US012590108B2

(12) United States Patent
Qin

(10) Patent No.: US 12,590,108 B2
(45) Date of Patent: Mar. 31, 2026

(54) BORACIC ACID COMPOUND

(71) Applicant: Phaeno Therapeutics Co., Ltd, Hangzhou (CN)

(72) Inventor: Donghui Qin, Hangzhou (CN)

(73) Assignee: Phaeno Therapeutics Co., Ltd, Hangzhou (CN)

( * ) Notice: Subject to any disclaimer, the term of this patent is extended or adjusted under 35 U.S.C. 154(b) by 503 days.

(21) Appl. No.: 18/042,002

(22) PCT Filed: Aug. 20, 2021

(86) PCT No.: PCT/CN2021/113815

§ 371 (c)(1),
(2) Date: Feb. 17, 2023

(87) PCT Pub. No.: WO2022/037680

PCT Pub. Date: Feb. 24, 2022

(65) Prior Publication Data

US 2024/0294554 A1 Sep. 5, 2024

(30) Foreign Application Priority Data

Aug. 20, 2020 (CN) ......................... 202010845001.1
Apr. 7, 2021 (CN) ......................... 202110373982.9

(51) Int. Cl.

| | |
|---|---|
| ***C07F 5/04*** | (2006.01) |
| ***A61K 31/407*** | (2006.01) |
| ***A61K 31/546*** | (2006.01) |
| ***A61K 31/69*** | (2006.01) |
| ***A61P 31/04*** | (2006.01) |

(52) U.S. Cl.
CPC .............. *C07F 5/04* (2013.01); *A61K 31/407* (2013.01); *A61K 31/546* (2013.01); *A61K 31/69* (2013.01); *A61P 31/04* (2018.01)

(58) Field of Classification Search
CPC ........................................................ C07F 5/04
See application file for complete search history.

(56) References Cited

U.S. PATENT DOCUMENTS

2010/0292185 A1 11/2010 Burns et al.

FOREIGN PATENT DOCUMENTS

| | | | |
|---|---|---|---|
| CN | 105026407 | A | 11/2015 |
| CN | 109415386 | A | 3/2019 |
| WO | 2010056827 | A1 | 5/2010 |
| WO | 2014089365 | A1 | 6/2014 |
| WO | 2016149393 | A1 | 9/2016 |
| WO | 2018005662 | A1 | 1/2018 |

OTHER PUBLICATIONS

Written opinion of the International Application No. PCT/CN2021/113815, Nov. 19, 2021, 3 pages.
Extended European Search Report of European Patent Application No. 21857768.2, Jul. 23, 2024, 8 pages.
Reaxys database accession No. XRN=30358082, 41405009, Sep. 22, 2016, 2 pages.

*Primary Examiner* — John S Kenyon
(74) *Attorney, Agent, or Firm* — Synergy IP Group AG; Lily Ackerman

(57) ABSTRACT

A new class of boronic acid compounds. Specifically disclosed are compounds represented by Formula (II) or (II'), pharmaceutically acceptable salts thereof or stereoisomers thereof, and the application thereof in the preparation of a medicament for treating diseases associated with bacterial infection.

(II)

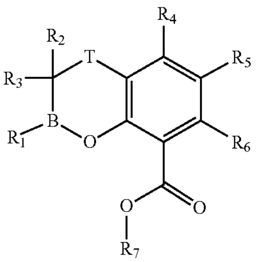

or (II')

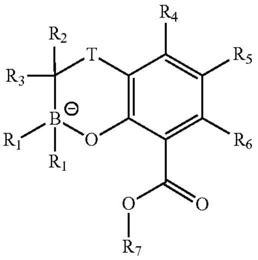

17 Claims, No Drawings

BORACIC ACID COMPOUND

CROSS REFERENCE TO RELATED APPLICATIONS

This application is a U.S. National Stage Application filed under 35 U.S.C. § 371 claiming the benefit of International Application No. PCT/CN2021/113815, filed on Aug. 20, 2021, which claims priority to and the benefit of Chinese Application No. 202110373982.9, filed on Apr. 7, 2021, and Chinese Application No. 202010845001.1, filed on Aug. 20, 2020, all of which are hereby incorporated herein by reference in their entireties.

TECHNICAL FIELD

The present invention relates to a new class of boronic acid compounds and specifically relates to compounds represented by Formula (II) or (II'), pharmaceutically acceptable salts thereof or stereoisomers thereof, and the application thereof in the preparation of a medicament for treating diseases associated with bacterial infection.

BACKGROUND ART

Since British scientist Fleming first discovered penicillin in 1928, β-lactam antibiotics have saved countless lives. With the emergence of various β-lactamases, β-lactam antibiotics are increasingly losing their due activities. For example, the proportion of serine hydrolases ESBLs, KPCs, and metallo-β-lactamases (MBLs) distributed in various bacteria is getting higher and higher, and the safety risks brought by bacteria to human beings are also increasing. A class of compounds, with phenylboronic acid as a representative, have significant inhibitory effects on metallo-β-lactamases (MBLs).

The appearance of medicaments of antibiotics combined with boronic acid β-lactamase inhibitors, with meropenem/vaborbactam as a representative, on the market has ignited hope for the development of boronic acid β-lactamase inhibitors. Rempex Pharmaceuticals, Inc. (WO 2018/005662 A1) reported a class of boronic acid β-lactamase inhibitors obtained by modifying phenylboronic acid. By optimizing this series of compounds, the compound QPX7728 was obtained, which is in the first phase of clinical development, and this compound is currently being promoted clinically by Qpex Biopharma, Inc. In addition, as boronic acid β-lactamase inhibitors, compounds currently under development also include VNRX-5133 (WO 2014/089365) developed by VenatoRx Pharmaceuticals, Inc., which is currently in the third clinical phase.

VNRX-5133

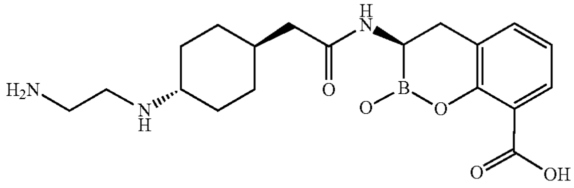

-continued

QPX7728

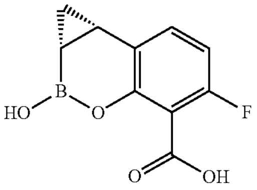

Based on the severe drug resistance situation, it is currently urgent to develop a new generation of broad-spectrum β-lactamase inhibitors to solve the current drug resistance problem. The boronic acid molecules of the present invention have corresponding potentials.

SUMMARY OF THE INVENTION

The present invention provides a compound represented by Formula (II) or (II') or a pharmaceutically acceptable salt thereof, (II)

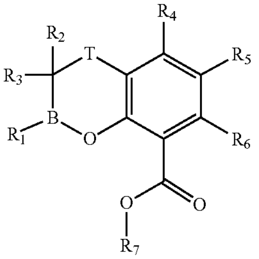

or (II')

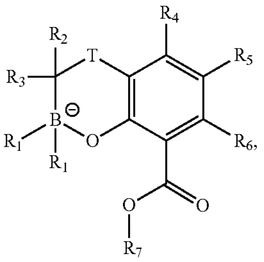

wherein B is boron;

T is —O—, —S—, or —Se—;

each $R_1$ is independently —OH or $C_{1-3}$ alkoxy;

$R_2$ and $R_3$ are each independently H or $C_{1-3}$ alkyl, wherein the $C_{1-3}$ alkyl is optionally substituted with 1, 2, or 3 substituents independently selected from F, Cl, Br, I, —OH, and —$OCH_3$;

$R_4$ is H, F, Cl, Br, I, $C_{1-3}$ alkyl, or $C_{1-3}$ alkoxy, wherein the $C_{1-3}$ alkyl and $C_{1-3}$ alkoxy are each independently and optionally substituted with 1, 2, or 3 substituents independently selected from F, Cl, Br, I, —OH, and —OCH;

$R_5$ is H, F, Cl, Br, I, or $C_{1-3}$ alkoxy;

$R_6$ is H, F, Cl, Br, I, —$OR_a$, or $C_{1-3}$ alkyl, wherein the $C_{1-3}$ alkyl is optionally substituted with 1, 2, or 3 substituents independently selected from F, Cl, Br, I, —OH, and —$OCH_3$;

or $R_5$ and $R_6$ together with the carbon atom to which they are attached form a 5-6-membered oxygen-containing non-aromatic heterocyclic ring, wherein the 5-6-membered oxygen-containing non-aromatic heterocyclic ring is optionally substituted with 1, 2, or 3 substituents independently selected from F, Cl, Br, I, —OH, and —$OCH_3$;

$R_7$ is H, $C_{1-3}$ alkyl, —$C(R_b)_2OC({=}O)R_c$, or —$C(R_b)_2OC({=}O)OR_c$, wherein the $C_{1-3}$ alkyl is optionally substituted with 1, 2, or 3 substituents independently selected from F, Cl, Br, I, —OH, and —$OCH_3$;

$R_a$ is H, $C_{1-6}$ alkyl,

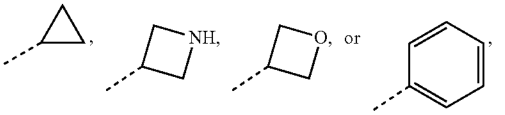

or wherein the $C_{1-6}$ alkyl,

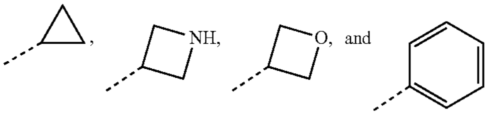

and are each independently and optionally substituted with 1, 2, or 3 $R_{a1}$;

each $R_b$ is independently H or $C_{1-3}$ alkyl;

$R_c$ is H, $C_{1-3}$ alkyl,

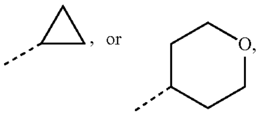

or wherein the $C_{1-3}$ alkyl,

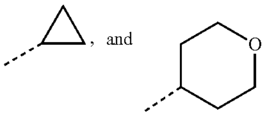

and are each independently and optionally substituted with 1, 2, or 3 $R_{c1}$;

each $R_{a1}$ is independently F, Cl, Br, I, $C_{1-3}$ alkyl, $C_{1-3}$ alkoxy,

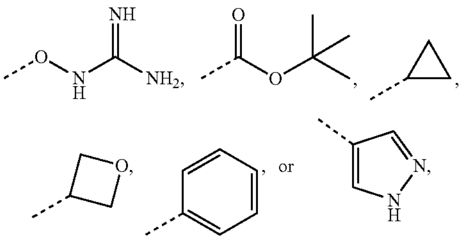

or wherein the $C_{1-3}$ alkyl, $C_{1-3}$ alkoxy,

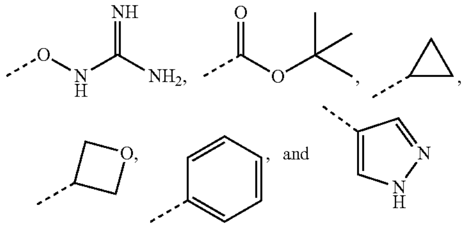

and are each independently and optionally substituted with 1, 2, or 3 R;

each $R_{c1}$ is independently F, Cl, Br, I, —OH, $C_{1-3}$ alkyl, or $C_{1-3}$ alkoxy; and each R is independently F, Cl, Br, I, —OH, or $C_{1-3}$ alkyl, wherein the $C_{1-3}$ alkyl is optionally substituted with 1, 2, or 3 substituents independently selected from F, Cl, Br, I, and

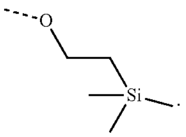

In some solutions of the present invention, the above-mentioned compound has a structure represented by Formula (II-1), (II'-1), (II-2), or (II'-2):

(II-1)

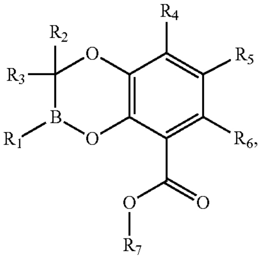

(II'-1)

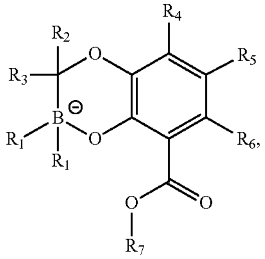

(II-2)

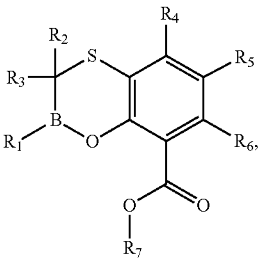

or

-continued (II'-2)

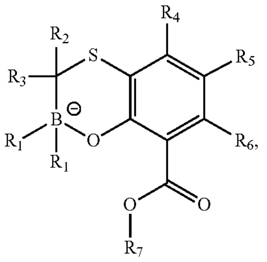

wherein $R_1$, $R_2$, $R_3$, $R_4$, $R_5$, $R_6$, and $R_7$ are as defined in the present invention.

In some solutions of the present invention, the above-mentioned compound has a structure represented by Formula (I) or (I'):

(I)

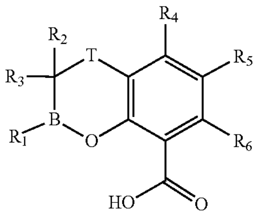

or (I')

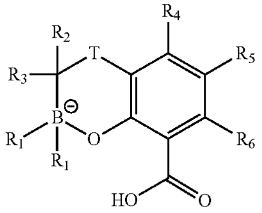

wherein T, $R_1$, $R_2$, $R_3$, $R_4$, $R_5$, and $R_6$ are as defined in the present invention.

The present invention provides a compound represented by Formula (I) or a pharmaceutically acceptable salt thereof, (I)

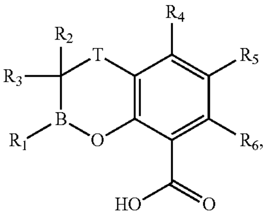

wherein B is boron;

T is —O—, —S—, or —Se—;

$R_1$ is —OH or $C_{1-3}$ alkoxy;

$R_2$ and $R_3$ are each independently H or $C_{1-3}$ alkyl, wherein the $C_{1-3}$ alkyl is optionally substituted with 1, 2, or 3 substituents independently selected from F, Cl, Br, I, —OH, and —$OCH_3$;

$R_4$ is H, F, Cl, Br, or I;

$R_5$ is H, F, Cl, Br, I, or $C_{1-3}$ alkoxy;

$R_6$ is H, F, Cl, Br, I, —$OR_a$, or $C_{1-3}$ alkyl, wherein the $C_{1-3}$ alkyl is optionally substituted with 1, 2, or 3 substituents independently selected from F, Cl, Br, I, —OH, and —$OCH_3$;

$R_a$ is H or $C_{1-3}$ alkyl, wherein the $C_{1-3}$ alkyl is optionally substituted with 1, 2, or 3 substituents independently selected from F, Cl, Br, I, and

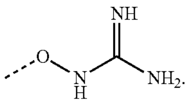

In some solutions of the present invention, the above-mentioned compound has a structure represented by Formula (I-1), (I'-1), (I-2), or (I'-2):

(I-1)

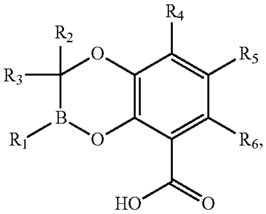

(I'-1)

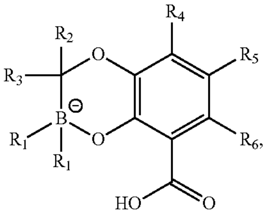

(I-2)

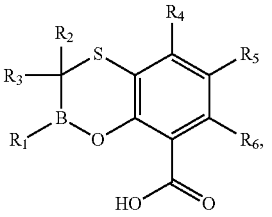

or (I'-2)

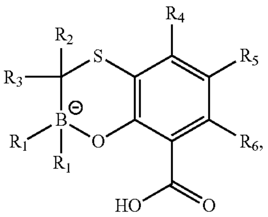

wherein $R_1$, $R_2$, $R_3$, $R_4$, $R_5$, and $R_6$ are as defined in the present invention. In some solutions of the present invention, the above-mentioned compound has a structure represented by Formula (I-1) or (I-2):

(I-1)

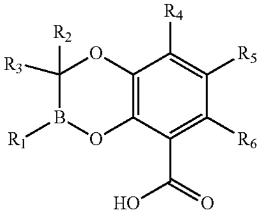

or (I-2)

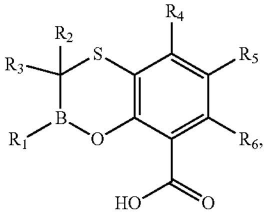

wherein $R_1$, $R_2$, $R_3$, $R_4$, $R_5$, and $R_6$ are as defined in the present invention.

In some solutions of the present invention, the above-mentioned pharmaceutically acceptable salt has a structure represented by Formula (I-3), (I-4), (I-5), or (I-6):

(I-3)

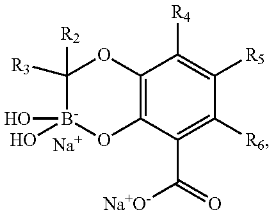

(I-4)

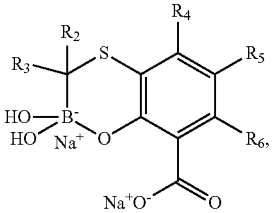

(I-5)

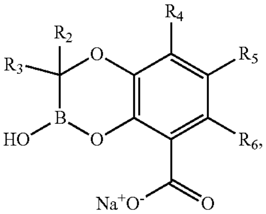

or (I-6)

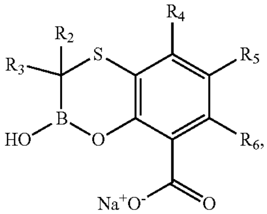

wherein $R_2$, $R_3$, $R_4$, $R_5$, and $R_6$ are as defined in the present invention.

In some solutions of the present invention, the above-mentioned pharmaceutically acceptable salt has a structure represented by Formula (I-3) or (I-4);

(I-3)

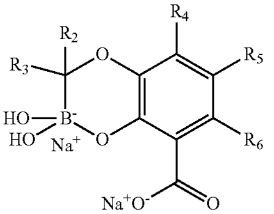

or (I-4)

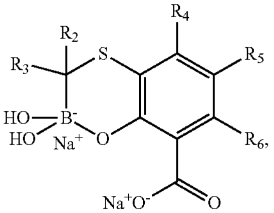

wherein $R_2$, $R_3$, $R_4$, $R_5$, and $R_6$ are as defined in the present invention.

In some solutions of the present invention, the above-mentioned each $R_1$ is independently —OH or —$OCH_3$, and the other variables are as defined in the present invention.

In some solutions of the present invention, the above-mentioned $R_1$ is —OH or —$OCH_3$, and the other variables are as defined in the present invention.

In some solutions of the present invention, the above-mentioned $R_2$ and $R_3$ are each independently H or —$CH_3$, and the other variables are as defined in the present invention.

In some solutions of the present invention, the above-mentioned $R_4$ is H, F, Cl, —$CH_3$, or —$OCH_2CH_3$, and the other variables are as defined in the present invention.

In some solutions of the present invention, the above-mentioned $R_5$ is H, F, Cl, or —$OCH_3$, and the other variables are as defined in the present invention.

In some solutions of the present invention, the above-mentioned each R is independently F, Cl, Br, I, —$CH_3$, or

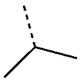

, wherein the —$CH_3$ or

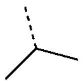

is each independently and optionally substituted with 1, 2, or 3 substituents independently selected from F, Cl, Br, I, and

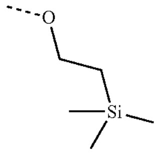, and the other variables are as defined in the present invention.

In some solutions of the present invention, the above-mentioned each R is independently F, Cl, Br, I, —$CH_3$,

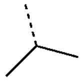, or 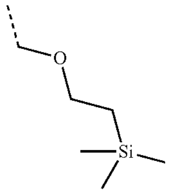, and the other variables are as defined in the present invention.

In some solutions of the present invention, the above-mentioned each $R_{a1}$ is independently F, Cl, Br, I, —$OCH_3$,

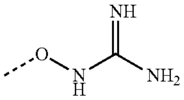, 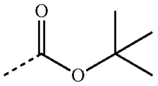, 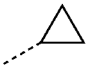, 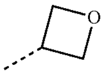, 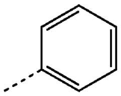, or 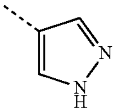, wherein the —$OCH_3$,

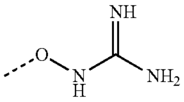, 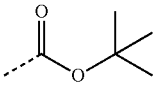, 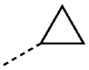, 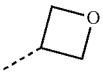, 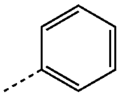, and 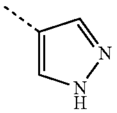

are each independently and optionally substituted with 1, 2, or 3 R, and R and the other variables are as defined in the present invention.

In some solutions of the present invention, the above-mentioned each $R_{a1}$ is independently F, Cl, Br, I, —$OCH_3$,

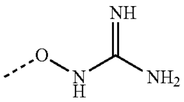, 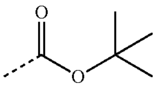, 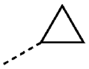, 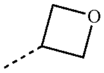, 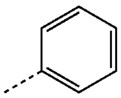, 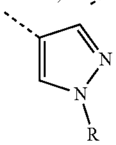, or

-continued

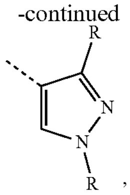, and R and the other variables are as defined in the present invention.

In some solutions of the present invention, the above-mentioned each $R_{a1}$ is independently F, Cl, Br, I, —$OCH_3$,

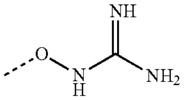, 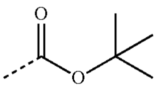, 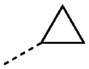, 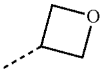, 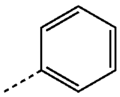, 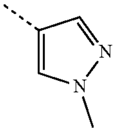, 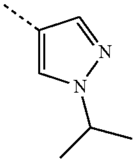, 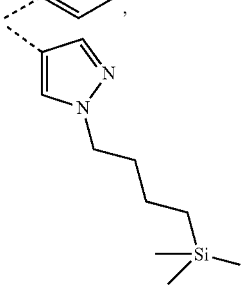, or 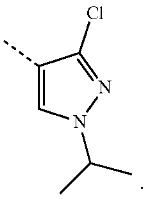.

In some solutions of the present invention, the above-mentioned $R_a$ is H, —$CH_3$, —$CH_2CH_3$,

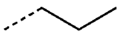, 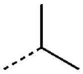, 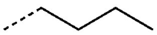, 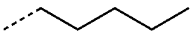, 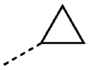, 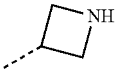, 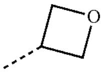, or 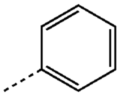, wherein the —$CH_3$, —$CH_2CH_3$,

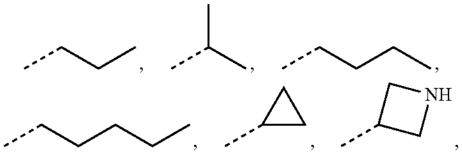

-continued

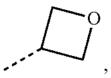

, and

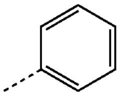

are each independently and optionally substituted with 1, 2, or 3 $R_{a1}$, and $R_{a1}$ and the other variables are as defined in the present invention.

In some solutions of the present invention, the above-mentioned $R_a$ is H, —$CH_3$,

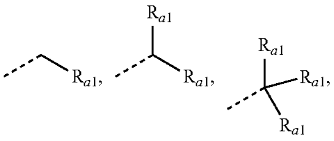

—$CH_2CH_3$,

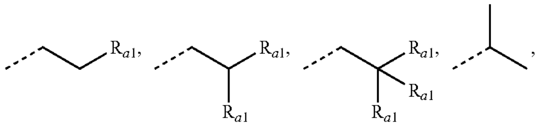

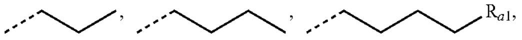

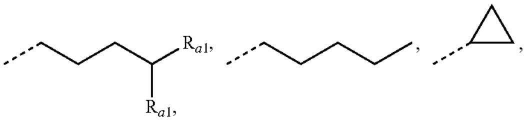

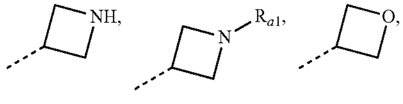

or

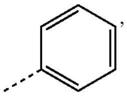

and $R_{a1}$ and the other variables are as defined in the present invention.

In some solutions of the present invention, the above-mentioned $R_a$ is H, —$CH_3$,

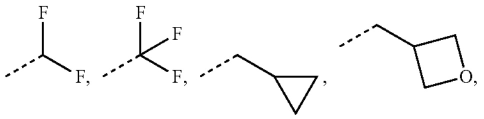

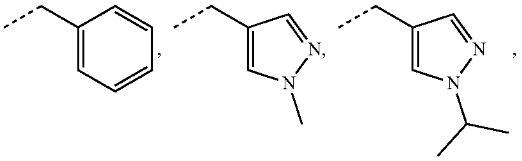

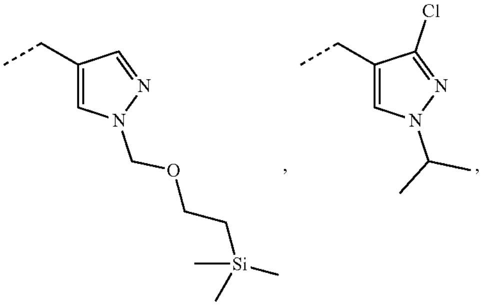

—$CH_2CH_3$,

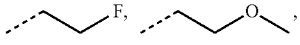

-continued

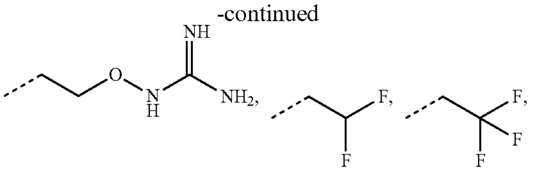

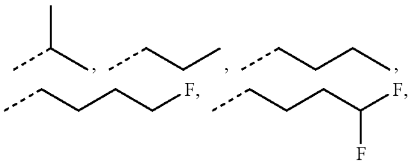

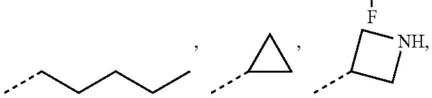

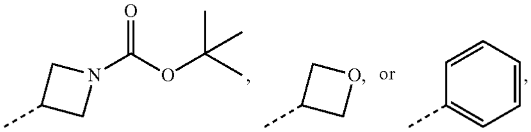

and the other variables are as defined in the present invention.

In some solutions of the present invention, the above-mentioned $R_a$ is H, —$CH_3$, or —$CH_2CH_3$, wherein the —$CH_3$ and —$CH_2CH_3$ are optionally substituted with 1, 2, or 3 substituents independently selected from F, Cl, Br, I, and

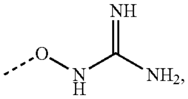

and the other variables are as defined in the present invention.

In some solutions of the present invention, the above-mentioned $R_a$ is H, —$CH_3$, —$CF_3$, —$CH_2CH_3$, or

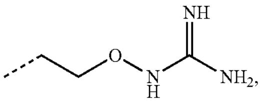

and the other variables are as defined in the present invention.

In some solutions of the present invention, the above-mentioned $R_6$ is H, F, Cl, Br, I, —$OR_a$, or —$CH_3$, wherein the —$CH_3$ is optionally substituted with 1, 2, or 3 substituents independently selected from F, Cl, Br, I, —OH, and —$OCH_3$, and $R_a$ and the other variables are as defined in the present invention.

In some solutions of the present invention, the above-mentioned $R_b$ is H, F, Cl, Br, I, —OH, —$OCH_3$, —$OCH_2CH_3$, —$CH_3$, —$CH_2OH$, —$CH_2OCH_3$,

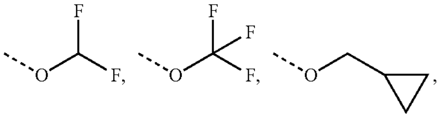

-continued

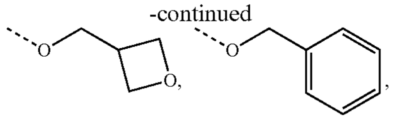

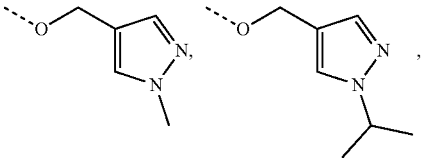

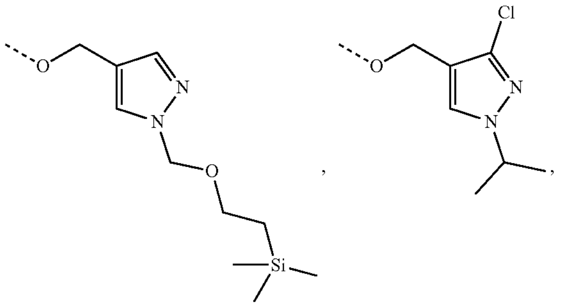

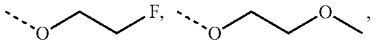

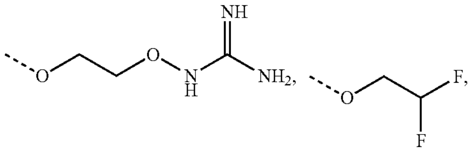

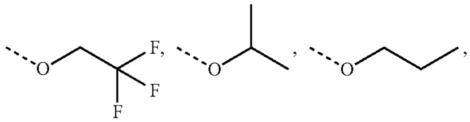

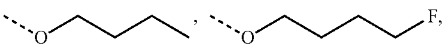

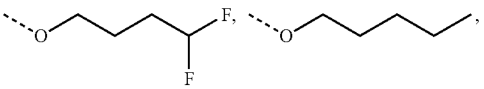

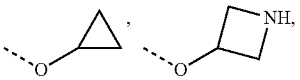

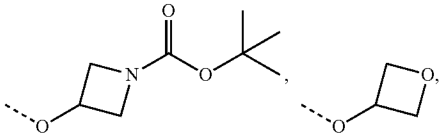

or

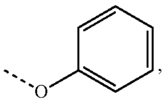

and the other variables are as defined in the present invention.

In some solutions of the present invention, the above-mentioned $R_b$ is H, F, Cl, Br, I, —OH, —$OCH_3$, —$OCF_3$, —$OCH_2CH_3$,

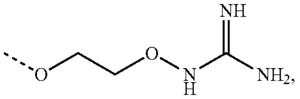

—$CH_3$, or —$CH_2OH$, and the other variables are as defined in the present invention.

In some solutions of the present invention, the above-mentioned structural unit

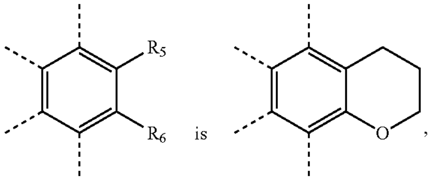

and the other variables are as defined in the present invention.

In some solutions of the present invention, the above-mentioned each $R_b$ is independently H, and the other variables are as defined in the present invention.

In some solutions of the present invention, the above-mentioned each $R_{c1}$ is independently —$OCH_3$, and the other variables are as defined in the present invention.

In some solutions of the present invention, the above-mentioned $R_c$ is H, —$CH_3$, —$CH_2CH_3$,

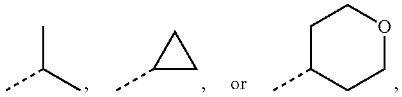

wherein the —$CH_3$, —$CH_2CH_3$,

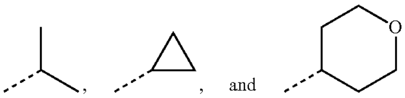

are each independently and optionally substituted with 1, 2, or 3 $R_{c1}$, and $R_{c1}$ and the other variables are as defined in the present invention.

In some solutions of the present invention, the above-mentioned $R_7$ is H,

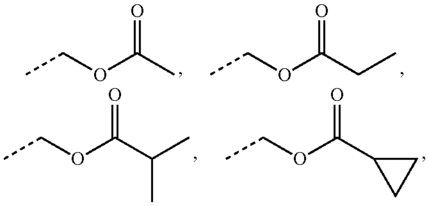

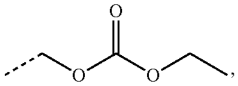

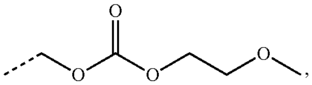

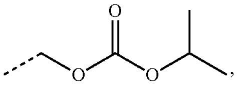

or

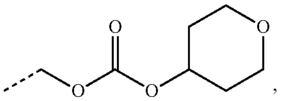

and the other variables are as defined in the present invention.
There are also some solutions of the present invention which are derived from arbitrary combinations of the above-mentioned variables.
The present invention further provides a compound of the following formula or a pharmaceutically acceptable salt thereof:
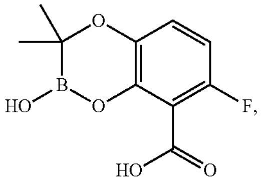
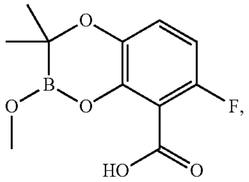
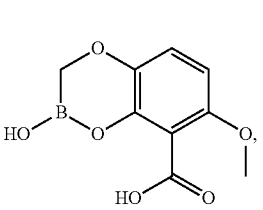
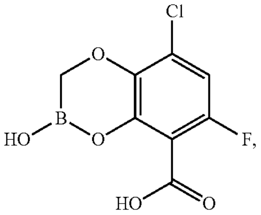
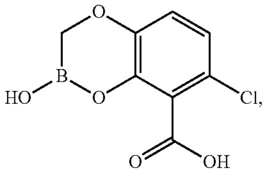
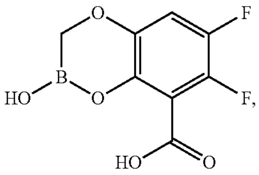
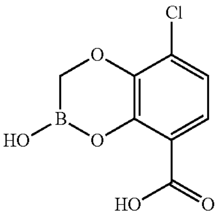
,
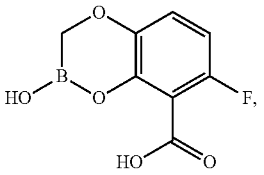
,
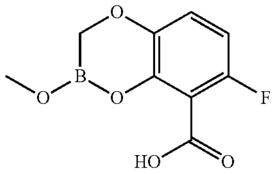
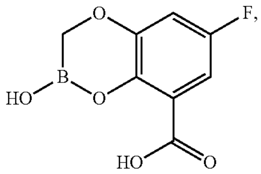
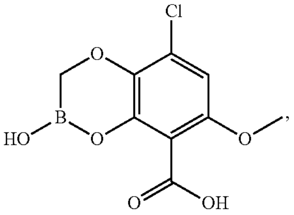
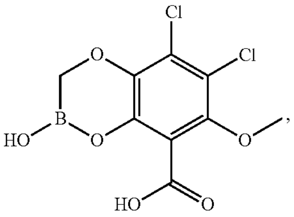
-continued
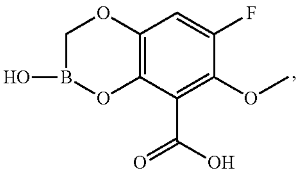
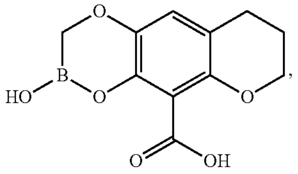
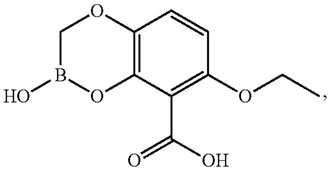
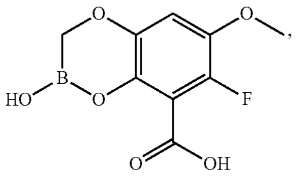
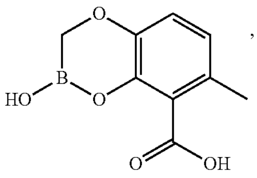
,
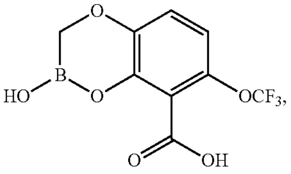
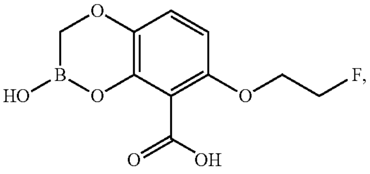
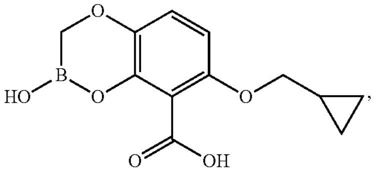
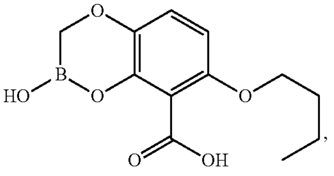
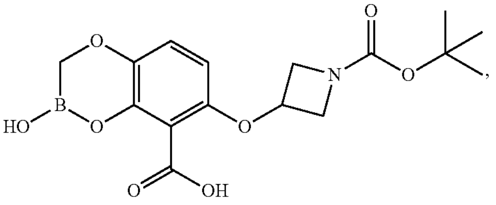

-continued
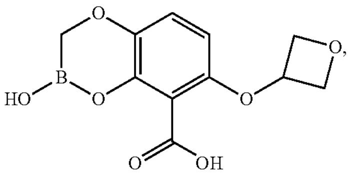
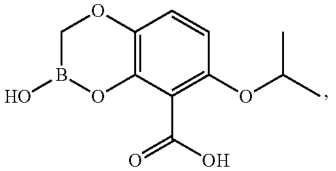
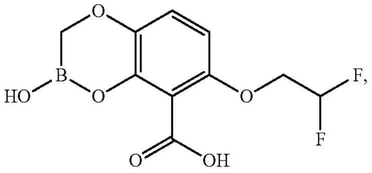
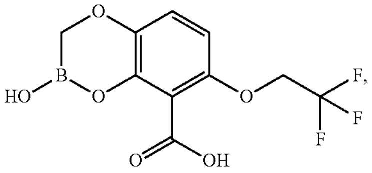
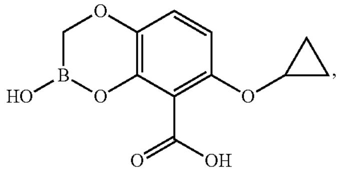
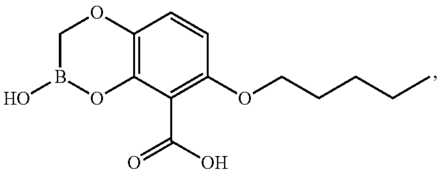
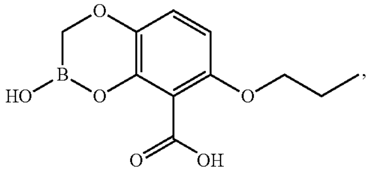
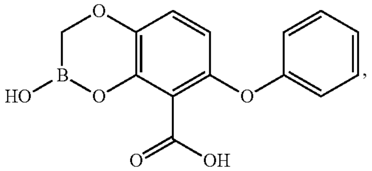
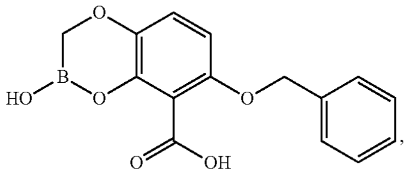
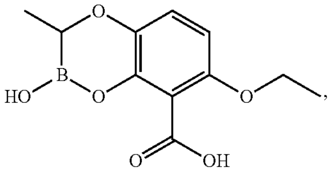
-continued
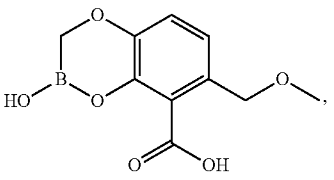
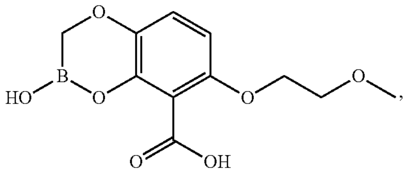
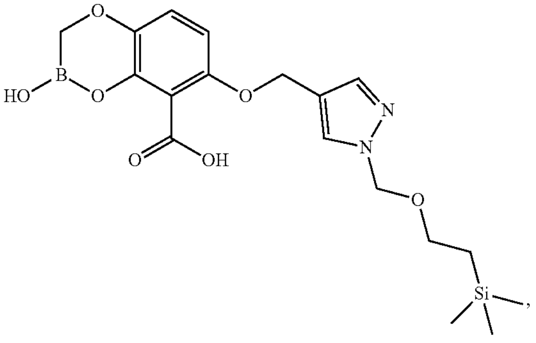
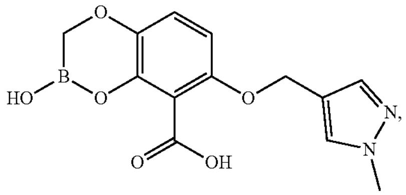
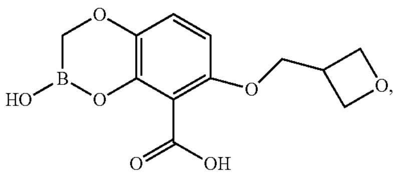
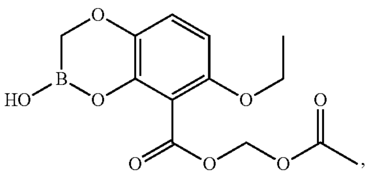
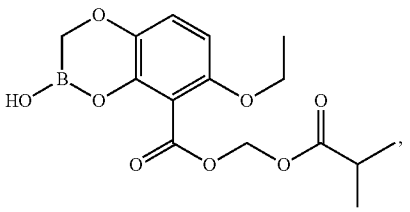
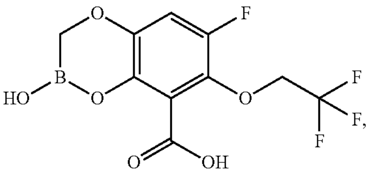

-continued
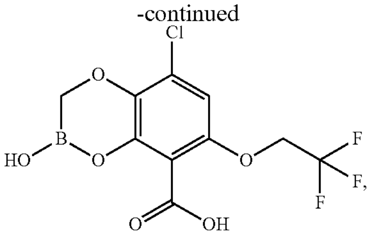
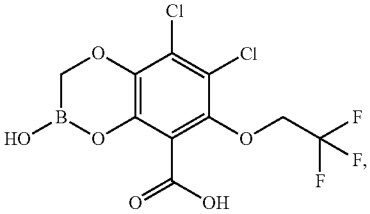
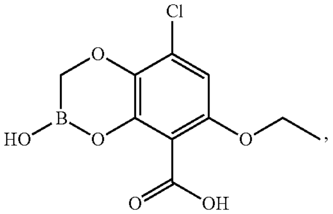
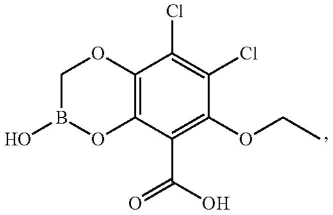
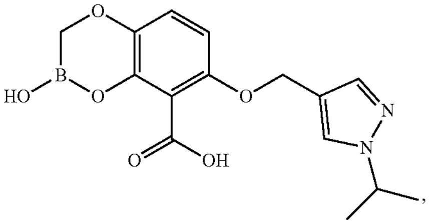
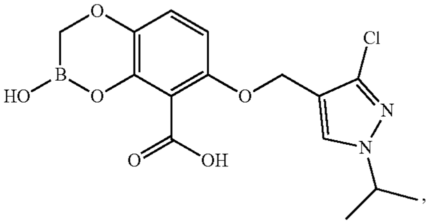
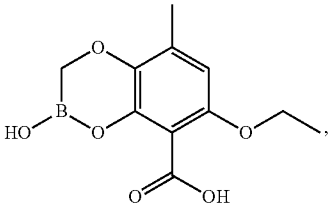
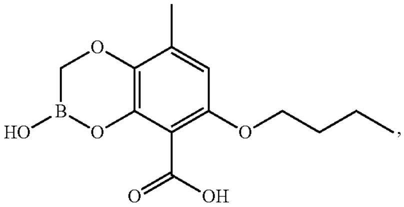
-continued
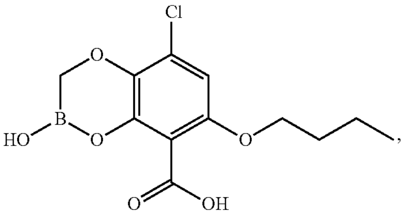
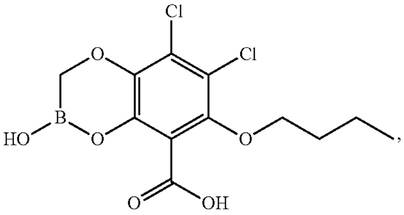
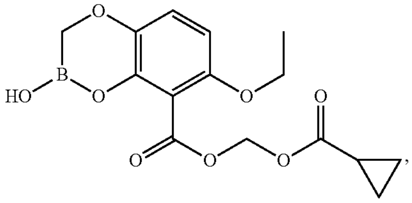
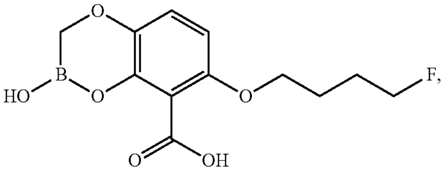
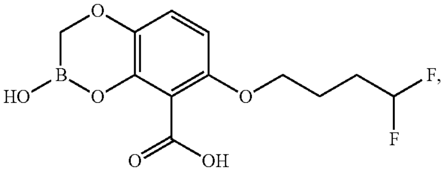
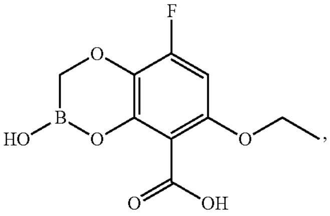
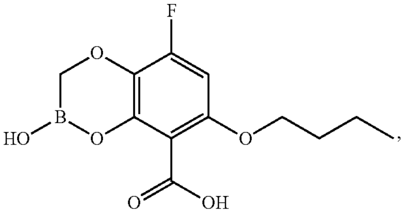
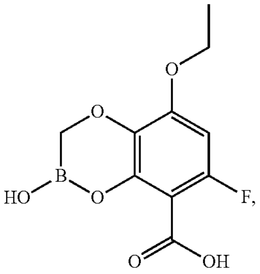

-continued
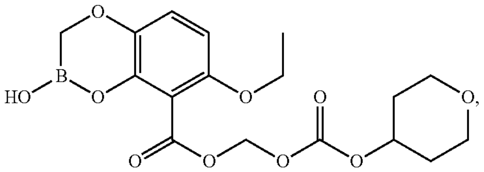
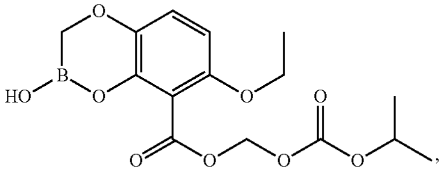
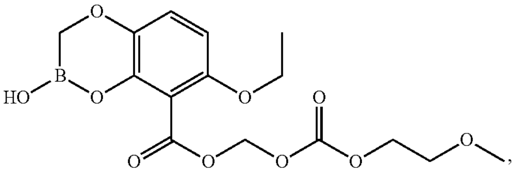
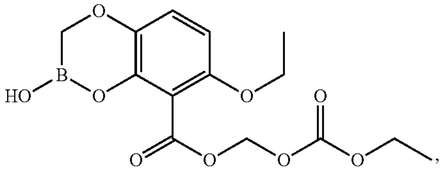
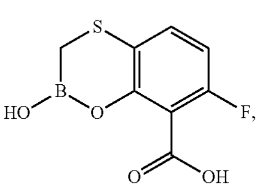
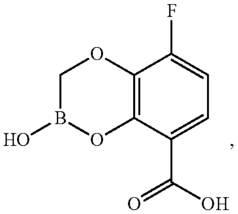
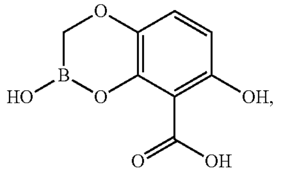
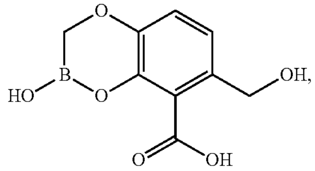
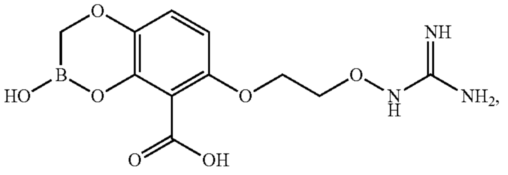
or
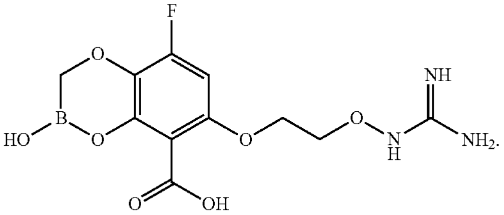
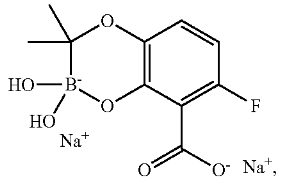
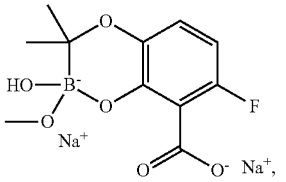
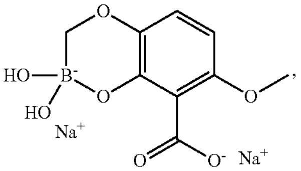
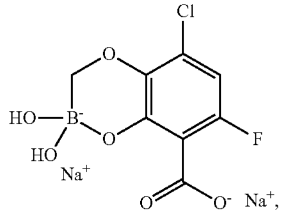
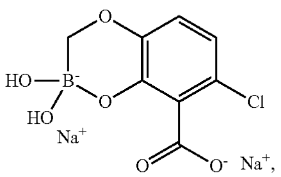
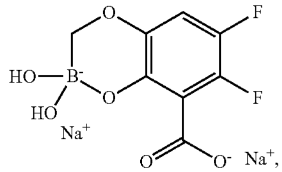
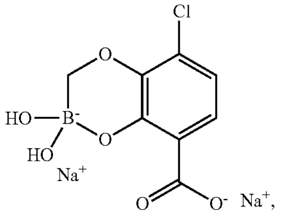
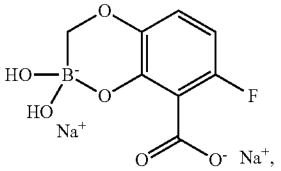
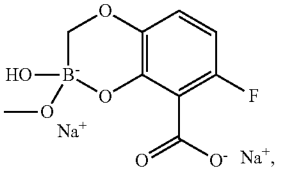
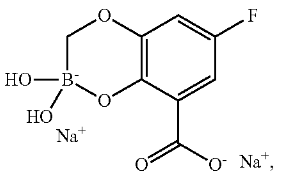
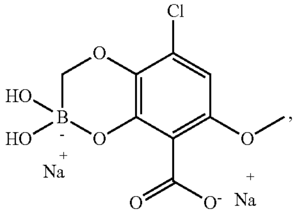
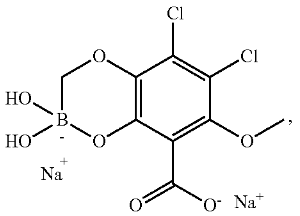
The present invention further provides a compound of the following formula:

-continued
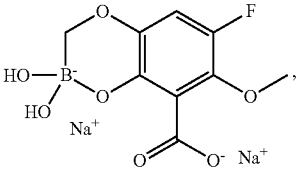
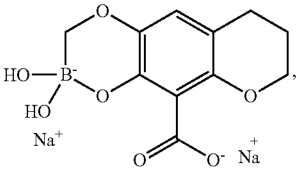
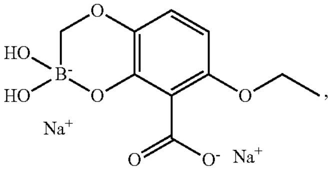
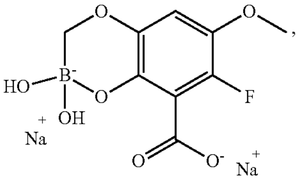
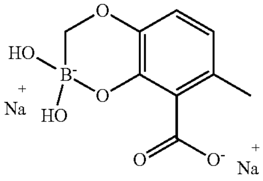
,
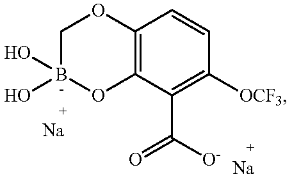
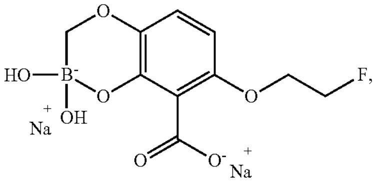
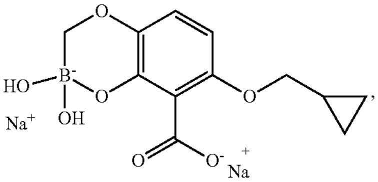
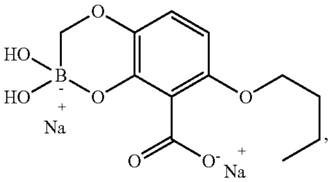
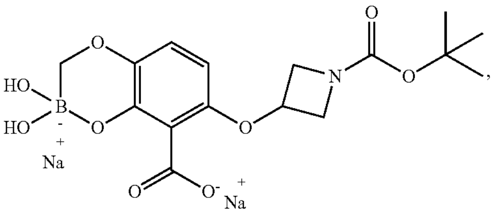
-continued
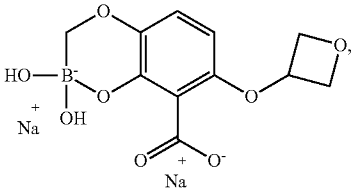
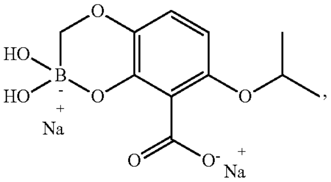
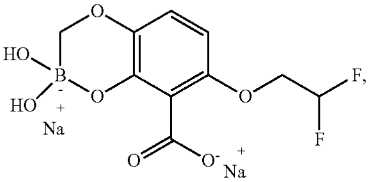
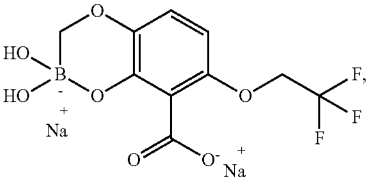
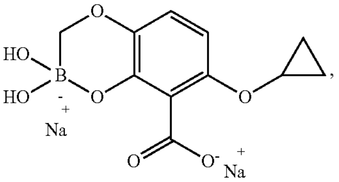
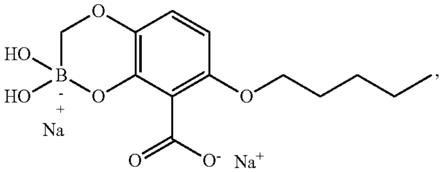
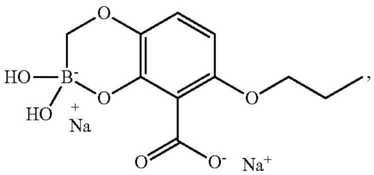
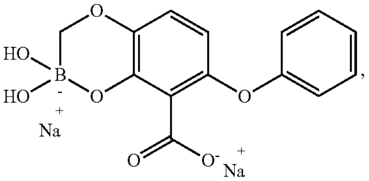
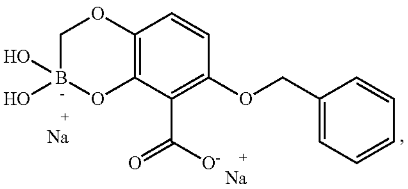

-continued
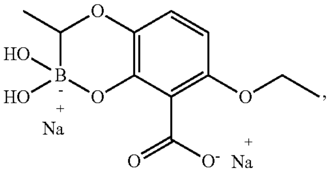
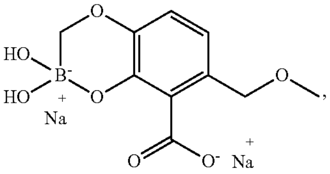
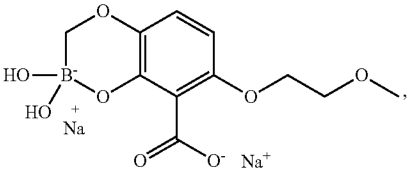
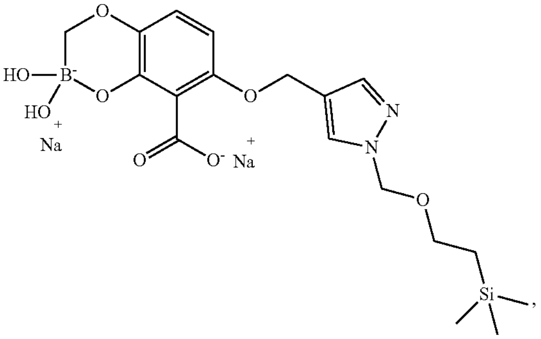
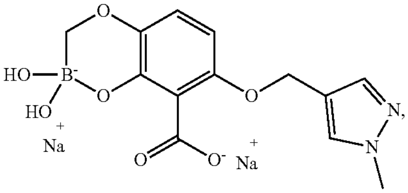
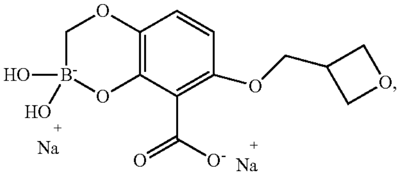
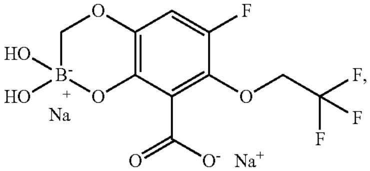
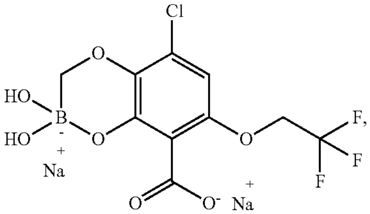
-continued
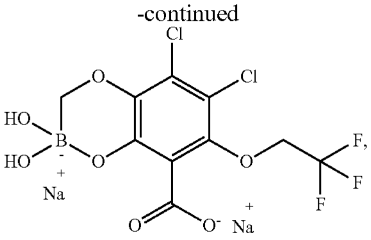
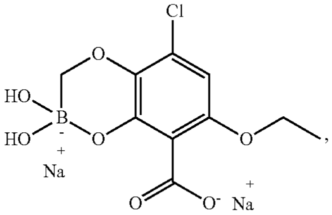
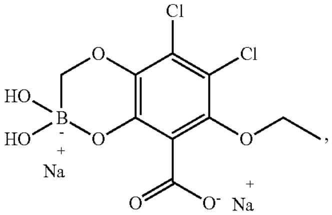
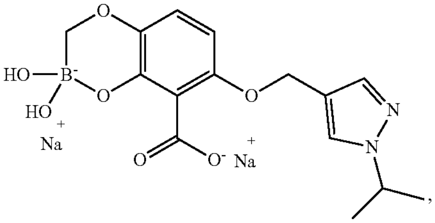
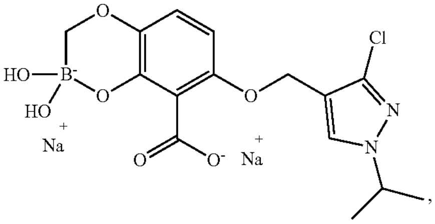
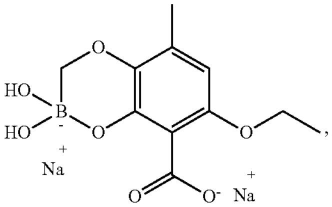
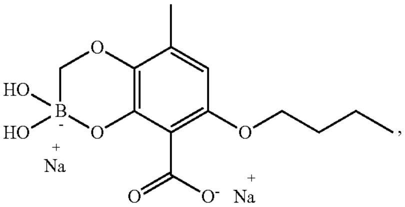
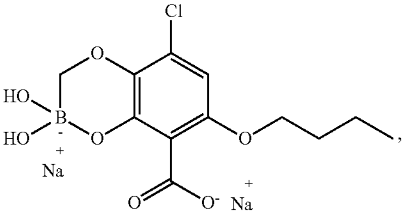

-continued
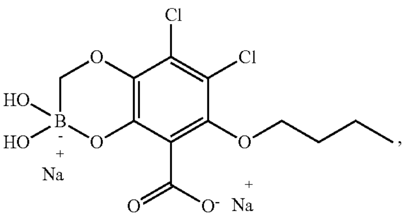
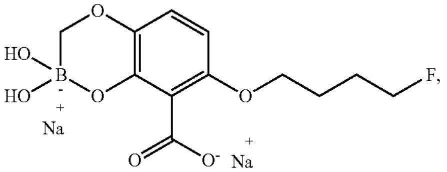
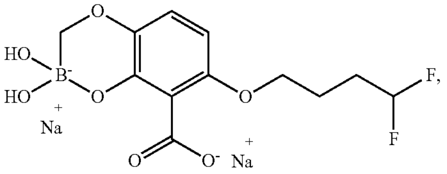
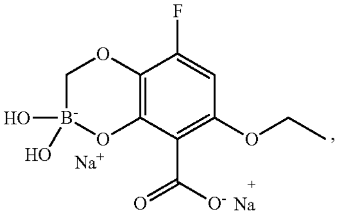
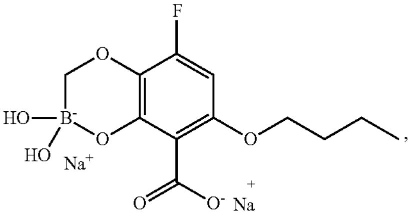
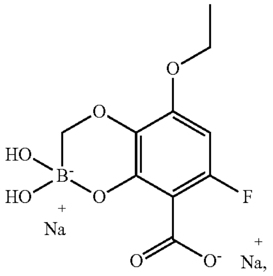
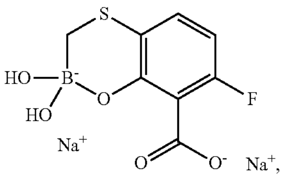
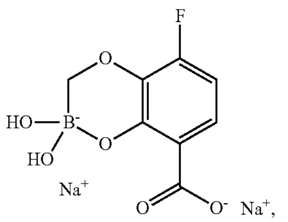
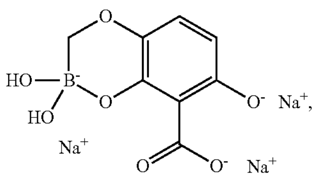
-continued
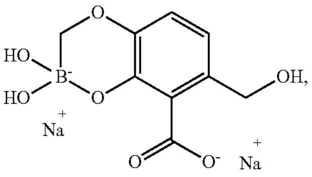
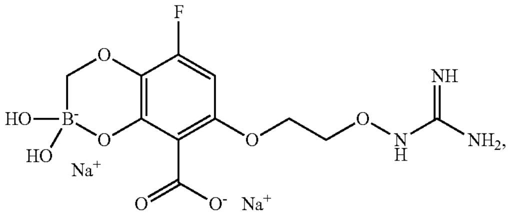
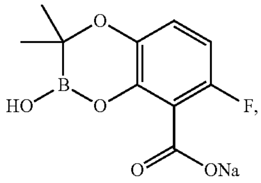
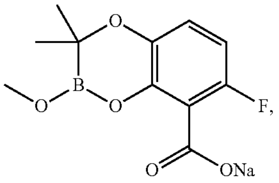
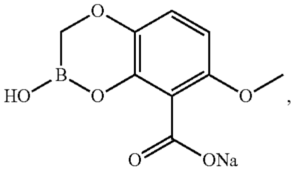
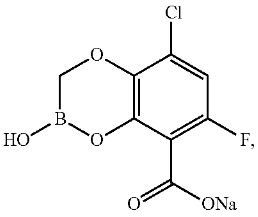
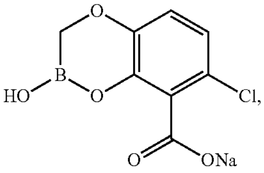
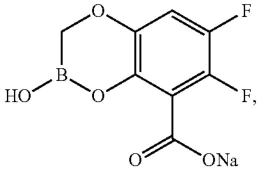
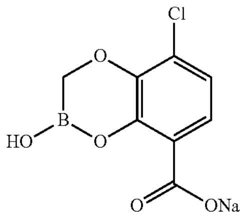
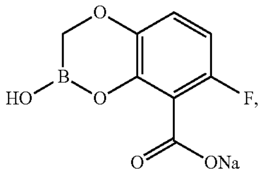
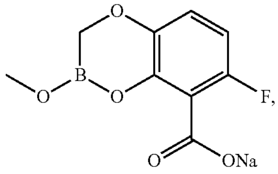
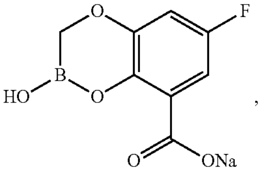
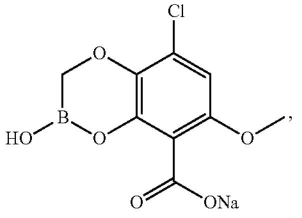

-continued
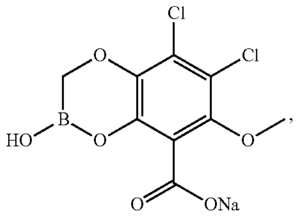
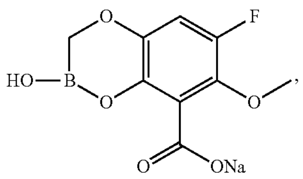
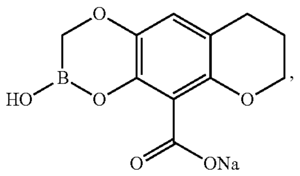
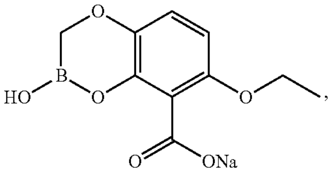
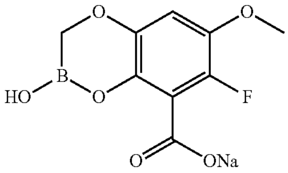
,
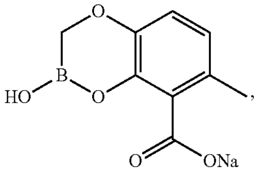
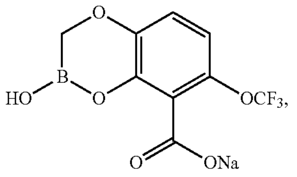
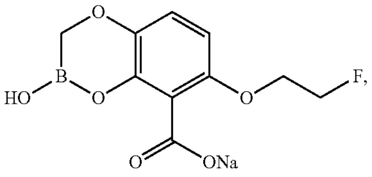
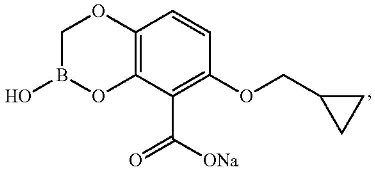
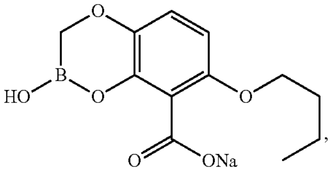
-continued
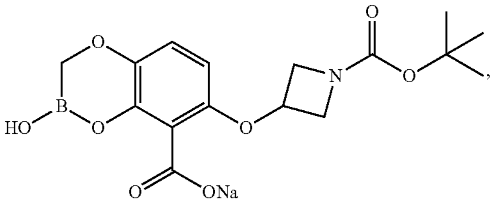
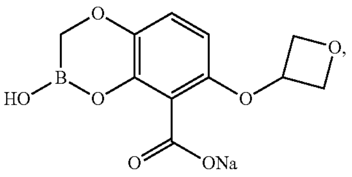
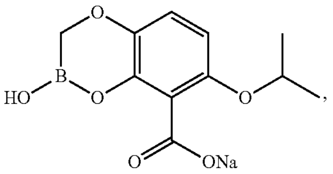
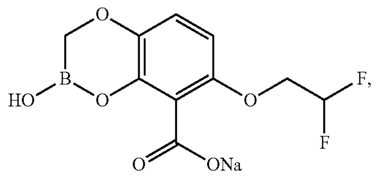
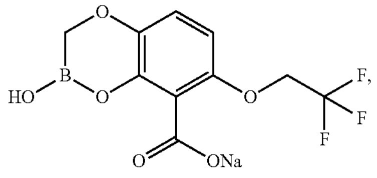
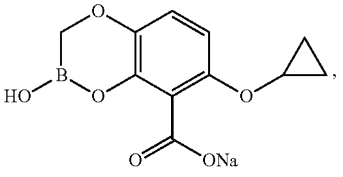
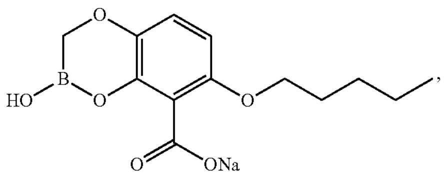
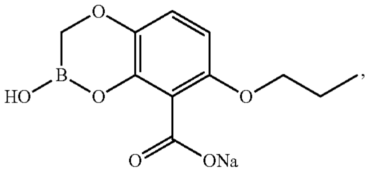
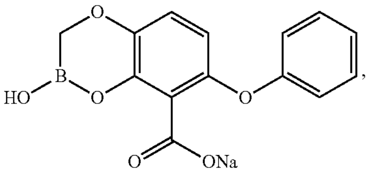

-continued
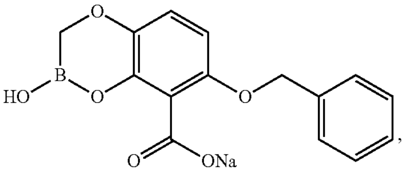
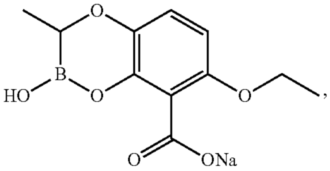
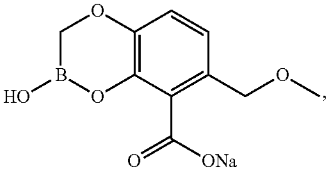
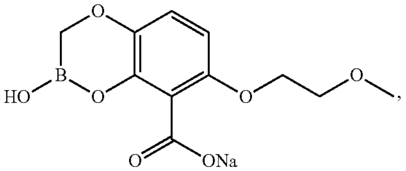
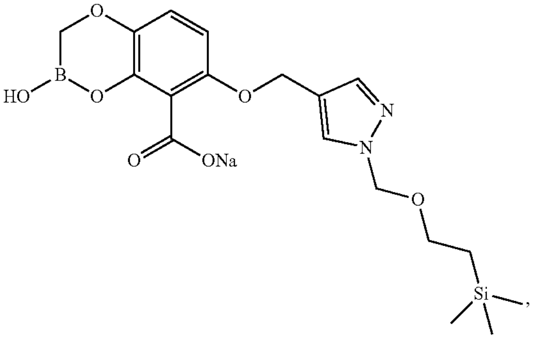
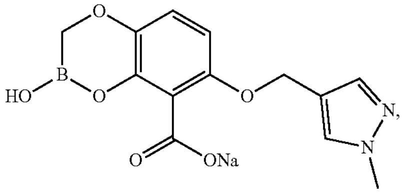
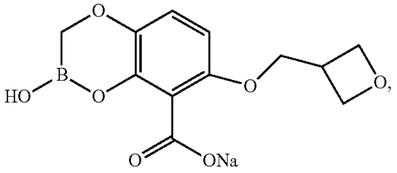
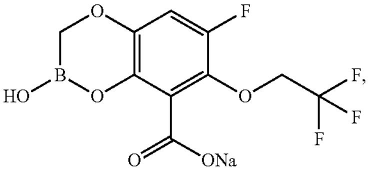
-continued
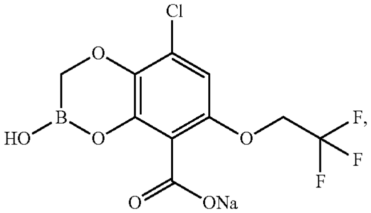
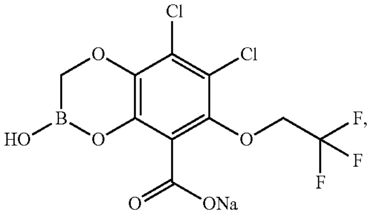
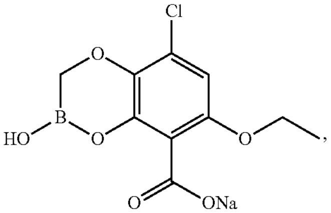
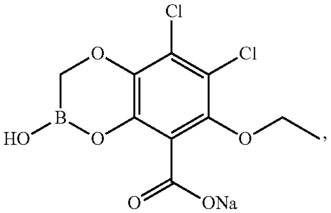
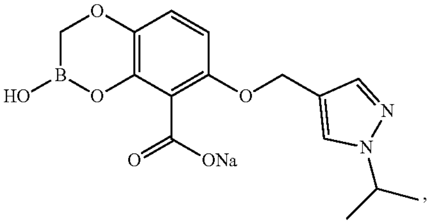
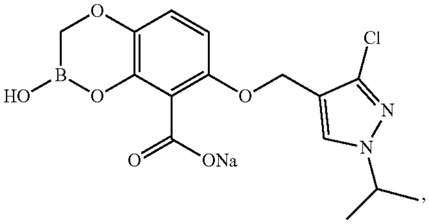
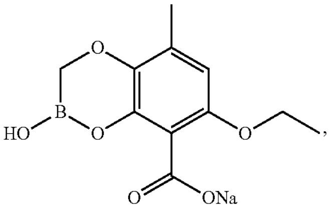
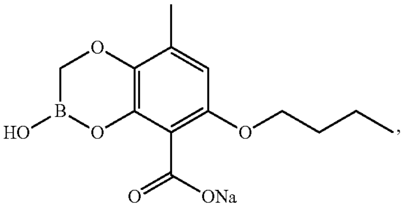

-continued

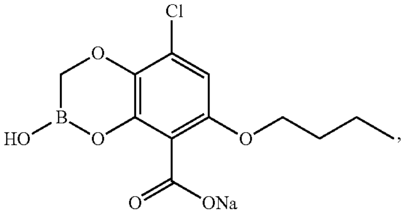

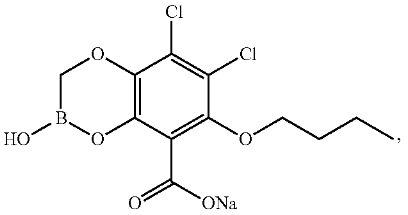

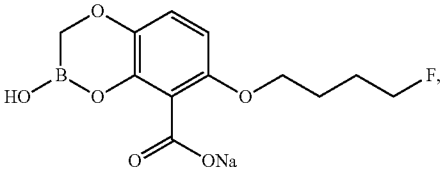

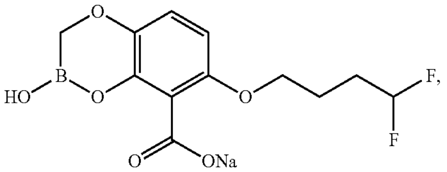

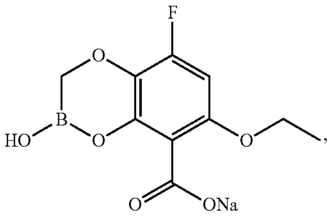

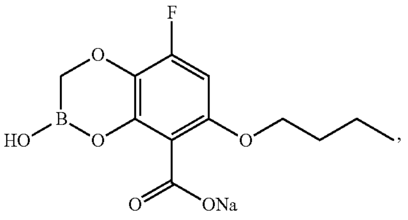

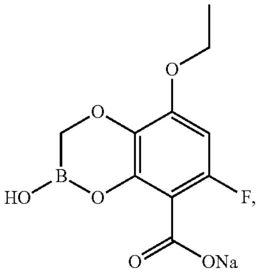

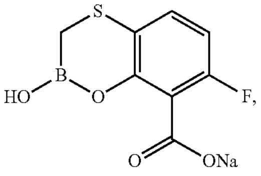

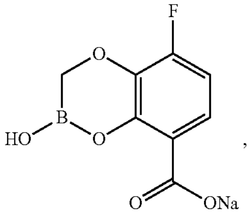

,

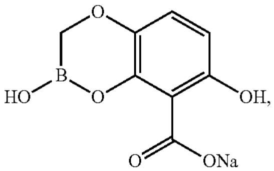

-continued

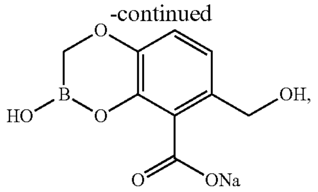

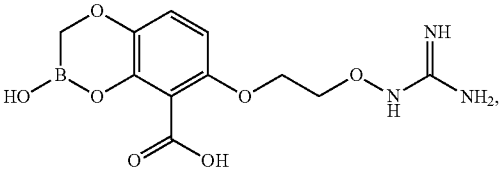

or

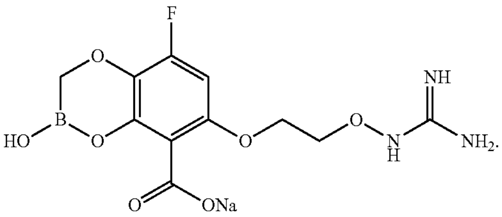

In some solutions of the present invention, the above-mentioned pharmaceutically acceptable salt is a sodium salt.

The present invention further provides a pharmaceutical composition, comprising a therapeutically effective amount of the above-mentioned compound or a pharmaceutically acceptable salt thereof, a β-lactam antibacterial agent, and a pharmaceutically acceptable carrier.

In some solutions of the present invention, the above-mentioned β-lactam antibacterial agent is based on penicillin, cephalosporin, cephamycin, oxacephem, carbapenem, or monocyclic lactam.

In some solutions of the present invention, the above-mentioned β-lactam antibacterial agent is amoxicillin, piperacillin, ticarcillin, azlocillin, mezlocillin, cefazolin, cefradine, cefotaxime, cefuroxime, cefaclor, cefotiam, cefprozil, cefotaxime, ceftriaxone, ceftazidime, cefoperazone, ceftizoxime, cefmenoxime, cefodizime, cefpodoxime, cefixime, ceftibuten, cefpirome, cefepime, cefoxitin, cefinetazole, panipenem, aztreonam, carumonam, cefoxitin, cefinetazole, latamoxef, flomoxef, imipenem, meropenem, ceftolozane, or cefiderocol. In some solutions of the present invention, the above-mentioned β-lactam antibacterial agent is meropenem.

The present invention further provides an application of the above-mentioned compound, a pharmaceutically acceptable salt thereof, or the above-mentioned pharmaceutical composition in the preparation of a β-lactamase inhibitor medicament.

The present invention further provides an application of the above-mentioned compound, a pharmaceutically acceptable salt thereof, or the above-mentioned pharmaceutical composition in the preparation of a medicament for treating a disease associated with bacterial infection. In some embodiments, the disease associated with bacterial infection is caused by bacteria that express β-lactamase. In some embodiments, the disease associated with bacterial infection is caused by *Klebsiella pneumoniae* or *Escherichia coli.*

Technical Effects

The present invention discloses a new class of boronic acid β-lactamase inhibitors, which have relatively strong antibacterial activity when used in combination with antibiotics, especially on various bacteria that express β-lactamase; have good solubility in water; have good exposure and excellent pharmacokinetic properties regardless of oral or intravenous administration; have good safety; can significantly restore the activity of antibiotics when used in combination with antibiotics; have good efficacy; and will be used for treating diseases associated with bacterial infection.

Definition and Description

Unless otherwise specified, the following terms and phrases used herein are intended to have the following meanings. A specific term or phrase should not be considered uncertain or unclear unless specifically defined but should be understood according to its common meaning. When a trade name appears herein, it is intended to refer to its corresponding commodity or its active ingredient.

The term "pharmaceutically acceptable" used here refers to compounds, materials, compositions and/or dosage forms that are within the range of reliable medical judgment, are suitable for contact with human and animal tissues without excessive toxicity, irritation, allergic reaction, or other issues or complications, and are commensurate with a reasonable benefit/risk ratio.

The term "pharmaceutically acceptable salt" refers to a salt of the compound of the present invention, which is prepared from a compound found in the present invention with a specific substituent and a relatively nontoxic acid or base. When the compound of the present invention contains a relatively acidic functional group, a base addition salt can be obtained by bringing such a compound into contact with a sufficient amount of base in a pure solution or a suitable inert solvent. Pharmaceutically acceptable alkali addition salts include sodium, potassium, calcium, ammonium, organic amine or magnesium salts or similar salts. When the compound of the present invention contains a relatively basic functional group, an acid addition salt can be obtained by bringing such a compound into contact with a sufficient amount of acid in a pure solution or a suitable inert solvent. Examples of pharmaceutically acceptable acid addition salts include salts of inorganic acids including, for example, hydrochloric acid, hydrobromic acid, nitric acid, carbonic acid, bicarbonate, phosphoric acid, monobasic phosphate, dihydrogen phosphate, sulfuric acid, bisulfate, hydroiodic acid, and phosphorous acid; and salts of organic acids including acids acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, methanesulfonic acid, and the like; and also includes salts of amino acids (such as arginine) and salts of organic acids such as glucuronic acid. Some specific compounds of the present invention contain basic and acidic functional groups, so they can be converted into any base or acid addition salt.

Pharmaceutically acceptable salts of the present invention can be synthesized by means of conventional chemical methods from parent compounds containing acid radicals or bases. Generally, such salts are prepared by reacting these compounds in the form of free acids or bases with stoichiometric amounts of appropriate bases or acids in water or an organic solvent or a mixture of both.

The compound of the present invention may exist in a specific geometric or stereoisomeric form. The present invention contemplates all such compounds, including cis and trans isomers, (−)- and (+)-enantiomers, (R)- and (S)-enantiomers, diastereomers, (D)-isomers, (L)-isomers, racemic mixtures thereof, and other mixtures, for example, enantiomerically or diastereomerically enriched mixtures, and all these mixtures are within the scope of the present invention. There may be other asymmetric carbon atoms in substituents such as alkyl. All these isomers and mixtures thereof are included in the scope of the present invention.

Unless otherwise specified, the term "enantiomer" or "optical isomer" refers to stereoisomers which are mirror images of each other.

Unless otherwise specified, the term "cis-trans isomer" or "geometric isomer" is caused by the fact that double bonds or single bonds of ring-forming carbon atoms cannot rotate freely.

Unless otherwise specified, the term "diastereomer" refers to a stereoisomer having two or more chiral centers in the molecule and having a non-mirror relationship between molecules.

Unless otherwise specified, "(+)" means dextrorotatory, "(−)" means levorotatory, and "(±)" means racemic.

Unless otherwise specified, the wedge-shaped solid bond ( ) and wedge-shaped dashed bond ( ) indicate the absolute configuration of a stereocenter, the straight solid bond ( ) and straight dashed bond ( ) indicate the relative configuration of the stereocenter, the wavy line ( ) indicates a wedge-shaped solid bond ( ) or wedge-shaped dashed bond ( ), or the wavy line ( ) indicates a straight solid bond ( ) and a straight dashed bond ( ).

Unless otherwise specified, the term "tautomer" or "tautomeric form" means that at room temperature, isomers with different functional groups are in dynamic equilibrium and can be rapidly transformed into each other. If tautomers are possible (such as in solution), the chemical equilibrium of tautomers can be achieved. For example, proton tautomer (also referred to as prototropic tautomer) includes mutual transformation by proton migration, such as keto-enol isomerization and imine-enamine isomerization. Valence tautomer includes the mutual transformation by recombination of some bonding electrons. A specific example of keto-enol tautomerization is the tautomerism between pentane-2,4-dione and 4-hydroxypent-3-en-2-one.

Unless otherwise specified, the term "enriched in an isomer", "isomer-enriched", "enriched in an enantiomer" or "enantiomer-enriched" means that the content of one isomer or enantiomer is less than 100%, and the content of the isomer or enantiomer is more than or equal to 60%, or more than or equal to 70%, or more than or equal to 80%, or more than or equal to 90%, or more than or equal to 95%, or more than or equal to 96%, or more than or equal to 97%, or more than or equal to 98%, or more than or equal to 99%, or more than or equal to 99.5%, or more than or equal to 99.6%, or more than or equal to 99.7%, or more than or equal to 99.8%, or more than or equal to 99.9%.

Unless otherwise specified, the term "isomeric excess" or "enantiomeric excess" refers to the difference between the relative percentages of two isomers or two enantiomers. For example, where the content of one isomer or enantiomer is 90% and the content of the other isomer or enantiomer is 10%, the isomeric or enantiomeric excess (ee value) is 80%.

Optically active (R)- and (S)-isomers and D and L isomers can be prepared by means of chiral synthesis or chiral reagents or other conventional techniques. If it is desired to obtain an enantiomer of a compound of the present invention, it can be prepared by means of asymmetric synthesis or derivatization with chiral auxiliaries, wherein the obtained diastereomer mixture is separated and the auxiliary group is cleaved to provide the pure desired enantiomer. Alternatively, when the molecule contains a basic functional group (such as amino) or an acidic functional group (such as carboxyl), it forms diastereomer salts with an appropriate optically active acid or base, diastereomers are then resolved by means of a conventional method known in the art, and a pure enantiomer is then recovered. In addition, the separation of enantiomers and diastereomers is usually accomplished by using chromatography, in which a chiral stationary phase is used, and optionally in combination with chemical derivatization (e.g., carbamate formation from amine).

The compound of the present invention may contain an unnatural proportion of atomic isotopes at one or more atoms that constitute the compound. For example, compounds can be labeled with radioisotopes, such as tritium ($^3H$), iodine-125 ($^{125}I$), or C-14 ($^{14}C$). As another example, deuterated drugs can be formed by replacing hydrogen with heavy hydrogen, and the bond between deuterium and carbon is stronger than that between ordinary hydrogen and carbon. Compared with non-deuterated drugs, deuterated drugs have the advantages of reducing toxic and side effects, increasing drug stability, enhancing curative effects, prolonging drug biological half-life, etc. The transformation of all isotopic compositions of the compounds of the present invention, whether radioactive or not, is included in the scope of the present invention.

The term "optional" or "optionally" means that the subsequently described event or condition may, but does not have to, occur, and the description includes the case where the event or condition occurs and the case where the event or condition does not occur.

With regard to drugs or pharmacologically active agents, the term "effective amount" or "therapeutically effective amount" refers to a sufficient amount of drugs or agents that are nontoxic but can achieve the expected effect. For the oral dosage form of the present invention, the "effective amount" of one active substance in the composition refers to the amount required to achieve the expected effect when used in combination with another active substance in the composition. The determination of the effective amount varies from person to person, depending on the age and general situation of the recipient and also on the specific active substance. The appropriate effective amount in individual cases can be determined by a person skilled in the art according to conventional trials.

The term "substituted" means that any one or more hydrogen atoms on a specific atom are replaced by substituents, which may include heavy hydrogen and hydrogen variants, as long as the valence state of the specific atom is normal, and the substituted compound is stable. When the substituent is oxygen (i.e., =O), it means that two hydrogen atoms are substituted. Oxygen substitution does not occur on aromatic groups. The term "optionally substituted" means that it may or may not be substituted. Unless otherwise specified, the type and number of substituents may be arbitrary on the basis of being chemically achievable.

When any variable (such as R) appears once or more times in the composition or structure of a compound, the definition thereof in each case is independent. Therefore, for example, if one group is substituted with 0-2 R, the group can optionally be substituted with at most two R, and R in each case has an independent option. In addition, a combination of substituents and/or variants thereof is allowed only if such a combination produces a stable compound.

When the number of a linking group is 0, such as $-(CRR)_0-$, it means that the linking group is a single bond.

When one variable is selected from a single bond, it means that the two groups connected thereby are directly connected. For example, when L in A-L-Z represents a single bond, it means that the structure is actually A-Z.

When a substituent is absent, it means that the substituent does not exist. For example, when X in A-X is absent, it means that the structure is actually A. Where it is not indicated via which atom the recited substituent is connected to the substituted group, such a substituent can be bonded via any atom, for example, pyridyl as a substituent can be connected to the substituted group via any carbon atom on the pyridyl ring.

When the recited linking group does not indicate the linking direction thereof, the linking direction thereof is arbitrary, for example, the linking group L in

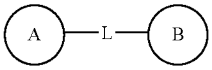

is -M-W-, and in this regard, the -M-W- may connect ring A and ring B in the same direction as the reading order from left to right to form

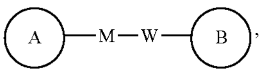, or may also connect ring A and ring B in the opposite direction to the reading order from left to right to form

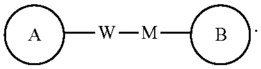.

In addition, a combination of the linking group, substituents and/or variants thereof is allowed only if such a combination produces a stable compound.

Unless otherwise specified, when a group has one or more linkable sites, any one or more sites of the group can be linked to other groups via chemical bonds. When the connection mode of the chemical bond is independent of location and there are H atoms in a site that can be connected, then when the chemical bond is connected, the number of H atoms in the site will correspondingly decrease with the number of the chemical bonds connected and become a group with the corresponding valence. The chemical bond that connects the site to another group can be represented by a straight solid bond (), a straight dashed bond (), or a wavy line (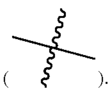).

For example, the straight solid bond in $-OCH_3$ means that it is connected to another group via the oxygen atom in this group; the straight dashed bond in

indicates that it is connected to another group via two ends of the nitrogen atom in this group; the wavy line in

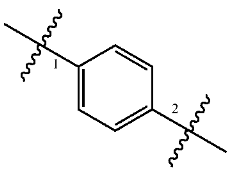 [SMILES: *c1ccc(*)cc1]

indicates that the phenyl group is connected to other groups via the carbon atoms at positions 1 and 2; and

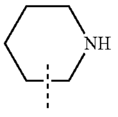

means that any linkable site on the piperidyl group can be connected to another group via a chemical bond, including at least four connection modes, i.e.,

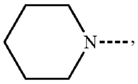, 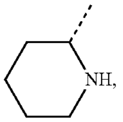, 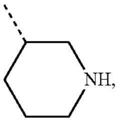, and 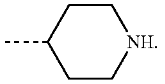.

Even if H atom is drawn on —N—,

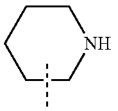

still includes groups having the connection mode

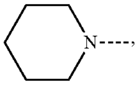, but when a chemical bond is connected, the number of H in this site will be correspondingly reduced by one to form a corresponding monovalent piperidyl group.

Unless otherwise specified, "B" in the present invention represents boron.

Unless otherwise specified, the term "$C_{1-3}$ alkyl" is used to denote a linear or branched saturated hydrocarbon group composed of 1 to 3 carbon atoms. The $C_{1-3}$ alkyl includes $C_{1-2}$ and $C_{2-3}$ alkyl, etc., and it may be monovalent (such as methyl), divalent (such as methylene), or multivalent (such as methine). Examples of $C_{1-3}$ alkyl include, but are not limited to, methyl (Me), ethyl (Et), propyl (including n-propyl and isopropyl), etc. Unless otherwise specified, "$C_{2-8}$ alkenyl" is used to denote a linear or branched hydrocarbon group composed of 2 to 8 carbon atoms and containing at least one carbon-carbon double bond that can be located at any position of the group. The $C_{2-8}$ alkenyl includes $C_{2-6}$, $C_{2-4}$, $C_{2-3}$, $C_4$, $C_3$, and $C_2$ alkenyl, etc., and it may be monovalent, divalent, or multivalent. Examples of $C_{2-8}$ alkenyl include, but are not limited to, vinyl, propenyl, butenyl, pentenyl, hexenyl, butadienyl, pentadienyl, hexadienyl, etc.

Unless otherwise specified, the term "$C_{1-6}$ alkyl" is used to denote a linear or branched saturated hydrocarbon group composed of 1 to 6 carbon atoms. The $C_{1-6}$ alkyl includes $C_{1-5}$, $C_{1-4}$, $C_{1-3}$, $C_{1-2}$, $C_{2-6}$, $C_{2-4}$, $C_6$, and $C_5$ alkyl, etc., and it may be monovalent (such as methyl), divalent (such as methylene), or multivalent (such as methine). Examples of $C_{1-6}$ alkyl include, but are not limited to, methyl (Me), ethyl (Et), propyl (including n-propyl and isopropyl), butyl (including n-butyl, isobutyl, s-butyl, and t-butyl), pentyl (including n-pentyl, isopentyl, and neopentyl), hexyl, etc.

Unless otherwise specified, the term "$C_{1-3}$ alkoxy" refers to those alkyl groups containing 1 to 3 carbon atoms that are attached to the rest of the molecule via an oxygen atom. The $C_{1-3}$ alkoxy includes $C_{1-2}$, $C_{2-3}$, $C_3$, and $C_2$ alkoxy, etc. Examples of $C_{1-3}$ alkoxy include, but are not limited to, methoxy, ethoxy, propoxy (including n-propoxy and isopropoxy), etc.

Unless otherwise specified, the term "5-6-membered oxygen-containing non-aromatic heterocyclic ring" refers to a monocyclic non-aromatic heterocyclic ring composed of 5-6 atoms and containing, in addition to one O, the same or different 0-3 heteroatoms selected from the heteroatoms O, N and S, wherein N is optionally quaternized, and the heteroatoms C and S can be optionally oxidized (i.e., C(=O) and $S(=O)_p$ where p is 1 or 2), including groups having a partially unsaturated cyclic group and a partially crosslinked structure. A non-aromatic heterocyclic ring may form a condensed ring with aryl or heteroaryl. The 5-6-membered oxygen-containing non-aromatic heterocyclic ring includes 5- and 6-membered oxygen-containing non-aromatic heterocyclic rings, etc. The 5-6-membered oxygen-containing non-aromatic heterocyclic ring includes 5-6-membered heterocyclic alkenyl. Examples of the 5-6-membered heterocyclic alkenyl include, but are not limited to,

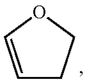, 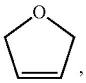, 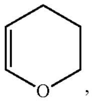, 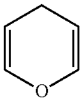, 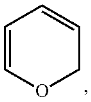, 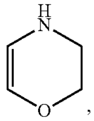, or 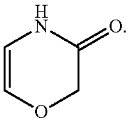.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and also includes any range of n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, $C_{9-12}$, etc. By the same reasoning, n-membered to n+m-membered means that the number of atoms on a ring is n to n+m, for example, 3-12-membered rings include 3-membered ring, 4-membered ring, 5-membered ring, 6-membered ring, 7-membered ring, 8-membered ring, 9-membered ring, 10-membered ring, 11-membered ring, and 12-membered ring, and also includes any range of n to n+m, for example, 3-12-membered rings include 3-6-membered ring, 3-9-membered ring, 5-6-membered ring, 5-7-membered ring, 6-7-membered ring, 6-8-membered ring, 6-10-membered ring, etc.

The term "leaving group" refers to a functional group or atom that can be substituted with another functional group or atom by means of a substitution reaction (such as a nucleophilic substitution reaction). For example, representative leaving groups include trifluoromethanesulfonate; chlorine, bromine, and iodine; sulfonate groups, such as mesylate, tosylate, p-bromobenzenesulfonate, and p-tosylate; and acyloxy, such as acetoxy and trifluoroacetoxy.

The term "protecting group" includes but is not limited to "amino protecting group", "hydroxyl protecting group", or "thiol protecting group". The term "amino protecting group" refers to a protecting group suitable for preventing side reactions at the amino nitrogen position. Representative amino protecting groups include, but are not limited to, formyl; acyl, such as alkanoyl (such as acetyl, trichloroacetyl, or trifluoroacetyl); alkoxycarbonyl, such as tert-butoxycarbonyl (Boc); arylmethoxycarbonyl, such as benzyloxycarbonyl (Cbz) and 9-fluorenylmethoxycarbonyl (Fmoc); arylmethyl, such as benzyl (Bn), triphenylmethyl (Tr), and 1,1-di-(4'-methoxyphenyl)methyl; and silyl, such as trimethylsilyl (TMS) and tert-butyldimethylsilyl (TBS). The term "hydroxyl protecting group" refers to a protecting group suitable for preventing hydroxyl side reactions. Representative hydroxyl protecting groups include, but are not limit to, alkyl such as methyl, ethyl, and tert-butyl; acyl, such as alkanoyl (such as acetyl); arylmethyl, such as benzyl (Bn), p-methoxybenzyl (PMB), 9-fluorenylmethyl (Fm), and diphenylmethyl (diphenylmethyl, DPM); and silyl, such as trimethylsilyl (TMS) and tert-butyldimethylsilyl (TBS).

The compound of the present invention can be prepared by means of various synthesis methods well known to those skilled in the art, including the specific embodiments listed below, embodiments formed by combining them with other chemical synthesis methods, and equivalent alternatives well known to those skilled in the art. Preferred embodiments include but are not limited to the examples of the present invention.

The structure of the compound of the present invention can be confirmed by means of a conventional method well known to those skilled in the art. If the present invention involves the absolute configuration of the compound, the absolute configuration can be confirmed by means of a conventional technical means in the art. For example, by means of single crystal X-ray diffraction (SXRD), the cultured single crystal is sent to Bruker D8 venture diffractometer to collect diffraction intensity data, wherein the light source is CuKα radiation, and the scanning mode is φ/ω scanning; and after relevant data is collected, a direct method (Shelxs97) is further used to analyze the crystal structure, whereupon the absolute configuration can be confirmed.

In the present invention, the following abbreviations are used: aq stands for aqueous; eq stands for equivalent; DCM stands for dichloromethane; DMF stands for N,N-dimethylformamide; DIPEA stands for diisopropylethylamine; EA stands for ethyl acetate; EtOAc stands for ethyl acetate; THF stands for tetrahydrofuran; MeCN stands for acetonitrile; NCS stands for N-chlorosuccinimide; NBS represents N-bromosuccinimide; PE stands for petroleum ether; TFA stands for trifluoroacetic acid; TFAA stands for trifluoroacetic anhydride; TEA stands for triethylamine; HPLC stands for high performance liquid chromatography; $Boc_2O$ stands for di-tert-butyl dicarbonate; DMAP stands for 4-dimethylaminopyridine; LDA stands for lithium diisopropylamide; DIAD stands for diisopropyl azodicarboxylate; SEM-Cl stands for 2-(trimethylsilyl)ethoxymethyl chloride; $CD_3OD$ stands for deuterated methanol; $CDCl_3$ stands for deuterated chloroform; $D_2O$ stands for deuterated water; CFU stands for colony forming unit; i.v stands for intravenous administration; i.p stands for intraperitoneal injection; $PPh_3$ stands for triphenylphosphine; $Pd(Pph3)_2Cl_2{\cdot}CH_2Cl_2$ stands for 1,1-bis(diphenylphosphino)ferrocenepalladium (II) dichloride dichloromethane complex; $Pd(Pph3)_2Cl_2$ stands for [1,1'-bis(diphenylphosphino)ferrocene]palladium dichloride; LiHMDS stands for lithium bis(trimethylsilyl) amide; and $LiAlH_4$ stands for lithium aluminum hydride.

DETAILED DESCRIPTION OF EMBODIMENTS

The present invention will be described in detail by means of the following examples, and these examples do not mean any unfavourable limitation to the present invention. The compound of the present invention can be prepared by means of various synthesis methods well known to those skilled in the art, including the specific embodiments listed below, embodiments formed by combining them with other chemical synthesis methods, and equivalent alternatives well known to those skilled in the art. Preferred embodiments include but are not limited to the examples of the present invention. It will be obvious to those skilled in the art that various changes and improvements can be made to the specific embodiments of the present invention without departing from the spirit and scope of the present invention.

Example 1

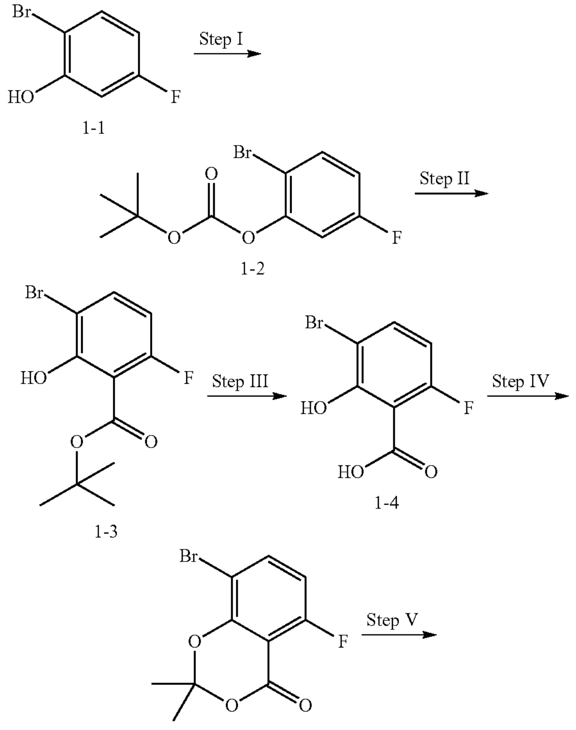

1-1

1-2

1-3

1-4

1-5

-continued

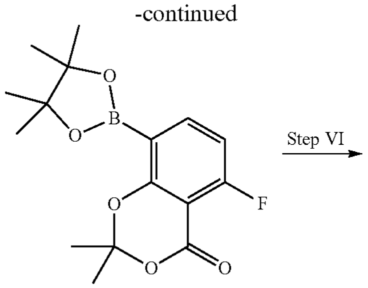

1-6

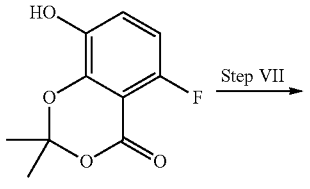

1-7

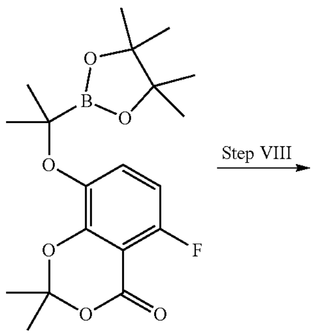

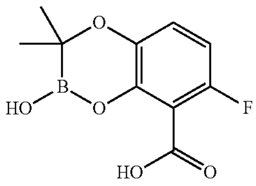

Compound 1

1-8

Step I: Preparation of Compound 1-2

DMAP (3.20 g, 26.18 mmol, 0.05 eq) and $Boc_2O$ (137.12 g, 628.28 mmol, 144.34 mL, 1.2 eq) were added to a solution of compound 1-1 (100 g, 523.57 mmol, 1 eq) in DCM (1000 mL). The mixed solution was stirred at 25° C. for 1 hour. The mixed solution was washed with 100 mL of a dilute HCl aqueous solution (0.5 mol/L); and the organic layer was dried over anhydrous $Na_2SO_4$, filtered, and concentrated under reduced pressure to obtain compound 1-2.

Step II: Preparation of Compound 1-3

LDA (2 M, 329.77 mL, 1.2 eq) was added dropwise to a solution of compound 1-2 in THF (1500 mL) at −70° C. and stirred for 2 hours. The mixed solution was washed with an HCl aqueous solution (2 mol/L, 500 mL) and extracted with EtOAc (100 mL×1). The organic phase was washed with brine (300 mL×1), then dried with anhydrous $Na_2SO_4$, and then filtered, and the filtrate was concentrated under reduced pressure to obtain a crude product. The crude product was washed with petroleum ether/ethyl acetate=3/1 (100 mL) and filtered, and the filter cake was dried to obtain product 1-3.

Step III: Preparation of Compound 1-4

TFA (79.57 g, 697.81 mmol, 51.67 mL, 6.55 eq) was added dropwise to a solution of compound 1-3 (31 g, 106.49 mmol, 1 eq) in DCM (50 mL). The mixed solution was then stirred at 20° C. for 12 hours. The reaction mixture was concentrated under reduced pressure to remove the solvent. The residue was washed with DCM (50 mL) and filtered under reduced pressure and the filter cake was dried to obtain compounds 1-4. $^1H$ NMR (400 MHz, $CD_3OD$) δ=7.74 (dd, J=5.5, 9.0 Hz, 1H), 6.67 (dd, J=8.9, 10.5 Hz, 1H).

Step IV: Preparation of Compound 1-5

Compound 1-4 (25 g, 106.38 mmol, 1 eq) was dissolved in a mixed solution of DMF (1.5 mL) and acetone (63.20 g, 1.09 mol, 80 mL, 10.23 eq). TFAA (151.00 g, 718.94 mmol, 100 mL, 6.76 eq) and TFA (10 mL) were added dropwise to the mixed solution at 0° C. The mixed solution was heated to 100° C. and stirred for 12 hours. The mixed solution was poured into saturated $Na_2CO_3$ (500 mL) and stirred for 10 minutes. It was then extracted with ethyl acetate (150 mL×2). The combined organic phases were washed with brine (15 mL×2), dried with anhydrous $Na_2SO_4$, filtered, and concentrated in vacuum. After the residue was purified by column chromatography ($SiO_2$, petroleum ether/ethyl acetate=1/0 to 20/1), the crude product was washed with PE (40 mL) and filtered, and the filter cake was dried under reduced pressure to obtain compound 1-5. $^1H$ NMR (400 MHz, $CDCl_3$) δ=7.72-7.63 (m, 1H), 6.78-6.65 (m, 1H), 1.77-1.64 (m, 6H).

Step V: Preparation of Compound 1-6

Under nitrogen protection, compound 1-5 (8.8 g, 31.99 mmol, 1 eq), bis(pinacolato)diboron (12.19 g, 47.99 mmol, 1.5 eq), 1,1-bis(diphenylphosphino)ferrocenepalladium(II) dichloride dichloromethane complex (5.23 g, 6.40 mmol, 0.2 eq) and potassium acetate (9.42 g, 95.98 mmol, 3 eq) were dissolved in dioxane (100 mL), and after displacement with $N_2$ 3 times, the mixed solution was then stirred at 65° C. for 5 hours. The reaction mixture was concentrated under reduced pressure to remove the solvent. The residue was purified by silica gel column chromatography (petroleum ether/ethyl acetate=1/0 to 10/1) to obtain compound 1-6.

Step VI: Preparation of Compound 1-7

Compound 1-6 (4.24 g, 13.16 mmol, 1 eq) was dissolved in a mixed solvent of tetrahydrofuran (40 mL) and water (20 mL), sodium perborate tetrahydrate (5.06 g, 32.91 mmol, 2.5 eq) was added at 0° C., and the mixture was then stirred at 25° C. for 1 hour under nitrogen protection. 20 mL of water was added to the reaction mixture, and the reaction mixture was extracted with ethyl acetate (20 mL×2), washed with brine (40 mL×1), dried over $Na_2SO_4$, filtered, and concentrated in vacuum. The crude product was washed and purified with petroleum ether (10 mL) and filtered, and the filter cake was dried in vacuum to obtain compound 1-7.

Step VII: Preparation of Compound 1-8

Compound 1-7 (457 mg, 1.84 mmol, 1 eq) and compound 2-(2-bromoprop-2-yl)-4,4,5,5-tetramethyl-1,3,2-dioxaborolane (389.49 mg, 1.84 mmol, 1 eq) were dissolved in DMF (5 mL), potassium carbonate (279.08 mg, 2.02 mmol, 1.1 eq) was added to the mixture at 25° C., and the mixture was then stirred at 25° C. for 12 hours. 15 mL of water was added to the mixture, and the reaction mixture was extracted with ethyl acetate (20 mL×3), washed with brine (20 mL×2), dried over anhydrous $Na_2SO_4$, filtered, and concentrated in vacuum. The residue was purified by silica gel flash column chromatography (petroleum ether/ethyl acetate=0/1 to 1/1) to obtain compound 1-8. LCMS (ESI) m/z: 381.2 (M+1).

Step VIII: Preparation of Compound 1

Compound 1-8 (37 mg, 97.31 μmol, 1 eq) was dissolved in isopropanol (1 mL), and NaOH (3 M, 64.88 μL, 2 eq) was added at 0° C. The mixture was then stirred at 25° C. for 2 hours. The reaction liquid was filtered and purified by preparative HPLC (chromatographic column: Waters Xbridge 150×25 mm×5 μm; mobile phase: 10 mmol/L ammonium bicarbonate aqueous solution and acetonitrile, the proportion of acetonitrile in the mobile phase was from 1% to 10%, 8 min) to obtain compound 1. $^1$H NMR (400 MHz, $CD_3OD$) δ=6.75 (dd, J=5.4, 8.8 Hz, 1H), 6.41 (dd, J=8.9, 10.5 Hz, 1H), 1.14 (s, 6H); LCMS (ESI) m/z: 223.1 (M−18+1).

Example 2

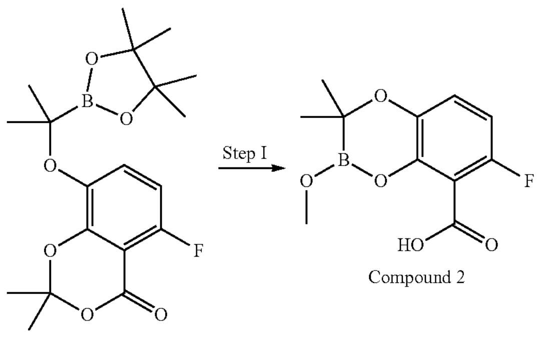

1-8

Compound 2

Step I: Preparation of Compound 2

Compound 1-8 (100 mg, 263.01 μmol, 1 eq) was dissolved in MeOH (2 mL), an aqueous sodium hydroxide solution (3 mol/L, 175.34 μL, 2 eq) was added to the mixture at 0° C., and the mixture was then stirred at 25° C. for 2 hours. The reaction mixture was separated and purified by preparative high performance liquid chromatography (chromatographic column: Waters Xbridge 150×25 mm×5 μm; mobile phase: 10 mmol/L ammonium bicarbonate aqueous solution and acetonitrile, the proportion of acetonitrile in the mobile phase was from 1% to 31%, 9 min) to obtain compound 2. $^1$H NMR (400 MHz, $CD_3OD$) δ=6.66 (dd, J=5.8, 8.9 Hz, 1H), 6.33 (t, J=9.0 Hz, 1H), 3.88 (s, 3H), 1.13 (s, 6H); LCMS (ESI) m/z; 255.1 (M+1).

Example 3

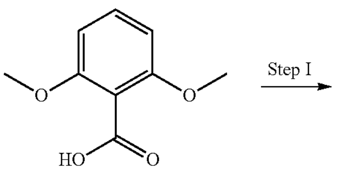

3-1

-continued

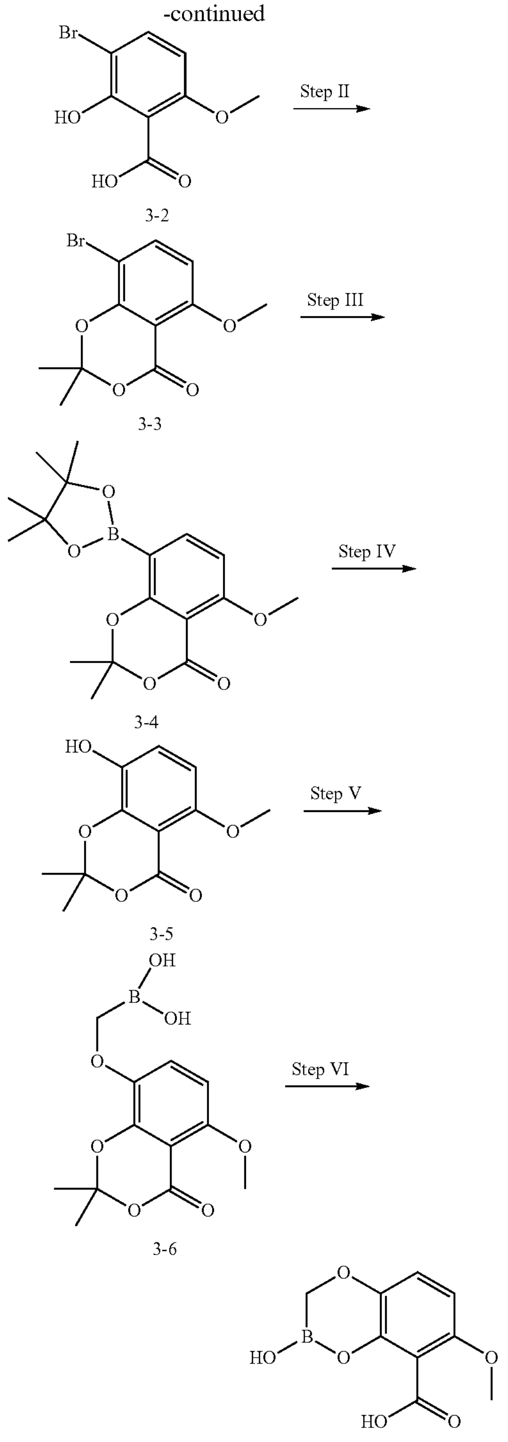

3-2

3-3

3-4

3-5

3-6

Compound 3

Step I: Preparation of Compound 3-2

Compound 3-1 (5 g, 27.45 mmol, 1 eq) was dissolved in chloroform (100 mL), liquid bromine (4.39 g, 27.45 mmol, 1.41 mL, 1 eq) was added to the mixture at 0° C., and the mixture was then stirred at 25° C. for 30 hours. The mixture was directly concentrated in vacuum, and the residue was washed and purified by (petroleum ether/ethyl acetate=5/1, 40 mL) to obtain compound 3-2. $^1$H NMR (400 MHz, $CDCl_3$) δ=12.87 (s, 1H), 7.62 (d, J=8.9 Hz, 1H), 6.40 (d, J=8.9 Hz, 1H), 4.02 (s, 3H).

Step II: Preparation of Compound 3-3

Compound 3-2 (5.44 g, 22.02 mmol, 1 eq) was dissolved in DMF (0.2 mL) and acetone (13.43 g, 231.24 mmol, 17 mL, 10.50 eq), and trifluoroacetic anhydride (31.71 g, 150.98 mmol, 21 mL, 6.86 eq) and trifluoroacetic acid (2 mL) were added to the mixture at 0° C. and then stirred at 100° C. for 12 hours. The reaction liquid was poured into a saturated sodium carbonate aqueous solution (100 mL), stirred for 10 minutes, extracted with ethyl acetate (50 mL×2), washed with brine (15 mL×2), dried over anhydrous $Na_2SO_4$, filtered, and concentrated in vacuum. Purification by silica gel flash column chromatography (petroleum ether/ethyl acetate=0/1 to 3/1) afforded compound 3-3. $^1$H NMR (400 MHz, $CDCl_3$) δ=7.60 (d, J=9.0 Hz, 1H), 6.51 (d, J=9.0 Hz, 1H), 3.89 (s, 3H), 1.68 (s, 6H); LCMS (ESI) m/z: 286.9 (M+1).

Step III: Preparation of Compound 3-4

Compound 3-3 (1.52 g, 5.29 mmol, 1 eq) was mixed with bis(pinacolato)diboron (3.36 g, 13.24 mmol, 2.5 eq) and dissolved in dioxane (15 mL), potassium acetate (1.56 g, 15.88 mmol, 3 eq) and 1,1-bis(diphenylphosphino)ferrocenepalladium(II) dichloride dichloromethane complex were added to the mixture, and the mixture was then stirred at 65° C. for 5 hours under nitrogen protection. Ethyl acetate (20 mL) was added to the mixed liquid, filtered, and concentrated in vacuum. 50 mL of water was added to the concentrated liquid and extracted with ethyl acetate (20 mL×2), and the organic phase was washed with brine (50 mL×1), dried over anhydrous $Na_2SO_4$, filtered, and concentrated in vacuum. The residue was purified by silica gel flash column chromatography (petroleum ether/ethyl acetate=0/1 to 5/1) to obtain compound 3-4. LCMS (ESI) m/z: 335.1 (M+1).

Step IV: Preparation of Compound 3-5

Compound 3-4 (1.45 g, 4.34 mmol, 1 eq) was dissolved in tetrahydrofuran (20 mL) and water (10 mL), and sodium perborate tetrahydrate (1.67 g, 10.85 mmol, 2.09 mL, 2.5 eq) was added to the mixture at 0° C. The mixture was stirred at 25° C. for 1 hour. 20 mL of water was added to the mixture and extracted with ethyl acetate (20 mL×2), and the organic phase was washed with brine (40 mL×1), dried over anhydrous $Na_2SO_4$, filtered, and concentrated in vacuum. The residue was purified by silica gel flash column chromatography (petroleum ether/ethyl acetate=20/1 to 0/1) to obtain compound 3-5. $^1$H NMR (400 MHz, $CDCl_3$) δ=7.08 (d, J=9.0 Hz, 1H), 6.48 (d, J=9.0 Hz, 1H), 3.84 (s, 3H), 1.68 (s, 6H); LCMS (ESI) m/z: 225.0 (M+1).

Step V: Preparation of Compound 3-6

2-Iodomethyl-boronic acid pinacol ester (1.00 g, 3.75 mmol, 3 eq) and compound 3-5 (280 mg, 1.25 mmol, 1 eq) were dissolved in acetonitrile (5 mL), and $K_2CO_3$ (258.90 mg, 1.87 mmol, 1.5 eq) was added to the mixture at 25° C. The mixture was then stirred at 65° C. for 4 hours under nitrogen protection. 10 mL of water was added to the mixture and extracted with ethyl acetate (10 mL×3), and the organic phase was washed with brine (20 mL×2), dried over anhydrous $Na_2SO_4$, filtered, and concentrated in vacuum to obtain compound 3-6. LCMS (ESI) m/z: 283.1 (M+1).

Step VI: Preparation of Compound 3

Compound 3-6 (355 mg, 1.26 mmol, 1 eq) was dissolved in isopropanol (2 mL), a sodium hydroxide aqueous solution (1 M, 3.78 mL, 3 eq) was added at 0° C., and the mixture was then stirred at 25° C. for 2 hours. After filtration, the filtrate was separated by preparative HPLC (chromatographic column: Waters Xbridge 150×25 mm×5 μm; mobile phase: 10 mmol/L ammonium bicarbonate aqueous solution and acetonitrile, the proportion of acetonitrile in the mobile phase was from 1% to 6%, 5 min) to obtain compound 3. $^1$H NMR (400 MHz, $CD_3OD$) δ=6.50 (d, J=8.7 Hz, 1H), 6.19 (d, J=8.8 Hz, 1H), 3.72 (s, 3H), 3.39 (s, 2H); LCMS (ESI) m/z: 207.0 (M−18+1).

Example 4

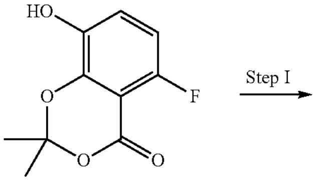

1-7

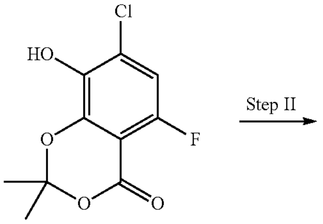

4-2

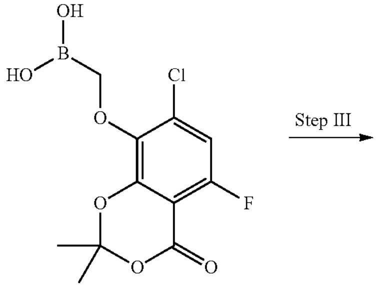

4-3

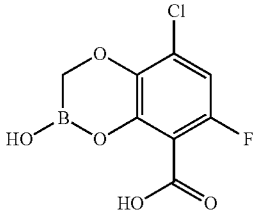

Compound 4

Step I: Preparation of Compound 4-2

Compound 1-7 (1 g, 4.71 mmol, 1 eq) was dissolved in acetic acid (15 mL), NCS (755.21 mg, 5.66 mmol, 1.2 eq)

was added, and the reaction liquid was then stirred at 105° C. for 12 hours under nitrogen protection. 20 mL of water was added to the mixture and extracted with ethyl acetate (20 mL×1), the combined organic phases were washed with brine (10 mL×1), dried over $Na_2SO_4$, filtered, and concentrated in vacuum, and the residue was purified by silica gel flash column chromatography (petroleum ether/ethyl acetate=10/0 to 8/1) to obtain compound 4-2. $^1H$ NMR (400 MHz, $CD_3OD$) δ=7.06-6.97 (m, 1H), 1.79 (s, 6H).

Step II: Preparation of Compound 4-3

Compound 4-2 (250 mg, 1.01 mmol, 1 eq) was dissolved in acetonitrile (5 mL), 2-iodomethyl-boronic acid pinacol ester (543.14 mg, 2.03 mmol, 2 eq) and potassium carbonate (210.16 mg, 1.52 mmol, 1.5 eq) were added, and the reaction mixture was then stirred at 60° C. for 3 hours under nitrogen protection. Water (20 mL) was added to the mixture and extracted with ethyl acetate (20 mL×1), and the combined organic phases were washed with brine (20 mL×1), dried over anhydrous $Na_2SO_4$, filtered, and concentrated in vacuum. Separation by preparative high performance liquid chromatography (chromatographic column: Phenomenex luna C18 150×40 mm×15 μm; mobile phase: a neat aqueous solution with 0.1% TFA and acetonitrile: the proportion of acetonitrile in the mobile phase was from 25-55%, 10 min) afforded compound 4-3.

Step III: Preparation of Compound 4

Compound 4-3 (200 mg, 656.89 μmol, 1 eq) was dissolved in isopropanol (2 mL), an NaOH aqueous solution (1 mol/L, 1.31 mL, 2 eq) was slowly added at 0° C. under nitrogen protection, and the reaction liquid was then heated to 25° C. and stirred for 1 hour under nitrogen protection. Purification by preparative HPLC (column: Waters Xbridge 150-25 mm×5 μm; mobile phase: 10 mmol/L ammonium bicarbonate aqueous solution and acetonitrile, the proportion of acetonitrile in the mobile phase was from 1% to 6%, 4 min) afforded compound 4. $^1H$ NMR (400 MHz, $CD_3OD$) δ=6.39 (d, J=8.8 Hz, 1H), 3.46 (s, 2H); LCMS (ESI) m/z: 246.9 (M+1).

Example 5

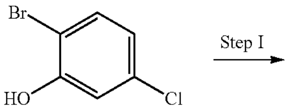

5-1

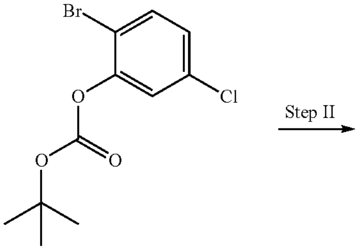

5-2

-continued

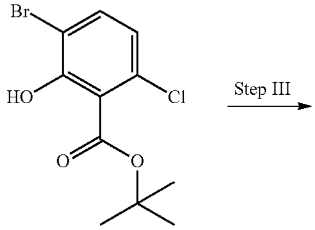

5-3

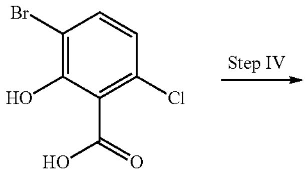

5-4

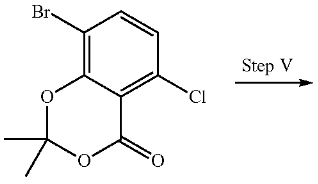

5-5

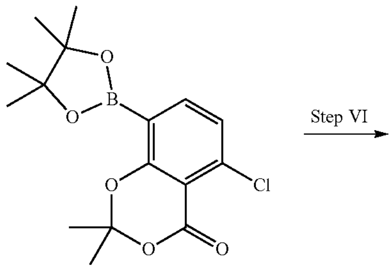

5-6

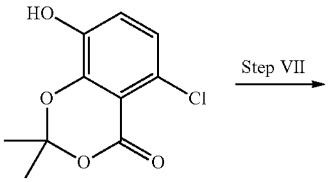

5-7

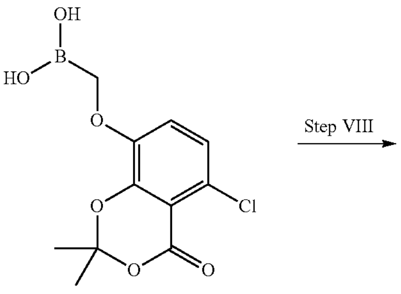

5-8

-continued

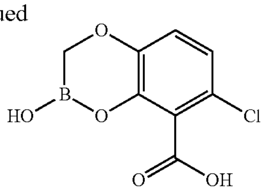

Compound 5

Step I: Preparation of Compound 5-2

Compound 5-1 (3.7 g, 17.84 mmol, 1 eq) was dissolved in DCM (40 mL), $BoC_2O$ (4.67 g, 21.40 mmol, 4.92 mL, 1.2 eq) and DMAP (108.95 mg, 891.77 μmol, 0.05 eq) were separately added, and the reaction mixture was then stirred at 25° C. for 16 hours under nitrogen protection. 20 mL of water was added to the mixture, the mixture was adjusted to pH=3-4 with 0.5 mol/L hydrochloric acid aqueous solution and extracted with dichloromethane (50 mL×2), the combined organic phases were washed with brine (100 mL×2), dried over anhydrous $Na_2SO_4$, and filtered, and the filtrate was concentrated under reduced pressure to obtain compound 5-2. $^1H$ NMR (400 MHz, $CDCl_3$) δ=7.45 (d, J=8.6 Hz, 1H), 7.16 (d, J=2.3 Hz, 1H), 7.04 (dd, J=2.3, 8.6 Hz, 1H), 1.49 (s, 9H).

Step II: Preparation of Compound 5-3

Compound 5-2 (5.4 g, 17.56 mmol, 1 eq) was dissolved in THF (60 mL), LDA (2 M, 10.53 mL, 1.2 eq) was slowly added at −78° C. under nitrogen protection, the reaction mixture was then stirred at −78° C. for 2 hours under nitrogen protection, $NH_4Cl$ (50 mL) was added to the mixture, the reaction was quenched, extracted with ethyl acetate (40 mL×3), and washed with brine (100 mL×2), the combined organic phases were dried over anhydrous $Na_2SO_4$, filtered, and concentrated in vacuum, and the residue was purified by silica gel flash column chromatography (petroleum ether/ethyl acetate=1/0 to 20/1) to obtain compound 5-3. $^1H$ NMR (400 MHz, $CDCl_3$) δ=11.61 (s, 1H), 7.44 (d, J=8.6 Hz, 1H), 6.78 (d, J=8.6 Hz, 1H), 1.57 (s, 9H).

Step III: Preparation of Compound 5-4

Compound 5-3 (1 g, 3.25 mmol, 1 eq) was dissolved in DCM (4 mL), trifluoroacetic acid (6.16 g, 54.02 mmol, 4 mL, 16.62 eq) was slowly added at 0° C. under nitrogen protection, the reaction mixture was then heated to 25° C. and stirred for 12 hours under nitrogen protection, concentrated in vacuum, then stirred with dichloromethane (5 mL) at room temperature, and filtered, the filter cake was washed with dichloromethane, and the filter cake was collected to obtain compound 5-4. $^1H$ NMR (400 MHz, $CD_3OD$) δ=7.59 (d, J=8.6 Hz, 1H), 6.93 (d, J=8.6 Hz, 1H).

Step IV: Preparation of Compound 5-5

Compound 5-4 (3.3 g, 13.12 mmol, 1 eq) was dissolved in TFA (20 mL), acetone (2.29 g, 39.37 mmol, 2.89 mL, 3 eq) was added, and TFAA (8.27 g, 39.37 mmol, 5.48 mL, 3 eq) and DMF (191.85 mg, 2.62 mmol, 201.94 μL, 0.2 eq) were then added to the reaction mixture at 0° C. under nitrogen protection, heated to 105° C. and stirred for 32 hours. After vacuum concentration, saturated $NaHCO_3$ (20 mL) was added, the mixture was extracted with ethyl acetate (20 mL×3) and washed with brine (50 mL×2), the organic phase was dried with anhydrous $Na_2SO_4$, filtered, and concentrated in vacuum, and the residue was purified by silica gel flash column chromatography (petroleum ether/ethyl acetate=20/1 to 0/1) to obtain compound 5-5. $^1H$ NMR (400 MHz, $CDCl_3$) δ=7.59 (d, J=8.6 Hz, 1H), 7.02 (d, J=8.6 Hz, 1H), 1.71 (s, 6H); LCMS (ESI) m/z: 292.8 (M+1).

Step V: Preparation of Compound 5-6

Compound 5-5 (1.4 g, 4.80 mmol, 1 eq), bis(pinacolato) diboron (1.83 g, 7.20 mmol, 1.5 eq), 1,1-bis(diphenylphosphino)ferrocenepalladium(II) dichloride dichloromethane complex (784.35 mg, 960.47 μmol, 0.2 eq), and potassium acetate (1.41 g, 14.41 mmol, 3 eq) were dissolved in anhydrous dioxane (20 mL). After displacement with nitrogen 3 times, the temperature was raised to 65° C., and after stirring for 5 hours, concentration in vacuum was performed. The residue was purified by silica gel flash column chromatography (petroleum ether/ethyl acetate=10/0 to 0/1) to obtain compound 5-6. LCMS (ESI) m/z: 339 (M+1).

Step VI: Preparation of Compound 5-7

Compound 5-6 (2.9 g, 8.56 mmol, 1 eq) was dissolved in THF (18 mL) and $H_2O$ (9 mL), sodium perborate tetrahydrate (2.64 g, 17.13 mmol, 3.29 mL, 2 eq) was added, and the reaction mixture was then stirred at 25° C. for 2 hours under nitrogen protection. $H_2O$ (10 mL) was added to the mixture and extracted with ethyl acetate (20 mL×3), the organic phase was washed with brine (50 mL×2), dried over $Na_2SO_4$, filtered, and concentrated in vacuum, and the residue was purified by silica gel flash column chromatography (petroleum ether/ethyl acetate=10/1 to 5/1) to obtain compound 5-7. LCMS (ESI) m/z: 229 (M+1).

Step VII: Preparation of Compound 5-8

Compound 5-7 (840 mg, 3.67 mmol, 1 eq) was dissolved in acetonitrile (10 mL), 2-iodomethyl-boronic acid pinacol ester (1.97 g, 7.35 mmol, 2 eq) and $K_2CO_3$ (761.69 mg, 5.51 mmol, 1.5 eq) were added, and the reaction mixture was then stirred at 60° C. for 3 hours under nitrogen protection. Water (10 mL) was added to the mixture and extracted with ethyl acetate (10 mL×3), and the organic phase was washed with brine (30 mL×2), dried over anhydrous $Na_2SO_4$, filtered, and concentrated in vacuum. Purification by silica gel flash column chromatography (petroleum ether/ethyl acetate=10/1 to 0/1) afforded compound 5-8. LCMS (ESI) m/z: 287 (M+1).

Step VIII: Preparation of Compound 5

Compound 5-8 (200 mg, 698.15 μmol, 1 eq) was dissolved in isopropanol (1 mL), an NaOH aqueous solution (1 mol/L, 1.40 mL, 2 eq) was slowly added at 0° C. under nitrogen protection, and the reaction mixture was then stirred at 0-25° C. for 1 hour under nitrogen protection. Purification by preparative HPLC (column: Waters Xbridge 150×25 mm×5 μm; mobile phase: 10 mmol/L ammonium bicarbonate aqueous solution and acetonitrile, the proportion of acetonitrile in the mobile phase was from 1% to 6%, 4 min) afforded compound 5. $^1H$ NMR (400 MHz, $CD_3OD$) δ=6.48 (s, 2H), 3.41 (s, 2H); LCMS (ESI) m/z: 229 (M+1); 211 (M−18+1).

Example 6

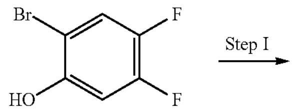

6-1

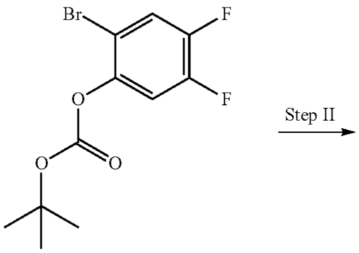

6-2

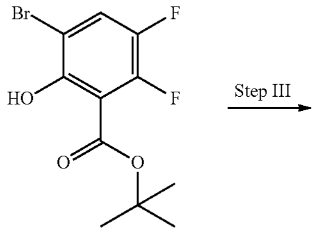

6-3

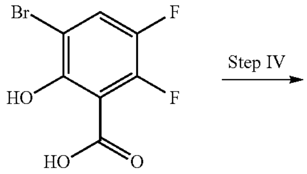

6-4

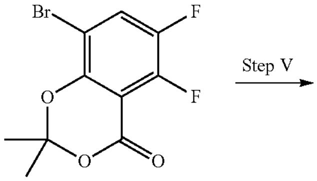

6-5

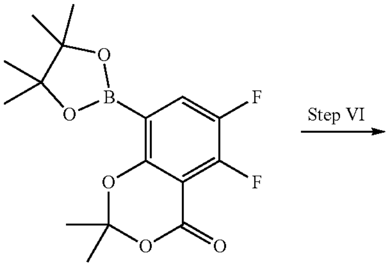

6-6

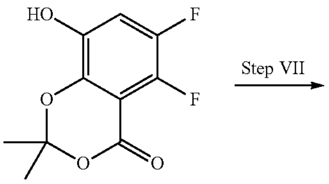

6-7

-continued

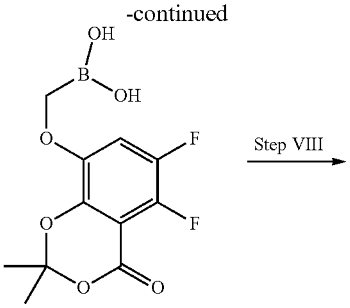

6-8

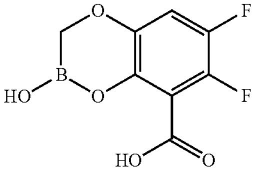

Compound 6

Step I: Preparation of Compound 6-2

Compound 6-1 (10 g, 47.85 mmol, 1 eq) was dissolved in DCM (100 mL), $Boc_2O$ (12.53 g, 57.42 mmol, 13.19 mL, 1.2 eq) and DMAP (292.28 mg, 2.39 mmol, 0.05 eq) were separately added, and the reaction mixture was then stirred at 25° C. for 16 hours under nitrogen protection. 50 mL of water was added to the mixture, the mixture was extracted with dichloromethane (50 mL×2), and the combined organic phases were washed with brine (100 mL×2), dried over $Na_2SO_4$, filtered, and concentrated in vacuum to obtain compound 6-2. $^1$H NMR (400 MHz, $CDCl_3$) δ=7.37 (dd, J=8.0, 9.3 Hz, 1H), 7.04 (dd, J=7.3, 10.1 Hz, 1H), 1.50 (s, 9H).

Step II: Preparation of Compound 6-3

Compound 6-2 (8.1 g, 26.20 mmol, 1 eq) was dissolved in THF (90 mL), LDA (2 M, 19.65 mL, 1.5 eq) was slowly added at −78° C. under nitrogen protection, the reaction mixture was then stirred at −78° C. for 2 hours under nitrogen protection, a saturated $NH_4Cl$ aqueous solution (50 mL) was added to the mixture, the mixture was extracted with ethyl acetate (40 mL×3), the combined organic phases were washed with brine (100 mL×2), dried over anhydrous $Na_2SO_4$, filtered, and concentrated in vacuum, and the residue was purified by silica gel flash column chromatography (petroleum ether/ethyl acetate=1/0 to 20/1) to obtain compound 6-3. $^1$H NMR (400 MHz, $CDCl_3$) δ=11.77 (s, 1H), 7.59-7.41 (m, 1H), 1.56 (s, 9H).

Step III: Preparation of Compound 6-4

Compound 6-3 (5.1 g, 16.50 mmol, 1 eq) was dissolved in DCM (15 mL), trifluoroacetic acid (23.10 g, 202.59 mmol, 15.00 mL, 12.28 eq) was slowly added at 0° C. under nitrogen protection, the reaction mixture was then heated to 25° C. and stirred for 2 hours under nitrogen protection, the mixture was concentrated under vacuum, washed with dichloromethane (25 mL) at room temperature, and filtered, and the filter cake was collected to obtain 6-4. $^1$H NMR (400 MHz, $CD_3OD$) δ=7.77 (dd, J=8.1, 9.9 Hz, 1H).

Step IV: Preparation of Compound 6-5

Compound 6-4 (2.5 g, 9.88 mmol, 1 eq) was dissolved in TFA (30 mL), acetone (1.72 g, 29.64 mmol, 2.18 mL, 3 eq) was added, and TFAA (6.23 g, 29.64 mmol, 4.12 mL, 3 eq) and DMF (144.46 mg, 1.98 mmol, 152.06 μL, 0.2 eq) were then added to the reaction mixture at 0° C. under nitrogen protection, heated to 105° C. and stirred for 32 hours. After vacuum concentration, saturated $NaHCO_3$ aqueous solution (50 mL) was added, the mixture was extracted with ethyl acetate (20 mL×3), the organic phase was washed with brine (50 mL×2), dried over anhydrous $Na_2SO_4$, filtered, and concentrated in vacuum, and the residue was purified by silica gel flash column chromatography (petroleum ether/ethyl acetate=20/1 to 0/1) to obtain compound 6-5. $^1$H NMR (400 MHz, $CDCl_3$) δ=7.60 (dd, J=7.7, 9.3 Hz, 1H), 1.71 (s, 6H); LCMS (ESI) m/z: 294 (M+1).

Step V: Preparation of Compound 6-6

Compound 6-5 (900 mg, 3.07 mmol, 1 eq), bis(pinacolato)diboron (1.17 g, 4.61 mmol, 1.5 eq), 1,1-bis(diphenylphosphino)ferrocenepalladium(II) dichloride dichloromethane complex (501.58 mg, 614.21 μmol, 0.2 eq), and potassium acetate (904.19 mg, 9.21 mmol, 3 eq) were dissolved in anhydrous dioxane (10 mL). After displacement with nitrogen 3 times, the temperature was raised to 65° C., and after stirring for 5 hours, concentration in vacuum was performed. Purification by silica gel flash column chromatography (petroleum ether/ethyl acetate=10/0 to 0/1) afforded compound 6-6. LCMS (ESI) m/z: 341 (M+1).

Step VI: Preparation of Compound 6-7

Compound 6-6 (680 mg, 2.00 mmol, 1 eq) was dissolved in THF (6 mL) and $H_2O$ (3 mL), sodium perborate tetrahydrate (922.82 mg, 6.00 mmol, 1.15 mL, 3 eq) was added, and the reaction mixture was then stirred at 25° C. for 2 hours under nitrogen protection. $H_2O$ (10 mL) was added to the mixture and extracted with ethyl acetate (30 mL×3), the organic phase was washed with brine (80 mL×2), dried over anhydrous $Na_2SO_4$, filtered, and concentrated in vacuum, and the residue was purified by silica gel flash column chromatography (petroleum ether/ethyl acetate=10/1 to 5/1) to obtain compound 6-7. LCMS (ESI) m/z: 231.4 (M+1).

Step VII: Preparation of Compound 6-8

Compound 6-7 (320 mg, 1.39 mmol, 1 eq) was dissolved in acetonitrile (5 mL), 2-iodomethyl-boronic acid pinacol ester (744.93 mg, 2.78 mmol, 2 eq) and $K_2CO_3$ (384.30 mg, 2.78 mmol, 2 eq) were added, and the reaction mixture was then stirred at 60° C. for 3 hours under nitrogen protection. Water (10 mL) was added to the mixture and extracted with ethyl acetate (30 mL×3), the organic phase was washed with brine (80 mL×2), dried over anhydrous $Na_2SO_4$, and filtered, and the filtrate was concentrated in vacuum. The residue was purified by preparative HPLC (column: Phenomenex luna C18 150×40 mm×15 m; mobile phase: an aqueous solution with 0.1% TFA and acetonitrile, the proportion of acetonitrile in the mobile phase was from 20% to 50%, 10 min) to obtain compound 6-8. $^1$H NMR (400 MHz, $CDCl_3$) δ=7.01 (dd, J=7.1, 11.5 Hz, 1H), 3.71 (s, 2H), 1.70 (s, 6H); LCMS (ESI) m/z: 288.9 (M+1).

Step VIII: Preparation of Compound 6

Compound 6-8 (100 mg, 347.21 μmol, 1 eq) was dissolved in isopropanol (2 mL), NaOH (1 M, 694.42 μLL, 2 eq) was slowly added at 0° C. under nitrogen protection, the reaction mixture was then gradually heated to 25° C. under nitrogen protection, and stirring was continued for 1 hour. The crude was purified by preparative HPLC (column: Waters Xbridge 150×25 mm×5 μm; mobile phase: 10 mmol/L ammonium bicarbonate aqueous solution and acetonitrile, the proportion of acetonitrile in the mobile phase was from 1% to 6%, 4 min) to obtain compound 6. $^1$H NMR (400 MHz, $CD_3OD$) δ=6.40 (br dd, J=8.3, 11.8 Hz, 1H), 3.40 (s, 2H); LCMS (ESI) m/z: 230.9 (M+1); 213 (M−18+1).

Example 7

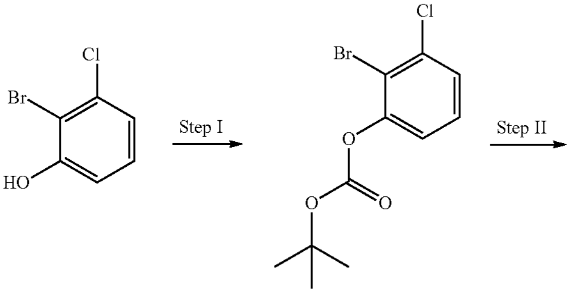

7-1 7-2

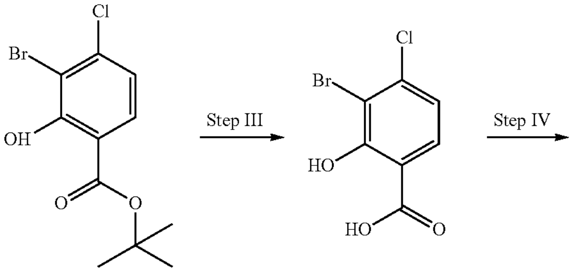

7-3 7-4

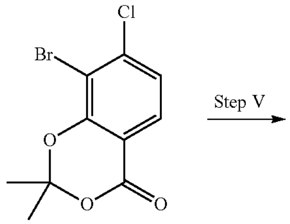

7-5

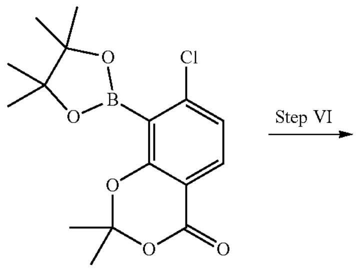

7-6

-continued

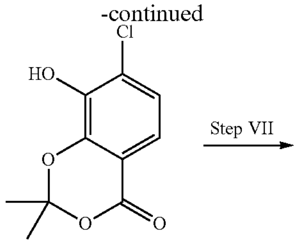

7-7

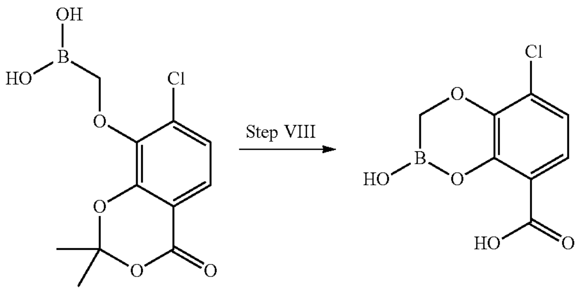

7-8 Compound 7

Step I: Preparation of Compound 7-2

$Boc_2O$ (12.62 g, 57.84 mmol, 13.29 mL, 1.2 eq) and DMAP (294.45 mg, 2.41 mmol, 0.05 eq) were added to a solution of compound 7-1 (10 g, 48.20 mmol, 1 eq) in DCM (100 mL), and the mixed solution was stirred at 25° C. for 1 hour. $H_2O$ (50 mL) was added to the mixed solution, and the mixed solution was extracted with ethyl acetate (50 mL×3). The combined organic phases were washed with brine (100 mL×2), dried with anhydrous $Na_2SO_4$, and filtered, and the filtrate was concentrated in vacuum to obtain compound 7-2. $^1H$ NMR (400 MHz, $CDCl_3$) δ=7.39 (dd, J=1.5, 8.0 Hz, 1H), 7.33-7.29 (m, 1H), 7.14 (dd, J=1.5, 8.2 Hz, 1H), 7.17-7.12 (m, 1H), 1.59 (s, 9H).

Step II: Preparation of Compound 7-3

LDA (2 M, 13.66 mL, 1.2 eq) was added to a solution of compound 7-2 (7 g, 22.76 mmol, 1 eq) in THF (100 mL). Additionally, the mixture was stirred at −70° C. for 2 hours. The mixed solution was completely quenched with $H_2O$ (20 mL) and extracted with EtOAc (40 mL×3). The combined organic phases were washed with an NaCl aqueous solution (100 mL×2), dried over anhydrous $Na_2SO_4$, filtered, and concentrated under reduced pressure. The residue was purified by silica gel chromatography (petroleum ether/ethyl acetate=1/0, 20/1) to obtain compound 7-3.

Step III: Preparation of Compound 7-4

TFA (38.50 g, 337.66 mmol, 25 mL, 20.36 eq) was added to a solution of compound 7-3 (5.1 g, 16.58 mmol, 1 eq) in DCM (25 mL) at 0° C. under nitrogen protection, and the solution was then stirred at 25° C. for 12 hours. The compound was concentrated in vacuum. The crude product was washed with DCM (25 mL) at 25° C. Compound 7-4 was obtained.

Step IV: Preparation of Compound 7-5

Compound 7-4 (3.0 g, 11.93 mmol, 1 eq) was dissolved in TFA (40 mL) at 0° C. and acetone (2.08 g, 35.79 mmol, 2.63 mL, 3 eq), TFAA (7.52 g, 35.79 mmol, 4.98 mL, 3 eq) and DMF (174.40 mg, 2.39 mmol, 183.58 μL, 0.2 eq) were added. The mixed solution was stirred at 20° C. for 0.5 hour. It was then heated to 105° C. and stirred for another 32 hours. The solution was concentrated in vacuum, an $NaHCO_3$ solution (20 mL) was then added, and the solution was extracted with ethyl acetate (30 mL×3). The combined organic phases were washed with brine (50 mL×2), dried with anhydrous $Na_2SO_4$, filtered, and concentrated in vacuum. The residue was purified by silica gel chromatography (petroleum ether/ethyl acetate=1/0 to 50/1), and the compound was then washed with petroleum ether (40 mL) at 25° C. Compound 7-5 was obtained. $^1H$ NMR (400 MHz, $CDCl_3$) δ=7.68 (d, J=8.7 Hz, 1H), 7.11 (d, J=8.5 Hz, 1H), 1.80 (s, 6H); LCMS (ESI) m/z: 292.8 (M+1).

Step V: Preparation of Compound 7-6

Under nitrogen protection, compound 7-5 (770 mg, 2.64 mmol, 1 eq), bis(pinacolato)diboron (1.01 g, 3.96 mmol, 1.5 eq), 1,1-bis(diphenylphosphino)ferrocenepalladium(II) dichloride dichloromethane complex (431.39 mg, 528.26 μmol, 0.2 eq), and potassium acetate (777.66 mg, 7.92 mmol, 3 eq) were added to 1,4-dioxane (3 mL), and after displacement with nitrogen at 25° C. 3 times, the mixed solution was then stirred at 65° C. for 5 hours in an $N_2$ atmosphere. The reaction mixture was concentrated under reduced pressure to remove the solvent. The residue was purified by silica gel chromatography (petroleum ether/ethyl acetate=100/1, 10/1) to obtain compound 7-6. LCMS (ESI) m/z: 339 (M+1).

Step VI: Preparation of Compound 7-7

Sodium perborate tetrahydrate (1.77 g, 11.52 mmol, 2.22 mL, 3 eq) was added to a solution of compound 7-6 (1.3 g, 3.84 mmol, 1 eq) in a mixture of THF (20 mL) and $H_2O$ (10 mL), and this mixed solution was stirred at 25° C. for 16 hours. $H_2O$ (10 mL) was added to the solution, and the aqueous phase was extracted with ethyl acetate (30 mL×3). The combined organic phases were washed with brine (80 mL×2), dried with anhydrous $Na_2SO_4$, filtered, and concentrated in vacuum. The residue was purified by silica gel column chromatography (petroleum ether/ethyl acetate=10/1, 5/1) to obtain compound 7-7. LCMS (ESI) m/z: 229 (M+1).

Step VII: Preparation of Compound 7-8

2-Iodomethyl-boronic acid pinacol ester (234.35 mg, 874.78 μmol, 2 eq) and $K_2CO_3$ (120.90 mg, 874.78 μmol, 2 eq) were added to a solution of compound 7-7 (100 mg, 437.39 μmol, 1 eq) in acetonitrile (3 mL) at 25° C. and then stirred at 60° C. for 3 hours. $H_2O$ (5 mL) was added to the solution, and the aqueous phase was adjusted to pH=3-4 with 0.5 mol/L HCl and extracted with ethyl acetate (10 mL×3). The combined organic phases were washed with brine (30 mL×2), dried with anhydrous $Na_2SO_4$, filtered, and concentrated in vacuum. Compound 7-8 was obtained. LCMS (ESI) m/z: 287 (M+1).

Step VIII: Preparation of Compound 7

An NaOH aqueous solution (1 M, 977.40 μL, 2 eq) was added to a solution of compound 7-8 (140 mg, 488.70 μmol, 1 eq) in isopropanol (1 mL) at 0° C. and then stirred at 25° C. for 1 hour. The solution was purified directly by preparative HPLC (column: Waters Xbridge 150×25 mm×5 μm; mobile phase: 10 mmol/L ammonium bicarbonate aqueous solution and acetonitrile, the proportion of acetonitrile in the mobile phase was from 1% to 6%, 4 min) to obtain compound 7. $^1$H NMR (400 MHz, $CD_3OD$) δ=6.49 (s, 2H), 3.41 (s, 2H); LCMS (ESI) m/z: 229 (M+1); 211 (M−18+1).

Example 8

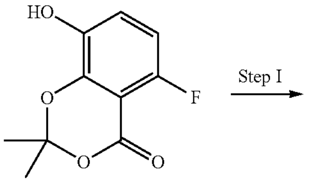

1-7

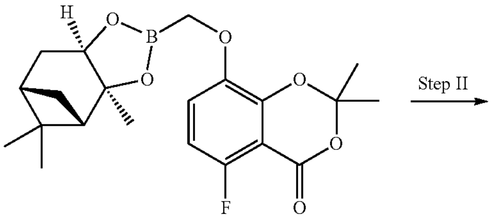

8-2

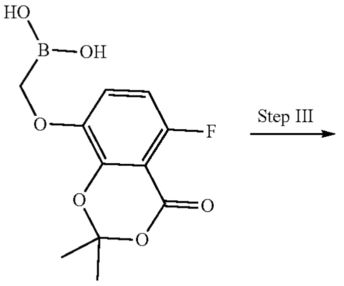

8-3

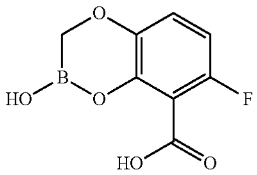

Compound 8

Step I: Preparation of Compound 8-2

$K_2CO_3$ (1.02 g, 7.35 mmol, 1.3 eq) and compound 1-7 (1.2 g, 5.66 mmol, 1 eq) were added to a solution of (1S,2S,6R,8S)-4-(bromomethyl)-2,9,9-trimethyl-3,5-dioxa-4-boratricyclo[6.1.1.0$^{2,6}$]decane (1.85 g, 6.79 mmol, 1.2 eq) in DMF (15 mL). The mixed solution was stirred at 20° C. for 12 hours. The reaction mixture was diluted with 50 mL of $H_2O$ and extracted with EtOAc (100 mL×2). The combined organic layers were washed with an NaCl aqueous solution (20 mL×2), dried over anhydrous $Na_2SO_4$, filtered, and concentrated under reduced pressure to obtain a residue. The residue was purified by silica gel column chromatography (petroleum ether/ethyl acetate=1/0 to 20/1) to obtain compound 8-2.

Step H: Preparation of Compound 8-3

$K_2CO_3$ (769.26 mg, 5.57 mmol, 2.5 eq) and $CH_3I$ (948.04 mg, 6.68 mmol, 415.81 μL, 3 eq) were added to a solution of compound 8-2 (900 mg, 2.23 mmol, 1 eq) in DMF (10 mL). The mixed solution was stirred at 20° C. for 12 hours, $H_2O$ (30 mL) was added to the reaction mixed solution, and filtered under reduced pressure, the filter cake was dried under reduced pressure to obtain a part of compound 8-3, the filtrate was extracted with EtOAc (30 mL×2), and the combined organic layers were dried over $Na_2SO_4$, filtered, and concentrated under reduced pressure to obtain the remaining compound 8-3. $^1$H NMR (400 MHz, DMSO-$d_6$) δ=8.21-7.93 (m, 2H), 7.29-7.17 (m, 1H), 7.03-6.91 (m, 1H), 3.77-3.61 (m, 2H), 1.71 (s, 6H).

Step III: Preparation of Compound 8

NaOH (2 M, 814.76 μL, 2 eq) was added to a solution of compound 8-3 (220 mg, 814.76 μmol, 1 eq) in i-PrOH (i.e., isopropanol, 2.5 mL) at 0° C. and stirred for 1 hour, and the reaction mixture was concentrated under reduced pressure to remove the solvent. The residue was purified by preparative HPLC (column: Waters Xbridge 150×25 mm×5 μm; mobile phase: 10 mmol/L ammonium bicarbonate aqueous solution and acetonitrile; the proportion of acetonitrile was from 1% to 6%, 4 min) to obtain compound 8. $^1$H NMR (400 MHz, $CD_3OD$) δ=6.49 (dd, J=5.8, 8.7 Hz, 1H), 6.29-6.18 (m, 1H), 3.43-3.38 (m, 2H); LCMS (ESI) m/z: 213.1 (M+1).

Example 9

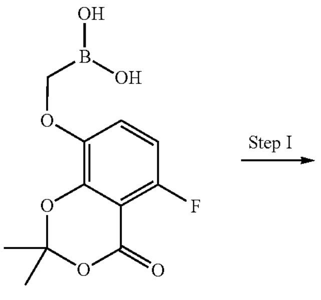

8-3

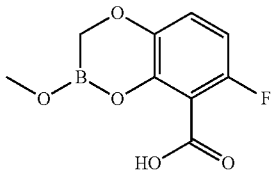

Compound 9

Step I: Preparation of Compound 9

An NaOH aqueous solution (2 M, 1.11 mL, 2 eq) was added dropwise to a solution of compound 8-3 (300 mg, 1.11 mmol, 1 eq) in MeOH (2.5 mL) at 0° C. and stirred for 1 hour. The reaction mixture was concentrated under reduced pressure to remove the solvent. The residue was purified by preparative HPLC (column: Waters Xbridge 150-25 mm×5 μm; mobile phase: 10 mol/L ammonium bicarbonate aqueous solution and acetonitrile, the proportion of acetonitrile in the mobile phase was from 1% to 26%, 9 min) to obtain compound 9. $^1$H NMR (400 MHz, $CD_3OD$) δ=6.69-6.58 (m, 1H), 6.31-6.20 (m, 1H), 3.86 (s, 3H), 3.38 (s, 2H); LCMS (ESI) m/z: 227.1 (M+1).

Example 10

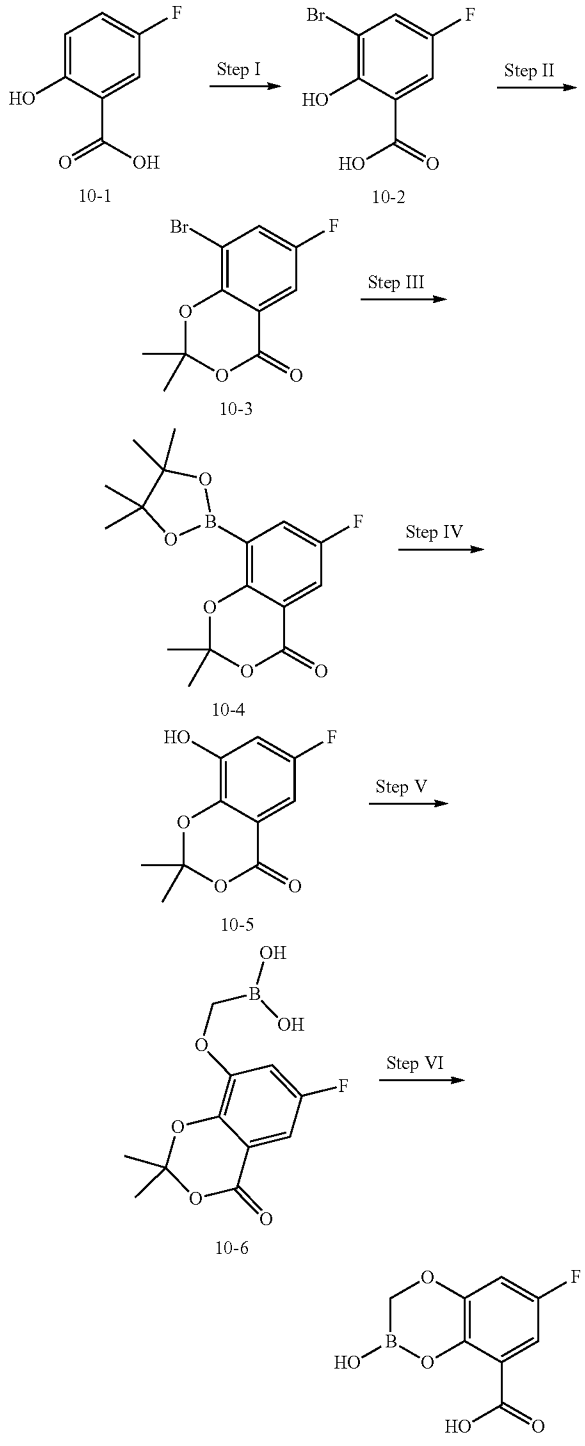

10-1, 10-2, 10-3, 10-4, 10-5, 10-6, Compound 10

Step I: Preparation of Compound 10-2

Compound 10-1 (10 g, 64.06 mmol, 1 eq) and NBS (12.54 g, 70.46 mmol, 1.1 eq) were added to AcOH (50 mL) at 25° C., and the mixed solution was stirred at 80° C. for 24 hours. The mixed solution was poured into water (115 mL) at 0° C. Filtration was then carried out and the filter cake was dried to obtain compound 10-2. $^1$H NMR (400 MHz, $CD_3OD$) δ=7.61 (ddd, J=3.1, 8.1, 11.2 Hz, 2H); LCMS (ESI) m/z: 234.9 (M+1).

Step II: Preparation of Compound 10-3

Compound 10-2 (12.74 g, 54.21 mmol, 1 eq) was dissolved in TFA (100 mL) at 0° C. and acetone (9.45 g, 162.63 mmol, 11.96 mL, 3 eq), TFAA (34.16 g, 162.63 mmol, 22.62 mL, 3 eq) and DMF (792.50 mg, 10.84 mmol, 834.21 μL, 0.2 eq) were added. It was then stirred at 25° C. for 1 hour. It was then heated to 100° C. and stirred for another 35 hours. The mixed solution was concentrated under reduced pressure to obtain a residue, an $NaHCO_3$ aqueous solution (500 mL) was added to the residue at 0° C., and the mixture was then extracted with EA (200 mL). The organic layer was washed with 100 mL of brine, dried over $Na_2SO_4$, filtered, and concentrated under reduced pressure to obtain a residue. The residue was purified by silica gel column chromatography (petroleum ether/ethyl acetate=0/1 to 10/1) to obtain compound 10-3. LCMS (ESI) m/z: 274.8 (M+1).

Step III: Preparation of Compound 10-4

Under nitrogen protection, compound 10-3 (1.78 g, 6.47 mmol, 1 eq), bis(pinacolato)diboron (2.46 g, 9.71 mmol, 1.5 eq), bis(triphenylphosphine)palladium dichloride (454.20 mg, 647.11 μmol, 0.1 eq), di-tert-butyl-[2-(2,4,6-triisopropylphenyl)phenyl]phosphine (549.58 mg, 1.29 mmol, 0.2 eq) and potassium acetate (1.91 g, 19.41 mmol, 3 eq) were added to dioxane (40 mL), and after displacement with $N_2$ 3 times, the mixed solution was then stirred at 55° C. for 5 hours under nitrogen protection. EA (20 mL) was added to the mixed solution, filtered, and concentrated under reduced pressure to obtain a residue. The reaction mixture was quenched by adding 50 mL of $H_2O$ to the residue, and the mixture was then extracted with EA (20 mL×2). The organic layer was washed with 50 mL of brine, dried over anhydrous $Na_2SO_4$, filtered, and concentrated under reduced pressure, and the obtained residue was purified by silica gel column chromatography (petroleum ether/ethyl acetate=1/0 to 0/1) to obtain compound 10-4.

Step IV: Preparation of Compound 10-5

Compound 10-4 (2.03 g, 6.30 mmol, 1 eq) was dissolved in a mixed solution of THF (20 mL) and water (10 mL) at 0° C., and sodium perborate tetrahydrate (2.91 g, 18.91 mmol, 3.64 mL, 3 eq) was further added. The mixed solution was stirred at 25° C. for 1 hour. Water (20 mL) was added to the reaction mixed solution, the solution was extracted with EA (20 mL×2), the combined organic layers were washed with brine (40 mL 1), dried with anhydrous $Na_2SO_4$, filtered, and concentrated under reduced pressure, and the obtained residue was purified by silica gel column chromatography (petroleum ether/ethyl acetate=20/1 to 0/1) to obtain compound 10-5. LCMS (ESI) m/z: 213.1 (M+1).

Step V: Preparation of Compound 10-6

2-iodomethyl-boronic acid pinacol ester (631.32 mg, 2.36 mmol, 2 eq) and compound 10-5 (250 mg, 1.18 mmol, 1 eq)

were dissolved in acetonitrile (5 mL) at 25° C., and $K_2CO_3$ (244.27 mg, 1.77 mmol, 1.5 eq) was added to the solution. It was then stirred at 65° C. for 4 hours. Water (10 mL) was added to the mixed solution, the solution was extracted with EA (10 mL×3), and the combined organic layers were washed with brine (20 mL×2), dried with $Na_2SO_4$, filtered, and concentrated under reduced pressure to obtain a residue. The crude product was purified by preparative HPLC (column: 3-Phenomenex Luna C18 75×30 mm×3 μm; mobile phase: an aqueous solution with 0.1% TFA and acetonitrile, the content of acetonitrile in the mobile phase was from 26-56%, 10 min) to obtain compound 10-6. LCMS (ESI) m/z: 270.9 (M+1).

Step VI: Preparation of Compound 10

NaOH (1 M, 740.69 μL, 2 eq) was added dropwise to a solution of compound 10-6 (100 mg, 370.35 μmol, 1 eq) in isopropanol (1 mL) at 0° C. The mixed solution was then stirred at 25° C. for 2 hours. The crude product was purified by preparative HPLC (column. Waters Xbridge 150×25 mm×5 μm; mobile phase: 10 mmol/L ammonium bicarbonate aqueous solution and acetonitrile, the proportion of acetonitrile in the mobile phase was from 1% to 6%, 4 min) to obtain compound 10. $^1H$ NMR (400 MHz, $D_2O$) δ=6.63 (dd, J=3.3, 8.8 Hz, 1H), 6.56 (dd, J=3.1, 9.9 Hz, 1H), 3.34 (s, 2H); LCMS (ESI) m/z: 212.8 (M+1).

Example 11

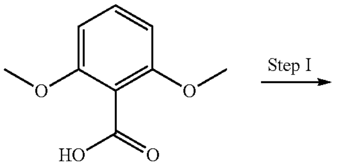

11-1

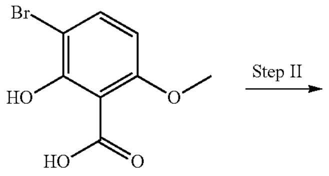

11-2

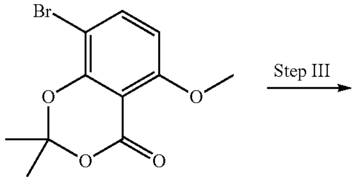

11-3

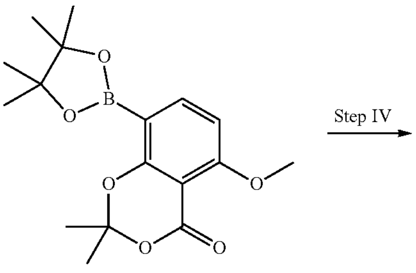

11-4

-continued

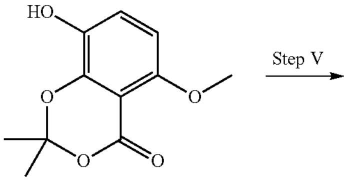

11-5

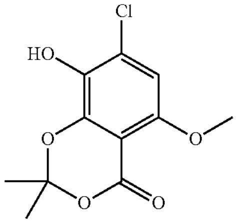
11-6

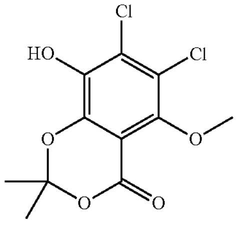
12-1

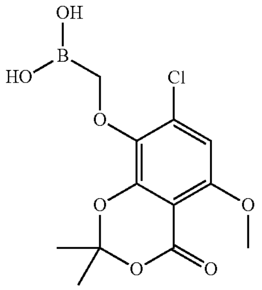
11-7

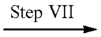

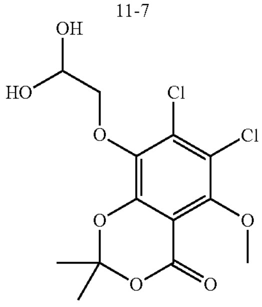
12-2

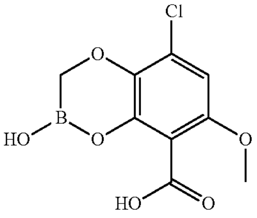
Compound 11

Step I: Preparation of Compound 11-2

Compound 11-1 (10 g, 54.89 mmol, 1 eq) was dissolved in chloroform (200 mL) at 0° C., and liquid bromine (8.77 g, 54.89 mmol, 2.83 mL, 1 eq) was then added. It was stirred at 25° C. for 30 hours. The mixture was concentrated under reduced pressure to obtain a residue. The crude product was washed with petroleum ether/ethyl acetate (150 mL, 5/1) at 25° C. for 30 minutes. After filtration, compound 11-2 was obtained. LCMS (ESI) m/z: 247.0 (M+1).

Step II: Preparation of Compound 11-3

Acetone (8.74 g, 150.46 mmol, 11.06 mL, 3 eq) was added to a solution of compound 11-2 (12.39 g, 50.15 mmol, 1 eq) in trifluoroacetic acid (100 mL), trifluoroacetic anhydride (31.60 g, 150.46 mmol, 20.93 mL, 3 eq) and DMF (733.14 mg, 10.03 mmol, 771.73 μL, 0.2 eq) were added at 0° C., and the mixture was then stirred at 25° C. for 1 hour, then heated to 100° C. and stirred for another 47 hours. The reaction mixture was concentrated under reduced pressure to obtain a residue, which was quenched by adding to sodium bicarbonate aqueous solution (500 mL) at 0° C. and then extracted with ethyl acetate (200 mL×1). The organic layer was washed with brine (100 mL×1), dried over anhydrous sodium sulfate, filtered, and concentrated under reduced pressure to obtain a residue. The crude product was purified by silica gel flash column chromatography (petroleum ether/ethyl acetate=1/0 to 5/1). 11-3 was obtained. $^1$H NMR (400 MHz, $CDCl_3$) δ=7.60 (d, J=9.0 Hz, 1H), 6.51 (d, J=9.0 Hz, 1H), 3.89 (s, 3H), 1.68 (s, 6H); LCMS (ESI) m/z: 288.9 (M+1).

Step III: Preparation of Compound 11-4

Compound 11-3 (3 g, 10.45 mmol, 1 eq), bis(pinacolato) diboron (3.98 g, 15.67 mmol, 1.5 eq), 1,1-bis(diphenylphosphino)ferrocenepalladium(II) dichloride dichloromethane complex (1.71 g, 2.09 mmol, 0.2 eq), and potassium acetate (3.08 g, 31.35 mmol, 3 eq) were mixed in dioxane (40 mL), and after displacement with nitrogen 3 times, and the mixture was then stirred at 65° C. for 12 hours in a nitrogen atmosphere. Ethyl acetate (50 mL) was added to the mixture, and the mixture was filtered, and concentrated under reduced pressure to obtain a residue. Water (50 mL) was added to the mixture, and the mixture was then extracted with ethyl acetate (20 mL×2). The organic layer was washed with 50 mL of brine, dried over anhydrous sodium sulfate, filtered, and concentrated under reduced pressure to obtain a residue. Purification by silica gel flash column chromatography (petroleum ether/ethyl acetate=0/1 to 5/1) afforded a crude product of 11-4. LCMS (ESI) m/z: 335.1 (M+1).

Step IV: Preparation of Compound 11-5

Compound 11-4 (1.23 g, 3.68 mmol, 1 eq) was added to tetrahydrofuran (12 mL) and water (6 mL) at 0° C., and sodium perborate tetrahydrate (1.70 g, 11.04 mmol, 2.12 mL, 3 eq) was added. The mixture was then stirred at 25° C. for 1 hour. Water (20 mL) was added to the reaction mixture, and the mixture was extracted with ethyl acetate (20 mL×2), and the combined organic layers were washed with brine (40 mL×1), dried with anhydrous sodium sulfate, filtered, and concentrated under reduced pressure to obtain a residue. Purification by silica gel flash column chromatography (petroleum ether/ethyl acetate=20/1 to 0/1) afforded a crude product of 11-5. LCMS (ESI) m/z: 225.0 (M+1).

Step V: Preparation of Compound 11-6

Compound 11-5 (365 mg, 1.63 mmol, 1 eq) and NCS (416.96 mg, 2.12 mmol, 1.3 eq) were mixed in tetrahydrofuran (10 mL), and the mixture was stirred at 50° C. for 5 hours. Water (20 mL) was added to the mixture, and the mixture was extracted with ethyl acetate (20 mL×2), the combined organic layers were then washed with brine (50 mL×1), dried with anhydrous sodium sulfate, filtered, and concentrated under reduced pressure to obtain a mixture of compounds 11-6 and 12-1, which was directly used in the next step of reaction. LCMS (ESI) m/z: 258.9 (M+1).

Step VI: Preparation of Compound 11-7

2-Iodomethyl-boronic acid pinacol ester (1.69 g, 6.32 mmol, 2 eq) and a crude product of compounds 11-6 and 12-1 (818 mg, 3.16 mmol, 1 eq) were mixed in acetonitrile (10 mL) at 25° C., and potassium carbonate (655.64 mg, 4.74 mmol, 1.5 eq) was added. The mixture was then stirred at 65° C. for 4 hours. Water (10 mL) was added to the mixture, the mixture was extracted with ethyl acetate (10 mL×3), the combined organic layers were washed with brine (20 mL×2), dried with anhydrous sodium sulfate, filtered, and concentrated under reduced pressure, and the obtained residue was purified by preparative HPLC (column: Phenomenex tuna C18 150×40 mm×15 μm; mobile phase: an aqueous solution with 0.1% TFA and acetonitrile; the proportion of acetonitrile in the mobile phase was from 23-53%, 8 min) to obtain compound 11-7, LCMS (ESI) m/z: 317.0 (M+1); and compound 12-2, LCMS (ESI) m/z: 351.1 (M+1).

Step VII: Preparation of Compound 11

Compound 11-7 (100 mg, 315.96 μmol, 1 eq) was dissolved in isopropanol (1 mL), sodium hydroxide aqueous solution (1 M, 631.91 μL, 2 eq) was added at 0° C., and the mixture was then stirred at 25° C. for 2 hours. The crude product was purified by preparative HPLC (column: Waters Xbridge 150×25 mm×5 μm; mobile phase: 10 mmol/L ammonium bicarbonate aqueous solution and acetonitrile, the proportion of acetonitrile in the mobile phase was from 1% to 6%, 4 min) to obtain compound 11. $^1$H NMR (400 MHz, $D_2O$)=6.64 (s, 1H), 3.69 (s, 3H), 3.22 (s, 2H); LCMS (ESI) m/z: 240.9 (M−18+1).

Example 12

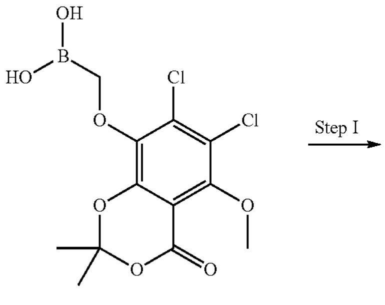

12-2

-continued

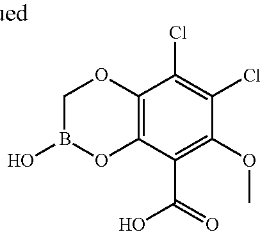

Compound 12

Step I: Preparation of Compound 12

Compound 12-2 (100 mg, 284.95 μmol, 1 eq) was dissolved in isopropanol (1 mL), and a sodium hydroxide aqueous solution (1 M, 569.89 μL, 2 eq) was added at 0° C. The mixture was then stirred at 25° C. for 2 hours. The crude product was purified by preparative HPLC (chromatographic column: Waters Xbridge 150×25 mm×5 μm; mobile phase: 10 mmol/L ammonium bicarbonate aqueous solution and acetonitrile, the proportion of acetonitrile in the mobile phase was from 1% to 6%, 4 min) to obtain compound 12. $^1$H NMR (400 MHz, $D_2O$) δδ=3.71 (s, 3H), 3.31 (s, 2H); LCMS (ESI) m/z: 274.9 (M−18+1).

Example 13

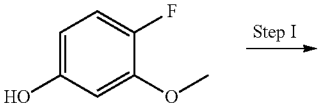

13-1

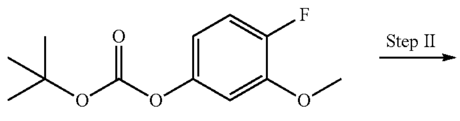

13-2

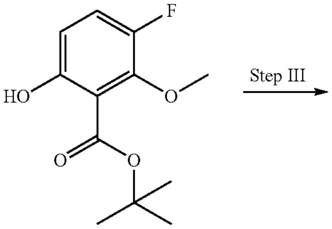

13-3

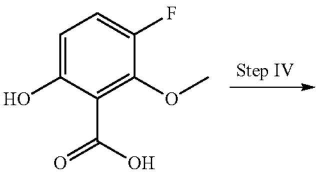

13-4

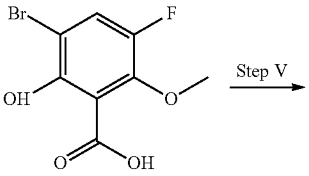

13-5

-continued

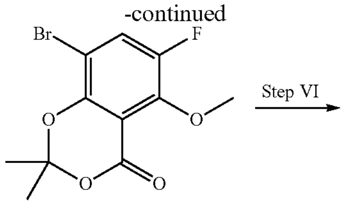

13-6

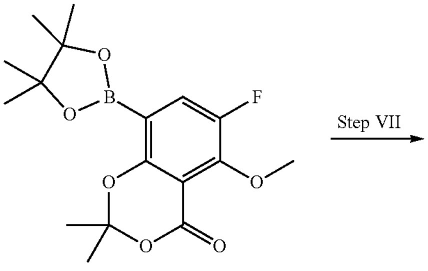

13-7

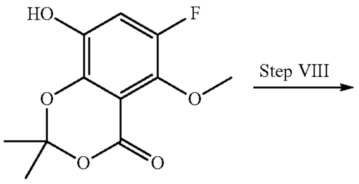

13-8

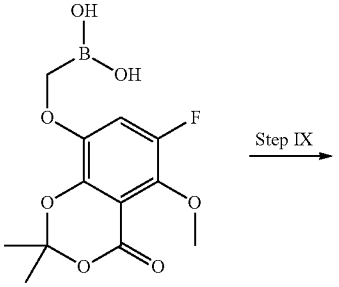

13-9

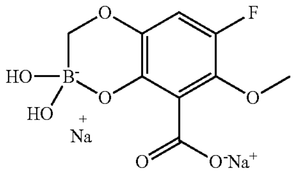

Compound 13

Step I: Preparation of Compound 13-2

Compound 13-1 (108 g, 70.36 mmol, 1 eq) was dissolved in dichloromethane (100 mL), $Boc_2O$ (16.89 g, 77.40 mmol, 17.78 mL, 1.1 eq) and DMAP (429.79 mg, 3.52 mmol, 0.05 eq) were added, and the mixture was stirred at 25° C. for 16 hours. Water (50 mL) was added to the reaction liquid, and the aqueous phase was extracted with ethyl acetate (50 mL×3). The combined organic phases were washed with brine (100 mL×2), dried with anhydrous sodium sulfate, filtered, and concentrated in vacuum to obtain compound 13-2. $^1$H NMR (400 MHz, $CDCl_3$) δ=6.98 (dd, J=8.9, 10.8 Hz, 1H), 6.73 (dd, J=2.8, 7.2 Hz, 1H), 6.67-6.60 (m, 1H), 3.81 (s, 3H), 1.49 (s, 9H).

Step II: Preparation of Compound 13-3

Compound 13-2 (16.9 g, 69.76 mmol, 1 eq) was dissolved in a solution of tetrahydrofuran (170 mL), lithium diisopropylamide (2 M, 41.86 mL, 1.2 eq) was added dropwise at −70° C. under nitrogen, and the mixture was stirred at −70° C. for 2 hours. The reaction mixture was diluted with 1N dilute hydrochloric acid (20 mL) and extracted with ethyl acetate (40 mL×3). The combined organic layers were washed with table salt aqueous solution (100 mL×2), dried over anhydrous sodium sulfate, filtered, and concentrated under reduced pressure. The residue was purified by silica gel chromatography (petroleum ether/ethyl acetate=1/0 to 20/1). Compound 13-3 was obtained. $^1$H NMR (400 MHz, $CDCl_3$) δ=7.17 (dd, J=9.2, 10.5 Hz, 1H), 6.67 (dd, J=4.1, 9.3 Hz, 1H), 3.91 (d, J=1.0 Hz, 3H), 1.66 (s, 9H).

Step III: Preparation of Compound 13-4

Trifluoroacetic acid (53.90 g, 472.71 mmol, 35 mL, 9.35 eq) was added to a solution of compound 13-3 (12.25 g, 50.57 mmol, 1 eq) in dichloromethane (35 mL) at 0° C., and the mixture was stirred at 25° C. for 16 hours. The solution was concentrated under reduced pressure, the obtained crude product was stirred with petroleum ether (70 mL) at 25° C. and filtered, and the filter cake was dried to obtain compound 13-4. $^1$H NMR (400 MHz, $CDCl_3$) δ=11.67 (s, 1H), 11.63-11.49 (m, 1H), 7.30-7.28 (m, 1H), 6.79 (dd, J=3.9, 9.4 Hz, 1H), 4.26 (d, J=2.9 Hz, 3H).

Step IV: Preparation of Compound 13-5

NBS (9.29 g, 52.18 mmol, 1.05 eq) was added in portions to a solution of compound 13-4 (9.25 g, 49.69 mmol, 1 eq) in dichloromethane (100 mL) at 0° C., and the solution was then stirred at 25° C. for 12 hours. The solution was concentrated in vacuum. The crude product was mixed with water (100 mL) and stirred at room temperature for 30 minutes. After filtration, compound 13-5 was obtained. $^1$H NMR (400 MHz, $CD_3OD$) δ=7.63 (d, J=10.6 Hz, 1H), 3.95 (d, J=1.3 Hz, 3H); LCMS (ESI) m/z: 265 (M+1).

Step V: Preparation of Compound 13-6

Acetone (8.14 g, 140.13 mmol, 10.30 mL, 3 eq), trifluoroacetic anhydride (29.43 g, 140.13 mmol, 19.49 mL, 3 eq) and DMF (682.82 mg, 9.34 mmol, 718.76 μL, 0.2 eq) were added to a solution of compound 13-5 (12.38 g, 46.71 mmol, 1 eq) in trifluoroacetic acid (130 mL) at 0° C. The mixture was stirred at 105° C. for 48 hours. The solution was concentrated in vacuum, a sodium bicarbonate solution (20 mL) was then added, and the solution was extracted with ethyl acetate (30 mL×3). The combined organic phases were washed with brine (50 mL×2), dried with anhydrous sodium sulfate, filtered, and concentrated in vacuum. The residue was purified by silica gel chromatography (petroleum ether/ethyl acetate=500/1 to 50/1), and the compound was then stirred with petroleum ether (100 mL) at 0° C. for 1 hour. After filtration, compound 13-6 was obtained. $^1$H NMR (400 MHz, $CDCl_3$) δ=7.57 (d, J=10.6 Hz, 1H), 4.08 (d, J=2.2 Hz, 3H), 1.77 (s, 6H); LCMS (ESI) m/z: 305 (M+1).

Step VI: Preparation of Compound 13-7

Compound 13-6 (2.7 g, 8.85 mmol, 1 eq), bis(pinacolato) diboron (8.99 g, 35.40 mmol, 4 eq), bis(triphenylphosphine) palladium dichloride (621.15 mg, 884.97 μmol, 0.1 eq), potassium acetate (3.47 g, 35.40 mmol, 4 eq), and di-tert-butyl-[2-(2,4,6-triisopropylphenyl)phenyl]phosphine (751.58 mg, 1.77 mmol, 0.2 eq) were mixed in dioxane (30 mL) at 25° C. and degassed, and after displacement with nitrogen 3 times, the mixture was then stirred at 65° C. for 5 hours in a nitrogen atmosphere. The reaction mixture was concentrated under reduced pressure to remove the solvent. The residue was purified by silica gel chromatography (petroleum ether/ethyl acetate=50/1 to 0/1) to obtain crude 13-7. LCMS (ESI) m/z: 353 (M+1).

Step VII: Preparation of Compound 13-8

Compound 13-7 (1 g, 2.84 mmol, 1 eq) was dissolved in tetrahydrofuran (10 mL) and water (5 mL), sodium perborate tetrahydrate (1.31 g, 8.52 mmol, 1.64 mL, 3 eq) was added, and the mixture was stirred at 25° C. for 16 hours. Water (30 mL) was added to the solution, and the aqueous phase was extracted with ethyl acetate (50 mL×3). The combined organic phases were washed with brine (150 mL×2), dried with anhydrous sodium sulfate, filtered, and concentrated in vacuum. The residue was purified by silica gel chromatography (petroleum ether/ethyl acetate=20/1 to 5/1) to obtain compound 13-8. $^1$H NMR (400 MHz, $CDCl_3$) δ=7.02 (d, J=11.6 Hz, 1H), 3.98 (d, J=0.9 Hz, 3H), 1.77 (s, 6H); LCMS (ESI) m/z: 242.9 (M+1).

Step VIII: Preparation of Compound 13-9

Compound 13-8 (1.7 g, 1.75 mmol, 25% purity, 1 eq) was dissolved in acetonitrile (20 mL), 2-iodomethyl-boronic acid pinacol ester (470.10 mg, 1.75 mmol, 1 eq) and potassium carbonate (363.79 mg, 2.63 mmol, 1.5 eq) were added at 20° C., and the mixture was then stirred at 60° C. for 3 hours. Water (5 mL) was added to the solution, and the aqueous phase was adjusted to pH=3-4 with 0.5 N dilute hydrochloric acid and extracted with ethyl acetate (10 mL×3). The combined organic phases were washed with brine (30 mL×2), dried with anhydrous sodium sulfate, filtered, and concentrated in vacuum. The crude product was purified by preparative HPLC (column: Zhongpu RD-C18 150×25 mm×3 μm; mobile phase: an aqueous solution with 0.1% TFA and acetonitrile, the proportion of acetonitrile in the mobile phase was from 17-47%, 10 min) to obtain compound 13-9. LCMS (ESI) m/z: 300.9 (M+1).

Step IX: Preparation of Compound 13

Compound 13-9 (60 mg, 199.97 t mol, 1 eq) was dissolved in isopropanol (0.5 mL), a sodium hydroxide aqueous solution (1 M, 399.94 μL, 2 eq) was added at 0° C., and the mixture was then stirred at 25° C. for 1 hour. Acetone was added to the solution, and the solution was filtered, and dried in vacuum. Compound 13 was obtained. $^1$H NMR (400 MHz, $CD_3OD$) δ=6.30 (d, J=12.4 Hz, 1H), 3.83 (s, 3H), 3.39 (s, 2H); LCMS (ESI) m/z: 242.9 (M+1); 224.9 (M−18+1).

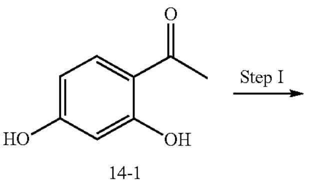

14-1

-continued

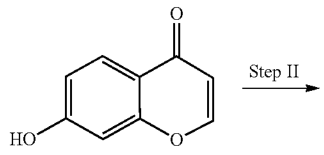

14-2

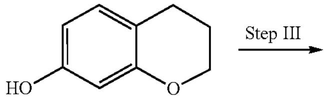

14-3

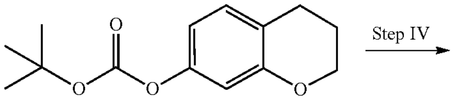

14-4

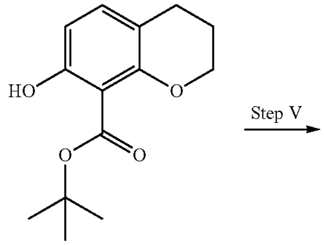

14-5

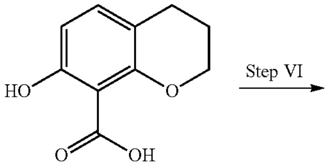

14-6

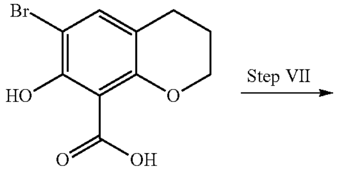

14-7

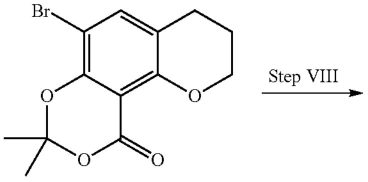

14-8

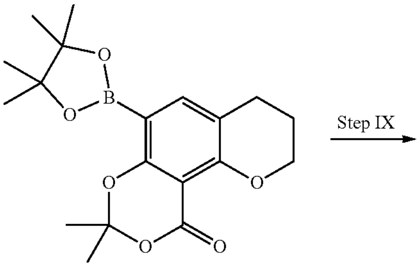

14-9

-continued

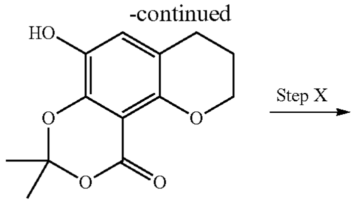

14-10

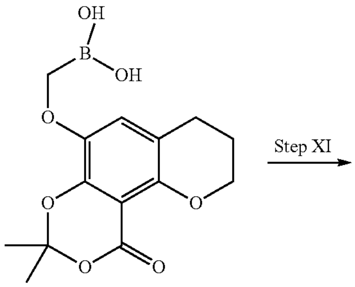

14-11

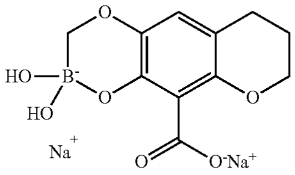

Compound 14

Step I: Preparation of Compound 14-2

$HClO_4$ (23.67 g, 164.93 mmol, 14.26 mL, 70% purity, 8.36e−1 eq) was added dropwise to a mixture of compound 14-1 (30 g, 197.18 mmol, 25.42 mL, 1 eq) and triethyl orthoformate (160.72 g, 1.08 mol, 180.38 mL, 5.5 eq) at 20° C., the temperature was controlled not to exceed 40° C., and the mixture was stirred at 20° C. for 1.5 hours. Subsequently, methyl tert-butyl ether (600 mL) was added and then filtered, the filter cake was collected and dissolved in $H_2O$ (200 mL), and the solution was stirred at 80° C. for 2 hours, extracted with 400 mL of ethyl acetate (200 mL×2), washed with 300 mL of aqueous saturated table salt, dried over $Na_2SO_4$, filtered, and concentrated under reduced pressure to obtain compound 14-2. $^1H$ NMR (400 MHz, DMSO-$d_6$) δ=10.78 (s, 1H), 8.15 (d, J=6.00 Hz, 1H), 7.87 (s, 1H), 6.92 (dd, J=8.76, 2.25 Hz, 1H), 6.85 (d, J=2.13 Hz, 1H), 6.22 (d, J=6.00 Hz, 1H).

Step II: Preparation of Compound 14-3

Compound 14-2 (23.89 g, 147.34 mmol, 1 eq) was dissolved in EtOH (240 mL), and Pd/C (4.78 g, 10% purity) was added at 20° C. under $N_2$. After displacement with hydrogen several times, the reaction product was stirred at 55° C. for 24 hours under $H_2$ (50 psi). Pd/C was removed by filtration, and the filtrate was distilled under reduced pressure to obtain a crude product. Purification by column chromatography ($SiO_2$, petroleum ether/ethyl acetate=10/1 to 8/1) afforded 14-3. $^1H$ NMR (400 MHz, DMSO-$d_6$) δ=9.16-9.10 (m, 1H), 6.89-6.81 (m, 1H), 6.32-6.27 (m, 1H), 6.20-6.15 (m, 1H), 4.13-4.06 (m, 2H), 2.70-2.61 (m, 2H), 1.95-1.85 (m, 2H).

Step III: Preparation of Compound 14-4

Compound 14-3 (14.23 g, 94.76 mmol, 1 eq) was dissolved in DCM (150 mL), DMAP (578.82 mg, 4.74 mmol, 0.05 eq) was added at room temperature, and $Boc_2O$ (24.82 g, 113.71 mmol, 26.12 mL, 1.2 eq) was then slowly added. The mixture was stirred at 20° C. for 4 hours. The reaction mixture was quenched with HCl (0.2 M, 50 mL) at 20° C., extracted with DCM (150 mL), washed with aqueous saturated table salt (100 mL), dried over $Na_2SO_4$, filtered, and concentrated under reduced pressure to obtain compound 14-4, which was directly used in the next step. $^1$H NMR (400 MHz, $CDCl_3$) δ=6.92 (d, J=8.25 Hz, 1H), 6.56 (s, 1H), 6.59-6.55 (m, 1H), 4.11-4.06 (m, 2H), 2.68 (t, J=6.50 Hz, 2H), 1.95-1.86 (m, 2H), 1.47 (s, 9H).

Step IV: Preparation of Compound 14-5

Compound 14-4 (24.47 g, 97.77 mmol, 1 eq) was dissolved in THF (240 mL), LDA (2 M, 58.66 mL, 1.2 eq) was slowly added dropwise under $N_2$, and the mixture was stirred at −20° C. for 1.5 hours. The reaction mixture was quenched with $NH_4Cl$ (300 mL) at −78° C., extracted with (400 mL) ethyl acetate, washed with aqueous saturated table salt (200 mL), dried over $Na_2SO_4$, filtered, and concentrated under reduced pressure to obtain a crude product, which was purified by column chromatography ($SiO_2$, petroleum ether/ethyl acetate=1/0) to obtain compound 14-5. LCMS (ESI) m/z: 195.2 (M−55).

Step V: Preparation of Compound 14-6

Compound 14-5 (16.55 g, 66.12 mmol, 1 eq) was dissolved in DCM (50 mL), and TFA (76.46 g, 670.59 mmol, 49.65 mL, 10.14 eq) was added at room temperature. The mixture was stirred at 20° C. for 1 hour. Concentration under reduced pressure afforded a crude product, the crude product was stirred with PE:EA=20:1 (126 mL) for 10 min at room temperature and filtered, and the filter cake was dried to obtain compound 14-6. $^1$H NMR (400 MHz, $CDCl_3$) δ=7.16 (d, J=8.56 Hz, 1H), 6.63 (d, J=8.56 Hz, 1H), 4.51-4.41 (m, 2H), 2.78 (t, J=6.48 Hz, 2H), 2.16-2.07 (m, 2H).

Step VI: Preparation of Compound 14-7

Compound 14-6 (15.22 g, 78.38 mmol, 1 eq) was dissolved in DCM (150 mL), and NBS (12.55 g, 70.54 mmol, 0.9 eq) was then added at room temperature. The mixture was stirred at 0° C. for 1 hour. The reaction mixture was diluted with 100 mL of $H_2O$, extracted with 100 mL of DCM, washed with 200 mL of brine (100 mL×2), dried over $Na_2SO_4$, filtered, and concentrated under reduced pressure to obtain a residue. The crude product was stirred with petroleum ether:ethyl acetate=20:1 (126 mL) at 20° C. for 30 minutes and filtered, and the filter cake was dried to obtain compound 14-7. $^1$H NMR (400 MHz, $CDCl_3$) δ=12.77-12.69 (m, 1H), 11.53-11.36 (m, 1H), 7.51-7.42 (m, 1H), 4.51-4.45 (m, 2H), 2.82-2.76 (m, 2H), 2.19-2.08 (m, 2H).

Step VII: Preparation of Compound 14-8

Compound 14-7 (13.82 g, 50.61 mmol, 1 eq) was dissolved in TFA (56 mL), acetone (29.39 g, 506.08 mmol, 37.21 mL, 10 eq) was added at 0° C., TFAA (31.89 g, 151.82 mmol, 21.12 mL, 3 eq) was added dropwise, and after displacement with nitrogen several times, the reaction product was stirred at 100° C. under $N_2$ for 48 hours. The product was concentrated under reduced pressure to remove the solvent, diluted with 200 mL of an $NaHCO_3$ saturated solution, and extracted with 300 mL of EA (100 mL×3). It was washed with aqueous saturated table salt (150 mL×1), dried over $Na_2SO_4$, filtered, and concentrated under reduced pressure to obtain a residue, which was purified by column chromatography ($SiO_2$, petroleum ether/ethyl acetate=50/1 to 5/1) to obtain compound 14-8. LCMS (ESI) m/z: 315.0 (M+3).

Step VIII: Preparation of Compound 14-9

Compound 14-8 (1 g, 1.60 mmol, 50/6 purity, 1 eq) was dissolved in dioxane (20 mL), and pinacol boronate (1.01 g, 3.99 mmol, 2.5 eq), potassium acetate (470.10 mg, 4.79 mmol, 3 eq) and Pd(dppf)$Cl_2$ (233.67 mg, 319.34 μmol, 0.2 eq) were then added under nitrogen flow. The mixture was stirred at 70° C. for 12 hours under nitrogen protection. The reaction mixture was filtered, then diluted with 40 mL of water, extracted with 60 mL of ethyl acetate (30 mL×2), washed with aqueous saturated table salt (60 mL×1), dried over $Na_2SO_4$, filtered, and concentrated under reduced pressure to obtain a residue. The residue was purified by column chromatography ($SiO_2$, petroleum ether/ethyl acetate=5/1 to 1/1) to obtain compound 14-9. LCMS (ESI) m/z: 361.2 (M+1).

Step IX: Preparation of Compound 14-10

Compound 14-9 (1.74 g, 4.82 mmol, 1 eq) was dissolved in a mixed solution of THF (10 mL) and $H_2O$ (10 mL). Sodium perborate tetrahydrate (1.48 g, 9.64 mmol, 2 eq) was added at 20° C., and the mixture was stirred at 20° C. for 1 hour. The reaction liquid was diluted with 20 mL of water, then extracted with 80 mL of ethyl acetate (40 mL×2), washed with aqueous saturated table salt (40 mL), dried with anhydrous $Na_2SO_4$, filtered, and concentrated in vacuum. The residue was purified by column chromatography ($SiO_2$, petroleum ether/ethyl acetate=10/1 to 4/1) to obtain compound 14-10. LCMS (ESI) m/z: 251.1 (M+1).

Step X: Preparation of Compound 14-11

Compound 14-10 (214 mg, 855.16 μmol, 1 eq) was dissolved in acetonitrile (2 mL), and 2-iodomethyl pinacol boronate (274.91 mg, 1.03 mmol, 1.2 eq) and $K_2CO_3$ (141.83 mg, 1.03 mmol, 1.2 eq) were added in sequence at room temperature; and after the addition was complete, displacement with nitrogen was performed 3 times, and the mixture was then stirred at 60° C. for 6 hours under $N_2$. The reaction mixture was concentrated under reduced pressure to remove the solvent acetonitrile. The residue was diluted with 20 mL of $H_2O$ and extracted with 100 mL of ethyl acetate (20 mL×5). The combined organic layers were washed with 30 mL of brine (30 mL×1), dried over $Na_2SO_4$, filtered, and concentrated under reduced pressure to obtain compound 14-11. LCMS (ESI) m/z: 309.1 (M+1).

Step XI: Preparation of Compound 14

Compound 14-11 (318 mg, 1.03 mmol, 1 eq) was dissolved in i-PrOH (1 mL), and NaOH (2 M, 1.03 mL, 2 eq) was added dropwise at room temperature. The mixture was stirred and reacted at 20° C. for 2 hours. The reaction mixture was diluted with 1 mL of $H_2O$ and purified by preparative HPLC (chromatographic column: Waters Xbridge 150-25 mm×5 μm; mobile phase: water with 10 mM $NH_4HCO_3$ and acetonitrile, the proportion of acetonitrile in the mobile phase was from 1% to 6%, 4 min) to obtain compound 14. LCMS (ESI) m/z: 251.0 (M+1); $^1$H NMR (400 MHz, $D_2O$) δ=6.34 (s, 1H), 4.02-3.95 (m, 2H), 3.20 (s, 2H), 2.55 (t, J=6.48 Hz, 2H), 1.88-1.79 (m, 2H).

Example 15

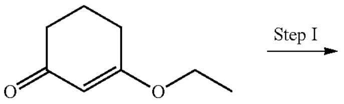

15-1

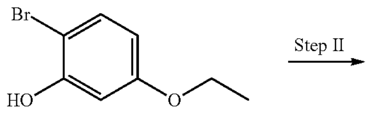

15-2

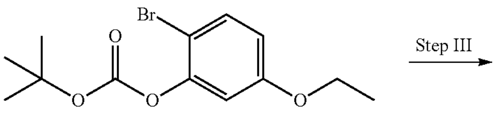

15-3

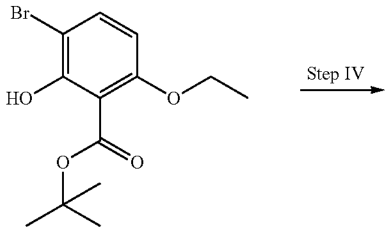

15-4

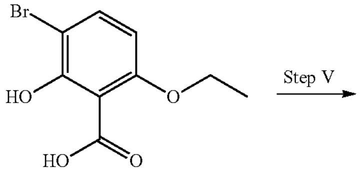

15-5

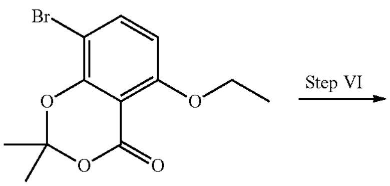

15-6

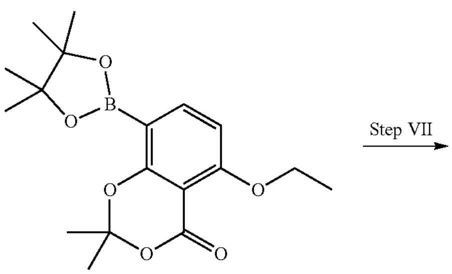

15-7

-continued

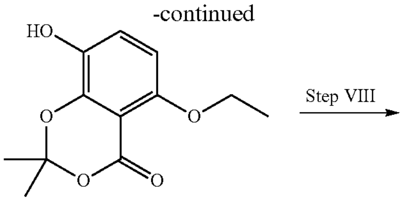

15-8

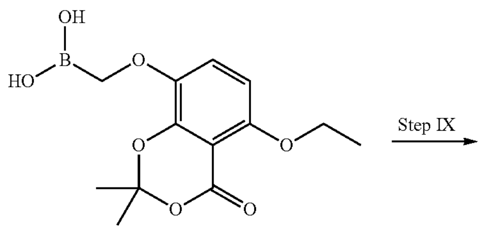

15-9

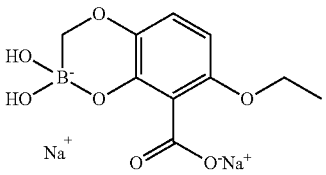

Compound 15

Step I: Preparation of Compound 15-2

LiHMDS (1 M THF solution, 363.82 mL, 3 eq) was dissolved in a toluene (150 mL) solution and cooled to −70° C., a solution of compound 15-1 (17 g, 121.27 mmol, 17.65 mL, 1 eq) in toluene (20 mL) was added within 3 minutes and stirred for 0.5 hour, a solution of 4-methylbenzenesulfonyl bromide (59.87 g, 254.67 mmol, 2.1 eq) in tetrahydrofuran (50 mL) was then added over 0.5 hour, LiHMDS (1M, 121.27 mL, 1 eq) was added, and after the addition was completed, the mixture was slowly heated to 20° C. and stirred for 0.5 hour. THF (50 mL) was added to the solution and the solution was stirred at 25° C. for another 0.5 hour. The reaction liquid was poured into $NH_4Cl$ (100 mL) and stirred for 10 minutes. The aqueous phase was extracted with ethyl acetate (100 mL×2). The combined organic phases were washed with brine (200 mL×2), dried with anhydrous $Na_2SO_4$, filtered, and concentrated in vacuum. The crude product was purified by silica gel chromatography (petroleum ether/ethyl acetate=1/0 to 100/1). Compound 15-2 was obtained. $^1H$ NMR (400 MHz, $CDCl_3$) δ=7.32 (d, J=8.9 Hz, 1H), 6.64-6.59 (m, 1H), 6.43 (dd, J=2.8, 8.9 Hz, 1H), 5.53 (s, 1H), 4.00 (q, J=7.0 Hz, 2H), 1.42 (t, J=7.0 Hz, 3H).

Step II: Preparation of Compound 15-3

Compound 15-2 (6.4 g, 29.48 mmol, 1 eq) was dissolved in dichloromethane (70 mL), $Boc_2O$ (7.08 g, 32.43 mmol, 7.45 mL, 1.1 eq) and DMAP (180.11 mg, 1.47 mmol, 0.05 eq) were added, and the mixture was stirred at 25° C. for 16 hours. $H_2O$ (50 mL) was added to the reaction liquid, and the aqueous phase was extracted with ethyl acetate (50 mL×3). The combined organic phases were washed with brine (100 mL×2), dried with anhydrous $Na_2SO_4$, filtered, and concentrated in vacuum to obtain compound 15-3 without purification. $^1H$ NMR (400 MHz, $CDCl_3$) δ=7.37 (d, J=8.9 Hz, 1H), 6.69 (d, J=2.8 Hz, 1H), 6.61 (dd, J=2.9, 8.9 Hz, 1H), 3.93 (q, J=7.0 Hz, 2H), 1.50 (s, 9H), 1.33 (t, J=7.0 Hz, 3H).

Step III: Preparation of Compound 15-4

Compound 15-3 (9 g, 28.38 mmol, 1 eq) was dissolved in a solution of tetrahydrofuran (90 mL), LDA (1 M, 34.05 mL, 1.2 eq) was added under nitrogen at −70° C., and the mixture was stirred at −70° C. for 2 hours. The reaction mixture was diluted with $NH_4Cl$ (50 mL) and extracted with ethyl acetate (50 mL×2). The combined organic layers were washed with an NaCl aqueous solution (100 mL×2), dried over $Na_2SO_4$, filtered, and concentrated under reduced pressure. The crude product was stirred with petroleum ether at 25° C. for 1 hour and filtered, and the filter cake was dried to obtain compound 15-4. $^1H$ NMR (400 MHz, $CDCl_3$) δ=12.29 (br s, 1H), 7.44 (d, J=8.9 Hz, 1H), 6.24 (d, J=8.9 Hz, 1H), 3.94 (q, J=6.9 Hz, 2H), 1.53 (s, 9H), 1.38 (t, J=7.0 Hz, 3H).

Step IV: Preparation of Compound 15-5

Compound 15-4 (5.15 g, 16.24 mmol, 1 eq) was dissolved in a solution of dichloromethane (20 mL), and trifluoroacetic acid (31.41 g, 275.47 mmol, 20.40 mL, 16.97 eq) was added under nitrogen at 0° C. It was heated to 25° C. and stirred for 2 hours. The compound was concentrated in vacuum. The crude product was stirred with petroleum ether (20 mL) at 25° C. for 2 hour and filtered, and the filter cake was dried to obtain compound 15-5. $^1H$ NMR (400 MHz, $CDCl_3$) δ=12.87 (s, 1H), 7.60 (d, J=8.8 Hz, 1H), 6.37 (d, J=8.9 Hz, 1H), 4.26 (q, J=7.1 Hz, 2H), 1.51 (s, 3H).

Step V: Preparation of Compound 15-6

Compound 15-5 (4.2 g, 16.09 mmol, 1 eq) was dissolved in a solution of TFA (10 mL), acetone (2.80 g, 48.26 mmol, 3.55 mL, 3 eq) was added, and trifluoroacetic anhydride (10.14 g, 48.26 mmol, 6.71 mL, 3 eq) and dimethylformamide (235.17 mg, 3.22 mmol, 247.55 μL, 0.2 eq) were added at 0° C. The mixture was stirred at 20° C. for 0.5 hour. It was then heated to 105° C. and stirred for another 32 hours. The solution was concentrated in vacuum, an $NaHCO_3$ solution (30 mL) was then added, and the solution was extracted with ethyl acetate (30 mL×3). The combined organic phases were washed with aqueous saturated table salt (50 mL×2), dried with anhydrous $Na_2SO_4$, filtered, and concentrated in vacuum. The crude product was purified by silica gel column chromatography (petroleum ether/ethyl acetate=100/0, 10/1) to obtain 15-6. LCMS: 302.9 (M+3); $^1H$ NMR (400 MHz, $CDCl_3$) δ=7.56 (d, J=9.1 Hz, 1H), 6.48 (d, J=9.1 Hz, 1H), 4.09 (q, J=7.0 Hz, 2H), 1.68 (s, 6H), 1.45 (t, J=7.0 Hz, 3H).

Step VI: Preparation of Compound 15-7

Compound 15-6 (2.1 g, 6.97 mmol, 1 eq), 4,4,5,5-tetramethyl-2-(4,4,5,5-tetramethyl-1,3,2-dioxaborolane-2-yl)-1,3,2-dioxaborolane (2.66 g, 10.46 mmol, 1.5 eq), Pd(dppf) $Cl_2 \cdot CH_2Cl_2$ (1.14 g, 1.39 mmol, 0.2 eq), and potassium acetate (2.05 g, 20.92 mmol, 3 eq) were dissolved in dioxane (20 mL), and after displacement with nitrogen 3 times, the mixture was then stirred at 65° C. for 5 hours under nitrogen protection. The reaction mixture was filtered and concentrated under reduced pressure to remove the solvent. The crude product was purified by column chromatography ($SiO_2$, petroleum ether/ethyl acetate=500/1 to 10/1) to obtain compound 15-7. LCMS: 349.0 (M+1).

Step VII: Preparation of Compound 15-8

Compound 15-7 (3.6 g, 10.34 mmol, 1 eq) was dissolved in a solution of tetrahydrofuran (30 mL) and water (15 mL), sodium perborate tetrahydrate (4.77 g, 31.02 mmol, 5.97 mL, 3 eq) was added, and the mixture was stirred at 25° C. for 2 hours. Water (10 mL) was added to the solution, the solution was adjusted to pH=3-4 with 0.5N HCl, the aqueous phase was extracted with ethyl acetate (30 mL×3). The combined organic phases were washed with brine (80 mL×2), dried with anhydrous $Na_2SO_4$, filtered, and concentrated in vacuum. The crude product was purified by silica gel column chromatography (petroleum ether/ethyl acetate=40/1 to 5/1) to obtain compound 15-8. LCMS: 239.0 (M+1); $^1H$ NMR (400 MHz, $CDCl_3$) δ=7.04 (d, J=9.0 Hz, 1H), 6.47 (d, J=9.2 Hz, 1H), 4.04 (q, J=7.0 Hz, 2H), 1.68 (s, 6H), 1.42 (t, J=7.0 Hz, 3H).

Step VIII: Preparation of Compound 15-9

Compound 15-8 (1.2 g, 5.04 mmol, 1 eq) was dissolved in a solution of acetonitrile (3 mL), 2-(iodomethyl)-4,4,5,5-tetramethyl-1,3,2-dioxaborolane (2.70 g, 10.07 mmol, 2 eq) and $K_2CO_3$ (1.39 g, 10.07 mmol, 2 eq) were added at 25° C., and the mixture was then stirred at 60° C. for 3 hours. $H_2O$ (5 mL) was added to the solution, and the aqueous phase was adjusted to pH=3-4 with 0.5 N HCl and extracted with ethyl acetate (10 mL×3). The combined organic phases were washed with brine (30 mL×2), dried with anhydrous $Na_2SO_4$, filtered, and concentrated in vacuum. The crude product was purified by preparative HPLC (chromatographic column: Phenomenex luna C18 (250×70 mm×15 μm); mobile phase: water (with 0.1% TFA) and acetonitrile; the content of acetonitrile in the mobile phase was from 15% to 45%, 12 min) to obtain compound 15-9. LCMS (ESI) m/z: 297.1 (M+1); $^1H$ NMR (400 MHz, $CDCl_3$) δ=7.07 (d, J=9.1 Hz, 1H), 6.47 (d, J=9.1 Hz, 1H), 4.08-4.03 (m, 2H), 3.70 (s, 2H), 1.67 (s, 6H), 1.43 (t, J=6.9 Hz, 3H).

Step IX: Preparation of Compound 15

Compound 15-9 (100 mg, 337.75 μmol, 1 eq) was dissolved in isopropanol (1.5 mL), NaOH (1 M, 675.49 μL, 2 eq) was added at 0° C., and the mixture was then stirred at 25° C. for 1 hour. Acetone was added to the solution, and the solution was filtered, and concentrated in vacuum to obtain compound 15. LCMS (ESI) m/z: 239.1 (M+1), 221 (M−18+1); $^1H$ NMR (400 MHz, $CD_3OD$) δ=6.46 (d, J=8.6 Hz, 1H), 6.16 (d, J=8.6 Hz, 1H), 3.96 (q, 0.1=7.0 Hz, 2H), 3.38 (s, 2H), 1.33 (t, J=7.0 Hz, 3H).

Example 16

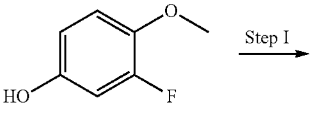

16-1

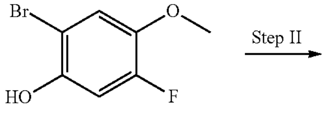

16-2

-continued

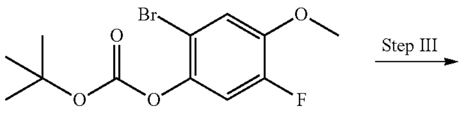

16-3

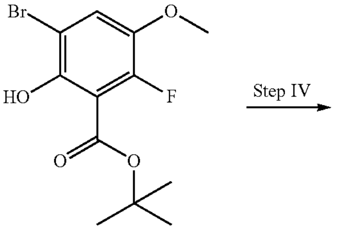

16-4

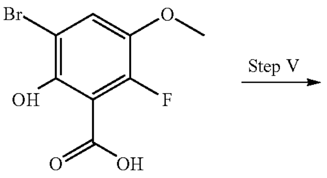

16-5

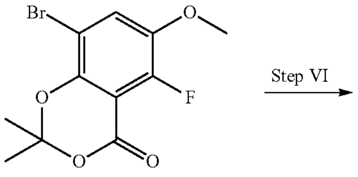

16-6

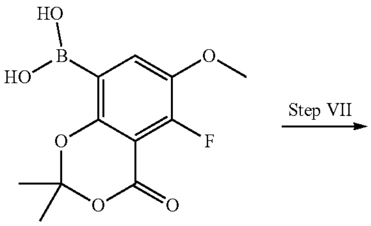

16-7

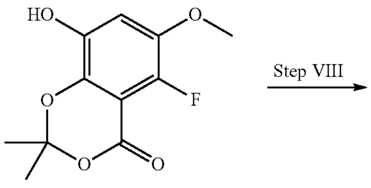

16-8

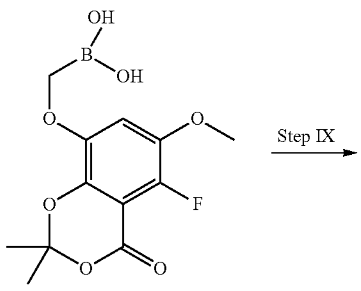

16-9

-continued

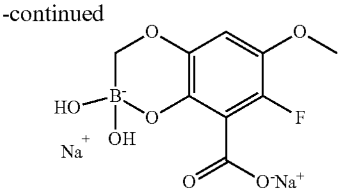

Compound 16

Step I: Preparation of Compound 16-2

Compound 16-1 (15 g, 105.54 mmol, 1 eq) was dissolved in dichloromethane (300 mL), liquid bromine (18.55 g, 116.09 mmol, 5.98 mL, 1.1 eq) was added, and the mixture was stirred at −15° C. for 1 hour. The mixture was then stirred at 10° C. for 1 hour. Sodium sulfite (5 mL) was added at 0-5° C. to quench the reaction mixture. It was extracted with ethyl acetate (10 mL). The organic layer was washed with brine (10 mL), dried with anhydrous sodium sulfate, filtered, and concentrated under reduced pressure to obtain compound 16-2. $^1$H NMR (400 MHz, $CDCl_3$) δ=6.98 (d, J=8.7 Hz, 1H), 6.76 (d, J=11.9 Hz, 1H), 3.77 (s, 3H).

Step II: Preparation of Compound 16-3

DMAP (641.18 mg, 5.25 mmol, 0.05 eq) and $Boc_2O$) (25.20 g, 115.46 mmol, 26.53 mL, 1.1 eq) were added to a solution of compound 16-2 (23.2 g, 104.97 mmol, 1 eq) in dichloromethane (200 mL). The mixture was stirred at 25° C. for 12 hours. Hydrochloric acid aqueous solution (1 mL, 0.5 N) was added at 0-5° C. to quench the reaction mixture. The separated organic layer was washed with 30 mL of brine, dried over anhydrous sodium sulfate, filtered, and concentrated under reduced pressure to obtain compound 16-3.

Step III: Preparation of Compound 16-4

Lithium diisopropylamide (1 M, 100.89 mL, 1.2 eq) was added to a solution of 16-3 (27 g, 84.08 mmol, 1 eq) in tetrahydrofuran (200 mL) at −78° C. The mixture was stirred at −78° C. for 2 hours. 100 mL of an ammonium chloride aqueous solution was added at −78° C. to quench the reaction mixture, which was then extracted with 250 mL of ethyl acetate. The organic layer was washed with 150 mL of brine, dried with anhydrous sodium sulfate, filtered, and concentrated under reduced pressure to obtain a residue. The residue was purified by silica gel flash column chromatography (petroleum ether/ethyl acetate=100/1 to 50/1) to obtain compound 16-4.

Step IV: Preparation of Compound 16-5

Trifluoroacetic acid (154.00 g, 1.35 mol, 100 mL, 18.86 eq) was added to a solution of compound 16-4 (23 g, 71.62 mmol, 1 eq) in dichloromethane (100 mL) at 0-5° C., and the mixture was stirred at 20° C. for 1 hour. The reaction mixture was concentrated under reduced pressure to obtain a residue. The crude product was stirred with dichloromethane (20 mL) and filtered, and the filter cake was dried to obtain compound 16-5. LCMS (ESI) m/z: 265.1/266.9 (M+1/M+3); $^1$H NMR (400 MHz, $CDCl_3$) δ=7.38 (d, J=8.6 Hz, 1H), 3.80 (s, 3H).

Step V: Preparation of Compound 16-6

Trifluoroacetic anhydride (25.36 g, 120.74 mmol, 16.79 mL, 4 eq), acetone (7.01 g, 120.74 mmol, 8.88 mL, 4 eq) and N,N-dimethylformamide (441.27 mg, 6.04 mmol, 464.49 μL, 0.2 eq) were added to a solution of compound 16-5 (8 g, 30.18 mmol, 1 eq) in trifluoroacetic acid (190 mL) at 0-5° C., and the mixture was stirred at 105° C. for 32 hours. The reaction mixture was concentrated, and the residue was diluted with water (100 mL) and extracted with ethyl acetate (50 mL×2). The combined organic layers were washed with brine (20 mL×2), dried over anhydrous sodium sulfate, filtered, and concentrated under reduced pressure to obtain a residue. The residue was purified by silica gel column chromatography (petroleum ether/ethyl acetate=50/1 to 5/1) to obtain compound 16-6. LCMS (ESI) m/z: 304.9 (M+1). $^1$H NMR (400 MHz, $CDCl_3$) δ=7.34 (d, J=82 Hz, 1H), 3.83 (s, 3H), 1.69 (s, 6H).

Step VI: Preparation of Compound 16-7

Compound 16-6 (1.1 g, 3.61 mmol, 1 eq), bis(pinacolato) diboron (2.75 g, 10.82 mmol, 3 eq), potassium acetate (1.06 g, 10.82 mmol, 3 eq), and tetrakis(triphenylphosphine)palladium (208.31 mg, 180.27 μmol, 0.05 eq) were mixed in dioxane (30 mL), and after displacement with $N_2$ 3 times, the mixture was then stirred at 65° C. for 17 h in a nitrogen atmosphere. The reaction mixture was concentrated under reduced pressure to remove the solvent. The residue was diluted with 50 mL of water and extracted with 50 mL of ethyl acetate. The organic layer was dried over anhydrous sodium sulfate, filtered, and concentrated under reduced pressure to obtain a residue. Purification by silica gel column chromatography (petroleum ether/ethyl acetate=20/1 to 5/1) afforded compound 16-7. LCMS (ESI) m/z: 270.9 (M+1).

Step VII: Preparation of Compound 16-8

Compound 16-7 (1 g, 3.70 mmol, 1 eq) was dissolved in tetrahydrofuran (10 mL) and water (10 mL), and sodium perborate tetrahydrate (1.71 g, 11.11 mmol, 2.14 mL, 3 eq) was added. The mixture was stirred at 20° C. for 5 hours. The reaction mixture was diluted with 20 mL of water and extracted with 20 mL of ethyl acetate. The organic layer was washed with 20 mL of brine, dried over anhydrous sodium sulfate, filtered, and concentrated under reduced pressure to obtain a residue. Purification by silica gel column chromatography (petroleum ether/ethyl acetate=20/1 to 2/1) afforded compound 16-8. LCMS (ESI) m/z: 243.0 (M+1).

Step VIII: Preparation of Compound 16-9

Compound 16-8 (340 mg, 1.40 mmol, 1 eq), 2-(iodomethyl)-4,4,5,5-tetramethyl-1,3,2-dioxaborolane (564.11 mg, 2.11 mmol, 1.5 eq), and potassium carbonate (291.03 mg, 2.11 mmol, 1.5 eq) were mixed in acetonitrile (5 mL) and degassed, and after displacement with nitrogen 3 times, the mixture was stirred at 60° C. for 1 h. 20 mL of water was added to quench the reaction mixture, which was then extracted with 20 mL of ethyl acetate. The organic layer was washed with 5 mL of aqueous saturated table salt, dried over anhydrous sodium sulfate, filtered, and concentrated under reduced pressure, and the residue was purified by thin layer chromatography (ethyl acetate). Compound 16-9 was obtained. $^1$H NMR (400 MHz, $CDCl_3$) δ=6.85 (d, J=7.7 Hz, 1H), 3.89 (s, 2H), 3.80 (s, 3H), 1.69 (s, 6H); LCMS (ESI) m/z: 300.8 (M+1).

Step IX: Preparation of Compound 16

A sodium hydroxide solution (2 M, 466.60 μL, 2 eq) was added to a solution of compound 16-9 (140 mg, 466.60 μmol, 1 eq) in isopropanol (1.6 mL) at 20° C. The mixture was stirred at 20° C. for 0.5 h and filtered, and the filter cake was purified by preparative HPLC (chromatographic column: Waters Xbridge 150×25 mm×5 μm; mobile phase: 10 mmol/L ammonium bicarbonate aqueous solution and acetonitrile; the proportion of acetonitrile in the mobile phase was from 1% to 6%, 4 min) to obtain compound 16. $^1$H NMR (400 MHz, $D_2O$) δ=6.43 (d, J=8.9 Hz, 1H), 3.72 (s, 3H), 3.24 (s, 2H). LCMS (ESI) m/z: 243.0 (M+1).

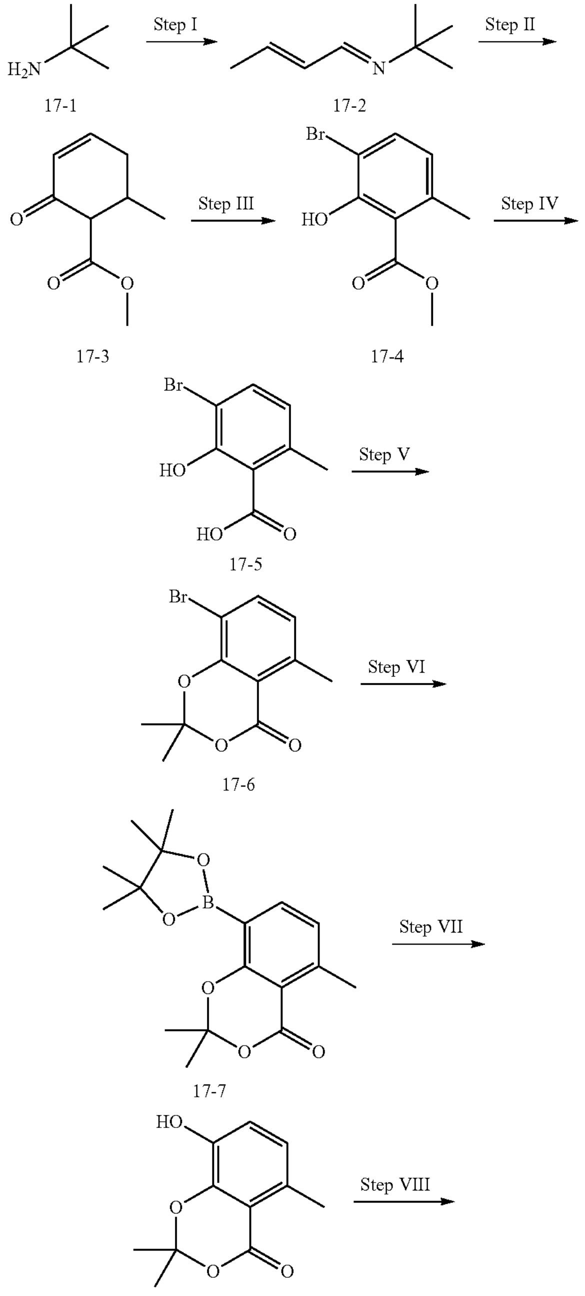

17-1

17-2

17-3

17-4

17-5

17-6

17-7

17-8

-continued

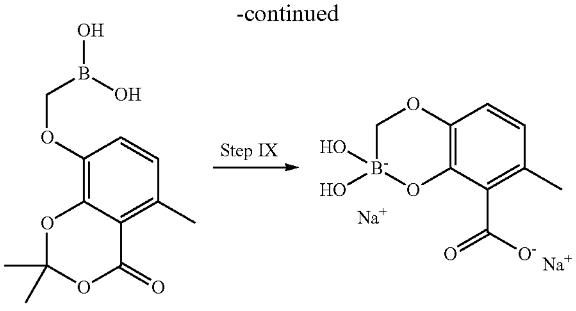

17-9

Compound 17

Step I: Preparation of Compound 17-2

Compound 17-1 (40 g, 546.92 mmol, 57.47 mL, 1 eq) and 4 Å molecular sieve (40 g) were dissolved in pentane (400 mL), but-2-ene (38.33 g, 546.92 mmol, 5.66 mL, 1 eq) was then added to the mixture at 25° C., and the mixture was stirred at 25° C. for 12 hours. Filtration and concentration under reduced pressure afforded compound 17-2.

Step II: Preparation of Compound 17-3

Compound 17-2 (63.26 g, 505.23 mmol, 1 eq) and 3-oxobutyrate were dissolved in toluene (500 mL), p-toluenesulfonic acid monohydrate (1.92 g, 10.10 mmol, 0.02 eq) was then added at 25° C., and then the mixture was then stirred at 25° C. for 72 hours. Water (500 mL) was added to the mixture, and the organic layer was washed with brine (200 mL), dried over $Na_2SO_4$, filtered, and concentrated under reduced pressure to obtain a residue. The residue was distilled at 80-95° C. to obtain compound 17-3. LCMS (ESI) m/z: 169.1 (M+1).

Step III: Preparation of Compound 17-4

Compound 17-3 (20.87 g, 124.09 mmol, 1 eq) was dissolved in acetic acid (150 mL), liquid bromine (39.66 g, 248.17 mmol, 12.79 mL, 2 eq) was then added to the mixture at 25° C., and the mixture was then stirred at 100° C. for 24 hours. The mixture was poured into water (300 mL), stirred at 25° C. for 15 minutes, filtered, and concentrated under reduced pressure to obtain a residue. The residue was purified by silica gel flash column chromatography (petroleum ether/ethyl acetate=1/0 to 1/1) to obtain compound 17-4. LCMS (ESI) m/z: 245.0/247.0 (M+1/M+3).

Step IV: Preparation of Compound 17-5

Compound 17-4 (10.52 g, 42.93 mmol, 1 eq) was dissolved in a mixed solvent of ethanol (80 mL) and water (38 mL), sodium hydroxide (5.15 g, 128.78 mmol, 710.00 μL, 3 eq) was then added to the mixture at 0° C., and the mixture was then stirred at 80° C. for 12 hours. The mixture was concentrated under reduced pressure, HCl (0.5 N) was added to the mixture to adjust pH to 2-3, the mixture was extracted with ethyl acetate (100 mL×3), and the combined organic layers were washed with brine (100 mL), dried with $Na_2SO_4$, filtered, and concentrated under reduced pressure to obtain compound 17-5. LCMS (ESI) m/z: 213.0 (M−18+1).

Step V: Preparation of Compound 17-6

Compound 17-5 (12.22 g, 52.89 mmol, 1 eq) was dissolved in trifluoroacetic acid (120 mL), acetone (18.43 g, 317.34 mmol, 23.33 mL, 6 eq), trifluoroacetic anhydride (33.33 g, 158.67 mmol, 22.07 mL, 3 eq) and DMF (773.19 mg, 10.58 mmol, 813.89 μL, 0.2 eq) were then added to the mixture at 0° C., and the mixture was then heated to 105° C. and stirred for 48 hours. The reaction mixture was concentrated under reduced pressure to obtain a residue, a sodium bicarbonate aqueous solution (300 mL) was added at 0° C., the mixture was extracted with ethyl acetate (200 mL), the combined organic layers were washed with brine (200 mL), dried with $Na_2SO_4$, filtered, and concentrated under reduced pressure, and the residue was purified by silica gel flash column chromatography (petroleum ether/ethyl acetate=1/0 to 0/1) to obtain compound 17-6. LCMS (ESI) m/z: 271.0 (M+1).

Step VI: Preparation of Compound 17-7

Compound 17-6 (1.23 g, 4.54 mmol, 1 eq), 4,4,5,5-tetramethyl-2-(4,4,5,5-tetramethyl-1,3,2-dioxaborolane-2-yl)-1,3,2-dioxaborolane (1.73 g, 6.81 mmol, 1.5 eq), bis(triphenylphosphine)palladium dichloride (318.45 mg, 453.70 μmol, 0.1 eq) and potassium acetate (1.34 g, 13.61 mmol, 3 eq) were dissolved in anhydrous dioxane (20 mL), the mixture was subjected to displacement with nitrogen 3 times, and the mixture was then stirred at 65° C. for 5 hours. The mixture was filtered and concentrated under reduced pressure to obtain a residue. The residue was purified by silica gel flash column chromatography (petroleum ether/ethyl acetate=1/0 to 0/1) to obtain compound 17-7. LCMS (ESI) m/z: 319.1 (M+1).

Step VII: Preparation of Compound 17-8

Compound 17-7 (1.02 g, 3.21 mmol, 1 eq) was dissolved in a mixed solvent of tetrahydrofuran (14 mL) and water (7 mL), sodium perborate tetrahydrate (1.48 g, 9.62 mmol, 1.85 mL, 3 eq) was added at 0° C., and the mixture was then stirred at 15° C. for 1 hour under nitrogen protection. 10 mL of water was added to the reaction mixture, and the reaction mixture was extracted with ethyl acetate (20 mL×3), washed with brine (30 mL×1), dried over $Na_2SO_4$, filtered, and concentrated in vacuum. The residue was purified by silica gel flash column chromatography (petroleum ether/ethyl acetate=20/1 to 0/1) to obtain compound 17-8. LCMS (ESI) m/z: 209.2 (M+1).

Step VIII: Preparation of Compound 17-9

Compound 2-(iodomethyl)-4,4,5,5-tetramethyl-1,3,2-dioxaborolane (468.35 mg, 1.75 mmol, 2 eq) and compound 17-8 (182 mg, 874.12 μmol, 1 eq) were dissolved in acetonitrile (5 mL), potassium carbonate (181.21 mg, 1.31 mmol, 1.5 eq) was added to the mixture at 25° C., and the mixture was then stirred at 65° C. for 4 hours. 10 mL of water was added to the mixture, and the mixture was extracted with ethyl acetate (20 mL×3), washed with brine (30 mL×2), dried over anhydrous $Na_2SO_4$, filtered, and concentrated in vacuum to obtain compound 17-9. $^1H$ NMR (400 MHz, $CD_3OD$) δ=7.19 (d, J=8.4 Hz, 1H), 6.92 (dd, J=0.7, 8.4 Hz, 1H), 3.88 (br s, 2H), 2.55 (s, 3H), 1.72 (s, 6H); LCMS (ESI) m/z: 267.1 (M+1).

Step IX: Preparation of Compound 17

Compound 17-9 (64 mg, 240.55 μmol, 1 eq) was dissolved in isopropanol (0.5 mL), sodium hydroxide (1 M, 601.38 μL, 2.5 eq) was added at 0° C., and the mixture was then stirred at 25° C. for 3 hours. The crude product was washed and purified with acetone (2 mL) and filtered, and the filter cake was dried in vacuum to obtain compound 17. $^1$H NMR (400 MHz, $D_2O$) δ=6.51 (d, J=8.1 Hz, 1H), 6.41 (dd, J=0.6, 8.1 Hz, 1H), 3.24 (s, 2H), 2.06 (s, 3H); LCMS (ESI) m/z: 209.1 (M+1), 191.1 (M−18+1).

Example 18

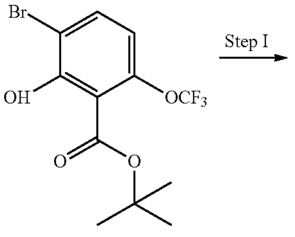

18-1

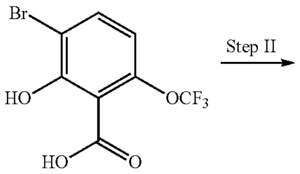

18-2

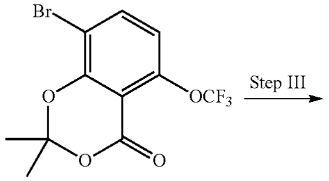

18-3

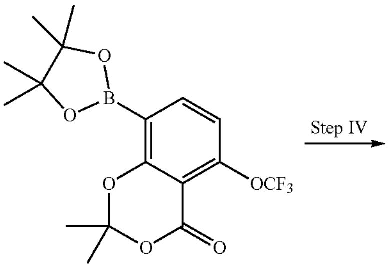

18-4

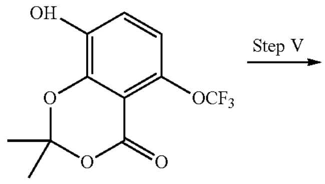

18-5

-continued

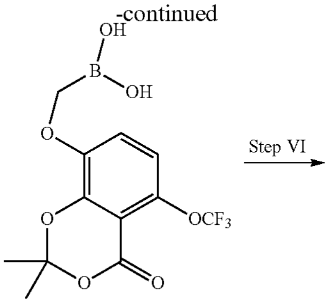

18-6

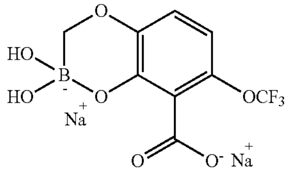

Compound 18

Step I: Preparation of Compound 18-2

Compound 18-1 (3 g, 8.40 mmol, 1 eq) was dissolved in dichloromethane (5 mL), and trifluoroacetic acid (957.85 mg, 8.40 mmol, 621.98 μL, 1 eq) was further added at 0-5° C. The mixture was stirred at 25° C. for 16 hours. The reaction mixture was concentrated under reduced pressure to obtain a residue. The crude product was stirred with dichloromethane (10 mL) and filtered, and the filter cake was dried to obtain product 18-2.

Step II: Preparation of Compound 18-3

Compound 18-2 (5.6 g, 18.60 mmol, 1 eq) was dissolved in trifluoroacetic acid (60 mL), and acetone (3.24 g, 55.81 mmol, 4.10 mL, 3 eq) was further added. After cooling to 0-5° C., trifluoroacetic anhydride (11.72 g, 55.81 mmol, 7.76 mL, 3 eq) and N,N-dimethylformamide (271.95 mg, 3.72 mmol, 286.26 μL, 0.2 eq) were added. The mixture was stirred at 105° C. for 16 hours. The reaction mixture was concentrated. The residue was diluted with sodium bicarbonate (30 mL) and extracted with ethyl acetate (20 mL×2). The combined organic layers were washed with brine (20 mL×2), dried over anhydrous sodium sulfate, filtered, and concentrated under reduced pressure to obtain a residue. The residue was purified by column chromatography ($SiO_2$, petroleum ether/ethyl acetate=100/1 to 50/1). Compound 18-3 was obtained. $^1$H NMR (400 MHz, $CDCl_3$) δ=7.82 (d, J=8.8 Hz, 1H), 7.16-6.79 (m, 1H), 1.86-1.75 (m, 6H).

Step III: Preparation of Compound 18-4

Dioxane (40 mL) was added to a mixture of compound 18-3 (3.4 g, 9.97 mmol, 1 eq), bis(pinacolato)diboron (10.13 g, 39.87 mmol, 4 eq), and potassium acetate (2.93 g, 29.91 mmol, 2 eq), Pd(dppf)$Cl_2$ (575.95 mg, 498.42 μmol, 0.05 eq) was further added, the mixture was degassed, and after displacement with nitrogen 3 times, the mixture was then heated to 40° C. and stirred for 16 hours in a nitrogen atmosphere. The reaction mixture was concentrated under reduced pressure to remove the solvent. The residue was diluted with 40 mL of water and extracted with 30 mL of ethyl acetate. The combined organic layers were washed with 30 mL of brine, dried over anhydrous sodium sulfate, filtered, and concentrated under reduced pressure to obtain 18-4. LCMS (ESI) m/z: 389.1 (M+1).

Step IV: Preparation of Compound 18-5

Compound 18-4 (3 g, 7.73 mmol, 1 eq) was added to a mixed solution of tetrahydrofuran (30 mL) and water (30 mL), followed by sodium perborate tetrahydrate (3.57 g, 23.19 mmol, 4.46 mL, 3 eq). The mixture was stirred at 20° C. for 1 hour. The reaction mixture was diluted with 20 mL of water and extracted with 20 mL of ethyl acetate. The combined organic layers were washed with 20 mL of brine, dried over sodium sulfate, filtered, and concentrated under reduced pressure to obtain a residue. The residue was purified by column chromatography ($SiO_2$, petroleum ether/ethyl acetate=1/0 to 5/1). 18-5 was obtained. LCMS (ESI) m/z: 279.0 (M+1); $^1H$ NMR (400 MHz, $CDCl_3$) δ=7.19 (d, J=8.9 Hz, 1H), 7.02-6.89 (m, 1H), 5.26 (br s, 1H), 1.86-1.75 (m, 6H).

Step V: Preparation of Compound 18-6

Compound 18-5 (800 mg, 2.88 mmol, 1 eq) was dissolved in acetonitrile (10 mL), 2-iodomethylboronic acid pinacol ester (1.54 g, 5.75 mmol, 2 eq) was then added to the solution, and potassium carbonate (596.18 mg, 4.31 mmol, 1.5 eq) was further added. The mixture was stirred at 65° C. for 4 hours. The reaction mixture was diluted with 15 mL of water and extracted with 15 mL of ethyl acetate. The combined organic layers were washed with 15 mL of brine, dried over sodium sulfate, filtered, and concentrated under reduced pressure to obtain a residue. The crude product was purified by preparative HPLC (chromatographic column: Phenomenex luna C18 250×50 mm×10 μm; mobile phase: water with 0.1% TFA and acetonitrile; the content of acetonitrile was from 30% to 55%, 17 min) to obtain compound 18-6. LCMS (ESI) m/z: 337.0 (M+1); $^1H$ NMR (400 MHz, $CDCl_3$) δ=6.99 (d, J=9.1 Hz, 1H), 6.86 (dd, 1=1.3, 9.0 Hz, 1H), 5.19 (br s, 1H), 3.94-3.88 (m, 2H), 1.70 (s, 6H).

Step VI: Preparation of Compound 18

Compound 18-6 (100 mg, 297.60 μmol, 1 eq) was dissolved in isopropanol (1 mL), and sodium hydroxide (1M, 595.19 μL, 2 eq) was further added. The mixture was stirred at 0° C. for 1 hour. The solution was filtered, washed with acetone, and concentrated in vacuum. No purification was performed. Compound 18 (30 mg) was obtained. LCMS (ESI) m/z: 279.0 (M+1); $^1H$ NMR (400 MHz, $D_2O$) δ=6.65-6.59 (m, 1H), 6.55 (d, J=1.5 Hz, 1H), 3.27 (s, 2H).

Example 19

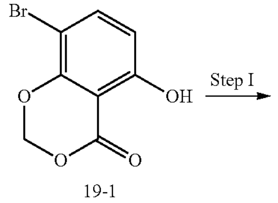

19-1

-continued

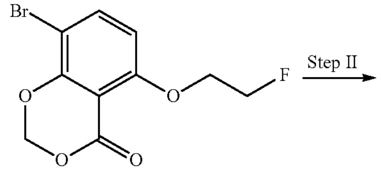

19-2

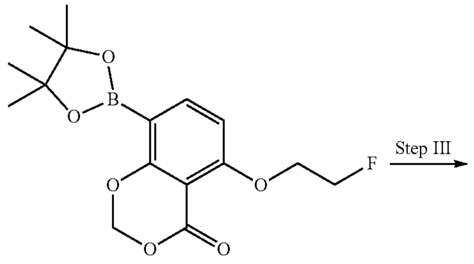

19-3

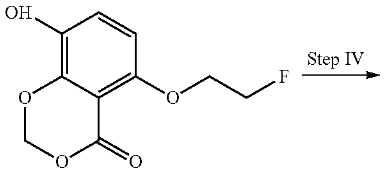

19-4

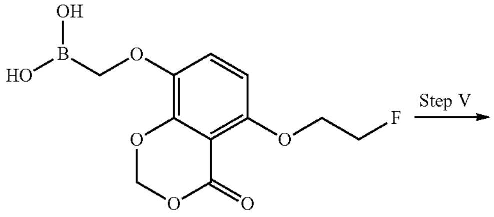

19-5

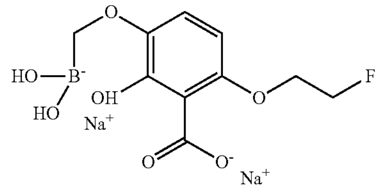
Compound 19

Step I: Preparation of Compound 19-2

Compound 19-1 (1 g, 4.08 mmol, 1 eq) was dissolved in a solution of dimethylformamide (10 mL), potassium phosphate (866.30 mg, 4.08 mmol, 1 eq) and 1-bromo-2-fluoroethane (777.19 mg, 6.12 mmol, 1.5 eq) was added at 25° C., and the mixture was then stirred at 65° C. for 16 hours. The residue was poured into water (10 mL). The aqueous phase was extracted with ethyl acetate (10 mL×2). The combined organic phases were washed with brine (30 mL×1), dried with anhydrous $Na_2SO_4$, filtered, and concentrated in vacuum. The residue was purified by silica gel chromatography (petroleum ether/ethyl acetate=20/1 to 3/1). Compound 19-2 was obtained. LCMS: 291 (M+1); $^1H$ NMR (400 MHz, $CDCl_3$) δ=7.64-7.59 (m, 1H), 6.58 (d, J=9.1 Hz, 1H), 5.58 (s, 2H), 4.85-4.81 (m, 1H), 4.72-4.70 (m, 1H), 4.33-4.30 (m, 1H), 4.27-4.23 (m, 1H).

Step II: Preparation of Compound 19-3

Compound 19-2 (500 mg, 1.72 mmol, 1 eq), 4,4,5,5-tetramethyl-2-(4,4,5,5-tetramethyl-1,3,2-dioxaborolane-2-yl)-1,3,2-dioxaborolane (1.74 g, 6.87 mmol, 4 eq), bis(triphenylphosphine)palladium dichloride (120.57 mg, 171.78 μmol, 0.1 eq), and potassium acetate (674.34 mg, 6.87 mmol, 4 eq) were dissolved in dioxane (10 mL), and after displacement with nitrogen, the mixture was then stirred at 65° C. for 16 hours in an $N_2$ atmosphere. The reaction mixture was concentrated under reduced pressure to remove the solvent. The residue was purified by silica gel chromatography (petroleum ether/ethyl acetate=10/1 to 0/1) to obtain compound 19-3. LCMS: 339.1 (M+1).

Step III: Preparation of Compound 19-4

Compound 19-3 (600 mg, 1.77 mmol, 1 eq) was dissolved in a solution of tetrahydrofuran (10 mL) and $H_2O$ (5 mL), sodium perborate tetrahydrate (273.02 mg, 1.77 mmol, 341.27 μL, 1 eq) was added, and the mixture was stirred at 25° C. for 0.5 h. Water (10 mL) was added to the solution, the solution was adjusted to pH=3-4 with 0.5N HCl, and the aqueous phase was extracted with ethyl acetate (30 mL×3). The combined organic phases were washed with brine (80 mL×2), dried with anhydrous $Na_2SO_4$, filtered, and concentrated in vacuum. The residue was purified by silica gel chromatography (petroleum ether/ethyl acetate=10/1 to 0/1). Compound 19-4 was obtained. LCMS: 229.1 (M+1).

Step IV: Preparation of Compound 19-5

Compound 19-4 (20 mg, 87.65 μmol, 1 eq) was dissolved in a solution of acetonitrile (2 mL), 2-(iodomethyl)-4,4,5,5-tetramethyl-1,3,2-dioxaborolane (46.96 mg, 175.30 μmol, 2 eq) and $K_2CO_3$ (24.23 mg, 175.30 μmol, 2 eq) were added at 25° C., and the mixture was then stirred at 65° C. for 2 hours. $H_2O$ (5 mL) was added to the solution, and the aqueous phase was adjusted to pH=3-4 with 0.5N HCl and extracted with ethyl acetate (10 mL×3). The combined organic phases were washed with brine (30 mL×2), dried with anhydrous $Na_2SO_4$, filtered, and concentrated in vacuum. Compound 19-5 was obtained. LCMS (ESI) m/z: 287.1 (M+1).

Step V: Preparation of Compound 19

Compound 19-5 (30 mg, 104.89 μmol, 1 eq) was dissolved in a solution of isopropanol (0.5 mL), NaOH (2 M, 104.89 μL, 2 eq) was added at 0° C., and the mixture was then stirred at 25° C. for 1 hour. The solution was filtered, and the filtered crude product was purified by preparative HPLC (column: Waters Xbridge 150×25 mm×5 μm; mobile phase: 10 mmol/L ammonium bicarbonate aqueous solution and acetonitrile; the content of acetonitrile was from 1% to 6%, 4 min). Compound 19 was obtained. LCMS (ESI) m/z: 257/239 (M+1/M−18+1); $^1$H NMR (400 MHz, $D_2O$) δ=6.55 (d, J=8.7 Hz, 1H), 6.28 (d, J=8.8 Hz, 1H), 4.66-4.59 (m, 2H), 4.20-4.15 (m, 1H), 4.13-4.07 (m, 1H), 3.22 (s, 2H).

Example 20

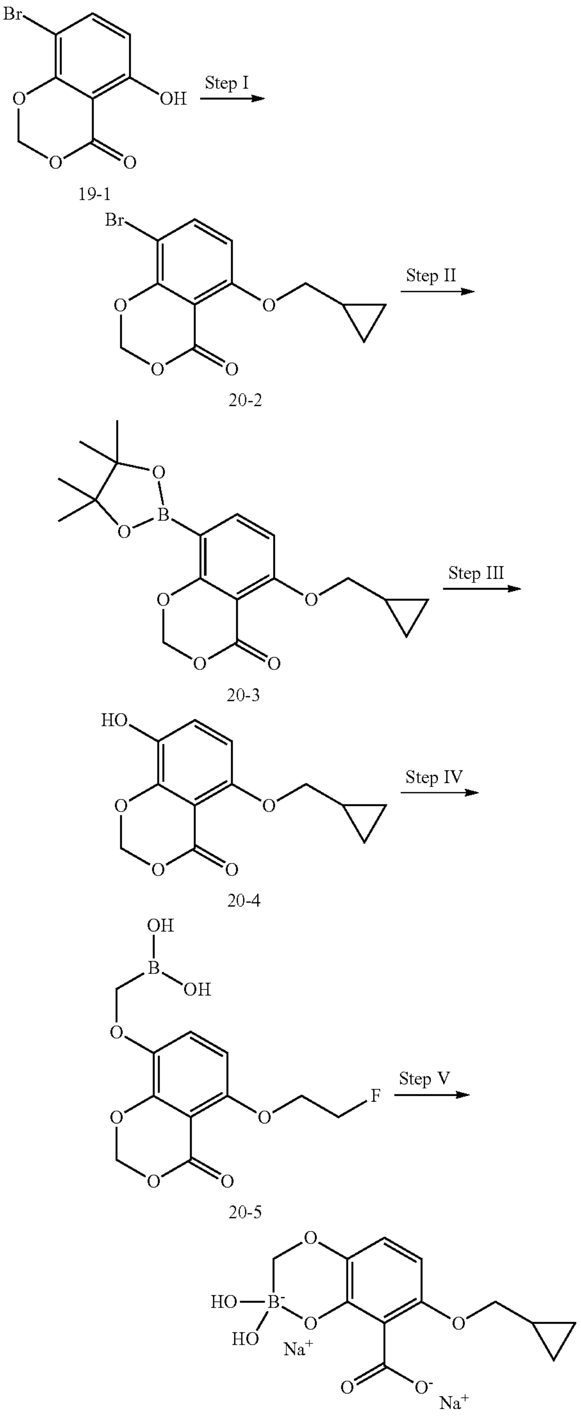

19-1
20-2
20-3
20-4
20-5
Compound 20

Step I: Synthesis of Compound 20-2

Compound 19-1 (600 mg, 2.45 mmol, 1 eq) was dissolved in DMF (6 mL), and potassium phosphate (1.30 g, 6.12 mmol, 2.5 eq) and bromomethylcyclopropane (495.87 mg, 3.67 mmol, 351.68 μL, 1.5 eq) were added. The mixture was stirred at 25° C. for 8 hours. The residue was diluted with 10 mL of EA and extracted with $H_2O$ (4 mL×2). The organic layer was washed with 8 mL of brine, dried over anhydrous sodium sulfate, filtered, and concentrated under reduced pressure, and the obtained residue was purified by column chromatography ($SiO_2$, petroleum ether/ethyl acetate=1/0 to 10/1). Compound 20-2 was obtained. $^1H$ NMR (400 MHz, $CDCl_3$) δ=7.66 (d, J=9.0 Hz, 1H), 6.62 (d, J=9.0 Hz, 1H), 5.66 (s, 2H), 3.99 (d, J=6.7 Hz, 2H), 1.37 (dddd, J=1.4, 3.3, 4.9, 6.5 Hz, 1H), 0.73-0.66 (m, 2H), 0.49-0.43 (m, 2H).

Step II: Synthesis of Compound 20-3

Dioxane (4 mL) was added to a mixture of compound 20-2 (150 mg, 501.48 μmol, 1 eq), bis(pinacolato)diboron (509.37 mg, 2.01 mmol, 2.5 eq), and potassium acetate (147.65 mg, 1.50 mmol, 3 eq), $Pd(dppf)Cl_2$ (81.90 mg, 100.30 μmol, 0.2 eq) was further added, the mixture was degassed, and after displacement with nitrogen 3 times, the mixture was stirred at 65° C. for 8 hours in a nitrogen atmosphere. The crude product 20-3 was used in the next step without further purification. LCMS (ESI) m/z: 347.1 (M+1).

Step III: Synthesis of Compound 20-4

Compound 20-3 (250 mg, 722.16 μmol, 1 eq) was added to a mixed solution of THF (4 mL) and $H_2O$ (4 mL), and sodium perborate tetrahydrate (222.22 mg, 1.44 mmol, 277.78 μL, 2 eq) was further added. The mixture was stirred at 0-5° C. for 1 hour. The reaction mixture was diluted with 20 mL of water and extracted with 20 mL of ethyl acetate. The combined organic layers were washed with 20 mL of brine, dried over sodium sulfate, filtered, and concentrated under reduced pressure to obtain a residue. The residue was purified by column chromatography ($SiO_2$, petroleum ether/ethyl acetate=1/0 to 5/1). Compound 20-4 was obtained. LCMS (ESI) m/z: 237.0 (M+1).

Step IV: Synthesis of Compound 20-5

Compound 20-4 (20 mg, 84.67 μmol, 1 eq) was dissolved in acetonitrile (1 mL), 2-iodomethylboronic acid pinacol ester (45.36 mg, 169.33 μmol, 2 eq) was added, and potassium carbonate (17.55 mg, 127.00 mol, 1.5 eq) was then added. The mixture was stirred at 65° C. for 4 hours. The reaction mixture was diluted with 15 mL of water and extracted with 15 mL of ethyl acetate. The combined organic layers were washed with 15 mL of brine, dried over sodium sulfate, filtered, and concentrated under reduced pressure to obtain a residue. 20-5 was obtained without purification.

Step V: Synthesis of Compound 20

Compound 20-5 (24 mg, 81.61 μmol, 1 eq) was dissolved in isopropanol (0.5 mL), and sodium hydroxide (2 M, 81.61 μL, 2 eq) was added. The mixture was stirred at 0° C. for 1 hour. The solution was filtered, washed with acetone, and concentrated in vacuum. The crude product was purified by preparative HPLC (column: Waters Xbridge 150-25 mm×5 μm; mobile phase: 10 mmol/L ammonium bicarbonate aqueous solution and acetonitrile; the content of acetonitrile was from 1% to 6%, 4 min). Compound 20 was obtained. LCMS (ESI) m/z: 265 (M+1); $^1H$ NMR (400 MHz, $CD_3OD$) δ=6.50 (br dd, J=2.4, 6.9 Hz, 1H), 6.18 (br d, J=8.3 Hz, 1H), 3.76 (d, J=6.6 Hz, 2H), 3.39 (br s, 2H), 1.97 (d, J=7.2 Hz, 1H), 1.29-1.15 (m, 2H), 0.53 (br d, J=6.7 Hz, 2H), 0.33 (br d, J=4.5 Hz, 2H).

Example 21

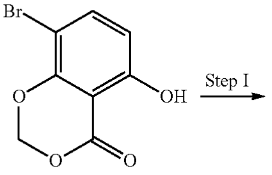

19-1

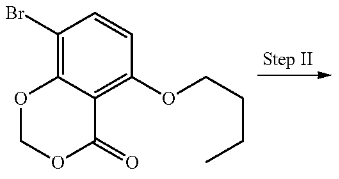

21-2

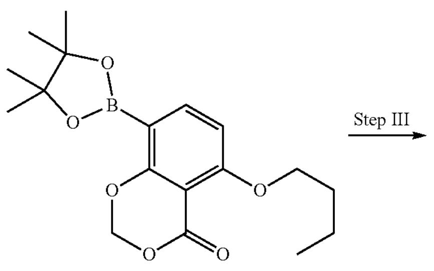

21-3

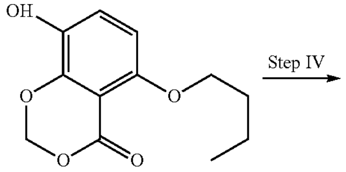

21-4

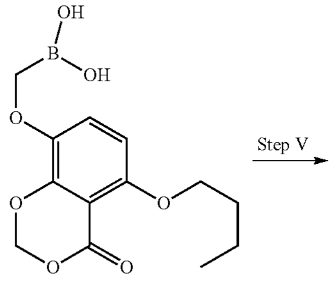

21-5

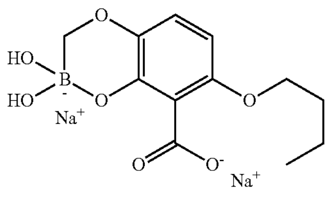

Compound 21

Step I: Synthesis of Compound 21-2

Compound 21-1 (600 mg, 2.45 mmol, 1 eq) was dissolved in N,N-dimethylformamide (6 mL), and potassium phosphate (1.30 g, 6.12 mmol, 2.5 eq) and 1-iodobutane (675.91 mg, 3.67 mmol, 417.23 µL, 1.5 eq) were further added. The mixture was stirred at 25° C. for 8 hours. The residue was diluted with 10 mL of water and extracted with 20 mL of ethyl acetate (10 mL×2). The combined organic layers were washed with 10 mL of brine, dried over sodium sulfate, filtered, and concentrated under reduced pressure to obtain a residue. No purification was performed. Compound 21-2 was obtained. $^1$H NMR (400 MHz, $CDCl_3$) δ=7.66 (d, J=9.0 Hz, 1H), 6.63 (d, J=9.0 Hz, 1H), 5.65 (s, 2H), 4.10 (t, J=6.5 Hz, 2H), 1.93-1.82 (m, 2H), 1.62-1.56 (m, 2H), 1.00 (t, J=7.4 Hz, 3H).

Step II: Synthesis of Compound 21-3

Dioxane (2 mL) was added to a mixture of compound 21-2 (490 mg, 1.63 mmol, 1 eq), bis(pinacolato)diboron (1.65 g, 6.51 mmol, 4 eq), and potassium acetate (479.08 mg, 4.88 mmol, 3 eq), Pd(dppf)$Cl_2$ (265.76 mg, 325.44 µmol, 0.2 eq) was further added, the mixture was then degassed, and after displacement with nitrogen 3 times, the mixture was then stirred at 65° C. for 8 hours in a nitrogen atmosphere. The residue was diluted with 10 mL of water and extracted with 20 mL of ethyl acetate (10 mL×2). The combined organic layers were washed with 10 mL of brine, dried over sodium sulfate, filtered, and concentrated under reduced pressure to obtain a residue. The residue was purified by column chromatography ($SiO_2$, petroleum ether/ethyl acetate=50/1 to 5/1). Compound 21-3 was obtained. LCMS (ESI) m/z: 349.1 (M+1).

Step III: Synthesis of Compound 21-4

Compound 21-3 (1.4 g, 4.02 mmol, 1 eq) was dissolved in a mixed solution of THF (4 mL) and $H_2O$ (4 mL), and sodium perborate tetrahydrate (1.24 g, 8.04 mmol, 1.55 mL, 2 eq) was further added. The mixture was stirred at 0-5° C. for 1 hour. The reaction mixture was diluted with 20 mL of water and extracted with 20 mL of EA. The combined organic layers were washed with 20 mL of brine, dried over sodium sulfate, filtered, and concentrated under reduced pressure to obtain a residue. The residue was purified by column chromatography ($SiO_2$, petroleum ether/ethyl acetate=1/0 to 5/1). Compound 21-4 was obtained.

Step IV: Synthesis of Compound 21-5

Compound 21-4 (300 mg, 1.26 mmol, 1 eq) was dissolved in acetonitrile (1.5 mL), 2-iodomethylboronic acid pinacol ester (674.71 mg, 2.52 mmol, 2 eq) was added, and potassium carbonate (261.06 mg, 1.89 mmol, 1.5 eq) was further added. The mixture was stirred at 25° C. for 4 hours. The reaction mixture was diluted with 15 mL of water and extracted with 15 mL of ethyl acetate. The combined organic layers were washed with 15 mL of brine, dried over sodium sulfate, filtered, and concentrated under reduced pressure to obtain a residue. The crude product was stirred in petroleum ether at 25° C. and filtered, and the filter cake was dried to obtain compound 21-5.

Step V: Synthesis of Compound 21

Compound 21-5 (80 mg, 270.20 µmol, 1 eq) was dissolved in isopropanol (1 mL), and sodium hydroxide (2 M, 270.20 µL, 2 eq) was added. The mixture was stirred at 0-5° C. for 1 hour. The solution was filtered, washed with acetone, and concentrated in vacuum. Compound 21 was obtained. LCMS (ESI) m/z: 249.1 (M−18+1); $^1$H NMR (400 MHz, $CD_3OD$) δ=6.45 (d, J=8.7 Hz, 1H), 6.15 (d, J=8.8 Hz, 1H), 3.90 (t, J=6.5 Hz, 2H), 3.38 (s, 2H), 1.71 (s, 2H), 1.57-1.45 (m, 2H), 0.96 (t, J=7.4 Hz, 3H).

Example 22

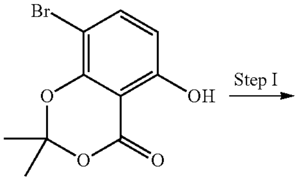

22-1

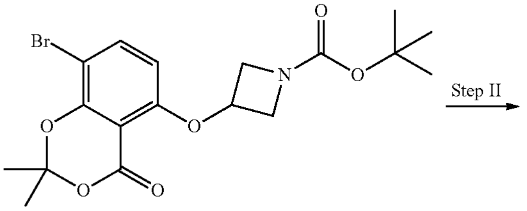

22-2

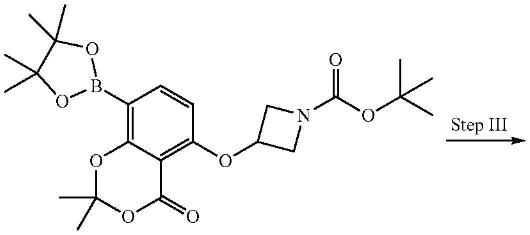

22-3

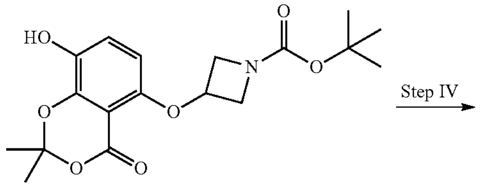

22-4

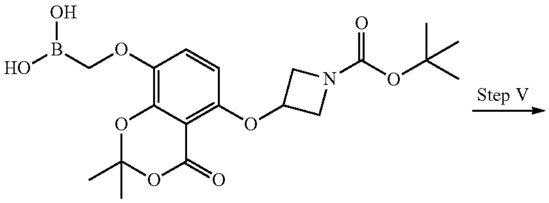

22-5

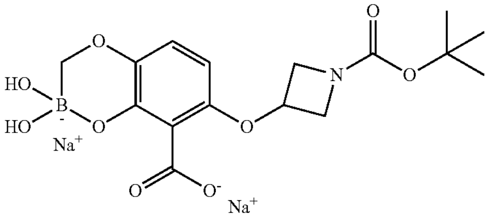

Compound 22

Step I: Synthesis of Compound 22-2

Compound 22-1 (3 g, 10.99 mmol, 1 eq) was dissolved in tetrahydrofuran (30 mL), tert-butyl 3-hydroxyazetidine-1-carboxylate (2.00 g, 11.54 mmol, 1.05 eq) was added, and triphenylphosphine (4.32 g, 16.48 mmol, 1.5 eq) was further added. After the addition was completed, DIAD (3.33 g, 16.48 mmol, 3.20 ml, 1.5 eq) was added dropwise at 20° C. The resulting mixture was stirred at 50° C. for 12 hours. The residue was purified by column chromatography ($SiO_2$, petroleum ether/ethyl acetate=10/1 to 4/1) to obtain compound 22-2.

Step II: Synthesis of Compound 22-3

A mixture of compound 22-2 (4.5 g, 10.51 mmol, 1 eq), bis(pinacolato)diboron (4.00 g, 15.76 moles, 1.5 eq), and potassium acetate (4.12 g, 42.03 mmol, 4 eq) was dissolved in dioxane (50 mL), Pd(dppf)$Cl_2$ (858.07 mg, 1.05 mmol, 0.1 eq) was lastly added, the mixture was degassed, and after displacement with nitrogen 3 times, the mixture was then stirred at 80° C. for 12 hours in a nitrogen atmosphere. The reaction mixture was filtered and concentrated under reduced pressure to obtain a residue. The residue was purified by column chromatography ($SiO_2$, petroleum ether/ethyl acetate=10/1 to 4/1). Compound 22-3 was obtained. LCMS (ESI) m/z: 420.1 (M−56+1).

Step III: Synthesis of Compound 22-4

Compound 22-3 (7 g, 5.89 mmol, 40% purity, 1 eq) was dissolved in a mixed solvent of tetrahydrofuran (20 mL) and water (10 mL), and sodium perborate tetrahydrate (2.27 g, 14.73 mmol, 2.5 eq) was added. The mixture was stirred at 20° C. for 1 hour. The mixture was filtered and concentrated under reduced pressure to obtain a residue. The residue was purified by column chromatography ($SiO_2$, petroleum ether/ethyl acetate=4/1 to 1/1). Compound 22-4 was obtained. LCMS (ESI) m/z: 310.0 (M−56+1).

Step IV: Synthesis of Compound 22-5

Compound 22-4 (650 mg, 1.78 mmol, 1 eq) was dissolved in acetonitrile (5 mL), and potassium carbonate (368.80 mg, 2.67 mmol, 1.5 eq) and 2-(iodomethyl)-4,4,5,5-tetramethyl-1,3,2-dioxaborolane (953.18 mg, 3.56 mmol, 2 eq) were added. The mixture was stirred at 60° C. for 3 hours. The reaction mixture was diluted with 20 mL of water and extracted with 20 mL of ethyl acetate. The combined organic layers were washed with 20 mL of aqueous saturated table salt, dried over sodium sulfate, filtered, and concentrated under reduced pressure to obtain a residue. The crude product was purified by preparative HPLC (column: Phenomenex luna C18 150×40 mm×15 μm; mobile phase: water with 0.1% TFA and acetonitrile; the content of acetonitrile was from 26% to 56%, 10 min). Compound 22-5 was obtained. LCMS (ESI) m/z: 368.1 (M−56+1); $^1$H NMR (400 MHz, $CDCl_3$) δ=7.12 (d, J=9.2 Hz, 1H), 6.31-6.14 (m, 1H), 4.99-4.87 (m, 1H), 4.37-4.31 (m, 2H), 4.15 (br dd, J=3.9, 9.7 Hz, 2H), 3.81-3.77 (m, 2H), 1.77 (s, 6H), 1.50-1.44 (m, 9H).

Step V: Synthesis of Compound 22

Compound 22-5 (50 mg, 118.14 μmol, 1 eq) was dissolved in isopropanol (1 mL), and sodium hydroxide (2 M, 118.14 μL, 2 eq) was further added. The mixture was stirred at 0-5° C. for 1 hour. The solution was filtered to obtain compound 22. LCMS (ESI) m/z: 310.1 (M−56+1); H NMR (400 MHz, $D_2O$) δ=6.51 (d, J=8.8 Hz, 1H), 6.02-5.84 (m, 1H), 4.84-4.79 (m, 1H), 4.27-4.14 (m, 2H), 4.02-3.84 (m, 3H), 1.44-1.27 (m, 10H).

Example 23

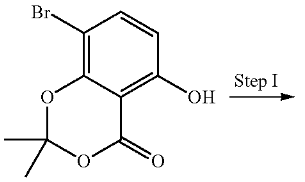

22-1

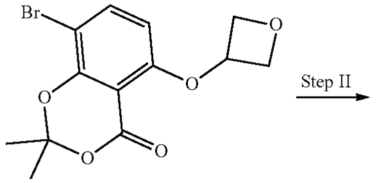

23-2

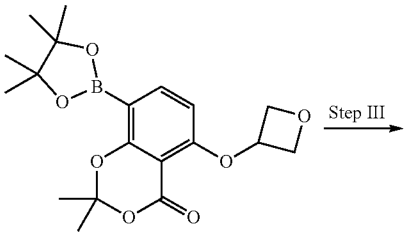

23-3

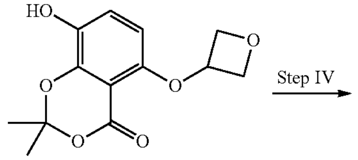

23-4

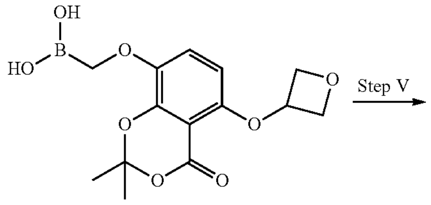

23-5

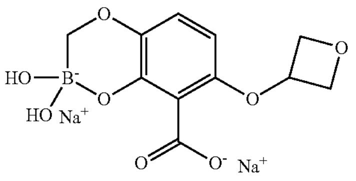

Compound 23

Step I: Preparation of Compound 23-2

Compound 22-1 (1 g, 3.66 mmol, 1 eq) was dissolved in a solution of dimethylformamide (10 mL), $K_2CO_3$ (1.01 g, 7.32 mmol, 2 eq) and 3-iodooxetane (1.01 g, 5.49 mmol, 1.5 eq) were added, and the mixture was stirred at 25° C. and then at 100° C. for 36 hours. The mixture was poured into ice water (15 mL) and stirred for 10 minutes. The aqueous phase was extracted with ethyl acetate (20 mL×2). It was washed with brine (30 mL×2), dried with anhydrous $Na_2SO_4$, filtered, and concentrated in vacuum. The residue was purified by silica gel chromatography (petroleum ether/ethyl acetate=30/1, 10/1). Compound 23-2 was obtained. LCMS: 329/331 (M+1/M+3); $^1$H NMR (400 MHz, $CDCl_3$) δ=7.54 (d, J=8.9 Hz, 1H), 5.99 (d, J=9.0 Hz, 1H), 5.19 (quin, J=5.8 Hz, 1H), 4.96-4.89 (m, 2H), 4.85-4.77 (m, 2H), 1.70 (s, 6H).

Step II: Preparation of Compound 23-3

Compound 23-2 (600 mg, 1.82 mmol, 1 eq), 4,4,5,5-tetramethyl-2-(4,4,5,5-tetramethyl-1,3,2-dioxaborolane-2-yl)-1,3,2-dioxaborolane (1.39 g, 0.5.47 mmol, 3 eq), Pd (dppf)$Cl_2$·$CH_2Cl_2$ (297.73 mg, 364.58 μmol, 0.2 eq), and potassium acetate (536.70 mg, 5.47 mmol, 3 eq) were dissolved in dioxane (3 mL), and after displacement with nitrogen at 25° C. 3 times, the mixture was heated to 65° C. and stirred for 16 hours under $N_2$. The reaction mixture was concentrated under reduced pressure to remove the solvent. The residue was purified by silica gel chromatography (petroleum ether/ethyl acetate=30/1 to 10/1). Compound 23-3 was obtained.

Step III: Preparation of Compound 23-4

Compound 23-3 (500 mg, 1.33 mmol, 1 eq) was dissolved in tetrahydrofuran (10 mL) and $H_2O$ (5 mL), and sodium perborate tetrahydrate (408.98 mg, 2.66 mmol, 511.22 μL, 2 eq) was added. The mixture was stirred at 25° C. for 0.5 hour. $H_2O$ (5 mL) was added to the solution, the solution was adjusted to pH=3-4 with 0.5N HCl, and the aqueous phase was extracted with ethyl acetate (10 mL×3). The combined organic phases were washed with brine (30 mL×2), dried with anhydrous $Na_2SO_4$, filtered, and concentrated in vacuum. The crude product was purified by silica gel column chromatography (petroleum ether/ethyl acetate=10/1 to 0/1). Compound 23-4 was obtained. LCMS: 267 (M+1).

Step IV: Preparation of Compound 23-5

Compound 23-4 (30 mg, 1.24 mmol, 1 eq) was dissolved in a solution of acetonitrile (5 mL), 2-(iodomethyl)-4,4,5,5-tetramethyl-1,3,2-dioxaborolane (664.10 mg, 2.48 mmol, 2 eq) and potassium carbonate (342.61 mg, 2.48 mmol, 2 eq) were added at 25° C., and the mixture was then stirred at 65° C. for 5 hours. $H_2O$ (5 mL) was added to the solution, and the aqueous phase was adjusted to pH=3-4 with 0.5 N HCl and extracted with ethyl acetate (10 mL×3). The combined organic phases were washed with brine (30 mL×2), dried with anhydrous $Na_2SO_4$, filtered, and concentrated in vacuum. The crude product was purified by preparative HPLC (column: Phenomenex luna C18 150×40 mm×15 μm; mobile phase: water with 0.1% TFA and acetonitrile; the content of acetonitrile was from 9% to 39/6, 10 min). Compound 23-5 was obtained. LCMS (ESI) m/z: 325 (M+1); $^1$H NMR (400 MHz, $CDCl_3$) δ=7.11 (d, J=9.0 Hz, 1H), 6.10 (d, J=9.0 Hz, 1H), 5.27-5.21 (m, 1H), 5.02-4.96 (m, 2H), 4.93-4.87 (m, 2H), 3.79 (s, 2H), 1.78 (s, 6H).

Step V: Preparation of Compound 23

Compound 23-5 (110 mg, 339.41 μmol, 1 eq) was dissolved in a solution of isopropanol (I mL), NaOH (2M, 339.41 μL, 2 eq) was added at 0° C., and the mixture was then stirred at 25° C. for 1 hour. Acetone (10 mL) was added to the mixture, and the mixture was stirred for 30 minutes and filtered to obtain compound 23. LCMS (ESI) m/z: 267.2 (M+1); $^1$H NMR (400 MHz, $D_2O$) δ=6.49 (d, J=8.8 Hz, 1H), 5.87 (d, J=8.8 Hz, 1H), 5.17-5.01 (m, 1H), 4.98-4.81 (m, 4H), 3.22 (s, 2H).

Example 24

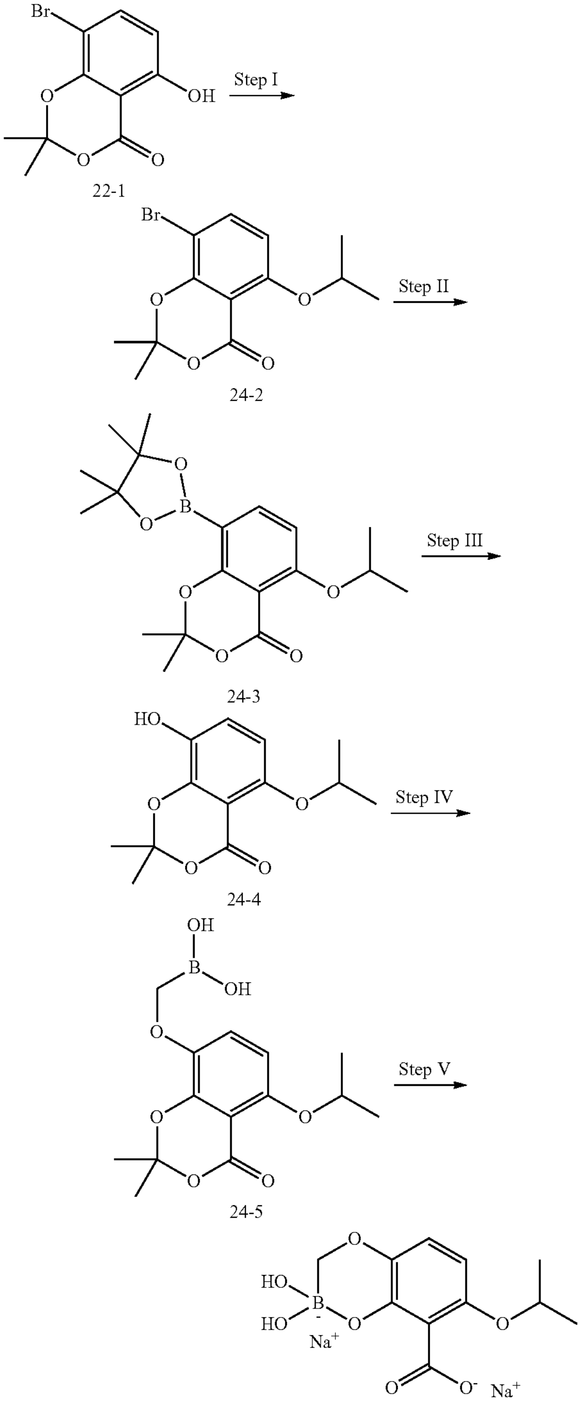

22-1
24-2
24-3
24-4
24-5
Compound 24

Step I: Synthesis of Compound 24-2

Compound 22-1 (500 mg, 1.83 mmol, 1 eq) was dissolved in N,N-dimethylformamide (4 mL), and potassium phosphate (971.63 mg, 4.58 mmol, 2.5 eq) and 2-iodopropane (466.87 mg, 2.75 mmol, 274.63 μL, 1.5 eq) were further added. The mixture was stirred at 50° C. for 8 hours. The residue was diluted with 10 mL of water and extracted with ethyl acetate (4 mL×2). The combined organic layers were washed with 8 mL of brine, dried over sodium sulfate, filtered, and concentrated under reduced pressure to obtain a residue. The residue was purified by column chromatography ($SiO_2$, petroleum ether/ethyl acetate=50/1 to 10/1). Compound 24-2 was obtained. LCMS (ESI) m/z: 315.1 (M+1); $^1$H NMR (400 MHz, $CDCl_3$) δ=7.54 (d, J=9.2 Hz, 1H), 6.54-6.46 (m, 1H), 4.62-4.49 (m, 1H), 1.67 (s, 6H), 1.39-1.33 (m, 6H).

Step II: Synthesis of Compound 24-3

Dioxane (4 mL) was added to a mixture of compound 24-2 (790 mg, 2.51 mmol, 1 eq), potassium acetate (738.03 mg, 7.52 mmol, 3 eq) and bis(pinacolato)diboron (2.55 g, 10.03 mmol, 4 eq), Pd(dppf)$Cl_2$ (409.41 mg, 501.33 μmol, 0.2 eq) was further added, and displacement was performed with nitrogen 3 times. The mixture was stirred at 65° C. for 8 hours. The residue was diluted with 15 mL of water and extracted with 20 mL of ethyl acetate (10 mL×2). The combined organic layers were washed with 10 mL of brine, dried over sodium sulfate, filtered, and concentrated under reduced pressure to obtain a residue. The residue was purified by column chromatography ($SiO_2$, petroleum ether/ethyl acetate=10/1 to 5/1) to obtain compound 24-3. LCMS (ESI) m/z: 363.1 (M+1).

Step III: Synthesis of Compound 24-4

Compound 24-3 (1.6 g, 4.42 mmol, 1 eq) was dissolved in a mixed solvent of tetrahydrofuran (2 mL) and water (2 mL), and sodium perborate tetrahydrate (1.36 g, 8.83 mmol, 2 eq) was added. The mixture was stirred at 20° C. for 1 hour. The reaction mixture was diluted with 20 mL of water and extracted with 20 mL of ethyl acetate. The combined organic layers were washed with 20 mL of brine, dried over sodium sulfate, filtered, and concentrated under reduced pressure to obtain a residue. The residue was purified by column chromatography ($SiO_2$, petroleum ether/ethyl acetate=1/0 to 5/1) to obtain compound 24-4. LCMS (ESI) m/z: 253.1 (M+1); $^1$H NMR (400 MHz, $CDCl_3$) δ=7.11 (d, J=9.0 Hz, 1H), 6.61-6.51 (m, 1H), 4.61-4.45 (m, 1H), 1.42-1.38 (m, 6H), 1.28 (s, 7H), 1.25 (s, 12H).

Step IV: Synthesis of Compound 24-5

Compound 24-4 (400 mg, 1.59 mmol, 1 eq) was dissolved in acetonitrile (1 mL), and 2-iodomethylboronic acid pinacol ester (849.59 mg, 3.17 mmol, 2 eq) and potassium carbonate (328.73 mg, 2.38 mmol, 1.5 eq) were added. The mixture was stirred at 65° C. for 4 hours. The reaction mixture was diluted with 15 mL of water and extracted with 15 mL of ethyl acetate. The combined organic layers were washed with 15 mL of brine, dried over sodium sulfate, filtered, and concentrated under reduced pressure to obtain a residue. The crude product was purified by preparative HPLC (chromatographic column: Phenomenex luna C18 150×40 mm×15 μm; mobile phase: water with 0.1% TFA and acetonitrile; the content of acetonitrile was from 20% to 50%, 10 min). Compound 24-5 was obtained. LCMS (ESI) m/z: 311.1 (M+1); $^1$H NMR (400 MHz, $CDCl_3$) δ=7.15 (d, J=9.1 Hz, 1H), 6.67-6.48 (m, 1H), 4.65-4.45 (m, 1H), 3.85-3.76 (m, 2H), 1.75 (s, 6H), 1.46-1.38 (m, 6H).

Step V: Synthesis of Compound 24

Compound 24-5 (180 mg, 580.45 μmol, 1 eq) was dissolved in isopropanol (1 mL), and sodium hydroxide (2 M, 580.45 μL, 2 eq) was added. The mixture was stirred at 0-5° C. for 1 hour. The solution was filtered, washed with acetone, and concentrated in vacuum. The crude product was purified by preparative HPLC (chromatographic column: Waters Xbridge 150×25 mm×5 μm; mobile phase: 10 mmol/L ammonium bicarbonate aqueous solution and acetonitrile; the content of acetonitrile was from 1% to 6%, 5 min). Compound 24 was added. LCMS (ESI) m/z: 253.1 (M+1); $^1$H NMR (400 MHz, $D_2O$) δ=6.49 (d, J=8.7 Hz, 1H), 6.25 (d, J=8.7 Hz, 1H), 4.26 (t, J=6.1 Hz, 1H), 3.18 (s, 2H), 1.13 (d, J=6.1 Hz, 6H).

Example 25

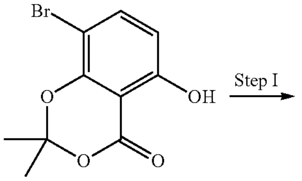

22-1

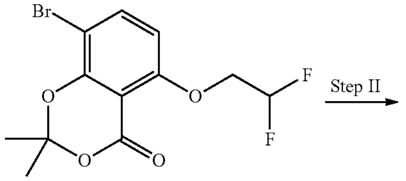

25-2

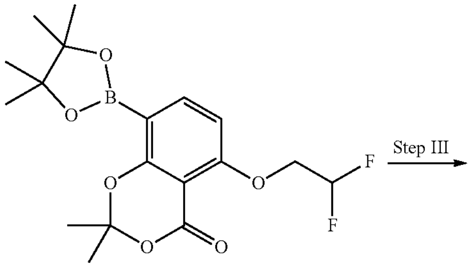

25-3

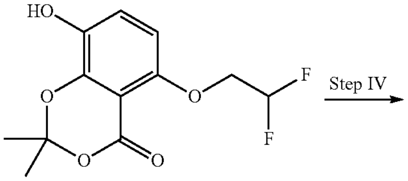

25-4

-continued

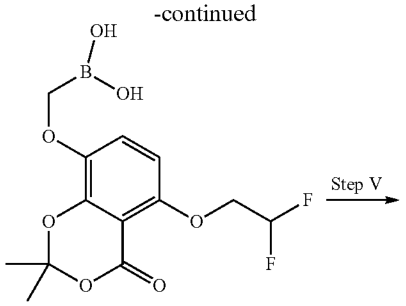

25-5

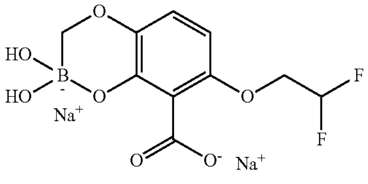

Compound 25

Step I: Synthesis of Compound 25-2

Compound 22-1 (800 mg, 2.93 mmol, 1 eq) was dissolved in N,N-dimethylformamide (7 mL), and potassium phosphate (1.55 g, 7.32 mmol, 2.5 eq) and 2-bromo-1,1-difluoroethane (636.94 mg, 4.39 mmol, 1.5 eq) were added. The mixture was stirred at 100° C. for 8 hours. The reaction mixture was diluted with 15 mL of water and extracted with 15 mL of ethyl acetate. The combined organic layers were washed with 15 mL of brine, dried over sodium sulfate, filtered, and concentrated under reduced pressure to obtain a residue. The residue was purified by column chromatography ($SiO_2$, petroleum ether/ethyl acetate=50/1 to 5/1). Compound 25-2 was obtained. LCMS (ESI) m/z: 339.1 (M+3); $^1$H NMR (400 MHz, $CDCl_3$) δ=7.62 (d, J=9.0 Hz, 1H), 6.51 (d, J=9.0 Hz, 1H), 6.33-5.94 (m, 1H), 4.21 (dt, J=4.2, 12.7 Hz, 2H), 1.73-1.67 (m, 6H).

Step II: Synthesis of Compound 25-3

A mixture of compound 25-2 (1 g, 2.97 mmol, 1 eq), potassium acetate (873.36 mg, 8.90 mmol, 3 eq) and bis (pinacolato)diboron (3.01 g, 11.87 mmol, 4 eq) was dissolved in dioxane (10 mL), Pd(dppf)$Cl_2$ (484.49 mg, 593.27 μmol, 0.2 eq) was further added, and displacement was performed with nitrogen 3 times. The mixture was stirred at 65° C. for 8 hours. The reaction mixture was diluted with 15 mL of water and extracted with 15 mL of ethyl acetate. The combined organic layers were washed with 15 mL of brine, dried over sodium sulfate, filtered, and concentrated under reduced pressure to obtain a residue. The residue was purified by column chromatography ($SiO_2$, petroleum ether/ethyl acetate=20/1 to 5/1). Compound 25-3 was obtained. LCMS (ESI) m/z: 385.1 (M+1); $^1$H NMR (400 MHz, $CDCl_3$) δ=7.77 (d, J=8.4 Hz, 1H), 6.55-6.52 (m, 1H), 6.37-5.99 (m, 1H), 4.29-4.17 (m, 2H), 1.64 (d, J=0.9 Hz, 6H), 1.31-1.13 (m, 12H).

Step III: Synthesis of Compound 25-4

Compound 25-3 (700 mg, 1.82 mmol, 1 eq) was dissolved in a mixed solvent of THF (4 mL) and $H_2O$ (4 mL), and sodium perborate tetrahydrate (560.69 mg, 3.64 mmol, 700.86 μL, 2 eq) was added. The mixture was stirred at 0-5° C. for 1 hour. The reaction mixture was diluted with 20 mL of water and extracted with 20 mL of ethyl acetate. The combined organic layers were washed with 20 mL of brine, dried over sodium sulfate, filtered, and concentrated under reduced pressure to obtain a residue. The residue was purified by column chromatography ($SiO_2$, petroleum ether/ethyl acetate=1/0 to 5/1). Compound 25-4 was added. LCMS (ESI) m/z: 275.1 (M+1); $^1$H NMR (400 MHz, $CDCl_3$) δ=7.07 (d, J=9.0 Hz, 1H), 6.56-6.50 (m, 1H), 6.30-5.94 (m, 1H), 4.21-4.11 (m, 2H), 1.71-1.67 (m, 6H).

Step IV: Synthesis of Compound 25-5

Compound 25-4 (190 mg, 692.88 μmol, 1 eq) was dissolved in acetonitrile (5 mL), 2-iodomethylboronic acid pinacol ester (371.25 mg, 1.39 mmol, 2 eq) was added, and potassium carbonate (143.64 mg, 1.04 mmol, 1.5 eq) was further added. The mixture was stirred at 65° C. for 4 hours. The reaction mixture was diluted with 15 mL of water and extracted with 15 mL of ethyl acetate. The combined organic layers were washed with 15 mL of brine, dried over sodium sulfate, filtered, and concentrated under reduced pressure to obtain a residue. The crude product was purified by preparative HPLC (chromatographic column: Phenomenex Luna C18 75×30 mm×3 μm; mobile phase: water with 0.1% TFA and acetonitrile; the content of acetonitrile was from 24% to 54%, 7 min). Compound 25-5 was obtained. LCMS (ESI) m/z: 333.1 (M+1); $^1$H NMR (400 MHz, $CDCl_3$) δ=7.16 (d, J=9.1 Hz, 1H), 6.63 (d, J=9.1 Hz, 1H), 6.44-6.02 (m, 1H), 4.26 (d, J=4.3 Hz, 2H), 3.90-3.75 (m, 2H), 1.83-1.73 (m, 6H).

Step V: Synthesis of Compound 25

Compound 25-5 (170 mg, 511.95 μmol, 1 eq) was dissolved in isopropanol (1.5 mL), and sodium hydroxide (2 M, 511.95 μL, 2 eq) was added. The mixture was stirred at 25° C. for 1 hour. The solution was filtered to obtain compound 25. LCMS (ESI) m/z: 257.0 (M−18+1); $^1$H NMR (400 MHz, $D_2O$) δ=6.54 (d, J=8.8 Hz, 1H), 6.27 (d, J=8.9 Hz, 1H), 6.07 (s, 1H), 4.12 (d, J=3.8 Hz, 2H), 3.21 (s, 2H).

Example 26

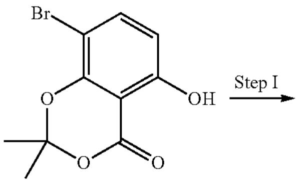

22-1

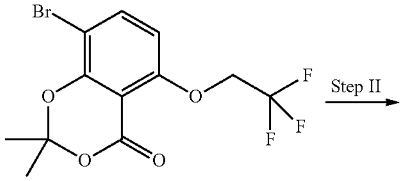

26-2

-continued

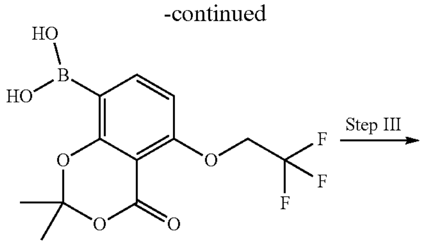

26-3

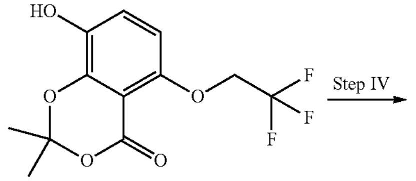

26-4

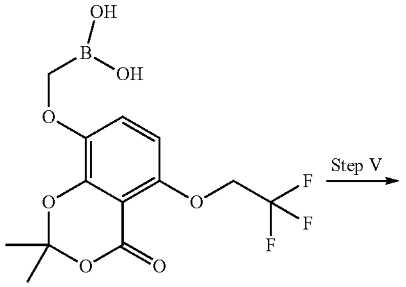

26-5

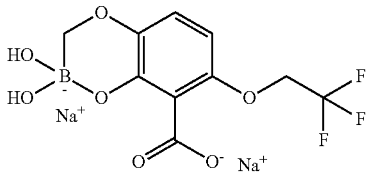

Compound 26

Step I: Preparation of Compound 26-2

Compound 22-1 (1 g, 3.66 mmol, 1 eq) and 2,2,2-trifluoroethyl trifluoromethanesulfonate (1.70 g, 7.32 mmol, 32.33 IL, 2 eq) were dissolved in N—N-dimethylformamide (10 mL), potassium carbonate (759.15 mg, 5.49 mmol, 1.5 eq) was added, the mixture was degassed, and after displacement with nitrogen 3 times, the mixture was then stirred at 95° C. for 2 hours. The reaction mixture was diluted with 20 mL of water and extracted with 20 mL of ethyl acetate. The organic layer was washed with 10 mL of brine, dried over anhydrous sodium sulfate, filtered, and concentrated under reduced pressure to obtain a residue. The residue was purified by silica gel flash column chromatography (petroleum ether/ethyl acetate=100/1 to 30/1) to obtain compound 26-2. $^1$H NMR (400 MHz, $CDCl_3$) δ=7.63 (d, J=8.9 Hz, 1H), 6.57 (d, J=9.0 Hz, 1H), 4.39 (d, J=8.1 Hz, 2H), 1.70 (s, 6H).

Step II: Preparation of Compound 26-3

Compound 26-2 (650 mg, 1.83 mmol, 1 eq), bis(pinacolato)diboron (929.64 mg, 3.66 mmol, 2 eq), potassium acetate (538.92 mg, 5.49 mmol, 3 eq), and Pd(dppf) $Cl_2 \cdot CH_2Cl_2$ (149.48 mg, 183.04 μmol, 0.1 eq) were dissolved in dioxane (10 mL), the mixture was degassed, and after displacement with nitrogen 3 times, the mixture was then stirred at 70° C. for 12 h in a nitrogen atmosphere. The reaction mixture was concentrated under reduced pressure to remove the solvent. The residue was diluted with 50 mL of water and extracted with 50 mL of ethyl acetate. The organic layer was dried over anhydrous sodium sulfate, filtered, and concentrated under reduced pressure to obtain a residue. The residue was purified by silica gel flash column chromatography (petroleum ether/ethyl acetate=20/1 to 5/1) to obtain compound 26-3.

Step III: Preparation of Compound 26-4

Compound 26-3 (900 mg, 2.81 mmol, 1 eq) was dissolved in tetrahydrofuran (10 mL) and water (10 mL), and sodium perborate tetrahydrate (865.39 mg, 5.62 mmol, 2 eq) was added. The mixture was stirred at 20° C. for 0.5 hour. The reaction mixture was diluted with 20 mL of water and extracted with 20 mL of ethyl acetate. The organic layer was washed with 20 mL of brine, dried over anhydrous sodium sulfate, filtered, and concentrated under reduced pressure to obtain a residue. Purification by silica gel flash column chromatography (petroleum ether/ethyl acetate=20/1 to 2/1) afforded compound 26-4. LCMS (ESI) m/z: 293.0 (M+1).

Step IV: Preparation of Compound 26-5

Compound 26-4 (400 mg, 1.37 mmol, 1 eq), 2-(iodomethyl)-4,4,5,5-tetramethyl-1,3,2-dioxaborolane (733.45 mg, 2.74 mmol, 2 eq), and potassium carbonate (283.79 mg, 2.05 mmol, 1.5 eq) were mixed in acetonitrile (5 mL), and after displacement with nitrogen 3 times, the mixture was then stirred at 60° C. for 3 hours in a nitrogen atmosphere. The reaction mixture was quenched by adding 20 mL of water and then extracted with 20 mL of ethyl acetate. The organic layer was washed with 5 mL of brine, dried with anhydrous sodium sulfate, filtered, and concentrated under reduced pressure to obtain a residue. The residue was stirred with petroleum ether (10 mL) and filtered, and the filter cake produced compound 26-5. $^1$H NMR (400 MHz, $CDCl_3$) δ=7.10 (d, J=9.0 Hz, 1H), 6.69 (d, J=9.0 Hz, 1H), 4.43 (q, J=8.4 Hz, 2H), 3.96 (s, 2H), 1.78 (s, 6H); LCMS (ESI) m/z: 351.0 (M+1).

Step V: Preparation of Compound 26

Compound 26-5 (100 mg, 285.67 μmol, 1 eq) was dissolved in isopropanol (1 mL), and a sodium hydroxide solution (2 M, 285.67 μL, 2 eq) was added. The mixture was stirred at 20° C. for 1 hour. Acetone (5 mL) was added, and the mixture was stirred for 1 h and then concentrated under reduced pressure, the obtained residue was purified by preparative HPLC (chromatographic column: Waters Xbridge 150×25 mm 5 μm; mobile phase: 10 mmol/L ammonium bicarbonate aqueous solution and acetonitrile; the proportion of acetonitrile in the mobile phase was from 1% to 6%, 4 min) to obtain compound 26. $^1$H NMR (400 MHz, $D_2O$) δ=6.58 (d, J=8.8 Hz, 1H), 6.31 (d, J=8.8 Hz, 1H), 4.37 (q, J=8.7 Hz, 2H), 3.24 (s, 2H). LCMS (ESI) m/z: 292.9 (M+1).

Example 27

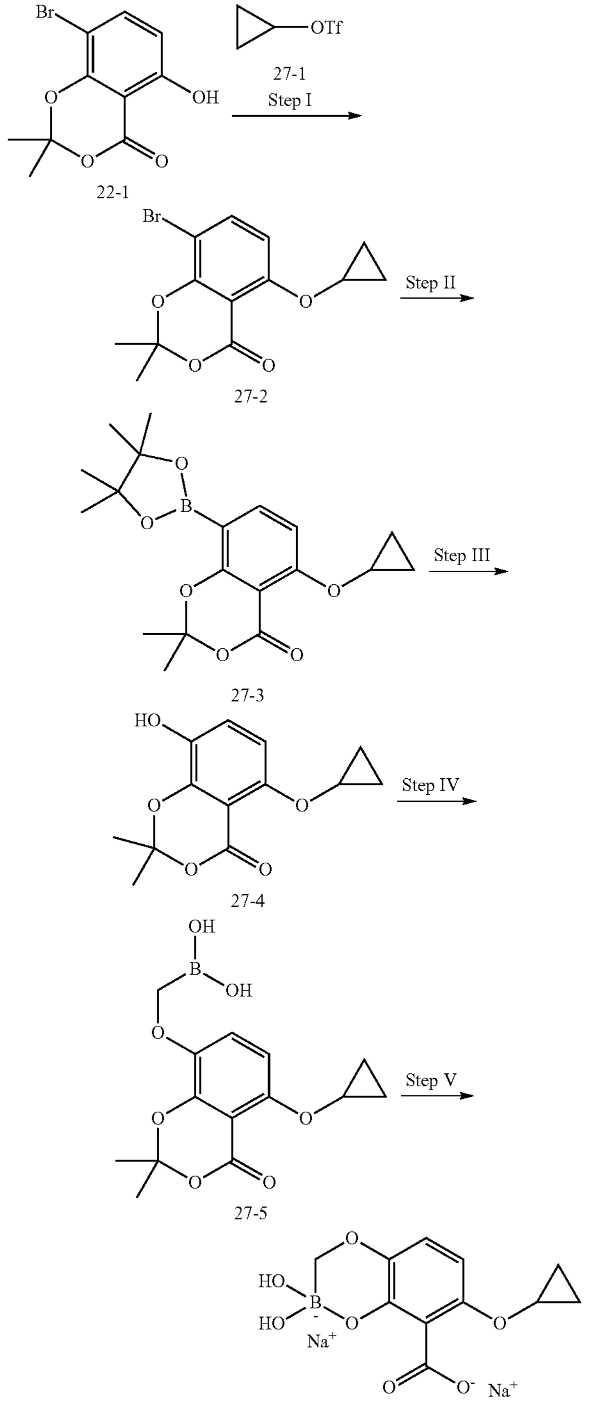

Compound 27

Step I: Preparation of Compound 27-2

Compound 22-1 (2 g, 7.32 mmol, 1 eq), compound 27-1 (2.09 g, 10.99 mmol, 32.33 uL, 1.5 eq) and potassium carbonate (1.52 g, 10.99 mmol, 1.5 eq) were mixed in N,N-dimethylformamide (10 mL), and after displacement with nitrogen 3 times, the reaction liquid was stirred at 75° C. for 12 hours. The reaction liquid was diluted with water (20 mL) and extracted with ethyl acetate (20 mL), and the organic phase was washed with aqueous saturated table salt (10 mL), dried with anhydrous sodium sulfate, filtered, and concentrated under reduced pressure to obtain a residue. The residue was purified by silica gel flash column chromatography (petroleum ether/ethyl acetate=100/1 to 30/1). 27-2 was obtained. LCMS (ESI) m/z: 312.9/314.9 (M+1/M+3); $^1$H NMR (400 MHz, $CDCl_3$) δ=7.60 (d, J=9.0 Hz, 1H), 6.92 (d, J=9.0 Hz, 1H), 3.78-3.68 (m, 1H), 1.67 (s, 6H), 0.92-0.73 (m, 4H).

Step II: Preparation of Compound 27-3

Compound 27-2 (340 mg, 1.09 mmol, 1 eq) was dissolved in dioxane (5 mL), potassium acetate (319.67 mg, 3.26 mol, 3 eq), bis(pinacolato)diboron (1.10 g, 4.34 mmol, 4 eq), and finally Pd(dppf)$Cl_2$ (177.34 mg, 217.15 μmol, 0.2 eq) were added. The mixture was stirred at 70° C. for 8 hours. The reaction mixture was diluted with 20 mL of water and extracted with 20 mL of ethyl acetate. The combined organic layers were washed with 20 mL of brine, dried over sodium sulfate, filtered, and concentrated under reduced pressure to obtain a residue. The residue was purified by column chromatography ($SiO_2$, petroleum ether/ethyl acetate=10/1 to 5/1) to obtain compound 27-3, which was used in the next step without further purification. LCMS (ESI) m/z: 361.1 (M+1).

Step III: Preparation of Compound 27-4

Compound 27-3 (1 g, 2.78 mmol, 1 eq) was dissolved in a mixed solvent of THF (4 mL) and $H_2O$ (4 mL), and sodium perborate tetrahydrate (854.28 mg, 5.55 mmol, 1.07 mL, 2 eq) was added. The mixture was stirred at 0-5° C. for 1 hour. The reaction mixture was diluted with 20 mL of water and extracted with 20 mL of ethyl acetate. The combined organic layers were washed with 20 mL of brine, dried over $Na_2SO_4$, filtered, and concentrated under reduced pressure to obtain a residue. The residue was purified by column chromatography ($SiO_2$, petroleum ether/ethyl acetate=1/0 to 5/1). Compound 27-4 was obtained. LCMS (ESI) m/z: 251.1 (M+1); $^1$H NMR (400 MHz, $CDCl_3$) δ=7.16 (d, J=9.2 Hz, 1H), 6.99-6.89 (m, 1H), 3.87-3.73 (m, 1H), 1.75 (s, 6H), 0.95-0.79 (m, 4H).

Step IV: Preparation of Compound 27-5

Compound 27-4 (100 mg, 399.61 μmol, 1 eq) was dissolved in MeCN (3 mL), and potassium carbonate (82.84 mg, 599.41 μmol, 1.5 eq) and 2-iodomethylboronic acid pinacol ester (214.11 mg, 799.21 μmol, 2 eq) were added. The mixture was stirred at 65° C. for 4 hours. The reaction mixture was diluted with 20 mL of water and extracted with 20 mL of ethyl acetate. The combined organic layers were washed with 20 mL of brine, dried over sodium sulfate, filtered, and concentrated under reduced pressure to obtain a residue. The crude product was purified by preparative HPLC (chromatographic column: Phenomenex Luna C18 75×30 mm×3 μm; mobile phase: water with 0.1% TFA and acetonitrile; the content of acetonitrile was from 24% to 54%, 7 min). Compound 27-5 was obtained. LCMS (ESI) m/z: 309.1 (M+1).

Step V: Preparation of Compound 27

Compound 27-4 (40 mg, 129.83 μmol, 1 eq) was dissolved in isopropanol (1 mL), and sodium hydroxide (2 M, 129.83 μL, 2 eq) was added. The mixture was stirred at 0° C. for 30 minutes. After filtration, compound 27 was obtained. LCMS (ESI) m/z: 251.1 (M+1), $^1$H NMR (400 MHz, $D_2O$) δ=6.52 (d, J=2.6 Hz, 2H), 3.73-3.60 (m, 1H), 3.18 (s, 2H), 0.61-0.52 (m, 4H).

Example 28

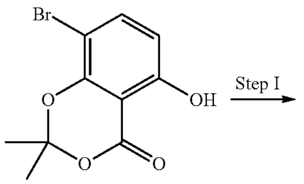

22-1

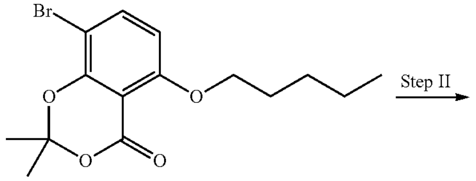

28-2

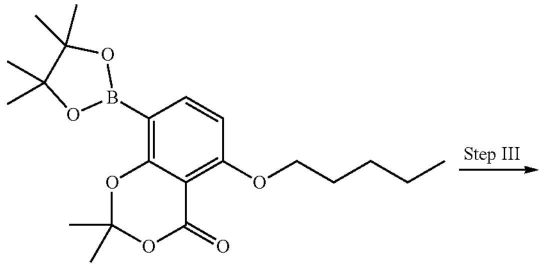

28-3

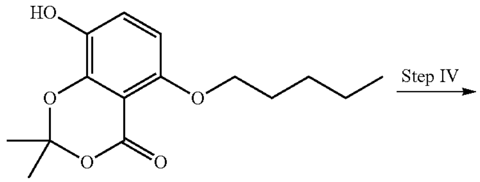

28-4

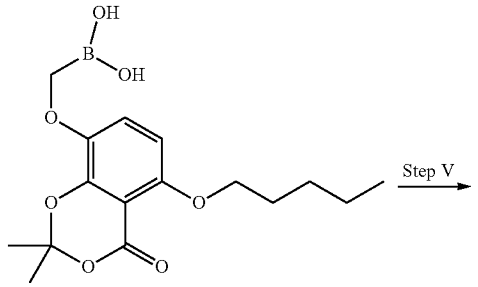

28-5

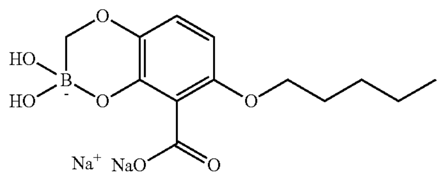

Compound 28

Step I: Synthesis of Compound 28-2

Compound 22-1 (850 mg, 3.11 mmol, 1 eq) was dissolved in N,N-dimethylformamide (5 mL), and potassium phosphate (1.65 g, 7.78 mmol, 2.5 eq) and 1-bromopentane (705.22 mg, 4.67 mmol, 582.83 μL, 1.5 eq) were added. The mixture was stirred at 70° C. for 4 hours. The reaction mixture was diluted with 15 mL of water and extracted with 15 mL of ethyl acetate. The combined organic layers were washed with 15 mL of brine, dried over sodium sulfate, filtered, and concentrated under reduced pressure to obtain a residue. The residue was purified by column chromatography ($SiO_2$, petroleum ether/ethyl acetate=50/1 to 5/I) to obtain compound 28-2. $^1$H NMR (400 MHz, $CDCl_3$) δ=7.55 (d, J=9.1 Hz, 1H), 6.48 (d, J=9.0 Hz, 1H), 3.99 (t, 1=6.8 Hz, 2H), 1.87-1.78 (m, 2H), 1.71-1.65 (m, 6H), 1.48-1.27 (m, 4H), 0.86 (t, J=7.2 Hz, 3H).

Step II: Synthesis of Compound 28-3

Compound 28-2 (950 mg, 2.77 mmol, 1 eq) was dissolved in dioxane (7 mL), potassium acetate (814.94 mg, 8.30 mmol, 3 eq), bis(pinacolato)diboron (2.81 g, 11.07 mmol, 4 eq), and finally Pd(dppf)$Cl_2$ (452.08 mg, 553.59 μmol, 0.2 eq) was added. The mixture was stirred at 80° C. for 6 hours. The reaction mixture was diluted with 15 mL of water and extracted with 15 mL of ethyl acetate. The combined organic layers were washed with 15 mL of brine, dried over sodium sulfate, filtered, and concentrated under reduced pressure to obtain a residue. The residue was purified by column chromatography ($SiO_2$, petroleum ether/ethyl acetate=1/0 to 5/1) to obtain product 28-3. LCMS (ESI) m/z: 391.1 (M+1).

Step III: Synthesis of Compound 28-4

Compound 28-3 (1.5 g, 3.84 mmol, 1 eq) was dissolved in tetrahydrofuran (4 mL) and water (4 mL), and sodium perborate tetrahydrate (1.18 g, 7.69 mmol, 1.48 mL, 2 eq) was added. The mixture was stirred at 20° C. for 1 h. The reaction mixture was diluted with 20 mL of water and extracted with 20 mL of ethyl acetate. The combined organic layers were washed with 20 mL of brine, dried over sodium sulfate, filtered, and concentrated under reduced pressure to obtain a residue. The residue was purified by column chromatography ($SiO_2$, petroleum ether/ethyl acetate=1/0 to 5/1). Compound 28-4 was obtained. LCMS (ESI) m/z: 281.1 (M+1).

Step IV: Synthesis of Compound 28-5

Compound 28-4 (350 mg, 1.25 mmol, 1 eq) was dissolved in acetonitrile (2 mL), and 2-iodomethylboronic acid pinacol ester (668.99 mg, 2.50 mmol, 2 eq) and potassium carbonate (258.85 mg, 1.87 mmol, 1.5 eq) were added. The mixture was stirred at 65° C. for 4 hours. The reaction mixture was diluted with 20 mL of water and extracted with 20 mL of ethyl acetate. The combined organic layers were washed with 20 mL of brine, dried over sodium sulfate, filtered, and concentrated under reduced pressure to obtain a residue. The crude product was stirred in PE at 25° C. for 20 minutes. 28-5 was obtained. LCMS (ESI) m/z: 339.1 (M+1); $^1$H NMR (400 MHz, $CDCl_3$) δ=7.15-7.09 (m, 1H), 6.58-6.47 (m, 1H), 4.03 (s, 2H), 3.92 (s, 2H), 1.92-1.86 (m, 2H), 1.76 (s, 6H), 1.53-1.46 (m, 2H), 1.40 (br d, J=6.9 Hz, 2H), 0.97-0.93 (m, 3H).

Step V: Synthesis of Compound 28

Compound 28-5 (110 mg, 325.29 μmol, 1 eq) was dissolved in isopropanol (1.5 mL), and sodium hydroxide (2 M, 325.29 μL, 2 eq) was added. The mixture was stirred at 0-5° C. for 1 hour. The solution was filtered to obtain compound 28. LCMS (ESI) m/z: 263.1 (M−18+1); $^1$H NMR (400 MHz, $D_2O$) δ=6.53 (d, J=8.8 Hz, 1H), 6.26 (br d, J=8.8 Hz, 1H), 3.87 (br t, 1=6.6 Hz, 2H), 3.21 (s, 2H), 1.66-1.51 (m, 2H), 1.36-1.17 (m, 4H), 0.86-0.75 (m, 3H).

Example 29

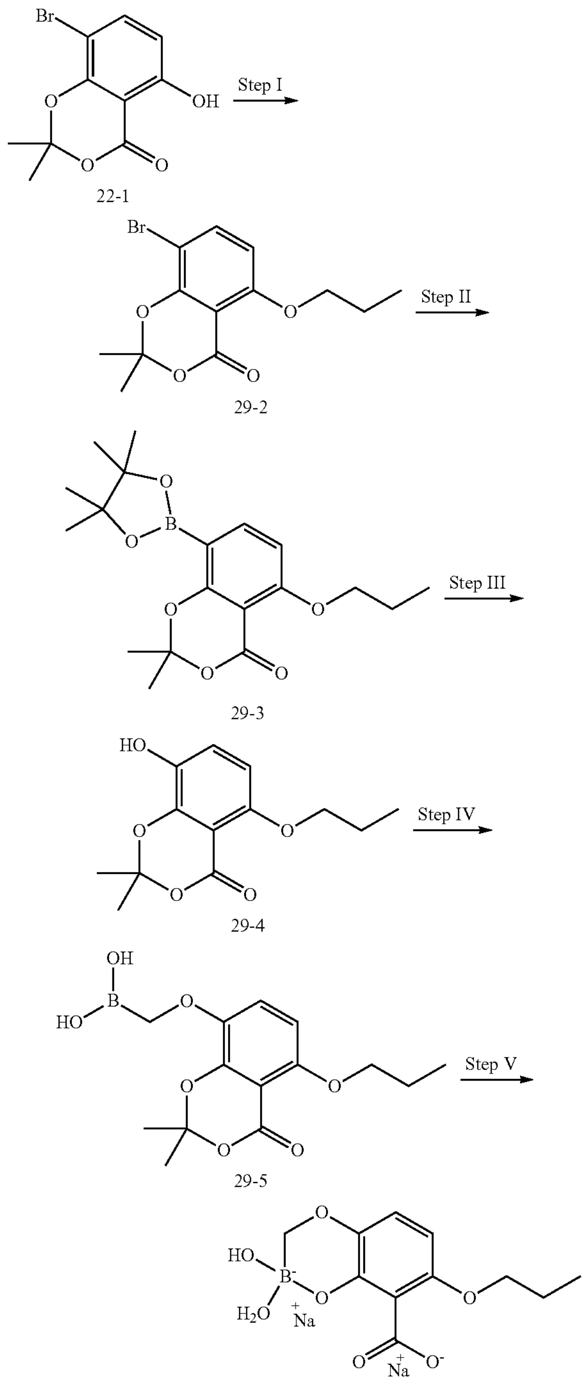

22-1

29-2

29-3

29-4

29-5

Compound 29

Step I: Preparation of Compound 29-2

Compound 22-1 (1 g, 3.66 mmol, 1 eq) was dissolved in a solution of dimethylformamide (10 mL), $K_2CO_3$ (1.01 g, 7.32 mmol, 2 eq) and 1-iodopropane (933.75 mg, 5.49 mmol, 536.64 μL, 1.5 eq) were added, and the mixture was stirred at 25° C. and then at 50° C. for 2 hours. The residue was poured into water (10 mL). The aqueous phase was extracted with ethyl acetate (10 mL×2). The combined organic phases were washed with brine (30 mL×1), dried with anhydrous $Na_2SO_4$, filtered, and concentrated in vacuum. The crude product was purified by silica gel chromatography (petroleum ether/ethyl acetate=30/1 to 10/1). Compound 29-2 was obtained. LCMS: 317 (M+3); $^1$H NMR (400 MHz, $CDCl_3$) δ=7.55 (d, J=9.1 Hz, 1H), 6.48 (d, J=9.1 Hz, 1H)), 3.96 (t, J=6.6 Hz, 2H), 1.84 (sxt, J=7.1 Hz, 2H), 1.68 (s, 6H), 1.02 (t, J=7.4 Hz, 3H).

Step II: Preparation of Compound 29-3

Compound 29-2 (1.1 g, 3.49 mmol, 1 eq), 4,4,5,5-tetramethyl-2-(4,4,5,5-tetramethyl-1,3,2-dioxaborolane-2-yl)-1,3,2-dioxaborolane (1.33 g, 5.24 mmol, 1.5 eq), Pd(dppf) $Cl_2 \cdot CH_2Cl_2$, and potassium acetate (1.03 g, 10.47 mmol, 3 eq) were dissolved in dioxane (3 mL), and after displacement with nitrogen at 25° C. 3 times, the mixture was then stirred at 75° C. for 16 hours under $N_2$. The reaction mixture was concentrated under reduced pressure to remove the solvent. The residue was poured into ice water (15 mL) and stirred for 10 minutes. The aqueous phase was extracted with ethyl acetate (30 mL×3). The combined organic phases were washed with brine (50 mL×2) and dried with $Na_2SO_4$. It was filtered with anhydrous $Na_2SO_4$ and concentrated in vacuum. The crude product was purified by silica gel chromatography (petroleum ether/ethyl acetate=10/1, 0/1). Compound 29-3 was obtained. LCMS: 363.2 (M+1).

Step III: Preparation of Compound 29-4

Compound 29-3 was dissolved in tetrahydrofuran (20 mL) and $H_2O$ (10 mL), sodium perborate tetrahydrate (220.88 mg, 1.44 mmol, 276.10 μL, 2 eq) was added, and the mixture was stirred and left to stand at 25° C. for 1 hour. $H_2O$ (10 mL) was added to the solution, the solution was adjusted to pH=3-4 with 0.5N HCl, and the aqueous phase was extracted with ethyl acetate (20 mL×3). The combined organic phases were washed with brine (50 mL×1), dried with anhydrous $Na_2SO_4$, filtered, and concentrated in vacuum. The residue was purified by silica gel chromatography (petroleum ether/ethyl acetate=10/1 to 5/1). Compound 29-4 was obtained. LCMS (ESI) m/z: 253.1 (M+1).

Step IV: Preparation of Compound 29-5

Compound 29-4 (300 mg, 1.19 mmol, 1 eq) was dissolved in a solution of acetonitrile (5 mL), 2-(iodomethyl)-4,4,5,5-tetramethyl-1,3,2-dioxaborolane (637.19 mg, 2.38 mmol, 2 eq) and $K_2CO_3$ (328.73 mg, 2.38 mmol, 2 eq) were added at 25° C., and the mixture was then stirred at 65° C. for 5 hours. $H_2O$ (5 mL) was added to the solution, and the aqueous phase was adjusted to pH=3-4 with 0.5 N HCl and extracted with ethyl acetate (10 mL×3). The combined organic phases were washed with brine (30 mL×2), dried with anhydrous $Na_2SO_4$, filtered, and concentrated in vacuum. The crude product was stirred in petroleum ether (10 mL) at 25° C. for 30 minutes and filtered, and the filter cake was dried to obtain compound 29-5. LCMS (ESI) m/z: 311 (M+1); $^1$H NMR (400 MHz, $CDCl_3$) δ=7.12 (d, J=9.1 Hz, 1H), 6.51 (d, J=9.3 Hz, 1H), 4.00 (t, J=6.6 Hz, 2H), 3.92 (s, 2H), 1.91 (s, J=7.1 Hz, 2H), 1.77 (s, 6H), 1.09 (t, J=7.4 Hz, 3H).

Step V: Preparation of Compound 29

Compound 29-5 (220 mg, 709.43 μmol, 1 eq) was dissolved in a solution of isopropanol (2 mL), NaOH (2 M, 709.43 μL, 2 eq) was added thereto at 0° C., and the mixture was then stirred at 25° C. for 1 hour. Acetone (10 mL) was added to the mixture, and the mixture was stirred for 30 minutes and filtered to obtain compound 29. LCMS (ESI) m/z: 253 (M+1); 235 (M−18+1); $^1H$ NMR (400 MHz, $D_2O$) δ=6.53 (d, J=8.6 Hz, 1H), 6.27 (d, J=8.8 Hz, 1H), 3.83 (t, J=6.6 Hz, 2H), 3.22 (s, 2H), 1.61 (qd, J=7.2, 14.0 Hz, 2H), 0.87 (t, J=7.4 Hz, 3H).

Example 30

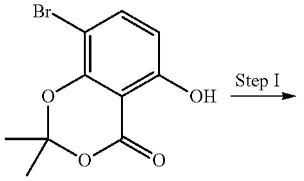

22-1

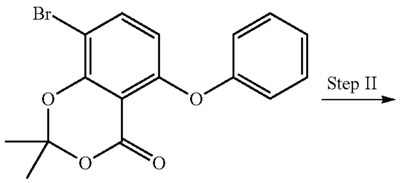

30-2

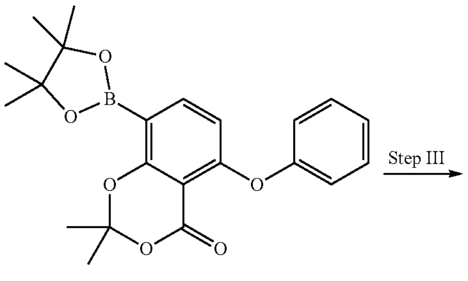

30-3

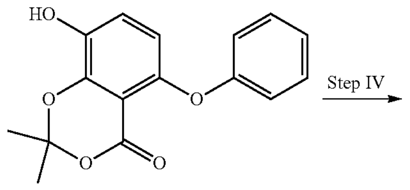

30-4

-continued

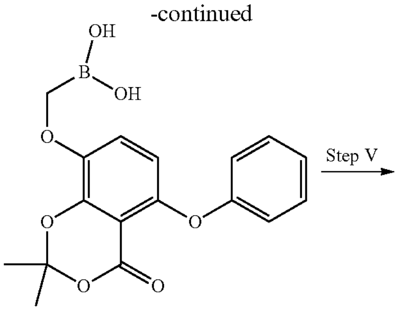

30-5

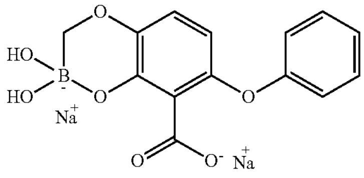

Compound 30

Step I: Synthesis of Compound 30-2

Compound 22-1 (2.24 g, 8.20 mmol, 1 eq) was dissolved in dichloromethane (20 mL) and stirred, 4 Å molecular sieve (2.24 g) was added to the solution, and phenylboronic acid (2 g, 16.40 mmol, 2 eq), copper acetate (3.35 g, 18.45 mmol, 2.25 eq) and pyridine (2.59 g, 32.81 mmol, 2.65 mL, 4 eq) were added in sequence. The mixture was stirred at 25° C. for 72 hours. The reaction mixture was diluted with 20 mL of water and extracted with 20 mL of ethyl acetate. The combined organic layers were washed with 20 mL of brine, dried over sodium sulfate, filtered, and concentrated under reduced pressure, and the obtained residue was purified by column chromatography ($SiO_2$, petroleum ether/ethyl acetate=60/1 to 40/1) to obtain compound 30-2. LCMS (ESI) m/z: 349.1 (M+1).

Step II: Synthesis of Compound 30-3

Compound 30-2 (430 mg, 1.23 mmol, 1 eq) was dissolved in dioxane (6 mL), potassium acetate (362.57 mg, 3.69 mmol, 3 eq), bis(pinacolato)diboron (1.25 g, 4.93 mmol, 4 eq), and finally Pd(dppf)$Cl_2$ (201.13 mg, 246.29 μmol, 0.2 eq) were added. After displacement with nitrogen 3 times, the mixture was stirred at 70° C. for 8 hours. The reaction mixture was diluted with 20 mL of water and extracted with 20 mL of ethyl acetate. The combined organic layers were washed with 20 mL of brine, dried over sodium sulfate, filtered, and concentrated under reduced pressure to obtain a residue. The residue was purified by column chromatography ($SiO_2$, petroleum ether/ethyl acetate=10/1 to 5/1) to obtain compound 30-3. LCMS (ESI) m/z: 397.1 (M+1).

Step III: Synthesis of Compound 30-4

Compound 30-3 (800 mg, 2.02 mmol, 1 eq) was dissolved in THF (5 mL) and water (5 mL), and sodium perborate tetrahydrate (621.28 mg, 4.04 mol, 776.60 μL, 2 eq) was added. The mixture was stirred at 0° C. for 1 hour. The reaction mixture was diluted with 20 mL of water and extracted with 20 mL of ethyl acetate. The combined organic layers were washed with 20 mL of brine, dried with sodium sulfate, filtered, and concentrated under reduced pressure, and the obtained residue was purified by column chromatography ($SiO_2$, petroleum ether/ethyl acetate=50/1 to 3/1) to obtain compound 30-4.

Step IV: Synthesis of Compound 30-5

Compound 30-4 (100 mg, 349.31 μmol, 1 eq) was dissolved in acetonitrile (3 mL), and potassium carbonate (72.42 mg, 523.96 μmol, 1.5 eq) and 2-iodomethylboronic acid pinacol ester (187.16 mg, 698.62 μmol, 2 eq) were added. The mixture was stirred at 65° C. for 4 hours. The reaction mixture was diluted with 20 mL of water and extracted with 20 mL of ethyl acetate. The combined organic layers were washed with 20 mL of brine, dried over sodium sulfate, filtered, and concentrated under reduced pressure to obtain a residue. The crude product was purified by preparative HPLC (chromatographic column: Phenomenex Synergi C18 150-25 mm×10 μm; mobile phase: water with 0.1% TFA and acetonitrile; the content of acetonitrile was from 38% to 68%, 10 min). Compound 30-5 was obtained. LCMS (ESI) m/z: 345.1 (M+1).

Step V: Synthesis of Compound 30

Compound 30-5 (30 mg, 87.18 μmol, 1 eq) was dissolved in a solution of isopropanol (1 mL), and sodium hydroxide (2 M, 87.18 μL, 2 eq) was added. The mixture was stirred at 0-5° C. for 30 minutes. The solution was filtered to obtain compound 30. LCMS (ESI) m/z: 287.1 (M+1); H NMR (400 MHz, $D_2O$) δ=7.33-7.21 (m, 2H), 7.05-6.87 (m, 3H), 6.59 (d, J=8.8 Hz, 1H), 6.21 (d, J=8.6 Hz, 1H), 3.27 (s, 2H).

Example 31

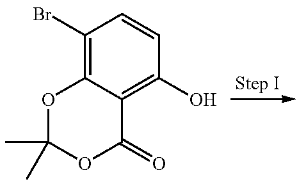

22-1

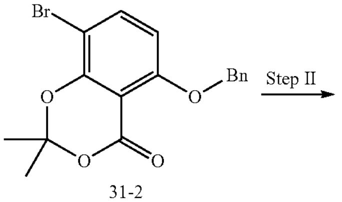

31-2

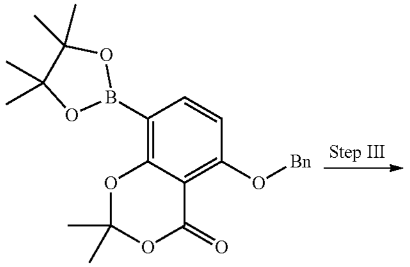

31-3

-continued

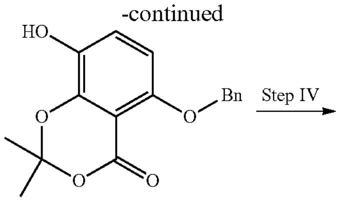

31-4

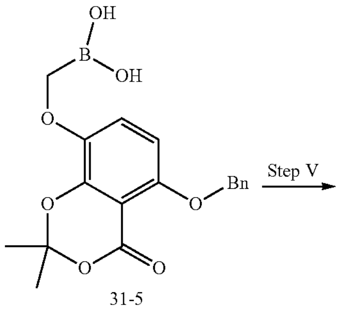

31-5

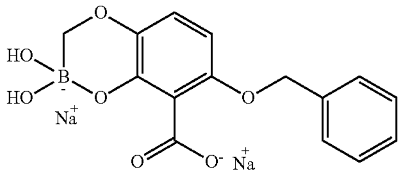

Compound 31

Step I: Preparation of Compound 31-2

Compound 22-1 (100 mg, 366.19 μmol, 1 eq) was dissolved in DMF (2 mL), and benzyl bromide (75.16 mg, 439.43 μmol, 52.19 μL, 1.2 eq) and $K_2CO_3$ (75.92 mg, 549.29 μmol, 1.5 eq) were then added in sequence at room temperature. The mixture was stirred at 50° C. for 24 hours. The reaction mixture was diluted with 5 mL of $H_2O$, extracted with 10 mL of EtOAc, washed with a saturated NaCl aqueous solution (10 mL×3), dried over anhydrous $Na_2SO_4$, filtered, and concentrated under reduced pressure to obtain compound 31-2. LCMS (ESI) m/z: 362.9 (M+1); $^1$H NMR (400 MHz, $CDCl_3$) δ=7.54 (d, J=9.1 Hz, 1H), 7.48-7.42 (m, 2H), 7.36-7.28 (m, 2H), 7.28-7.21 (m, 1H), 6.54 (s, 1H), 5.19 (s, 2H), 1.69 (s, 6H).

Step II: Preparation of Compound 31-3

Compound 31-2 (1.34 g, 3.68 mmol, 1 eq), bis(pinacolato)diboron (1.87 g, 7.37 mmol, 2 eq), and potassium acetate (1.08 g, 11.05 mmol, 3 eq) were dissolved in dioxane (12 mL), Pd(dppf)$Cl_2$ (269.55 mg, 368.39 μmol, 0.1 eq) was further added, the mixture was degassed and purged with $N_2$ 3 times, and the mixture was then stirred at 70° C. for 12 hours under $N_2$ protection. The reaction mixture was diluted with 30 mL of $H_2O$ and extracted with 40 mL of EA (20 mL×2). The combined organic layers were washed with 30 mL of brine, dried over $Na_2SO_4$, filtered, and concentrated under reduced pressure to obtain a residue. The residue was purified by column chromatography ($SiO_2$, petroleum ether/ethyl acetate=10/1) to obtain compound 31-3. LCMS (ESI) m/z: 411.3 (M+1).

Step III: Preparation of Compound 31-4

Compound 31-3 (1.57 g, 3.83 mmol, 1 eq) was dissolved in a mixed solvent of THF (7 mL) and $H_2O$ (7 mL), and sodium perborate tetrahydrate (1.18 g, 7.65 mmol, 1.47 mL, 2 eq) was then added. The mixture was stirred at 20° C. for 30 min. The solution was adjusted to pH 7-8 with 1N HCl and then extracted with EA (20 mL×2). The combined organic phases were washed with brine (20 mL×2), dried with anhydrous $Na_2SO_4$, filtered, and concentrated in vacuum. The residue was purified by column chromatography ($SiO_2$, petroleum ether/ethyl acetate=10/1 to 5/1) to obtain 31-4. $^1H$ NMR (400 MHz, $CDCl_3$) δ=7.54 (d, J=7.46 Hz, 2H), 7.40 (t, J=7.46 Hz, 2H), 7.33 (d, 1=7.34 Hz, 1H), 7.11 (d, J=9.05 Hz, 1H), 6.60 (d, J=9.05 Hz, 1H), 5.22 (s, 2H), 1.78 (s, 6H).

Step IV: Preparation of Compound 31-5

Compound 31-4 (467 mg, 1.56 mmol, 1 eq) was dissolved in acetonitrile (5 mL), 2-iodomethyl pinacol boronate (833.21 mg, 3.11 mmol, 2 eq) and $K_2CO_3$ (322.39 mg, 2.33 mmol, 1.5 eq) were added in sequence, and the mixture was then stirred at 60° C. for 3 hours under $N_2$. The reaction mixture was diluted with 20 mL of $H_2O$, extracted with 60 mL of EA (20 mL×3), washed with 30 mL of brine, dried over $Na_2SO_4$, filtered, and concentrated under reduced pressure to obtain a residue. The crude product was stirred with petroleum ether at 25° C. for 30 min and filtered, and the filter cake was dried to obtain 31-5. $^1H$ NMR (400 MHz, $CDCl_3$) δ=7.60-7.51 (m, 2H), 7.43-7.35 (m, 2H), 7.32 (br d, J=7.21 Hz, 1H), 7.08 (d, J=9.05 Hz, 1H), 6.56 (d, J=9.05 Hz, 1H), 5.21 (s, 2H), 3.92 (s, 2H), 1.77 (s, 6H).

Step V: Preparation of Compound 31

Compound 31-5 (535 mg, 1.49 mmol, 1 eq) was dissolved in i-PrOH (2 mL), and NaOH (2 M, 1.64 mL, 2.2 eq) was added at room temperature. The mixture was stirred at room temperature for 1 hour. The solution was filtered to obtain compound 31. LCMS (ESI) m/z: 301.1 (M+1), $^1H$ NMR (400 MHz, $D_2O$) δ=7.44-7.40 (m, 1H), 7.44-7.39 (m, 1H), 7.41-7.39 (m, 1H), 7.36 (t, J=7.47 Hz, 2H), 7.30 (br d, J=7.03 Hz, 1H), 6.49 (d, J=8.78 Hz, 1H), 6.26 (d, J=8.78 Hz, 1H), 4.99 (s, 2H), 3.22 (s, 2H).

Example 32

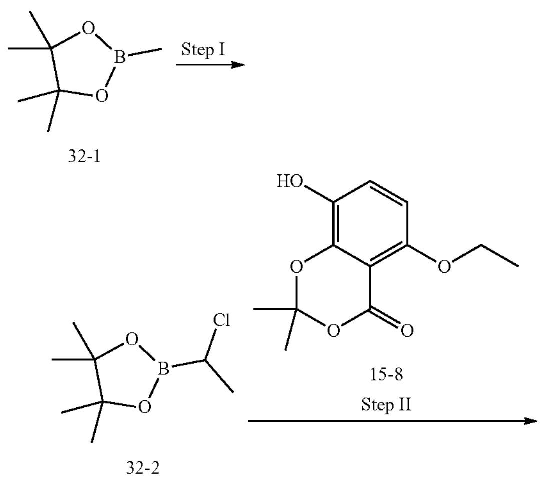

32-1

15-8

32-2

-continued

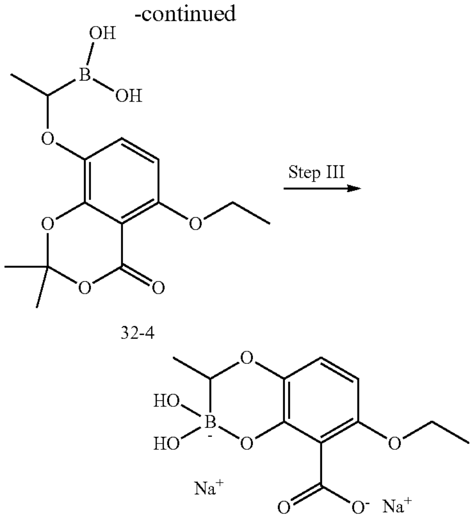

32-4

Compound 32

Step I: Preparation of Compound 32-2

At −100° C. to −90° C., n-butyllithium (2.5 M, 16.90 mL, 1.2 eq) was added dropwise to a solution of dichloromethane (4.49 g, 52.82 mmol, 3.40 mL, 1.5 eq) in tetrahydrofuran (50 mL), and the mixture was stirred at −100° C. to −90° C. for 30 minutes. Subsequently, at −100° C. to −90° C., a solution of 2,4,4,5,5-pentamethyl-1,3,2-dioxaborolane (5 g, 35.21 mmol, 1 eq) in tetrahydrofuran (10 mL) was added dropwise, zinc dichloride (1 M, 28.17 mL, 0.8 eq) was then added dropwise, and the mixture was then heated to 25° C. and stirred again for 12 h. The reaction mixture was quenched by adding 50 mL of an ammonium chloride aqueous solution at 0° C., then diluted with 50 mL of brine and extracted with 100 mL of ethyl acetate. The organic layer was washed with 50 mL of brine, dried over anhydrous sodium sulfate, filtered, and concentrated under reduced pressure to obtain compound 32-2. $^1H$ NMR (400 MHz, $CDCl_3$) δ=3.44 (m, 1H), 1.56-1.41 (m, 3H), 1.33-1.14 (m, 12H).

Step II: Preparation of Compound 32-4

Potassium carbonate (232.06 mg, 1.68 mmol, 2 eq), potassium iodide (278.72 mg, 1.68 mmol, 2 eq) and compound 32-2 (319.81 mg, 1.68 mmol, 2 eq) were added to a solution of compound 15-8 (200 mg, 839.50 μmol, 1 eq) in acetonitrile (2 mL). The mixture was stirred at 65° C. for 3 hours. The reaction mixture was concentrated under reduced pressure to remove the solvent. The residue was diluted with 10 mL of water and extracted with 20 mL of ethyl acetate (10 mL×2). The combined organic layers were washed with 10 mL of brine, dried over anhydrous sodium sulfate, filtered, and concentrated under reduced pressure to obtain compound 32-4.

Step III: Preparation of Compound 32

Compound 32-4 (260 mg, 838.42 μmol, 1 eq) was dissolved in a solution of isopropanol (2.6 mL), and sodium hydroxide (2 M, 838.42 μL, 2 eq) was added. The mixture was stirred at 20° C. for 1 h, sodium hydroxide (2 M, 838.42 μL, 2 eq) was then added, and the mixture was stirred again at 20° C. for 1 h. The mixture was filtered to obtain a filtrate. The residue was purified by preparative HPLC (chromatographic column: Waters Xbridge C18 150×50 mm×10 μm; mobile phase: water with 10 mmol/L ammonium bicarbonate and acetonitrile; the proportion of acetonitrile in the mobile phase was from 1%/6-12%, 10 min). Compound 32 was obtained. $^1$H NMR (400 MHz, $D_2O$) δ=6.52 (br d, J=8.6 Hz, 1H), 6.27 (br d, J=8.6 Hz, 1H), 3.92 (q, J=6.7 Hz, 2H), 3.30 (br d, J=7.1 Hz, 1H), 1.32-1.06 (m, 6H). LCMS (ESI) m/z: 252.9 (M+1).

Example 33

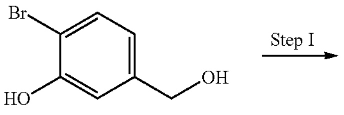

33-1

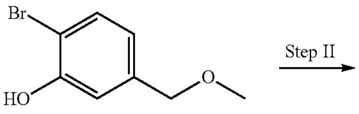

33-2

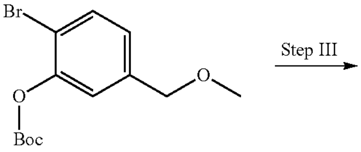

33-3

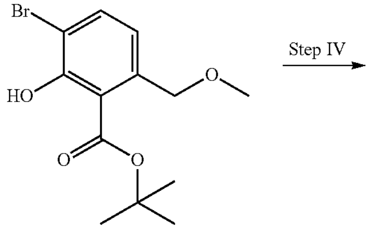

33-4

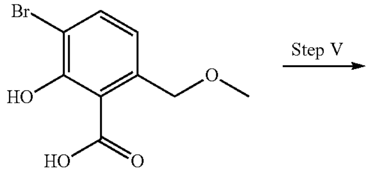

33-5

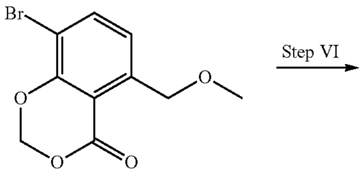

33-6

-continued

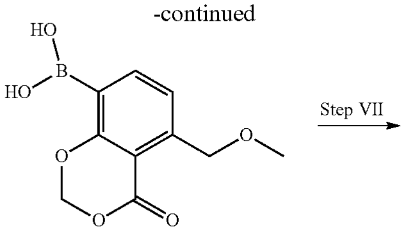

33-7

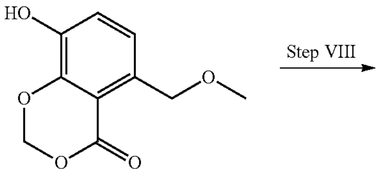

33-8

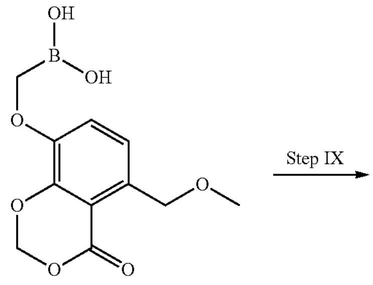

33-9

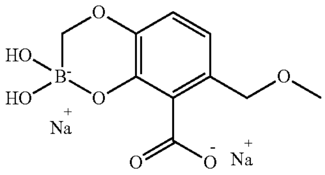

Compound 33

Step I: Preparation of Compound 33-2

Sodium hydride (2.04 g, 50.98 mmol, 60% purity, 2.3 eq) was added to a solution of compound 33-1 (4.5 g, 22.16 mmol, 1 eq) in tetrahydrofuran (45 mL) at a temperature of 0-5° C., the mixture was then stirred at 0-5° C. for 0.5 h, and iodomethane (3.46 g, 24.38 mmol, 1.52 mL, 1.1 eq) was then added. The mixture was stirred at 0-5° C. for another 0.5 h, then heated to 25° C., and stirred at 25° C. for another 11 h. The reaction mixture was quenched by adding 50 mL of an ammonium chloride aqueous solution at 0-5° C. and then extracted with 50 mL of ethyl acetate. The organic layer was washed with 20 mL of brine, dried over anhydrous sodium sulfate, filtered, and concentrated under reduced pressure to obtain a residue. Purification by silica gel flash column chromatography (petroleum ether/ethyl acetate=50/1 to 20/1) afforded compound 33-2. $^1$H NMR (400 MHz, $CDCl_3$) δ=7.35 (d, J=8.2 Hz, 1H), 6.94 (d, J=2.0 Hz, 1H), 6.72 (dd, J=2.0, 8.2 Hz, 1H), 5.43 (s, 1H), 4.32 (s, 2H), 3.31 (s, 3H).

Step II: Preparation of Compound 33-3

Compound 33-2 (4 g, 18.43 mmol, 1 eq) was dissolved in a solution of dichloromethane (40 mL), DMAP (112.57 mg, 921.41 μmol, 0.05 eq) was added, and $Boc_2O$ (4.83 g, 22.11 mmol, 5.08 mL, 1.2 eq) was then added. The mixture was stirred at 20° C. for 12 hours. The reaction mixture was quenched by adding a hydrochloric acid aqueous solution (0.2 N, 10 mL), and the separated organic layer was then washed with 10 mL of brine, dried over anhydrous sodium sulfate, filtered, and concentrated under reduced pressure to obtain compound 33-3.

Step III: Preparation of Compound 33-4

At −70° C. to −60° C., n-butyllithium (2.5 M, 9.51 mL, 1.3 eq) was added dropwise to a solution of diisopropylamine (2.41 g, 23.77 mmol, 3.36 mL, 1.3 eq) in tetrahydrofuran (10 mL), and the mixture was then stirred at 0° C. for 15 minutes to obtain a lithium diisopropylamide solution. The above-mentioned lithium diisopropylamide solution was slowly added to a solution of compound 33-3 (5.8 g, 18.29 mmol, 1 eq) in tetrahydrofuran (58 mL) at −70° C. to −60° C. The mixture was stirred at −70° C. to −60° C. for 1 hour. The reaction mixture was quenched by adding an ammonium chloride aqueous solution (50 mL) at −78° C. and then extracted with 50 mL of ethyl acetate, and the organic layer was washed with 50 mL of brine, dried over anhydrous sodium sulfate, filtered, and concentrated under reduced pressure to obtain compound 33-4.

Step IV: Preparation of Compound 33-5

Compound 33-4 (5.8 g, 18.29 mmol, 1 eq) was dissolved in a solution of dichloromethane (25 mL), and trifluoroacetic acid (38.50 g, 337.66 mmol, 25 mL, 18.47 eq) was added. The mixture was stirred at 20° C. for 20 minutes. The mixture was concentrated to obtain a residue. The residue was purified by preparative HPLC (column: Phenomenex luna C18 250×50 mm×10 μm; mobile phase: water with 1% trifluoroacetic acid and acetonitrile; the proportion of acetonitrile in the mobile phase was from 30% to 60%, 20 to 22 min) to obtain compound 33-5. $^1$H NMR (400 MHz, $CDCl_3$) δ=7.73 (d, J=8.0 Hz, 1H), 6.82 (d, J=8.0 Hz, 1H), 4.70 (s, 2H), 3.53 (s, 3H).

Step V: Preparation of Compound 33-6

Compound 33-5 (1.4 g, 5.36 mmol, 1 eq), dichloromethane (6.60 g, 77.71 mmol, 5 mL, 14.49 eq), and potassium phosphate (2.50 g, 11.80 mmol, 2.2 eq) were mixed in N,N-dimethylformamide (20 mL), the mixture was degassed, and after displacement with nitrogen 3 times, the mixture was then stirred at 100° C. for 48 hours in a nitrogen atmosphere. The reaction mixture was concentrated, then quenched by adding 30 mL of water, and extracted with 30 mL of ethyl acetate. The organic layer was washed with 20 mL of brine (10 mL×2), dried over anhydrous sodium sulfate, filtered, and concentrated under reduced pressure to obtain a residue. Purification by silica gel flash column chromatography (petroleum ether/ethyl acetate=50/1 to 20/1) afforded compound 33-6. $^1$H NMR (400 MHz, $CDCl_3$) δ=7.71 (d, J=8.4 Hz, 1H), 7.30 (d, J=8.4 Hz, 1H), 5.61 (s, 2H), 4.79 (s, 2H), 3.44 (s, 3H).

Step VI: Preparation of Compound 33-7

Compound 33-6 (800 mg, 2.93 mmol, 1 eq), 4,4,5,5-tetramethyl-2-(4,4,5,5-tetramethyl-1,3,2-dioxaborolane-2-yl)-1,3,2-dioxaborolane (1.49 g, 5.86 mmol, 2 eq), potassium acetate (862.52 mg, 8.79 mmol, 3 eq), and Pd(dppf)$Cl_2 \cdot CH_2Cl_2$ (239.24 mg, 292.95 μmol, 0.1 eq) were mixed in dioxane (10 mL), the mixture was degassed, and after displacement with nitrogen 3 times, the mixture was then stirred at 70° C. for 12 h in a nitrogen atmosphere. The reaction mixture was concentrated under reduced pressure to remove the solvent. The residue was diluted with 20 mL of water and extracted with 20 mL of ethyl acetate. The organic layer was dried over anhydrous sodium sulfate, filtered, and concentrated under reduced pressure to obtain a residue. The residue was purified by silica gel flash column chromatography (petroleum ether/ethyl acetate=20/1 to 10/1). Compound 33-7 was obtained. LCMS (ESI) m/z: 239.2 (M+1).

Step VII: Preparation of Compound 33-8

Compound 33-7 (1.1 g, 4.62 mmol, 1 eq) was dissolved in a solution of tetrahydrofuran (10 mL) and water (10 mL). Sodium perborate tetrahydrate (1.42 g, 9.24 mmol, 1.78 mL, 2 eq) was added. The mixture was stirred at 20° C. for 0.5 hour. The reaction mixture was diluted with 20 mL of water and extracted with 20 mL of ethyl acetate. The organic layer was washed with 20 mL of brine, dried over anhydrous sodium sulfate, filtered, and concentrated under reduced pressure to obtain a residue. The residue was purified by silica gel flash column chromatography (petroleum ether/ethyl acetate=10/1 to 3/1). Compound 33-8 was obtained. $^1$H NMR (400 MHz, $CDCl_3$) δ=7.26-7.20 (d, J=8.4 Hz, 1H), 7.15-7.09 (d, J=8.4 Hz, 1H), 5.61 (s, 2H), 5.37 (s, 1H), 4.76 (s, 2H), 3.42 (s, 3H); LCMS (ESI) m/z: 233.0 (M+23).

Step VIII: Preparation of Compound 33-9

Compound 33-8 (100 mg, 475.78 μmol, 1 eq), 2-(iodomethyl)-4,4,5,5-tetramethyl-1,3,2-dioxaborolane (165.70 mg, 618.51 μmol, 1.3 eq), and potassium carbonate (85.48 mg, 618.51 μmol, 1.3 eq) were mixed in acetonitrile (1 mL), the mixture was degassed, and after displacement with nitrogen 3 times, the mixture was then stirred at 60° C. for 4 hours in a nitrogen atmosphere. The reaction mixture was diluted with 10 mL of water and extracted with 10 mL of ethyl acetate. The organic layer was washed with 10 mL of brine, dried with anhydrous sodium sulfate, filtered, and concentrated under reduced pressure to obtain compound 33-9. The crude product was used in the next step without purification.

Step IX: Preparation of Compound 33

Compound 33-9 (127 mg, 473.83 μmol, 1 eq) was dissolved in isopropanol (1 mL), sodium hydroxide (2 M, 521.22 μL, 2.2 eq) was added, and the mixture was stirred at 20° C. for 1 hour. The mixture was filtered to obtain a filtrate. The residue was purified by preparative HPLC (chromatographic column: Waters Xbridge 150×25 mm×5 μm; mobile phase: water with 10 mmol/L ammonium bicarbonate and acetonitrile; the proportion of acetonitrile in the mobile phase was from 1% to 6%, 4 min) to obtain compound 33. $^1$H NMR (400 MHz, $D_2O$) δ=6.64-6.52 (m, 2H), 4.29 (s, 2H), 3.26 (s, 2H), 3.23 (s, 3H).

Example 34

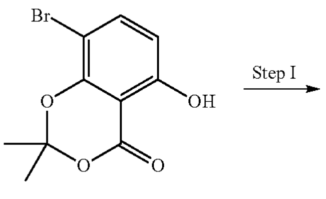

22-1

-continued

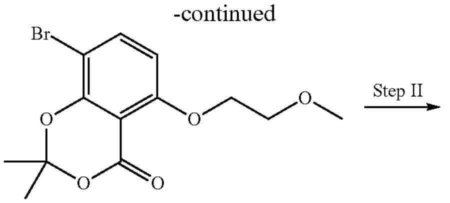

34-2

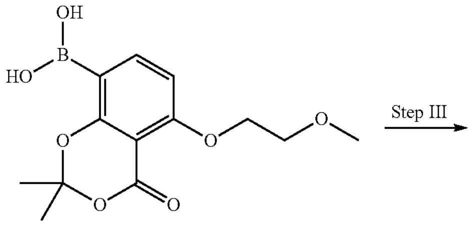

34-3

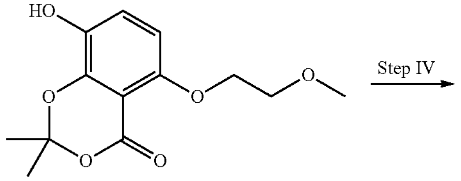

34-4

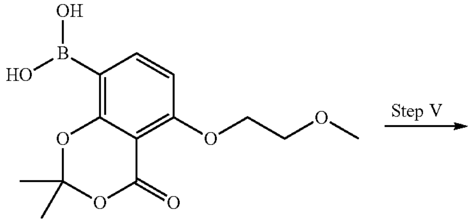

34-5

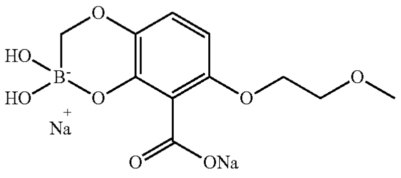

Compound 34

Step I: Preparation of Compound 34-2

Compound 22-1 (2 g, 7.32 mmol, 1 eq) and 2-methoxyethanol (668.76 mg, 8.79 mmol, 1.2 eq) were dissolved in tetrahydrofuran (20 mL), and triphenylphosphine (2.31 g, 8.79 mmol, 1.2 eq) and diisopropyl azodicarboxylate (1.78 g, 8.79 mmol, 1.71 ml, 1.2 eq) were added. The mixture was stirred at 20° C. for 0.5 hour. The reaction mixture was quenched by adding 0.1 ml of water and then concentrated under reduced pressure to obtain a residue. Purification by silica gel flash column chromatography (petroleum ether/ethyl acetate=10/1 to 6/1) afforded compound 34-2.

Step II: Preparation of Compound 34-3

Compound 34-2 (4 g, 7.25 mmol, 60% purity, 1 eq), bis(pinacolato)diboron (3.68 g, 14.49 mmol, 2 eq), potassium acetate (2.13 g, 21.74 mmol, 3 eq), and Pd(dppf) $Cl_2 \cdot CH_2Cl_2$ (591.84 mg, 724.73 μmol, 0.1 eq) were mixed in dioxane (50 mL), the mixture was degassed, and after displacement with nitrogen 3 times, the mixture was then stirred at 70° C. for 12 h in a nitrogen atmosphere. The reaction mixture was concentrated under reduced pressure to remove the solvent. The residue was diluted with 50 mL of water and extracted with 50 mL of ethyl acetate. The organic layer was dried over anhydrous sodium sulfate, filtered, and concentrated under reduced pressure to obtain a residue. Purification by silica gel flash column chromatography (petroleum ether/ethyl acetate=5/1 to 1/1) afforded compound 34-3. LCMS (ESI) m/z: 297.0 (M+1).

Step III: Preparation of Compound 34-4

Compound 34-3 (3.5 g, 11.82 mmol, 1 eq) was dissolved in tetrahydrofuran (20 mL) and water (20 mL), and sodium perborate tetrahydrate (3.64 g, 23.64 mmol, 4.55 mL, 2 eq) was added. The mixture was stirred at 20° C. for 0.5 hour. The reaction mixture was diluted with 50 mL of water and extracted with 50 mL of ethyl acetate. The organic layer was washed with 20 mL of brine, dried over anhydrous sodium sulfate, filtered, and concentrated under reduced pressure to obtain a residue. The residue was purified by silica gel flash column chromatography (petroleum ether/ethyl acetate=3/1 to 1/1). Compound 34-4 was obtained. LCMS (ESI) m/z: 269.0 (M+1); $^1H$ NMR (400 MHz, $CDCl_3$) δ=7.14 (d, J=9.0 Hz, 1H), 6.61 (d, J=9.0 Hz, 1H), 4.24-4.17 (m, 2H), 3.90-3.79 (m, 2H), 3.55-3.47 (m, 3H), 1.77 (s, 6H).

Step IV: Preparation of Compound 34-5

Compound 34-4 (300 mg, 1.12 mmol, 1 eq), 2-(iodomethyl)-4,4,5,5-tetramethyl-1,3,2-dioxaborolane (389.47 mg, 1.45 mmol, 1.3 eq), and potassium carbonate (200.93 mg, 1.45 mmol, 1.3 eq) were mixed in acetonitrile (3 mL), the mixture was degassed, and after displacement with nitrogen 3 times, it was then stirred at 60° C. for 4 hours in a nitrogen atmosphere. The reaction mixture was diluted with 10 mL of water and extracted with 10 mL of ethyl acetate. The aqueous layer was then adjusted to pH<3 with a hydrochloric acid aqueous solution (1 N) and then extracted with 10 mL of ethyl acetate, and the organic layer was washed with 10 mL of brine, dried over anhydrous sodium sulfate, filtered, and concentrated under reduced pressure to obtain compound 34-5. LCMS (ESI) m/z: 326.9 (M+1).

Step V: Preparation of Compound 34

Compound 34-5 (350 mg, 1.07 mmol, 1 eq) was dissolved in isopropanol (3 mL), and a sodium hydroxide aqueous solution (3M, 787.07 μL, 2.2 eq) was added. The mixture was stirred at 20° C. for 1 hour. The mixture was filtered to obtain a filtrate. The residue was purified by preparative HPLC (chromatographic column: Waters Xbridge 150×25 mm×5 μm; mobile phase: 10 mmol/L ammonium bicarbonate aqueous solution and acetonitrile; the proportion of acetonitrile in the mobile phase was from 1% to 6%, 4 min) to obtain compound 34. $^1H$ NMR (400 MHz, $D_2O$) δ=6.55 (d, J=8.7 Hz, 1H), 6.25 (d, J=8.8 Hz, 1H), 4.05-3.96 (m, 2H), 3.75-3.65 (m, 2H), 3.35 (s, 3H), 3.22 (s, 2H). LCMS (ESI) m/z: 269.0 (M+1).

Example 35

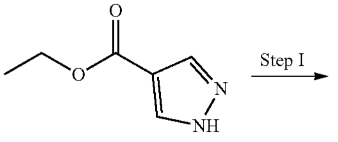

35-1

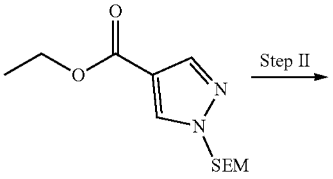

35-2

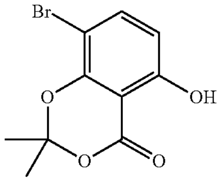

22-1

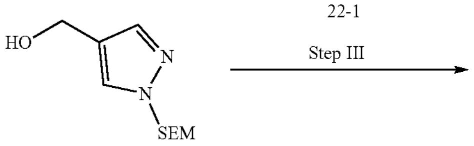

35-3

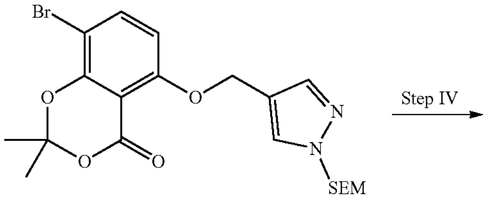

35-5

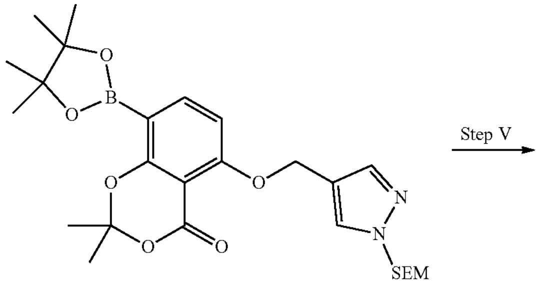

35-6

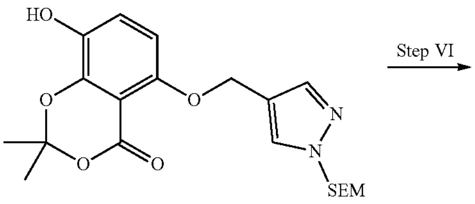

35-7

-continued

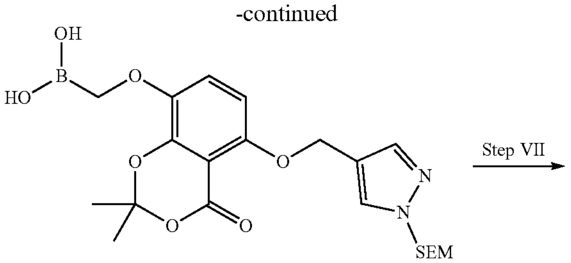

35-8

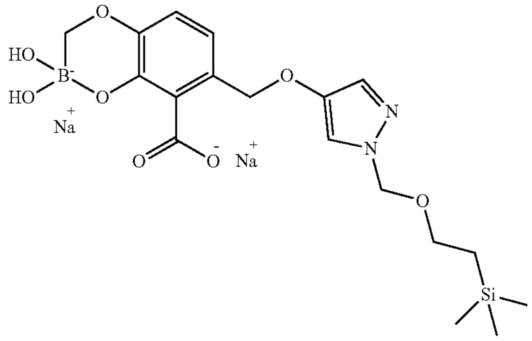

Compound 35

Step I: Preparation of Compound 35-2

Compound 35-1 (4 g, 28.54 mmol, 1 eq) was dissolved in a solution of tetrahydrofuran (40 mL), and NaH (1.71 g, 42.81 mmol, 60% purity, 1.5 eq) was added at 0° C. Subsequently, after stirring for 30 minutes, SEM-$C_1$ (7.14 g, 42.81 mmol, 7.58 mL, 1.5 eq) was slowly added, and the mixture was heated to 25° C. and stirred for 3 hours. The solution was poured into water (60 mL) and extracted with ethyl acetate (50 mL×2). The combined organic phases were washed with brine (100 mL×2), dried with anhydrous $Na_2SO_4$, filtered, and concentrated in vacuum to obtain compound 35-2. LCMS (ESI) m/z: 271.2 (M+1).

Step II: Preparation of Compound 35-3

$LiAlH_4$ (1.50 g, 39.52 mmol, 1.39 eq) was suspended in a solution of tetrahydrofuran (70 mL), a solution of ethyl 1-(2-trimethylsilylethoxymethyl)pyrazole-4-carboxylate (i.e., compound 35-2, 7.7 g, 28.48 mmol, 1 eq) in tetrahydrofuran (30 mL) was added dropwise under stirring at 10-20° C., and the mixture was stirred at 20° C. for 13 hours. $H_2O$ (1.5 mL) was slowly added dropwise to the solution at 0° C., 15% NaOH solution (1.5 mL) was added, $H_2O$ (4.5 mL) was added, the mixture was stirred for 10 minutes and filtered, and the filtrate was concentrated in vacuum. The residue was purified by silica gel chromatography (petroleum ether/ethyl acetate=10/1, 0/1) to obtain compound 35-3. LCMS (ESI) m/z: 229.2 (M+1); $^1H$ NMR (400 MHz, $CDCl_3$) δ=7.56 (d, J=13.8 Hz, 2H), 5.41 (s, 1H), 4.62 (s, 1H), 3.58 (dd, J=7.7, 8.8 Hz, 2H), 2.28 (br s, 1H), 1.01-0.86 (m, 2H), 0.01-0.02 (m, 9H).

Step III: Preparation of Compound 35-5

Compound 22-1 (3 g, 10.99 mmol, 1 eq) was dissolved in a solution of THF (30 mL), [1-(2-trimethylsilylethoxymethyl)pyrazol-4-yl]methanol (i.e., compound 35-3, 3.01 g, 13.18 mmol, 1.2 eq), and $PPh_3$ (5.76 g, 21.97 mmol, 2 eq) were added, DIAD (4.44 g, 21.97 mmol, 4.27 ml, 2 eq) was slowly added at 0° C., and the mixture was heated to 25° C. and stirred for 16 hours. $H_2O$ (30 mL) was added to the solution, and the solution was extracted with ethyl acetate (40 mL×1). The combined organic phases were washed with brine (40 mL×1), dried with anhydrous $Na_2SO_4$, filtered, and concentrated in vacuum. The crude product was purified by silica gel chromatography (petroleum ether/ethyl acetate=20/1 to 10/1) to obtain compound 35-5. LCMS: 483.2 (M+1).

Step IV: Preparation of Compound 35-6

Compound 35-5 (3.9 g, 8.07 mmol, 1 eq) was added to 4,4,5,5-tetramethyl-2-(4,4,5,5-tetramethyl-1,3,2-dioxaborolane-2-yl)-1,3,2-dioxaborolane (3.07 g, 12.10 mmol, 1.5 eq), $Pd(dppf)Cl_2{\cdot}CH_2Cl_2$ (329.41 mg, 403.37 μmol, 0.05 eq), and potassium acetate (2.38 g, 24.20 mmol, 3 eq), and the mixture was dissolved in dioxane (40 mL) and stirred at 25° C. and then at 70° C. for 12 hours. $H_2O$ (50 mL) was added to the solution, and the mixed solution was extracted with ethyl acetate (50 mL×2). The combined organic phases were washed with brine (100 mL×1), dried with anhydrous $Na_2SO_4$, filtered, and concentrated in vacuum. The crude product was purified by silica gel chromatography (petroleum ether/ethyl acetate=10/1 to 0/I). Compound 35-6 was obtained. LCMS: 531.2 (M+1).

Step V: Preparation of Compound 35-7

Compound 35-6 was dissolved in tetrahydrofuran (30 mL) and $H_2O$ (15 mL), sodium perborate tetrahydrate (2.20 g, 14.33 mmol, 2.76 mL, 2 eq) was added, and the mixture was stirred for 2 hours. $H_2O$ (40 mL) was added to the solution, and the solution was extracted with ethyl acetate (40 mL×2). The combined organic phases were washed with brine (50 mL×2), dried with anhydrous $Na_2SO_4$, filtered, and concentrated in vacuum. The crude product was purified by silica gel chromatography (petroleum ether/ethyl acetate=5/1 to 0/1) to obtain compound 35-7. LCMS (ESI) m/z: 421.2 (M+1).

Step VI: Preparation of Compound 35-8

Compound 35-7 (460.00 mg, 1.09 mmol) was dissolved in acetonitrile (5 mL), the mixture was then stirred at 25° C., 2-(iodomethyl)-4,4,5,5-tetramethyl-1,3,2-dioxaborolane (351.65 mg, 1.31 mmol, 1.2 eq) and $K_2CO_3$ (196.54 mg, 1.42 mmol, 1.3 eq) were added, and the mixture was then stirred at 60° C. for 2 hours. $H_2O$ (5 mL) was added to the solution, and the aqueous phase was extracted with ethyl acetate (10 mL×3). The combined organic phases were washed with brine (30 mL×2), dried with anhydrous $Na_2SO_4$, filtered, and concentrated in vacuum. The crude product was purified by preparative HPLC (column: Phenomenex luna C18 150×40 mm×15 μm; mobile phase: water with 0.225% formic acid and acetonitrile; the content of acetonitrile was from 37% to 67%, 10 minutes). Compound 35-8 was obtained. LCMS (ESI) m/z: 479.2 (M+1).

Step VII: Preparation of Compound 35

Compound 35-8 (100 mg, 209.04 μmol, 1 eq) was dissolved in isopropanol (1 mL), NaOH (3 M, 139.36 μL, 2 eq) was added, and the mixture was stirred at 0° C. and then at 25° C. for 1 hour. The mixture was filtered to obtain compound 35-9. LCMS (ESI) m/z: 421 (M+1); $^1$H NMR (400 MHz, $D_2O$) δ=7.92 (s, 1H), 7.75 (s, 1H), 6.62 (d, J=8.7 Hz, 1H), 6.35 (d, J=8.8 Hz, 1H), 5.49 (s, 2H), 5.02 (s, 2H), 3.72-3.60 (m, 2H), 3.34 (s, 2H), 0.99-0.88 (m, 2H), 0.00 (s, 9H).

Example 36

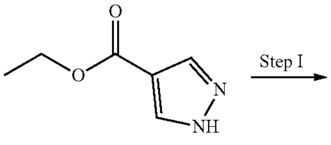

35-1

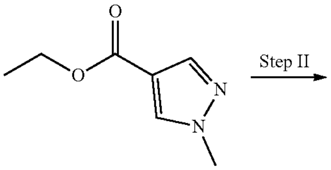

36-2

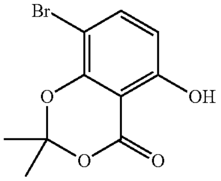

22-1

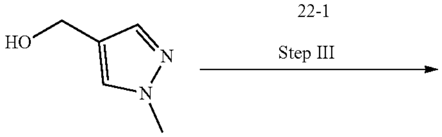

36-3

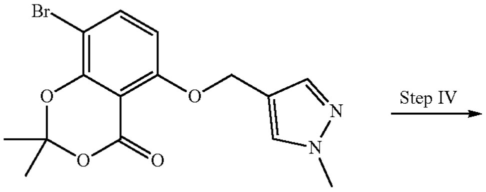

36-5

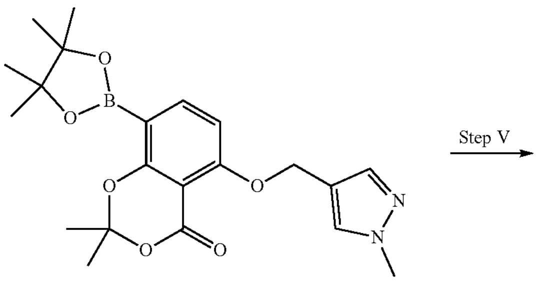

36-6

-continued

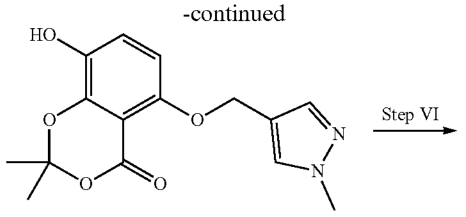

36-7

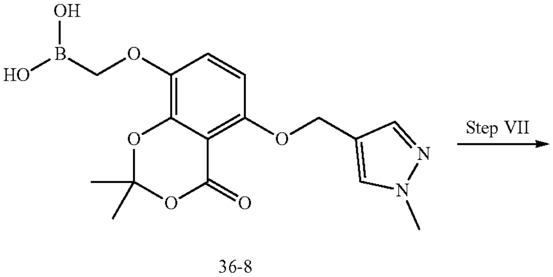

36-8

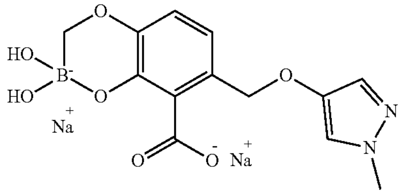

Compound 36

Step I: Preparation of Compound 36-2

Compound 35-1 (3 g, 21.41 mmol, 1 eq) was dissolved in a solution of dimethylformamide (75 mL), $Cs_2CO_3$ (17.44 g, 53.53 mmol, 2.5 eq) and iodomethane (3.04 g, 21.41 mmol, 1.33 mL, 1 eq) were added, and the mixture was stirred at 25° C. for 12 hours. The solution was concentrated in vacuum, $H_2O$ (20 mL) was added, and the mixture was extracted with ethyl acetate (30 mL×2). The combined organic phases were washed with brine (50 mL×1), dried with anhydrous $Na_2SO_4$, filtered, and concentrated in vacuum to obtain compound 36-2. LCMS (ESI) m/z: 155.3 (M+1).

Step I: Preparation of Compound 36-3

$LiAlH_4$ (1.3 g, 34.26 mmol, 1.60 eq) was dissolved in a solution of THF (30 mL), a solution of ethyl 1-methylpyrazole-4-carboxylate (i.e., compound 36-2, 3.3 g, 21.41 mmol, 1 eq) in THF (10 mL) was added dropwise at 10-20° C., and the mixture was stirred at 20° C. for 1 hour. $H_2O$ (1.3 mL) was slowly added dropwise to the solution at 0° C., 15% NaOH solution (1.3 mL) was added, $H_2O$ (3.9 mL) was added, the mixture was stirred for 10 minutes and filtered, the filtrate was concentrated in vacuum to obtain compound 36-3.

Step III: Preparation of Compound 36-5

Compound 22-1 (1.7 g, 6.23 mmol, 1 eq) was dissolved in a solution of tetrahydrofuran (30 mL), compound 36-3 (698.04 mg, 6.23 mmol, 1 eq) and $PPh_3$ (3.27 g, 12.45 mmol, 2 eq) were added, DIAD (2.52 g, 12.45 mmol, 2.42 mL, 2 eq) was slowly added dropwise at 0° C., and the mixture was then stirred at 20° C. for 1 hour. $H_2O$ (10 mL) was added to the solution, and the solution was extracted with ethyl acetate (20 mL×1). The combined organic phases were washed with brine (20 mL×1), dried with anhydrous $Na_2SO_4$, filtered, and concentrated in vacuum. Purification by silica gel chromatography (petroleum ether/ethyl acetate=5/1 to 0/1) afforded compound 36-5. LCMS: 367/369.0 (M+1/M+3).

Step IV: Preparation of Compound 36-6

Compound 36-5 (1.3 g, 4.27 mmol, 1.0 eq), 4,4,5,5-tetramethyl-2-(4,4,5,5-tetramethyl-1,3,2-dioxaborolane-2-yl)-1,3,2-dioxaborolane (1.63 g, 6.41 mmol, 1.5 eq), potassium acetate (1.26 g, 12.82 mmol, 3 eq) and Pd(dppf)$Cl_2 \cdot CH_2Cl_2$ (348.88 mg, 427.21 μmol, 0.1 eq) were mixed in dioxane (15 mL) at 25° C., and the mixture was then stirred at 75° C. for 12 hours. $H_2O$ (15 mL) was added to the solution, and the aqueous phase was extracted with ethyl acetate (20 mL×3). The combined organic phases were washed with brine (50 mL×2), dried with anhydrous $Na_2SO_4$, filtered, and concentrated in vacuum. The residue was purified by silica gel chromatography (petroleum ether/ethyl acetate=5/1 to 1/2). Compound 36-6 was obtained. LCMS: 415.3 (M+1).

Step V: Preparation of Compound 36-7

Compound 36-6 (1.3 g, 3.14 mmol, 1 eq) was dissolved in tetrahydrofuran (16 mL) and $H_2O$ (8 mL), sodium perborate tetrahydrate (482.83 mg, 3.14 mmol, 603.54 μL, 1 eq) was added, and the mixture was stirred for 2 hours. $H_2O$ (40 mL) was added to the solution, and the solution was extracted with ethyl acetate (40 mL×2). The combined organic phases were washed with brine (50 mL×2), dried with anhydrous $Na_2SO_4$, filtered, and concentrated in vacuum. The residue was purified by silica gel chromatography (petroleum ether/ethyl acetate=5/1 to 0/1). Compound 36-7 was obtained. LCMS (ESI) m/z: 305.1 (M+1); $^1H$ NMR (400 MHz, $CDCl_3$) δ=7.52 (s, 1H), 7.45 (s, 1H), 7.05 (d, J=9.0 Hz, 1H), 6.55 (d, J=9.0 Hz, 1H), 4.98 (s, 2H), 3.82 (s, 3H), 1.67 (s, 6H).

Step VI: Preparation of Compound 36-8

Compound 36-7 (250 mg, 821.57 μmol, 1 eq) was dissolved in a solution of acetonitrile (4 mL), 2-(iodomethyl)-4,4,5,5-tetramethyl-1,3,2-dioxaborolane (264.12 mg, 985.88 μmol, 1.2 eq) and $K_2CO_3$ (147.61 mg, 1.07 mmol, 1.3 eq) were added, and the mixture was stirred at 25° C. and then at 60° C. for 7 hours. Water (5 mL) was added to the solution, and the solution was then adjusted to pH=3-4 with 1N HCl and extracted with ethyl acetate (10 mL×3). The combined organic phases were washed with brine (30 mL×2), dried with anhydrous $Na_2SO_4$, filtered, and concentrated in vacuum. Compound 36-8 was obtained. LCMS (ESI) m/z: 363.2 (M+1).

Step VII: Preparation of Compound 36

Compound 36-8 (250 mg, 690.34 μmol, 1 eq) was dissolved in i-PrOH (2 mL), NaOH (3 M, 460.23 μL, 2 eq) was added at 0° C., and the mixture was then stirred at 25° C. for 1 hour. The solution was filtered, and the filtrate was directly purified. The crude product was purified by preparative HPLC (column: Waters Xbridge 150×25 mm×5 μm; mobile phase: 10 mmol/L ammonium bicarbonate aqueous solution and acetonitrile; the content of acetonitrile was from 1% to 6%, 4 min). Compound 36 was obtained. LCMS (ESI) m/z. 305 (M+1), 327 (M+23); $^1$H NMR (400 MHz, $D_2O$) δ=7.59 (s, 1H), 7.50 (s, 1H), 6.55 (d, J=8.8 Hz, 1H), 6.30 (d, J=8.7 Hz, 1H), 4.86 (s, 2H), 3.77 (s, 3H), 3.23 (s, 2H).

Example 37

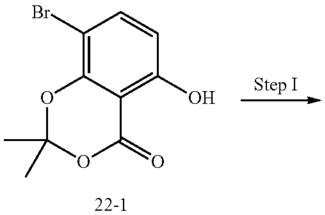

22-1

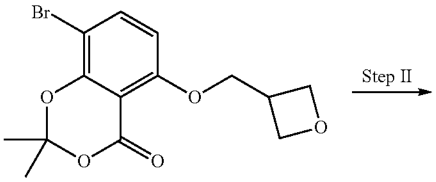

37-2

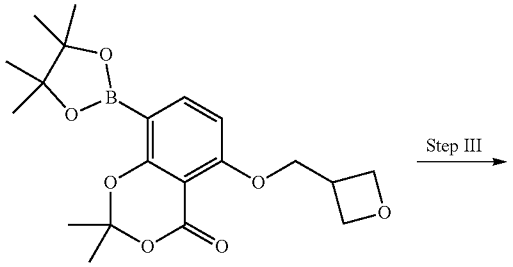

37-3

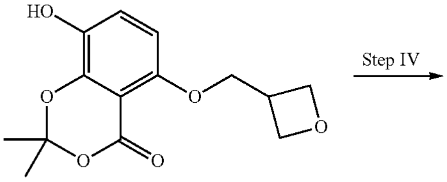

37-4

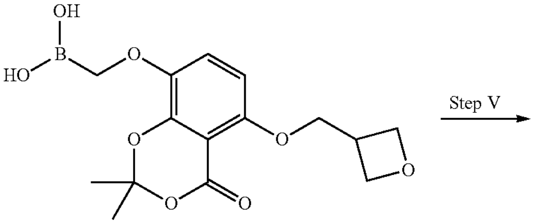

37-5

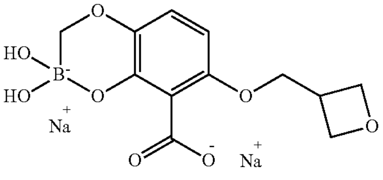

Compound 37

Step I: Preparation of Compound 37-2

22-1 (2 g, 7.32 mmol, 1 eq) and oxetan-3-ylmethanol (774.32 mg, 8.79 mmol, 1.2 eq) were dissolved in a tetrahydrofuran solution (30 mL), and $PPh_3$ (2.88 g, 10.99 mmol, 1.5 eq) and DIAD (2.22 g, 10.99 mmol, 2.14 mL, 1.5 eq) were added. The mixture was stirred at 20° C. for 5 hours. The reaction mixture was diluted with 100 mL of $H_2O$ and extracted with 200 mL of EA (100 mL×2). The combined organic layers were washed with 100 mL of brine, dried over $Na_2SO_4$, filtered, and concentrated under reduced pressure to obtain a residue. The residue was purified by column chromatography ($SiO_2$, petroleum ether/ethyl acetate=5/1 to 3/1) to obtain 37-2.

Step II: Preparation of Compound 37-3

Compound 37-2 (1.39 g, 4.05 mmol, 1 eq), bis(pinacolato)diboron (2.57 g, 10.12 mmol, 2.5 eq), Pd(dppf)$Cl_2$ (592.33 mg, 809.51 μmol, 0.2 eq), and potassium acetate (1.19 g, 12.14 mmol, 3 eq) were dissolved in dioxane (26 mL), and the mixture was then stirred at 70° C. four 12 hours under $N_2$. The reaction mixture was diluted with 20 mL of $H_2O$, extracted with 60 mL of EA, washed with 60 mL of brine, dried over $Na_2SO_4$, filtered, and concentrated under reduced pressure to obtain a residue. The residue was purified by column chromatography ($SiO_2$, petroleum ether/ethyl acetate=3/1 to 1/1) to obtain compound 37-3. LCMS (ESI) m/z: 391.2 (M+1).

Step III: Preparation of Compound 37-4

Compound 37-3 (3.8 g, 9.74 mmol, 1 eq) was dissolved in a mixed solvent of THF (38 mL) and $H_2O$ (38 mL), sodium perborate tetrahydrate (2.25 g, 14.61 mmol, 1.5 eq) was added at room temperature, the mixture was degassed, and after displacement with $N_2$ 3 times, the mixture was then stirred at 20° C. for 1.5 hours under $N_2$. The reaction mixture was filtered, then diluted with 20 mL of $H_2O$, and extracted with 40 mL of EA (20 mL×2). The combined organic layers were washed with 40 mL of brine, dried over $Na_2SO_4$, filtered, and concentrated under reduced pressure to obtain a residue. Purification by column chromatography ($SiO_2$, petroleum ether/ethyl acetate=10/1 to 2/1) afforded compound 37-4. LCMS (ESI) m/z; 281.2 (M+1).

Step IV: Preparation of Compound 37-5

Compound 37-4 (140 mg, 499.51 μmol, 1 eq) was dissolved in acetonitrile (2 mL), 2-iodomethyl pinacol boronate (200.73 mg, 749.27 μmol, 1.5 eq) and $Na_2CO_3$ (79.42 mg, 749.27 μmol, 1.5 eq) were added at room temperature, the mixture was degassed, and after displacement with $N_2$ 3 times, the mixture was then stirred at 60° C. for 6 hours under $N_2$. The reaction mixture was diluted with 30 mL of $H_2O$, adjusted to pH=4 with citric acid, then extracted with EA (20 mL×5), washed with 40 mL of brine, dried over $Na_2SO_4$, filtered, and concentrated under reduced pressure to obtain compound 37-5. LCMS (ESI) m/z: 339.2 (M+1).

Step V: Preparation of Compound 37

Compound 37-5 (90 mg, 266.18 μmol, 1 eq) was dissolved in i-PrOH (1 mL), and NaOH (2 M, 266.18 μL, 2 eq) was added. The mixture was stirred at 20° C. for 1 hour. The reaction mixture was diluted with 1 mL of $H_2O$. The mixture was purified by preparative HPLC (chromatographic column: Waters Xbridge 150×25 mm×5 μm; mobile phase: water with 10 mM $NH_4HCO_3$ and acetonitrile; the proportion of acetonitrile in the mobile phase was from 1% to 6%, 4 min) to obtain compound 37. LCMS (ESI) m/z: 281.1 (M+1). $^1$H NMR (400 MHz, $D_2O$) δ=6.55 (d, J=8.8 Hz, 1H), 6.29 (d, J=8.8 Hz, 1H), 4.79 (dd, J=6.4, 8.1 Hz, 2H), 4.53 (t, J=6.3 Hz, 2H), 4.08 (d, J=6.4 Hz, 2H), 3.32 (tt, J=6.3, 8.0 Hz, 1H), 3.22 (s, 2H).

Example 38

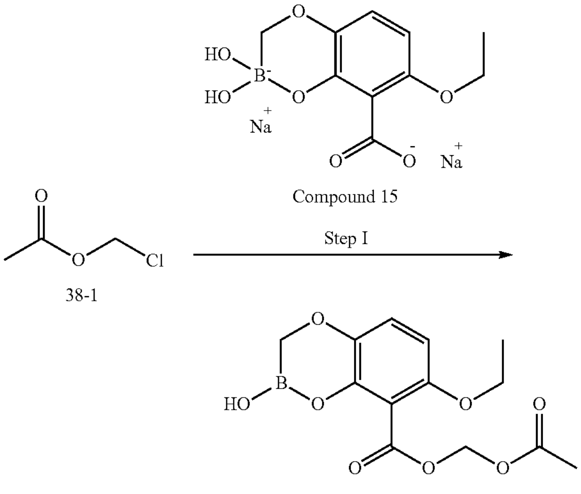

Compound 15

38-1

Compound 38

Compound 38-1 (100 mg, 333.36 μmol, 1 eq), compound 15 (72.35 mg, 666.71 μmol, 2 eq), $K_2CO_3$ (92.15 mg, 666.71 μmol, 2 eq), and potassium iodide (110.67 mg, 666.71 μmol, 2 eq) were dissolved in DMF (2 mL), and after displacement with nitrogen 3 times, the mixture was stirred at 50° C. for 12 hours under $N_2$; and the reaction mixture was diluted with 1 mL of $H_2O$ and 1 mL of acetonitrile, and purified by preparative HPLC (column: Waters Xbridge 150-25 mm×5 μm; mobile phase; an aqueous solution with 10 mmol/L ammonium bicarbonate and acetonitrile; the proportion of acetonitrile in the mobile phase was from 13% to 43%, 10 min). Compound 38 was obtained. LCMS (ESI) m/z: 620.1 (2M); $^1$H NMR (400 MHz, $CD_3OD$) δ=6.66 (d, J=8.7 Hz, 1H), 6.25 (br d, J=8.8 Hz, 1H), 5.90 (s, 2H), 3.95 (q, J=7.0 Hz, 2H), 3.41 (s, 2H), 2.13 (s, 3H), 1.31 (t, J=7.0 Hz, 3H).

Example 39

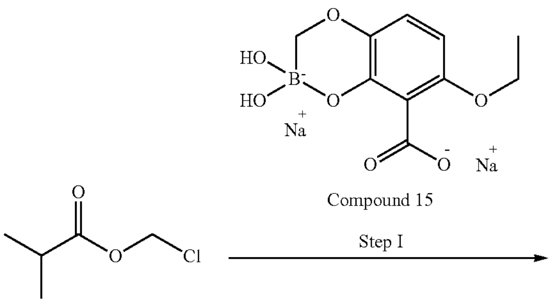

Compound 15

39-1

-continued

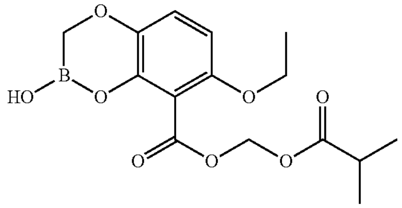

Compound 39

Step I: Preparation of Compound 142

Compound 15 (100 mg, 333.36 μmol, 1 eq), chloromethyl 2-methylpropionate (91.06 mg, 666.71 μmol, 2 eq), potassium iodide (166.01 mg, 1.00 mmol, 3 eq), and potassium carbonate (46.07 mg, 333.36 μmol, 1 eq) were mixed in N,N-dimethylformamide (1 mL), the mixture was degassed, and after displacement with nitrogen 3 times, the mixture was then stirred at 50° C. for 12 h in a nitrogen atmosphere. The reaction mixture was quenched by adding 0.5 mL of water and then filtered to obtain a filtrate. The residue was purified by preparative HPLC (column: Waters Xbridge 150×25 mm×5 μm; mobile phase: 10 mmol/L ammonium bicarbonate aqueous solution and acetonitrile; the proportion of acetonitrile in the mobile phase was from 7% to 40%, 9 min). Compound 39 was obtained. $^1$H NMR (400 MHz, $CD_3OD$) δ=6.64 (d, J=8.8 Hz, 1H), 6.22 (d, J=8.8 Hz, 1H), 5.91 (s, 2H), 4.00-3.90 (m, 2H), 3.39 (s, 2H), 2.70-2.59 (m, 1H), 1.30 (t, J=7.0 Hz, 3H), 1.23-1.19 (m, 6H).

Example 40

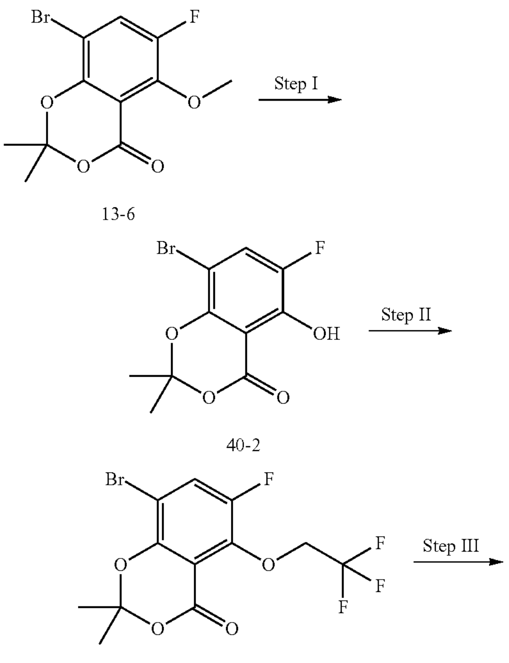

13-6

40-2

40-3

-continued

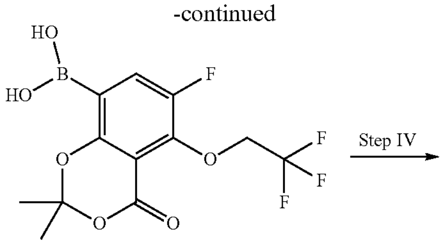

40-4

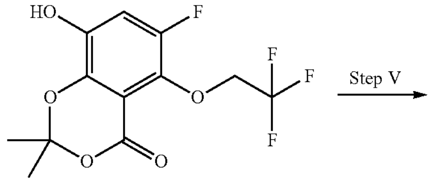

40-5

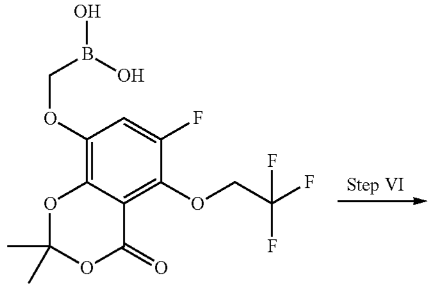

40-6

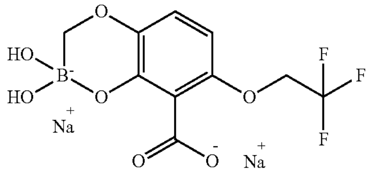

Compound 40

Step I: Synthesis of Compound 40-2

Compound 13-6 (2.6 g, 8.52 mmol, 1 eq) was dissolved in dichloromethane (30 mL), and boron trichloride (1M, 17.04 mL, 2 eq) was obtained. The mixture was stirred at −40° C. for 1 hour. Sodium bicarbonate (30 mL) was added to the mixture, and the reaction mixture was then diluted with 20 mL of water and extracted with 20 mL of ethyl acetate. The organic layer was washed with 10 mL of brine, dried over sodium sulfate, filtered, and concentrated under reduced pressure to obtain a residue. The residue was purified by column chromatography ($SiO_2$, petroleum ether/ethyl acetate=50/1 to 20/1) to obtain compound 40-2. LCMS (ESI) m/z: 291.0 (M+1).

Step II: Synthesis of Compound 40-3

Compound 40-2 (1.5 g, 5.15 mmol, 1 eq) was dissolved in N,N-dimethylformamide (20 mL), and potassium carbonate (1.07 g, 7.73 mmol, 1.5 eq) and 2,2,2-trifluoroethyl trifluoromethanesulfonate (2.39 g, 10.31 mmol, 2 eq) were added. The mixture was stirred at 80° C. for 2 hours. The reaction mixture was diluted with 20 mL of water and extracted with 20 mL of ethyl acetate. The combined organic layers were washed with 20 mL of brine (20 mL×1), dried over sodium sulfate, filtered, and concentrated under reduced pressure to obtain a residue. The crude product was stirred with petroleum ether at 25° C. for 30 minutes and filtered, and the filter cake was dried to obtain compound 40-3.

Step III: Synthesis of Compound 40-4

Compound 40-3 (1 g, 2.68 mmol, 1 eq) was dissolved in dioxane (30 mL), bis(pinacolato)diboron (1.36 g, 5.36 mmol, 2 eq), potassium acetate (789.13 mg, 8.04 mmol, 3 eq), and finally Pd(dppf)$Cl_2$ (437.76 mg, 536.06 μmol, 0.2 eq) were added, and the mixture was stirred at 60° C. for 8 hours. The reaction mixture was diluted with 20 mL of water and extracted with 20 mL of ethyl acetate. The combined organic layers were washed with 20 mL of brine, dried over sodium sulfate, filtered, and concentrated under reduced pressure to obtain a residue. The residue was purified by column chromatography ($SiO_2$, petroleum ether/ethyl acetate=10/1 to 0/1). 40-4 was obtained. LCMS (ESI) m/z: 339.0 (M+1).

Step IV: Synthesis of Compound 40-5

Compound 40-4 (1.5 g, 4.44 mmol, 1 eq) was dissolved in a mixed solution of THF (5 mL) and $H_2O$ (5 mL), and sodium perborate tetrahydrate (1.37 g, 8.88 mmol, 1.71 mL, 2 eq) was added. The mixture was stirred at 20° C. for 1 hour. The reaction mixture was diluted with 20 mL of water and extracted with 20 mL of ethyl acetate. The combined organic layers were washed with 40 mL of brine (20 mL×2), dried over sodium sulfate, filtered, and concentrated under reduced pressure to obtain a residue. The residue was purified by column chromatography ($SiO_2$, petroleum ether/ethyl acetate=3/1 to 1/1). 40-5 was obtained. LCMS (ESI) m/z: 311.0 (M+1).

Step V: Synthesis of Compound 40-6

Compound 40-5 (200 mg, 644.75 μmol, 1 eq) was dissolved in acetonitrile (3 mL), potassium carbonate (133.67 mg, 967.12 μmol, 1.5 eq) and 2-iodomethylboronic acid pinacol ester (345.46 mg, 1.29 mmol, 2 eq) were added, and the mixture was stirred at 65° C. for 4 hours. The reaction mixture was diluted with 20 mL of water and extracted with 30 mL of ethyl acetate (15 mL×2). The combined organic layers were washed with aqueous saturated table salt (20 mL×1), dried over sodium sulfate, filtered, and concentrated under reduced pressure to obtain compound 40-6. LCMS (ESI) m/z: 369.1 (M+1).

Step VI: Synthesis of Compound 40

Compound 40-6 (130 mg, 353.22 μmol, 1 eq) was dissolved in isopropanol (2 mL), and sodium hydroxide (2 M, 353.22 μL, 2 eq) was added. The mixture was stirred at 25° C. for 0.5 hour. The reaction mixture was concentrated under reduced pressure to obtain a residue. The crude product was purified by preparative HPLC (column: Waters Xbridge 150×25 mm×5 μm; mobile phase: water with 10 mM $NH_4HCO_3$ and acetonitrile; the proportion of acetonitrile in the mobile phase was from 1% to 20%, 8 min) to obtain compound 40. LCMS (ESI) m/z: 311.0 (M+1); $^1$H NMR (400 MHz, $D_2O$) δ=8.35 (br d, J=12.4 Hz, 1H), 8.06-7.93 (m, 1H), 5.93-5.65 (m, 2H), 4.86-4.82 (m, 1H), 4.67-4.59 (m, 1H), 4.51 (br d, J=11.4 Hz, 1H).

Example 41

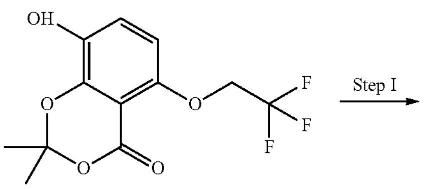

26-4

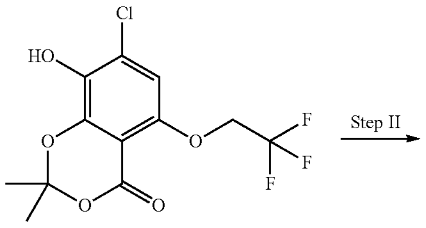

41-2

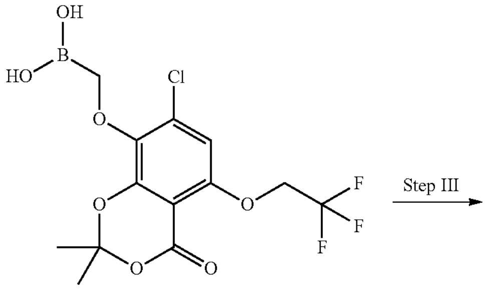

41-3

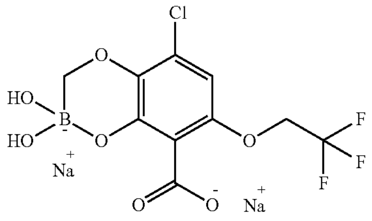

Compound 41

Step I: Preparation of Compound 41-2

Compound 26-4 (1 g, 3.42 mmol, 1 eq) was dissolved in THF (10 mL), and dichlorodimethylhydantoin (876.52 mg, 4.45 mmol, 1.3 eq) was added at room temperature. After the mixture was stirred at 50° C. for 4 hours, the reaction mixture was concentrated under reduced pressure to remove the solvent. The residue was diluted with 20 mL of $H_2O$, extracted with 40 mL of EA (20 mL×2), washed with 40 mL of brine, dried with $Na_2SO_4$, filtered, and concentrated under reduced pressure, and after purification by column chromatography ($SiO_2$, petroleum ether/ethyl acetate=5/1 to 4/1), compound 41-2 was obtained. LCMS (ESI) M/Z: 327.1 (M+1).

Step II: Preparation of Compound 41-3

Compound 41-2 (774 mg, 2.37 mmol, 1 eq), 2-iodomethylboronic acid pinacol ester (952.18 mg, 3.55 mmol, 1.5 eq), and $K_2CO_3$ (392.98 mg, 2.84 mmol, 1.2 eq) were dissolved in acetonitrile (8 mL), and displacement performed with nitrogen 3 times. The mixture was stirred at 60° C. for 3 hours under nitrogen protection. The residue was diluted with 20 mL of $H_2O$, extracted with 100 mL of EA (50 mL×2), washed with 100 mL of brine, dried with $Na_2SO_4$, filtered, and concentrated under reduced pressure to obtain a crude product, which was purified by preparative HPLC (chromatographic column: Phenomenex Synergi Max-RP 250×50 mm×10 μm; mobile phase: water with 0.1% TFA and acetonitrile, the proportion of acetonitrile in the mobile phase was from 25% to 55%, 23 min) to obtain compound 41-3. LCMS (ESI) m/z: 385.1 (M+1).

Step III: Preparation of Compound 41

Compound 41-3 (200 mg, 520.16 μmol, 1 eq) was dissolved in i-PrOH (2 mL), and an NaOH aqueous solution (2 M, 520.16 μL, 2 eq) was added dropwise at room temperature. The mixture was stirred at 20° C. for 1 hour. the reaction mixture was diluted with 1 mL of $H_2O$ and purified by preparative HPLC (chromatographic column: Waters Xbridge 150×25 mm×5 μm; mobile phase: water with 10 mM $NH_4HCO_3$ and acetonitrile, the proportion of acetonitrile in the mobile phase was from 1% to 12%, 6 min) to obtain compound 41. LCMS (ESI) m/z: 327.0 (M+1). $^1H$ NMR (400 MHz, $D_2O$) δ=6.50 (s, 1H), 4.37 (q, J=8.59 Hz, 2H), 3.31 (s, 2H).

Example 42

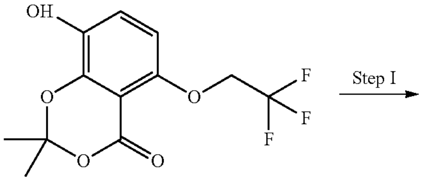

26-4

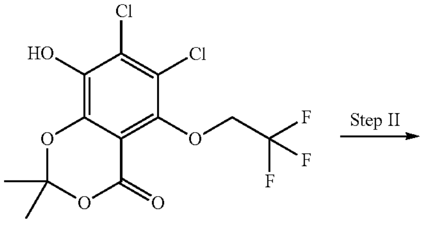

42-2

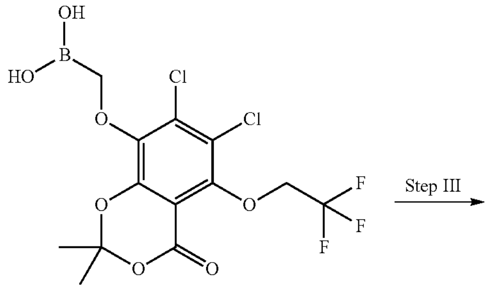

42-3

-continued

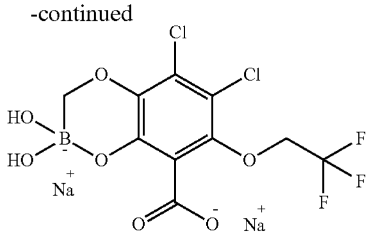

Compound 42

Step I: Preparation of Compound 42-2

Compound 26-4 (1 g, 3.42 mmol, 1 eq) was dissolved in THF (10 mL), and dichlorodimethylhydantoin (876.52 mg, 4.45 mmol, 1.3 eq) was added at room temperature. After the mixture was stirred at 50° C. for 4 hours, the reaction mixture was concentrated under reduced pressure to remove the solvent. The residue was diluted with 20 mL of $H_2O$, extracted with 40 mL of EA (20 mL×2), washed with 40 mL of brine, dried with $Na_2SO_4$, filtered, and concentrated under reduced pressure, and purification column chromatography ($SiO_2$, petroleum ether/ethyl acetate=5/1 to 4/1) afforded compound 42-2. LCMS (ESI) m/z: 361.1 (M+1).

Step II: Preparation of Compound 42-3

Compound 42-2 (774 mg, 2.37 mmol, 1 eq), 2-iodomethylboronic acid pinacol ester (952.18 mg, 3.55 mmol, 1.5 eq), and $K_2CO_3$ (392.98 mg, 2.84 mmol, 1.2 eq) were dissolved in acetonitrile (8 mL), and displacement performed with nitrogen 3 times. The mixture was stirred at 60° C. for 3 hours under nitrogen protection. The residue was diluted with 20 mL of $H_2O$, extracted with 100 mL of EA (50 mL×2), washed with 100 mL of brine, dried with $Na_2SO_4$, filtered, and concentrated under reduced pressure to obtain a crude product, which was purified by preparative HPLC (chromatographic column: Phenomenex Synergi Max-RP 250×50 mm×10 μm; mobile phase: water with 0.1% TFA and acetonitrile, the proportion of acetonitrile in the mobile phase was from 25% to 55%, 23 min) to obtain compound 42-3. LCMS (ESI) m/z: 419.1 (M+1).

Step III: Preparation of Compound 42

Compound 42-3 (70 mg, 167.09 μmol, 1 eq) was dissolved in i-PrOH (1 mL), and an NaOH aqueous solution (2 M, 167.09 μL, 2 eq) was added dropwise at room temperature. The mixture was stirred at 20° C. for 1 hour. The reaction mixture was diluted with $H_2O$ (1 mL) and purified by preparative HPLC (chromatographic column: Waters Xbridge 150×25 mm×5 μm; mobile phase: water with 10 mM $NH_4HCO_3$ and acetonitrile, the proportion of acetonitrile in the mobile phase was from 2% to 32%, 9 min) to obtain compound 42. LCMS (ESI) m/z: 361.0 (M+1); $^1H$ NMR (400 MHz, $D_2O$) δ=4.41 (q, J=8.63 Hz, 2H), 3.39 (s, 2H).

Example 43

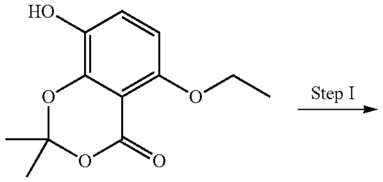

15-8

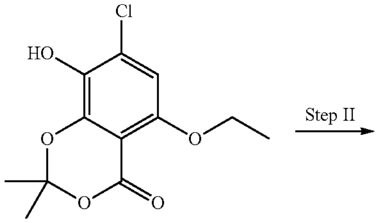

43-2

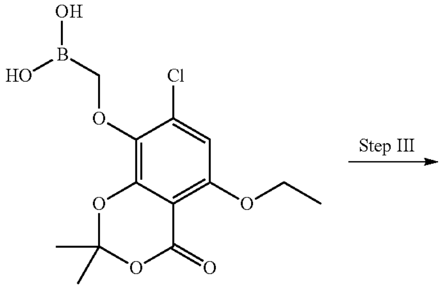

43-3

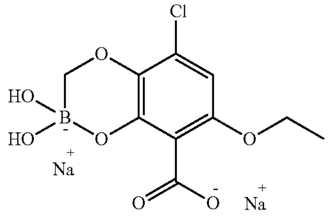

Compound 43

Step I: Preparation of Compound 43-2

Compound 15-8 (1.6 g, 6.72 mmol, 1 eq) was dissolved in THF (16 mL), and dichlorodimethylhydantoin (1.32 g, 6.72 mmol, 1 eq) was added at room temperature. After the mixture was stirred at 50° C. for 4 hours, the reaction mixture was concentrated under reduced pressure to remove the solvent. The residue was diluted with 20 mL of $H_2O$, extracted with 100 mL of EA (50 mL×2), washed with 100 mL of brine, dried with $Na_2SO_4$, filtered, and concentrated under reduced pressure to obtain a crude product. The crude product was purified by preparative HPLC (chromatographic column: Phenomenex luna C18 (250×70 mm, 10 μm); mobile phase: water (with 0.1% TFA) and acetonitrile, the proportion of acetonitrile in the mobile phase was from 30% to 60%, 25 min) to obtain 43-2. LCMS (ESI) m/z: 273.1 (M+1).

Step II: Preparation of Compound 43-3

Compound 43-2 (500 mg, 1.83 mmol, 1 eq), 2-iodomethylboronic acid pinacol ester (589.48 mg, 2.20 mmol, 1.2 eq), and $K_2CO_3$ (304.11 mg, 2.20 mmol, 1.2 eq) were dissolved in acetonitrile (5 mL), and displacement performed with nitrogen 3 times. The mixture was stirred at 60° C. for 4 hours under nitrogen protection. The residue was diluted with 20 mL of $H_2O$, adjusted to pH=4 with 2 M hydrochloric acid, extracted with 200 mL of EA (50 mL×4), washed with 200 mL of brine, dried with $Na_2SO_4$, filtered, and concentrated under reduced pressure to obtain compound 43-3. LCMS (ESI) m/z: 331.1 (M+1).

Step III: Preparation of Compound 43

Compound 43-3 (739 mg, 2.24 mmol, 1 eq) was dissolved in i-PrOH (7.5 mL), and NaOH (89.43 mg, 2.24 mmol, 1 eq) was added dropwise at room temperature. The mixture was stirred at 20° C. for 1 hour. The reaction mixture was diluted with 4 mL of $H_2O$ and purified by preparative HPLC (chromatographic column: Waters Xbridge 150×25 mm×5 μm; mobile phase: 10 mM $NH_4HCO_3$ aqueous solution and acetonitrile, the proportion of acetonitrile in the mobile phase was from 1% to 10%, 5 min) to obtain compound 43. LCMS (ESI) m/z: 255.1 (M+1-18). $^1$H NMR (400 MHz, $D_2O$) δ=6.70-6.53 (m, 1H), 3.86 (br d, J=6.24 Hz, 2H), 3.21-2.79 (m, 2H), 1.15 (t, J=7.03 Hz, 3H).

Example 44

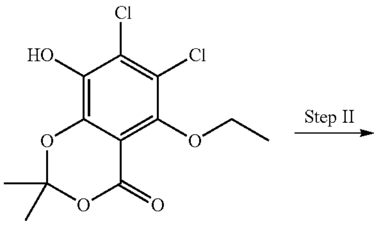

44-1

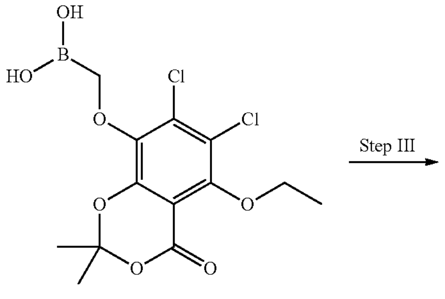

44-2

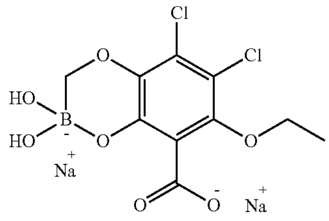

Compound 44

Step I: Synthesis of Compound 44-2

Compound 44-1 (350 mg, 1.14 mmol, 1 eq) was dissolved in acetonitrile (5 mL), and potassium carbonate (236.26 mg, 1.71 mmol, 1.5 eq) and 2-iodomethylboronic acid pinacol ester (396.89 mg, 1.48 mmol, 1.3 eq) were added. The mixture was stirred at 65° C. for 4 hours. The reaction mixture was diluted with 20 mL of water and extracted with ethyl acetate 30 mL (15 mL×2), it was then adjusted to pH 5-7 with hydrochloric acid (0.5 N) and extracted with 15 mL of ethyl acetate (15 mL×1) and the combined organic layers were washed with 20 mL of brine (20 mL×1), dried with sodium sulfate, filtered, and concentrated under reduced pressure to obtain a residue. Compound 44-2 was obtained. LCMS (ESI) m/z: 365.1 (M+1).

Step II: Synthesis of Compound 44

Compound 44-2 (310 mg, 849.38 μmol, 1 eq) was dissolved in isopropanol (3 mL), and sodium hydroxide (2 M, 849.38 μL, 2 eq) was added. The mixture was stirred at 25° C. for 1 hour. The reaction mixture was concentrated under reduced pressure to obtain a residue. The crude product was purified by preparative HPLC (column: Waters Xbridge 150×25 mm×5 μm; mobile phase: 10 mmol/L ammonium bicarbonate aqueous solution and acetonitrile, the proportion of acetonitrile in the mobile phase was from 1% to 12%, 6 min). Compound 44 was obtained. LCMS (ESI) m/z: 289.0 (M−18+1); $^1$H NMR (400 MHz, $D_2O$) δ=3.97 (d, J=7.1 Hz, 2H), 3.35 (s, 2H), 1.26 (t, J=7.1 Hz, 3H).

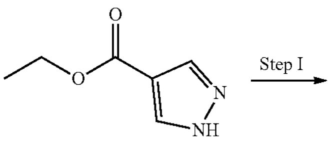

35-1

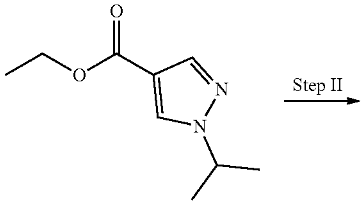

45-2

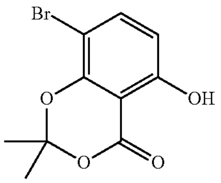

22-1

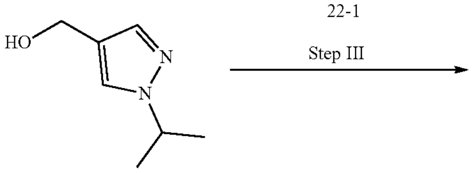

45-3

-continued

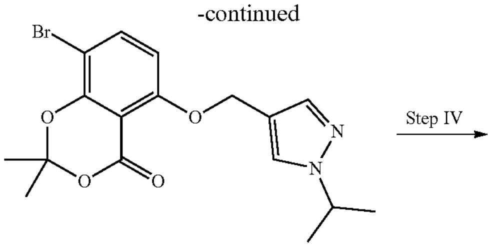

45-5

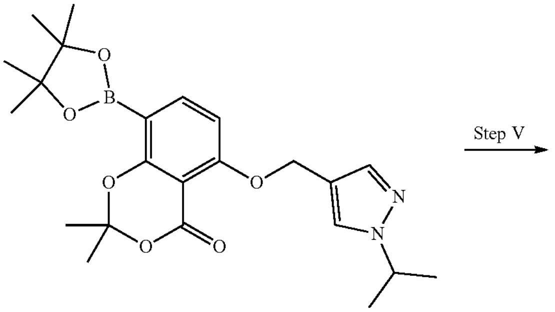

45-6

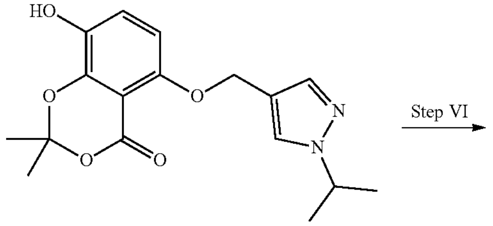

45-7

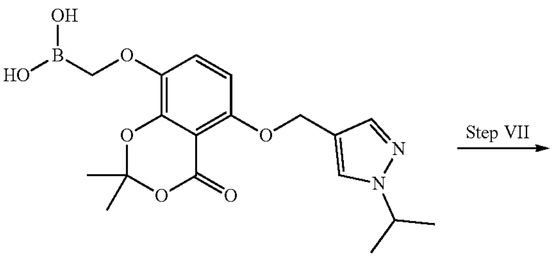

45-8

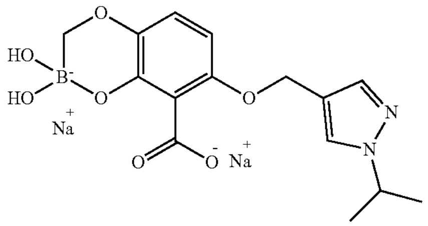

Compound 45

Step I: Preparation of Compound 45-2

Cesium carbonate (11.16 g, 34.25 mmol, 1.2 eq) and 2-iodopropane (5.82 g, 34.25 mmol, 3.42 mL, 1.2 eq) were added to solution of compound 35-1 (4 g, 28.54 mmol, 1 eq) in N,N-dimethylformamide (40 mL). The mixture was stirred at 40° C. for 1 hour. The reaction mixture was quenched by adding 50 mL of water and then extracted with 100 mL of ethyl acetate (50 mL×2). The combined organic layers were washed with 100 mL of brine (50 mL×2), dried over anhydrous sodium sulfate, filtered, and concentrated under reduced pressure to obtain compound 45-2.

Step II: Preparation of Compound 45-3

At 0-5° C., lithium aluminum hydride (1.15 g, 30.18 mmol, 1.1 eq) was added to tetrahydrofuran (50 mL), a solution of compound 45-2 (5 g, 27.44 mmol, 1 eq) in tetrahydrofuran (20 mL) was slowly added dropwise, and the mixture was stirred at 20° C. for 1 hour. At 0-10° C., water (1.15 mL), a sodium hydroxide solution (with a mass content of 15%, 1.15 mL), and water (3.45 mL) were added in sequence to quench the reaction mixture, the reaction mixture was then stirred at 20° C. for about 15 min, 2 g of magnesium sulfate was then added, and the mixture was then filtered, and concentrated under reduced pressure to obtain compound 45-3.

Step III: Preparation of Compound 45-5

At 0-5° C., triphenylphosphine (2.31 g, 8.79 mmol, 1.2 eq) and DIAD (1.78 g, 8.79 mmol, 1.71 mL, 1.2 eq) were added to compound 22-1 (2 g, 7.32 mmol, 1 eq) and compound 45-3 (1.23 g, 8.79 mmol, 1.2 eq) in tetrahydrofuran (20 mL). The mixture was stirred at 20° C. for 1 hour. The reaction mixture was concentrated under reduced pressure, and the residue was purified by silica gel flash column chromatography (petroleum ether/ethyl acetate=5/1 to 3/1). 45-5 was obtained. LCMS (ESI) m/z: 395.0/396.9 (M+1/M+3).

Step IV: Preparation of Compound 45-6

Compound 45-5 (2.6 g, 6.58 mmol, 1 eq), 4,4,5,5-tetramethyl-2-(4,4,5,5-tetramethyl-1,3,2-dioxaborolane-2-yl)-1,3,2-dioxaborolane (3.34 g, 13.16 mmol, 2 eq), Pd(dppf)$Cl_2$ (481.33 mg, 657.82 μmol, 0.1 eq), and potassium acetate (1.94 g, 19.73 mmol, 3 eq) were mixed in a dioxane solution (30 mL), the mixture was degassed, and after displacement with nitrogen 3 times, the mixture was then stirred at 70° C. for 12 hours in a nitrogen atmosphere. The reaction mixture was quenched by adding 50 mL of water and then extracted with 100 mL of ethyl acetate (50 mL×2). The combined organic layers were washed with 50 mL of brine, dried over anhydrous sodium sulfate, filtered, and concentrated under reduced pressure to obtain a residue. The residue was purified by silica gel flash column chromatography (petroleum ether/ethyl acetate=4/1 to 2/1). Compound 45-6 was obtained. LCMS (ESI) m/z: 443.2 (M+1).

Step V: Preparation of Compound 45-7

Compound 45-6 (1.4 g, 3.17 mmol, 1 eq) was dissolved in tetrahydrofuran (10 mL) and water (10 mL), and sodium perborate tetrahydrate (973.99 mg, 6.33 mmol, 1.22 mL, 2 eq) was added. The mixture was stirred at 20° C. for 0.5 hour. The reaction mixture was diluted with 50 mL of water and extracted with 50 mL of ethyl acetate. The organic layer was washed with 50 mL of brine, dried over anhydrous sodium sulfate, filtered, and concentrated under reduced pressure to obtain a residue. The residue was purified by silica gel flash column chromatography (petroleum ether/ethyl acetate=3/1 to 1/1). Compound 45-7 was obtained. LCMS (ESI) m/z: 333.0 (M+1). $^1$H NMR (400 MHz, $CDCl_3$) δ=7.69 (s, 11H), 7.57 (s, 1H), 7.14 (d, J=9.0 Hz, 11H), 6.65 (d, J=9.0 Hz, 1H), 5.16 (s, 1H), 5.07 (s, 2H), 4.57-4.45 (m, 1H), 1.77 (s, 6H), 1.52 (d, J=6.7 Hz, 6H).

Step VI: Preparation of Compound 45-8

Compound 45-7 (200 mg, 601.78 μmol, 1 eq), 2-(iodomethyl)-4,4,5,5-tetramethyl-1,3,2-dioxaborolane (153.15 mg, 571.69 μmol, 0.95 eq), and potassium carbonate (91.49 mg, 661.95 μmol, 1.1 eq) were mixed in acetonitrile (3 mL), the mixture was degassed, and after displacement with nitrogen 3 times, the mixture was then stirred at 60° C. for 4 hours in a nitrogen atmosphere. The reaction mixture was diluted with 10 mL of water and extracted with 10 mL of ethyl acetate, and the organic layer was then dried with anhydrous sodium sulfate, filtered, and concentrated under reduced pressure to obtain a part of crude product. The aqueous layer was then adjusted to pH<5 with hydrochloric acid (1 N) and extracted with 10 mL of ethyl acetate, and the organic matter was dried over anhydrous sodium sulfate, filtered, and concentrated under reduced pressure to obtain a residue. Compound 45-8 was obtained. The crude product was used in the next step without purification. LCMS (ESI) m/z: 391.0 (M+1).

Step VII: Preparation of Compound 45

Compound 45-8 (80 mg, 205.03 μmol, 1 eq) was dissolved in isopropanol (1 mL), and a sodium hydroxide solution (2 M, 205.03 μL, 2 eq) was added. The mixture was stirred at 20° C. for 1 hour. The mixture was filtered to obtain a filtrate. The filtrate was purified by preparative HPLC (chromatographic column: Waters Xbridge 150-25 mm×5 μm; mobile phase: 10 mmol/L ammonium bicarbonate aqueous solution and acetonitrile; the proportion of acetonitrile in the mobile phase was from 0% to 10%, 7 min). Compound 45 was obtained. $^1$H NMR (400 MHz, $D_2O$) δ=7.69 (s, 1H), 7.51 (s, 1H), 6.49 (dd, J=6.8, 8.5 Hz, 1H), 6.22 (dd, J=8.7, 14.7 Hz, 1H), 4.83 (s, 2H), 4.48-4.33 (m, 1H), 3.21 (d, J=12.5 Hz, 2H), 1.34 (d, J=6.8 Hz, 6H); LCMS (ESI) m/z: 333.3 (M+1).

Example 46

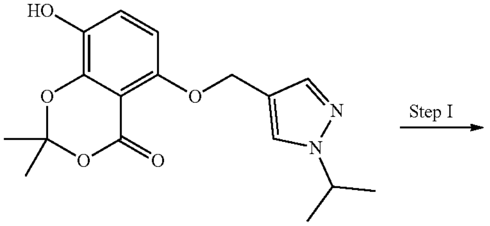

45-7

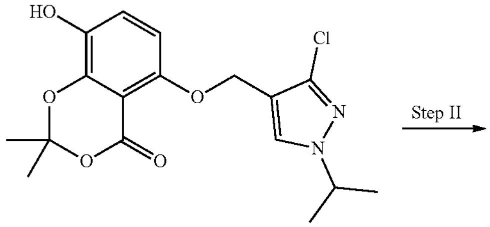

46-2

-continued

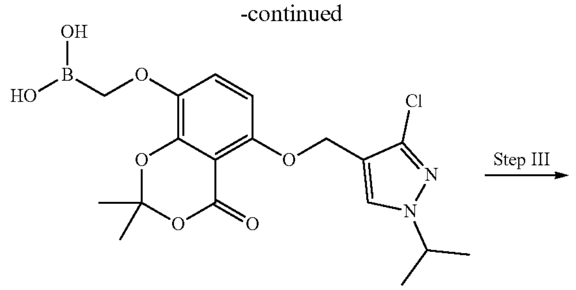

46-3

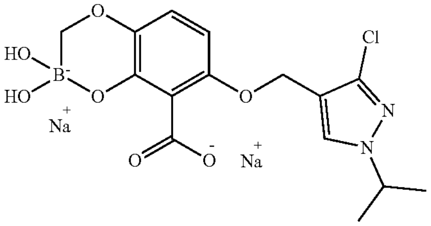

Compound 46

Step I: Preparation of Compound 46-2

Dichlorodimethylhydantoin (156.50 mg, 794.34 μmol, 0.6 eq) was added to a solution of compound 45-7 (440 mg, 1.32 mmol, 1 eq) in tetrahydrofuran (10 mL). The mixture was stirred at 45° C. for 3 hours. The reaction mixture was concentrated under reduced pressure to obtain a residue. Purification by silica gel flash column chromatography (petroleum ether/ethyl acetate=5/1 to 4/1) afforded compound 46-2. LCMS (ESI) m/z: 367.0 (M+1).

Step II: Preparation of Compound 46-3

Compound 46-2 (80.00 mg, 218.11 μmol, 1 eq), 2-(iodomethyl)-4,4,5,5-tetramethyl-1,3,2-dioxaborolane (58.43 mg, 218.11 μmol, 1 eq), and potassium carbonate (33.16 mg, 239.92 μmol, 1.1 eq) were mixed in acetonitrile (2 mL), the mixture was degassed, and after displacement with nitrogen 3 times, the mixture was then stirred at 60° C. for 3 hours in a nitrogen atmosphere. The reaction mixture was diluted with 5 mL of water and extracted with 5 mL of ethyl acetate. The aqueous layer was then adjusted to pH<3 with a hydrochloric acid aqueous solution (1N) and then extracted with 5 mL of ethyl acetate, and the organic layer was washed with 5 mL of brine, dried over anhydrous sodium sulfate, filtered, and concentrated under reduced pressure to obtain compound 46-3. LCMS (ESI) m/z: 425.0 (M+1).

Step III: Preparation of Compound 46

Compound 46-3 (92.00 mg, 216.65 μmol, 1 eq) was dissolved in isopropanol (1 mL), and a sodium hydroxide solution (3 M, 158.88 μL, 2.2 eq) was added. The mixture was stirred at 20° C. for 1 hour. The mixture was filtered to obtain a filtrate. The residue was purified by preparative HPLC (chromatographic column: Waters Xbridge 150×25 mm×5 μm; mobile phase: 10 mmol/L ammonium bicarbonate aqueous solution and acetonitrile; the proportion of acetonitrile in the mobile phase was from 1% to 6%, 4 min) to obtain compound 46. $^1$H NMR (400 MHz, $D_2O$) δ=6.20 (d, J=12.8 Hz, 1H), 3.87 (q, J=7.0 Hz, 2H), 3.23 (s, 2H), 1.18 (t, J=7.0 Hz, 3H); LCMS (ESI) m/z: 367.0 (M+1).

Example 47

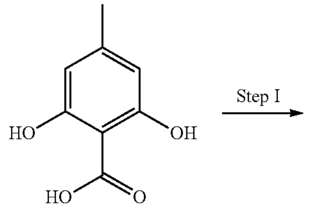

47-1

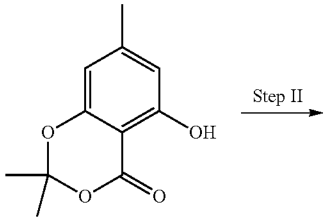

47-2

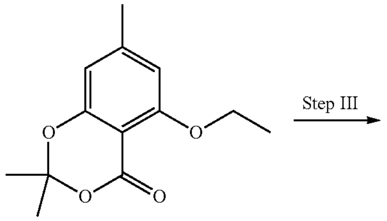

47-3

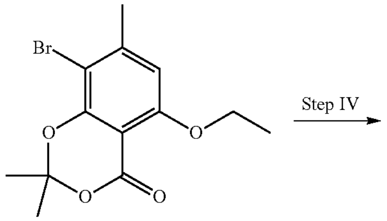

47-4

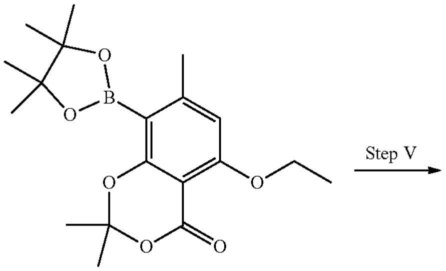

47-5

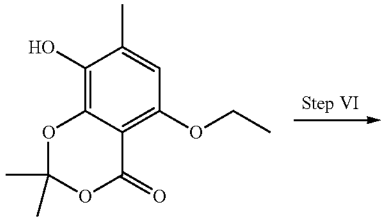

47-6

-continued

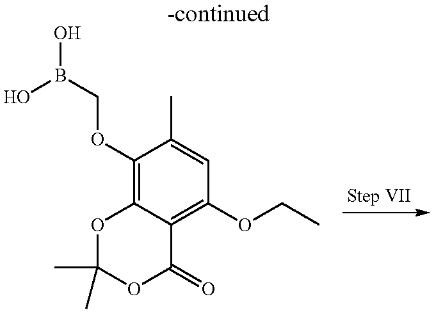

47-7

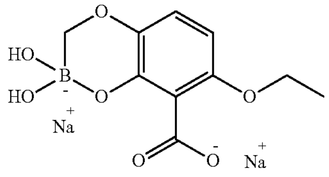

Compound 47

Step I: Preparation of Compound 47-2

Compound 47-1 (2 g, 11.89 mmol, 1 eq) was dissolved in DME (10 mL), acetone (898.05 mg, 15.46 mmol, 1.14 mL, 1.3 eq), DMAP (72.66 mg, 594.72 μmol, 0.05 eq) and sulfoxide chloride (1.84 g, 15.46 mmol, 1.12 mL, 1.3 eq) were then added to the mixture at 0° C., and the mixture was then stirred at 0-15° C.; for 16 hours. 20 ml of a saturated $NaHCO_3$ aqueous solution was added to the mixture, and the aqueous solution was then extracted with methyl tert-butyl ether (20 mL×3). The combined organic solutions were washed with 100 mL of a saturated NaCl aqueous solution and dried with anhydrous $Na_2SO_4$, and the solution was concentrated under reduced pressure. The residue was purified by silica gel flash column chromatography (petroleum ether/ethyl acetate=1/0 to 80/1) to obtain compound 47-2. $^1$H NMR (400 MHz, $CDCl_3$) δ=10.16 (s, 1H), 6.38 (s, 1H), 6.20 (s, 1H), 2.24 (s, 3H), 1.66 (s, 6H).

Step II: Preparation of Compound 47-3

Compound 47-2 (1.42 g, 6.82 mmol, 1 eq) and iodoethane (1.28 g, 8.18 mmol, 654.57 IL, 1.2 eq) were dissolved in DMF (10 mL), potassium carbonate (1.13 g, 8.18 mmol, 1.2 eq) was added to the mixture at 15° C., and the mixture was then stirred at 50° C. for 16 hours. The mixture was poured into water (30 mL) and extracted with ethyl acetate (30 mL×3), and the combined organic layers were washed with brine (50 mL 2), dried with $Na_2SO_4$, filtered, and concentrated under reduced pressure to obtain a residue. The residue was purified by silica gel flash column chromatography (petroleum ether/ethyl acetate=1/0 to 20/1) to obtain compound 47-3. $^1$H NMR (400 MHz, $CDCl_3$) δ=6.48-6.30 (m, 2H), 4.17 (q, J=7.0 Hz, 2H), 2.35 (s, 3H), 1.71 (s, 6H), 1.53 (t, J=6.9 Hz, 3H).

Step III: Preparation of Compound 47-4

Compound 47-3 (3.38 g, 14.31 mmol, 1 eq) and NBS (2.80 g, 15.74 mmol, 1.1 eq) were dissolved in tetrahydrofuran (40 mL), and the mixture was then stirred at 40° C. for 4 hours. The mixture was poured into water (50 mL) and extracted with ethyl acetate (50 mL×3), and the combined organic layers were washed with brine (100 mL), dried with $Na_2SO_4$, filtered, and concentrated under reduced pressure to obtain a residue. The crude product was washed and purified with petroleum ether (30 mL), filtered, the filter cake was dried in vacuum to obtain compound 47-4. $^1H$ NMR (400 MHz, $CDCl_3$) δ=6.58 (s, 1H), 4.17 (q, J=7.0 Hz, 2H), 2.46 (s, 3H), 1.76 (s, 6H), 1.53 (t, J=7.0 Hz, 3H).

Step IV: Preparation of Compound 47-5

Compound 47-4 (3.46 g, 10.98 mmol, 1 eq), 4,4,5,5-tetramethyl-2-(4,4,5,5-tetramethyl-1,3,2-dioxaborolane-2-yl)-1,3,2-dioxaborolane (5.58 g, 21.96 mmol, 2 eq), potassium acetate (3.23 g, 32.94 mmol, 3 eq) and Pd(dppf)$Cl_2$·$CH_2Cl_2$ (896.55 mg, 1.10 mmol, 0.1 eq) were dissolved in anhydrous dioxane (80 mL) the mixture was then subjected to displacement with nitrogen 3 times, and finally, the mixture was then stirred at 75° C. for 16 hours under nitrogen protection. The mixture was poured into water (100 mL) and extracted with ethyl acetate (100 mL×3), and the combined organic layers were washed with brine (100 mL), dried with $Na_2SO_4$, filtered, and concentrated under reduced pressure to obtain a residue. The residue was purified by silica gel flash column chromatography (petroleum ether/ethyl acetate=1/0 to 2/1) to obtain compound 47-5. LCMS (ESI) m/z: 363.2 (M+1).

Step V: Preparation of Compound 47-6

Compound 47-5 (4.64 g, 12.81 mmol, 1 eq) was dissolved in a mixed solvent of tetrahydrofuran (50 mL) and water (25 mL), sodium perborate tetrahydrate (3.94 g, 25.62 mmol, 4.93 mL, 2 eq) was added at 0° C., and the mixture was then stirred at 15° C. for 1 hour under nitrogen protection. 30 mL of water was added to the reaction mixture, and the reaction mixture was extracted with ethyl acetate (50 mL×3), washed with brine (100 mL×1), dried over $Na_2SO_4$, filtered, and concentrated in vacuum. The residue was purified by silica gel flash column chromatography (petroleum ether/ethyl acetate=20/1 to 0/1) to obtain compound 47-6. $^1H$ NMR (400 MHz, $CDCl_3$) δ=6.43 (s, 1H), 5.19-4.82 (m, 1H), 4.12 (q, J=7.0 Hz, 2H), 2.31 (s, 3H), 1.76 (s, 6H), 1.50 (t, J=7.0 Hz, 3H); LCMS (ESI) m/z: 253.2 (M+1).

Step VI: Preparation of Compound 47-7

Compound 2-(iodomethyl)-4,4,5,5-tetramethyl-1,3,2-dioxaborolane (190.52 mg, 711.16 μmol, 1.3 eq) and compound 47-6 (138 mg, 547.05 μmol, 1 eq) were dissolved in acetonitrile (2 mL), potassium carbonate (113.41 mg, 820.57 μmol, 1.5 eq) was added to the mixture at 15° C., and the mixture was then stirred at 60° C. for 2 hours. 10 mL of water was added to the mixture, and the mixture was extracted with ethyl acetate (20 mL×3), washed with brine (30 mL×2), dried over anhydrous $Na_2SO_4$, filtered, and concentrated in vacuum to obtain compound 47-7. LCMS (ESI) m/z: 311.1 (M+1).

Step VII: Preparation of Compound 47

Compound 47-7 (100 mg, 322.47 μmol, 1 eq) was dissolved in isopropanol (0.5 mL), sodium hydroxide (2 M, 322.47 μL, 2 eq) was added at 0° C., and the mixture was then stirred at 15° C. for 2 hours. The reaction liquid was filtered, and purified by preparative HPLC (chromatographic column: Waters Xbridge 150-25 mm×5 μm; mobile phase: water with 10 mmol/L ammonium bicarbonate and acetonitrile, the proportion of acetonitrile in the mobile phase was from 1% to 6%, 4 min) to obtain compound 47. $^1H$ NMR (400 MHz, $D_2O$) δ=6.21 (s, 1H), 3.93 (q, 1=7.1 Hz, 2H), 3.24 (s, 2H), 2.03 (s, 3H), 1.21 (t, J=7.0 Hz, 3H); LCMS (ESI) m/z: 253.1 (M+1).

Example 48

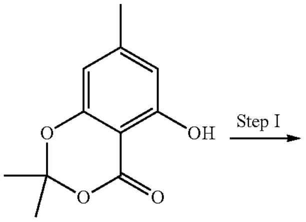

47-2

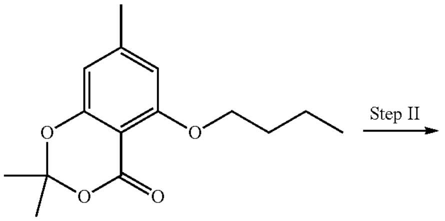

48-2

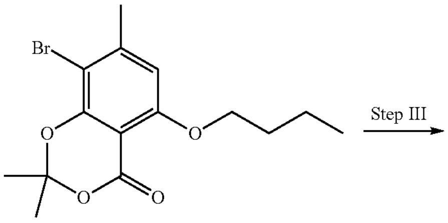

48-3

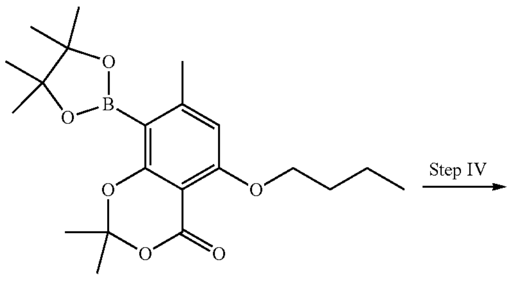

48-4

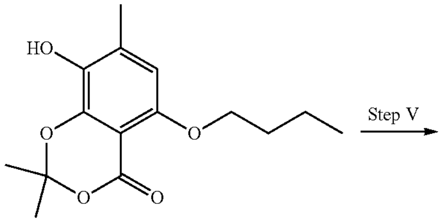

48-5

-continued

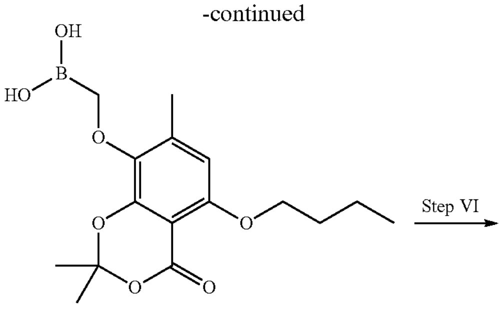

48-6

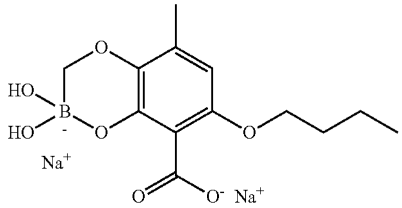

Compound 48

Step I: Preparation of Compound 48-2

Compound 47-2 (2 g, 9.61 mmol, 1 eq) and 1-bromobutane (1.58 g, 11.53 mmol, 1.24 mL, 1.2 eq) were dissolved in DMF (20 mL), potassium carbonate (1.59 g, 11.53 mmol, 1.2 eq) was then added to the mixture at 15° C., and the mixture was then stirred at 50° C. for 16 hours. The mixture was poured into water (50 mL) and extracted with ethyl acetate (50 mL×3), and the combined organic layers were washed with brine (100 mL), dried with $Na_2SO_4$, filtered, and concentrated under reduced pressure to obtain a residue. The residue was purified by silica gel flash column chromatography (petroleum ether/ethyl acetate=1/0 to 5/1) to obtain compound 48-2. $^1$H NMR (400 MHz, $CDCl_3$) δ=6.45-6.31 (m, 2H), 4.08 (t, J=6.6 Hz, 2H), 2.35 (s, 3H), 1.94-1.83 (m, 2H), 1.70 (s, 6H), 1.57 (dd, J=7.4, 15.1 Hz, 2H), 1.00 (t, J=7.4 Hz, 3H).

Step II: Preparation of Compound 48-3

Compound 48-2 (1.87 g, 7.07 mmol, 1 eq) and NBS (1.39 g, 7.78 mmol, 1.1 eq) were dissolved in anhydrous tetrahydrofuran (30 mL), and the mixture was then stirred at 40° C. for 4 hours. The mixture was poured into water (50 mL) and extracted with ethyl acetate (50 mL×3), and the combined organic layers were washed with brine (100 mL), dried with $Na_2SO_4$, filtered, and concentrated under reduced pressure to obtain a residue. The crude product was washed and purified with petroleum ether (20 mL) and filtered, and the filter cake was dried in vacuum to obtain compound 48-3.

Step III: Preparation of Compound 48-4

Compound 48-3 (2.61 g, 7.60 mmol, 1 eq), 4,4,5,5-tetramethyl-2-(4,4,5,5-tetramethyl-1,3,2-dioxaborolane-2-yl)-1,3,2-dioxaborolane (3.86 g, 15.21 mmol, 2 eq), potassium acetate (2.24 g, 22.81 mmol, 3 eq) and Pd(dppf) $Cl_2 \cdot CH_2Cl_2$ (621.02 mg, 760.46 μmol, 0.1 eq) were dissolved in anhydrous dioxane (50 mL) the mixture was then subjected to displacement with nitrogen 3 times, and finally, the mixture was then stirred at 75° C. for 16 hours. The mixture was poured into water (100 mL) and extracted with ethyl acetate (100 mL×3), and the combined organic layers were washed with brine (100 mL), dried with $Na_2SO_4$, filtered, and concentrated under reduced pressure to obtain a residue. The residue was purified by silica gel flash column chromatography (petroleum ether/ethyl acetate=I/O to 2/1) to obtain compound 48-4. LCMS (ESI) m/z: 391.1 (M+1).

Step IV: Preparation of Compound 48-5

Compound 48-4 (576 mg, 1.48 mmol, 1 eq) was dissolved in a mixed solvent of tetrahydrofuran (10 mL) and water (5 mL), sodium perborate tetrahydrate (454.16 mg, 2.95 mmol, 567.70 μL, 2 eq) was added at 0° C., and the mixture was then stirred at 15° C. for 1 hour under nitrogen protection. 20 mL of water was added to the reaction mixture, and the reaction mixture was extracted with ethyl acetate (20 mL×3), washed with brine (50 mL×1), dried over $Na_2SO_4$, filtered, and concentrated in vacuum. The residue was purified by silica gel flash column chromatography (petroleum ether/ethyl acetate=20/1 to 0/1) to obtain compound 48-5. LCMS (ESI) m/z: 281.2 (M+1).

Step V: Preparation of Compound 48-6

Compound 2-(iodomethyl)-4,4,5,5-tetramethyl-1,3,2-dioxaborolane (152.44 mg, 569.00 μmol, 1.1 eq) and compound 48-5 (145 mg, 517.27 μmol, 1 eq) were dissolved in acetonitrile (5 mL), potassium carbonate (107.24 mg, 775.91 μmol, 1.5 eq) was added to the mixture at 15° C., and the mixture was then stirred at 60° C. for 2 hours. 10 mL of water was added to the mixture, and the mixture was extracted with ethyl acetate (20 mL×3), washed with brine (30 mL×2), dried over anhydrous $Na_2SO_4$, filtered, and concentrated in vacuum to obtain compound 48-6. LCMS (ESI) m/z: 339.0 (M+1).

Step VI: Preparation of Compound 48

Compound 48-6 (176 mg, 520.46 μmol, 1 eq) was dissolved in isopropanol (1 mL), sodium hydroxide (3 M, 346.98 μL, 2 eq) was added at 0° C., and the mixture was then stirred at 15° C. for 2 hours. The reaction liquid was filtered to obtain compound 48. $^1$H NMR (400 MHz, $D_2O$) δ=6.19 (s, 1H), 3.85 (t, J=6.5 Hz, 2H), 3.28-3.18 (m, 2H), 2.11-1.97 (m, 3H), 1.63-1.52 (m, 2H), 1.38-1.26 (m, 2H), 0.82 (t, J=7.4 Hz, 3H); LCMS (ESI) m/z: 339.2 (M+1).

Example 49

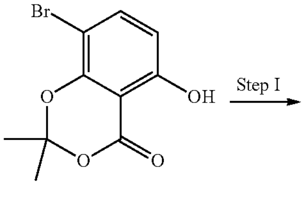

47-2

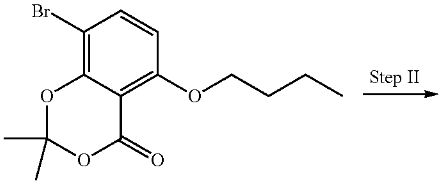

48-2

-continued

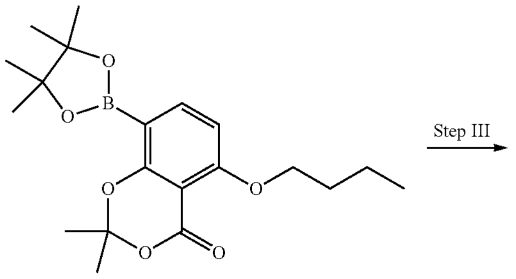

49-3

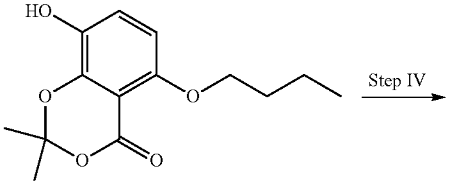

49-4

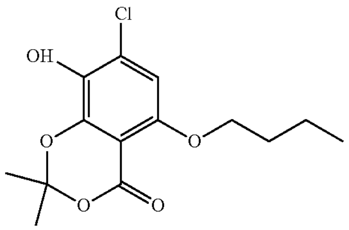

49-5

Step V

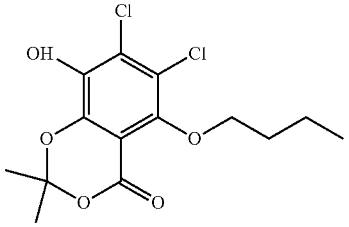

49-6

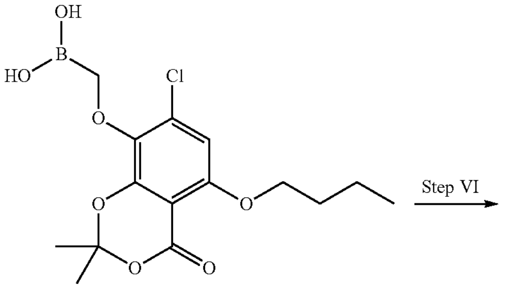

49-7

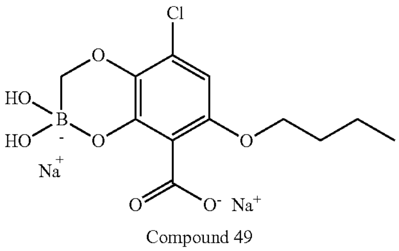

Compound 49

Step I: Synthesis of Compound 49-2

Compound 22-1 (4 g, 14.65 mmol, 1 eq) was dissolved in N,N-dimethylformamide (30 mL), and potassium phosphate (7.77 g, 36.62 mmol, 2.5 eq) and 1-iodobutane (4.04 g, 21.97 mmol, 2.50 mL, 1.5 eq) were added. The mixture was stirred at 25° C. for 8 hours. The residue was diluted with 10 mL of water and extracted with 20 mL of ethyl acetate (10 mL×2). The combined organic layers were washed with 10 mL of brine, dried over sodium sulfate, filtered, and concentrated under reduced pressure to obtain a residue. No purification was performed. 49-2 was obtained. LCMS (ESI) m/z: 329.1 (M+1).

Step I: Synthesis of Compound 49-3

Compound 49-2 (4.3 g, 13.06 mmol, 1 eq) was dissolved in dioxane (50 mL), and bis(pinacolato)diboron (6.63 g, 26.13 mmol, 2 eq), potassium acetate (3.85 g, 39.19 mmol, 3 eq), and finally Pd(dppf)$Cl_2$·$CH_2Cl_2$ (2.13 g, 2.61 mmol, 0.2 eq) were added. The mixture was stirred at 65° C. for 8 hours, and the reaction mixture was diluted with 20 mL of water and extracted with 20 mL of ethyl acetate. The combined organic layers were washed with 20 mL of brine, dried over sodium sulfate, filtered, and concentrated under reduced pressure to obtain a residue. The residue was purified by silica gel flash column chromatography (petroleum ether/ethyl acetate=5/1 to 0/1). Compound 49-3 was obtained. LCMS (ESI) m/z: 377.2 (M+1).

Step II: Synthesis of Compound 49-4

Compound 49-3 (6.3 g, 16.74 mmol, 1 eq) was dissolved in tetrahydrofuran (30 mL) and water (30 mL), and sodium perborate tetrahydrate (5.15 g, 33.49 mmol, 6.44 mL, 2 eq) was added. The mixture was stirred at 20° C. for 1 hour. The reaction mixture was diluted with 20 mL of water and extracted with 20 mL of ethyl acetate. The combined organic layers were washed with 20 mL of brine, dried over sodium sulfate, filtered, and concentrated under reduced pressure to obtain a residue. The residue was purified by silica gel flash column chromatography (petroleum ether/ethyl acetate=20/1 to 4/1). Compound 49-4 was obtained. LCMS (ESI) m/z: 267.2 (M+1).

Step IV: Synthesis of Compound 49-5 and 49-6

Compound 49-4 (1.55 g, 5.82 mmol, 1 eq) was dissolved in tetrahydrofuran (20 mL), and dichlorodimethylhydantoin (1.15 g, 5.82 mmol, 1 eq) was added. The mixture was stirred at 50° C. for 4 hours. The reaction mixture was diluted with 20 mL of water and extracted with 20 mL of ethyl acetate. The combined organic layers were washed with 20 mL of brine, dried over sodium sulfate, filtered, and concentrated under reduced pressure to obtain a residue. The crude product was purified by preparative HPLC (chromatographic column: Phenomenex luna C18 250×70 mm×10 μm; mobile phase: water (with 1% trifluoroacetic acid) and acetonitrile, the proportion of acetonitrile in the mobile phase was from 50% to 80%, 20 min). Compound 49-5 was obtained. LCMS (ESI) m/z: 301.1 (M+1). Compound 49-6 was obtained. LCMS (ESI) m/z: 335.1 (M+1).

Step V: Synthesis of Compound 49-7

49-5 (380 mg, 1.26 mmol, 1 eq) was dissolved in acetonitrile (5 mL), and potassium carbonate (261.96 mg, 1.90 mmol, 1.5 eq) and 2-iodomethylboronic acid pinacol ester (440.06 mg, 1.64 mmol, 1.3 eq) were added. The mixture was stirred at 65° C. for 4 hours. The reaction mixture was diluted with 20 mL of water and extracted with ethyl acetate (20 mL×2). The combined organic layers were washed with aqueous saturated table salt (20 mL), dried over sodium sulfate, filtered, and concentrated under reduced pressure to obtain compound 49-7. LCMS (ESI) m/z: 359.1 (M+1).

Step VI: Synthesis of Compound 49

Compound 49-7 (400 mg, 1.12 mmol, 1 eq) was dissolved in isopropanol (3 mL), sodium hydroxide (2 M, 1.12 mL, 2 eq) was added, and the mixture was stirred at 25° C. for 1 hour. The reaction mixture was concentrated under reduced pressure to obtain a residue, which resulted in compound 49 without purification. LCMS (ESI) m/z: 283.1 (M−18+1); $^1$H NMR (400 MHz, $D_2O$) δ=6.66 (s, 1H), 3.96-3.86 (m, 2H), 3.29-3.19 (m, 2H), 1.70-1.57 (m, 2H), 1.43-1.26 (m, 2H), 0.85 (t, J=7.4 Hz, 3H).

Example 50

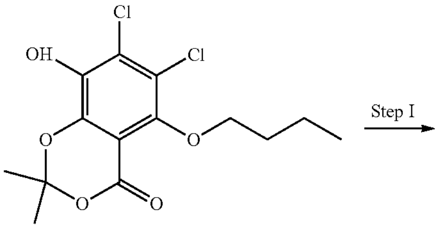

49-6

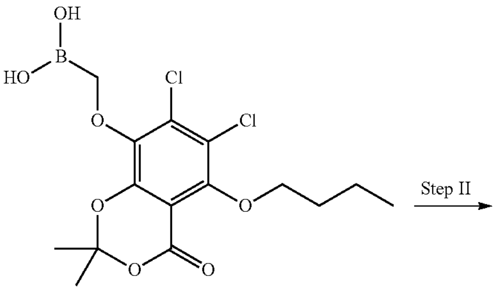

50-2

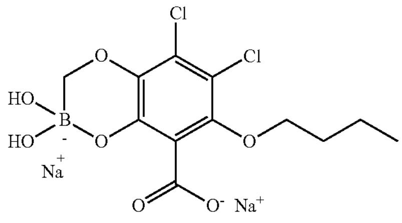

Compound 50

Step I: Synthesis of Compound 50-2

Compound 49-6 (400 mg, 1.19 mmol, 1 eq) was dissolved in acetonitrile (5 mL), and potassium carbonate (247.41 mg, 1.79 mmol, 1.5 eq) and 2-iodomethylboronic acid pinacol ester (415.62 mg, 1.55 mmol, 1.3 eq) were added. It was stirred at 65° C. for 8 hours. The reaction mixture was diluted with 20 mL of water and extracted with 40 mL (20 mL×2) of ethyl acetate. The combined organic layers were washed with 20 mL of brine (20 mL×1), dried over sodium sulfate, filtered, and concentrated under reduced pressure to obtain a residue. Compound 50-2 was obtained without purification. LCMS (ESI) m/z: 393.0 (M+1).

Step II: Synthesis of Compound 50

Compound 50-2 (500 mg, 1.27 mmol, 1 eq) was dissolved in isopropanol (3 mL), and sodium hydroxide (2M, 1.27 mL, 2 eq) was added. The mixture was stirred at 25° C. for 1 hour. The reaction mixture was concentrated under reduced pressure to obtain a residue. The residue was purified by preparative HPLC (column: Waters Xbridge 150-25 mm×5 μm; mobile phase: 10 mmol/L ammonium bicarbonate aqueous solution and acetonitrile, the proportion of acetonitrile in the mobile phase was from 1% to 30%, 9 min). Compound 50 was obtained. LCMS (ESI) m/z: 317.0 (M−18+1); $^1$H NMR (400 MHz, $D_2O$) δ=3.93 (t, J=6.5 Hz, 2H), 3.39 (s, 2H), 1.71-1.56 (m, 2H), 1.44-1.32 (m, 2H), 0.90-0.80 (m, 3H).

Example 51

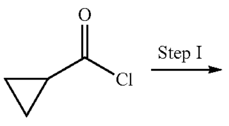

51-1

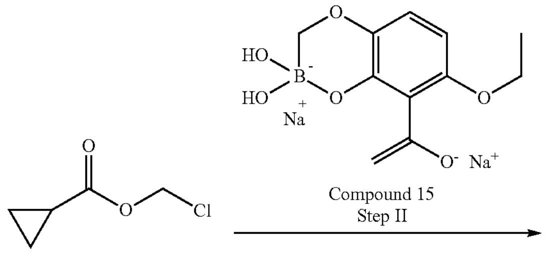

Compound 15

51-2

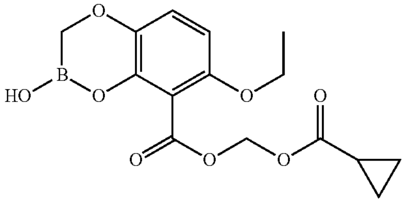

Compound 51

Step I: Preparation of Compound 51-2

At 0-5° C., zinc chloride (1 M, 1.91 mL, 0.02 eq) was added to a mixture of 51-1 (10 g, 95.66 mmol, 8.70 mL, 1 eq) and paraformaldehyde (2.87 g, 95.66 mmol, 2.64 mL, 1 eq), and the mixture was then stirred at 20° C. for 12 h in a nitrogen atmosphere. It was then heated to 90° C. and stirred for another 4 hours. The reaction mixture was concentrated under reduced pressure to remove the solvent. The crude product was distilled under reduced pressure (70° C., 133 Pa pressure/oil pump). Compound 51-2 was obtained. $^1$H NMR (400 MHz, $CDCl_3$) δ=5.64 (s, 2H), 1.61 (qd, J=4.1, 8.4 Hz, 1H), 1.08-0.99 (m, 2H), 0.96-0.86 (m, 2H).

Step I: Preparation of Compound 51

Compound 15 (100 mg, 333.36 μmol, 1 eq), compound 51-2 (89.71 mg, 666.72 μmol, 2 eq), potassium iodide (166.01 mg, 1.00 mmol, 3 eq), and potassium carbonate (92.15 mg, 666.72 μmol, 2 eq) were mixed in N,N-dimethylformamide (1 mL), the mixture was degassed, and after displacement with nitrogen 3 times, the mixture was then stirred at 50° C. for 12 h in a nitrogen atmosphere. The reaction mixture was quenched by adding 0.5 mL of water and then filtered to obtain a filtrate. Purification by preparative HPLC (chromatographic column: Waters Xbridge 150×25 mm×5 μm; mobile phase: water with 10 mmol/L ammonium bicarbonate and acetonitrile; the proportion of acetonitrile in the mobile phase was from 7% to 37%, 8 min) afforded compound 51. LCMS (ESI) m/z: 672.0 (2M), $^1$H NMR (400 MHz, $CD_3OD$ δ=6.67 (d, J=8.8 Hz, 1H), 6.25 (d, J=8.9 Hz, 1H), 5.90 (s, 2H), 3.96 (d, J=7.0 Hz, 2H), 3.42 (s, 2H), 1.75-1.66 (m, 1H), 1.32 (t, J=7.0 Hz, 3H), 1.09-0.90 (m, 4H).

Example 52

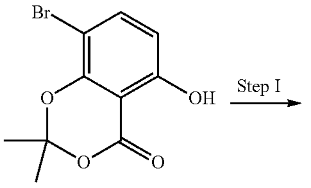

22-1

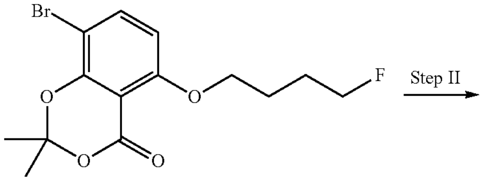

52-2

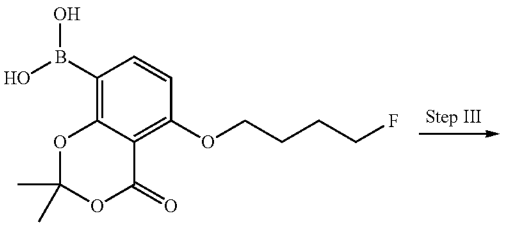

52-3

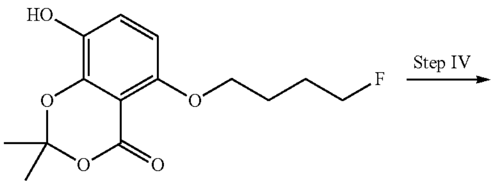

52-4

-continued

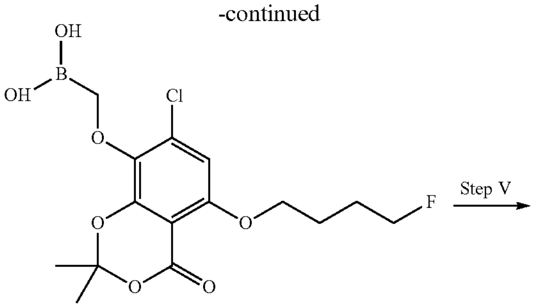

52-5

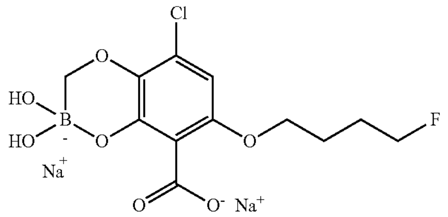

Compound 52

Step I: Synthesis of Compound 52-2

Compound 22-1 (2 g, 7.32 mmol, 1 eq) was dissolved in N,N-dimethylformamide (20 mL), and potassium carbonate (1.52 g, 10.98 mmol, 1.5 eq) and 1-bromo-4-fluorobutane (1.48 g, 9.52 mmol, 1.02 mL, 1.3 eq) was added. The mixture was stirred at 25° C. for 8 hours. The residue was diluted with 10 mL of water and extracted with ethyl acetate (10 mL×2), and the combined organic layers were washed with 10 mL of brine, dried with sodium sulfate, filtered, and concentrated under reduced pressure to obtain compound 52-2.

Step II: Synthesis of Compound 52-3

Compound 52-2 (2.6 g, 7.49 mmol, 1 eq) was dissolved in dioxane (50 mL), bis(pinacolato)diboron (3.80 g, 14.98 mmol, 2 eq), potassium acetate (2.20 g, 22.47 mmol, 3 eq), and finally Pd(dppf)$Cl_2$ (1.22 g, 1.50 mmol, 0.2 eq) were added, and displacement was performed with nitrogen 3 times. The mixture was stirred at 65° C. for 8 hours. The reaction mixture was diluted with 20 mL of water and extracted with 20 mL of ethyl acetate. The combined organic layers were washed with 20 mL of brine, dried over sodium sulfate, filtered, and concentrated under reduced pressure, and the obtained residue was purified by column chromatography ($SiO_2$, petroleum ether/ethyl acetate=5/1 to 0/1) to obtain compound 52-3. LCMS (ESI) m/z: 313.0 (M+1).

Step III: Synthesis of Compound 52-4

Compound 52-3 (3.4 g, 8.62 mmol, 1 eq) was dissolved in tetrahydrofuran (15 mL) and water (15 mL), and sodium perborate tetrahydrate (2.65 g, 17.25 mmol, 3.32 mL, 2 eq) was added. The mixture was stirred at 20° C. for 1 hour. The reaction mixture was diluted with 20 mL of water and extracted with 20 mL of ethyl acetate. The combined organic layers were washed with 40 mL of brine (20 mL×2), dried over sodium sulfate, filtered, and concentrated under reduced pressure to obtain a residue. The residue was purified by column chromatography ($SiO_2$, petroleum ether/ethyl acetate=10/1 to 1/1) to obtain compound 52-4. LCMS (ESI) m/z: 285.0 (M+1).

Step IV: Synthesis of Compound 52-5

Compound 52-4 (200 mg, 703.53 μmol, 1 eq) was dissolved in acetonitrile (3 mL), and potassium carbonate (145.85 mg, 1.06 mmol, 1.5 eq) and 2-iodomethylboronic acid pinacol ester (245.02 mg, 914.59 μmol, 1.3 eq) were added. The mixture was stirred at 65° C. for 8 hours. The reaction mixture was diluted with 20 mL of water and extracted with 40 mL (20 mL×2) of ethyl acetate. The combined organic layers were washed with 20 mL of brine (20 mL×1), dried over sodium sulfate, filtered, and concentrated under reduced pressure to obtain compound 52-5. LCMS (ESI) m/z: 343.0 (M+1).

Step V: Synthesis of Compound 52

Compound 52-5 (200 mg, 584.58 μmol, 1 eq) was dissolved in isopropanol (2 mL), and sodium hydroxide (2 M, 584.58 μL, 2 eq) was added. The mixture was stirred at 25° C. for 1 hour. The reaction mixture was concentrated under reduced pressure to obtain a residue. Purification by preparative HPLC (chromatographic column: Waters Xbridge 150×25 mm×5 μm; mobile phase: water with 10 mM $NH_4HCO_3$ and acetonitrile, the proportion of acetonitrile in the mobile phase was from 1% to 15%, 9 min) afforded compound 52. LCMS (ESI) m/z: 267.0 (M−18+1); $^1$H NMR (400 MHz, $D_2O$) δ=6.54 (d, J=8.7 Hz, 1H), 6.28 (d, J=8.7 Hz, 1H), 4.56 (t, J=5.9 Hz, 1H), 4.44 (br t, J=5.7 Hz, 1H), 3.92 (t, J=6.1 Hz, 2H), 3.22 (s, 2H), 1.87-1.66 (m, 4H), 1.14 (s, 1H).

Example 53

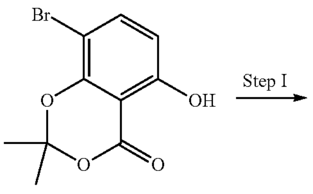

22-1

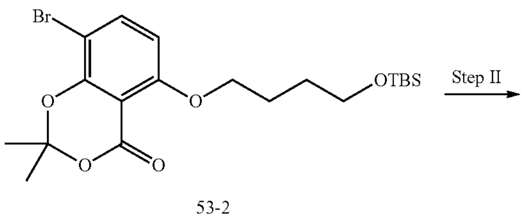

53-2

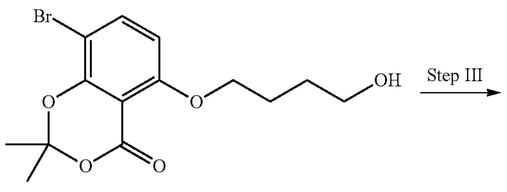

53-3

-continued

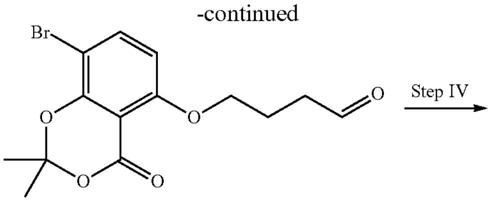

53-4

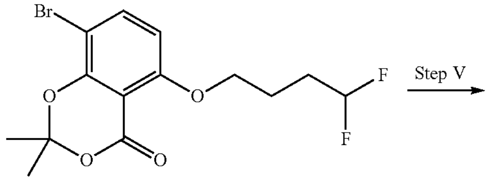

53-5

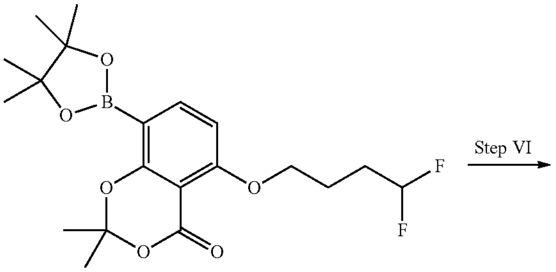

53-6

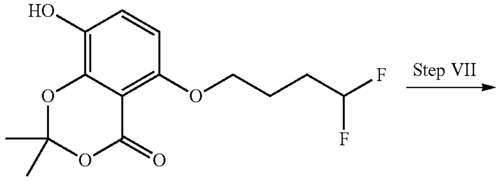

53-7

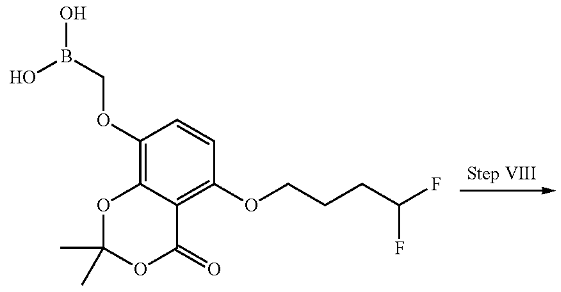

53-8

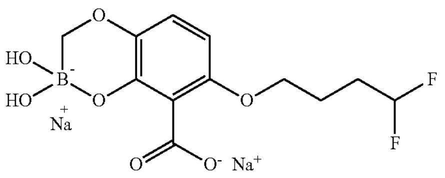

Compound 53

Step I: Preparation of Compound 53-2

Compound 22-1 (2.63 g, 9.63 mmol, 1 eq) and 4-bromobutoxy-tert-butyl-dimethylsilane (2.83 g, 10.59 mmol, 1.1 eq) were dissolved in DMF (30 mL), potassium carbonate (2.00 g, 14.44 mmol, 1.5 eq) was then added to the mixture at 15° C., and finally, the mixture was stirred at 80° C. for 16 hours. Water (50 mL) was added to the mixture, the mixture was extracted with ethyl acetate (100 mL×3), the combined organic layers were washed with brine (100 mL×2), dried with $Na_2SO_4$, filtered, and concentrated under reduced pressure, and the residue was purified by silica gel flash column chromatography (petroleum ether/ethyl acetate=1/0 to 0/1) to obtain compound 53-2. LCMS (ESI) m/z: 460.9 (M+3).

Step II: Preparation of Compound 53-3

Compound 53-2 (1.85 g, 4.03 mmol, 1 eq) was dissolved in anhydrous dichloromethane (20 mL), N,N-diethylethylamine·trihydrofluoride (6.49 g, 40.27 mmol, 6.56 mL, 10 eq) was then added to the mixture at 0° C., and the mixture was then stirred at 25° C. for 2 hours. Water (30 mL) was added to the mixture, the mixture was extracted with dichloromethane (30 mL×2), and the combined organic layers were washed with brine (100 mL), dried with $Na_2SO_4$, filtered, and concentrated under reduced pressure to obtain compound 53-3.

Step III: Preparation of Compound 53-4

Compound 53-3 (1.5 g, 4.35 mmol, 1 eq) was dissolved in anhydrous dichloromethane (20 mL), Dess-Martin periodinane (2.40 g, 5.65 mmol, 1.75 mL, 1.3 eq) was added to the mixture at 0° C., and the mixture was then stirred at 15° C. for 16 hours. The reaction mixture was quenched by adding 50 mL of a saturated sodium thiosulfate aqueous solution and extracted with dichloromethane (50 mL 2). The combined organic layers were washed with saturated sodium bicarbonate (50 mL) and brine (100 mL), dried over $Na_2SO_4$, filtered, and concentrated under reduced pressure to obtain compound 53-4. LCMS (ESI) m/z: 343.0 (M+1).

Step IV: Preparation of Compound 53-5

Compound 53-4 (1.5 g, 4.37 mmol, 1 eq) was dissolved in anhydrous dichloromethane (20 mL), diethylaminosulfur trifluoride (1.41 g, 8.74 mmol, 1.16 mL, 2 eq) was added to the mixture at 0° C., and the mixture was then stirred at 25° C. for 3 hours. The reaction mixture was poured into cooled saturated sodium bicarbonate (50 mL) and extracted with dichloromethane (50 mL×2), and the combined organic layers were washed with brine (100 mL), dried with $Na_2SO_4$, filtered, and concentrated under reduced pressure to obtain a residue. The residue was purified by silica gel flash column chromatography (petroleum ether/ethyl acetate=50/1 to 5/1) to obtain compound 53-5. LCMS (ESI) m/z: 367.0 (M+3).

Step V: Preparation of Compound 53-6

Compound 53-5 (774 mg, 2.12 mmol, 1 eq), 4,4,5,5-tetramethyl-2-(4,4,5,5-tetramethyl-1,3,2-dioxaborolane-2-yl)-1,3,2-dioxaborolane (1.08 g, 4.24 mmol, 2 eq), potassium acetate (624.05 mg, 6.36 mmol, 3 eq) and Pd(dppf) $Cl_2 \cdot CH_2Cl_2$ (346.19 mg, 423.92 μmol, 0.2 eq) were dissolved in anhydrous dioxane (20 mL) the mixture was then subjected to displacement with nitrogen 3 times, and finally, the mixture was then stirred at 75° C. for 16 hours under nitrogen protection. Water (20 mL) was added to the mixture, the mixture was extracted with ethyl acetate (30 mL×3), the combined organic layers were washed with brine (50 mL), dried with $Na_2SO_4$, filtered, and concentrated under reduced pressure, and the residue was purified by silica gel flash column chromatography (petroleum ether/ethyl acetate=1/0 to 2/1) to obtain compound 53-6. LCMS (ESI) m/z: 413.2 (M+1).

Step VI: Preparation of Compound 53-7

Compound 53-6 (1 g, 2.43 mmol, 1 eq) was dissolved in a mixed solvent of tetrahydrofuran (10 mL) and water (5 mL), sodium perborate tetrahydrate (373.24 mg, 2.43 mmol, 466.55 μL, 1 eq) was added at 0° C., and the mixture was then stirred at 15° C. for 1 hour under nitrogen protection. 20 mL of water was added to the reaction mixture, and the reaction mixture was extracted with ethyl acetate (20 mL×3), washed with brine (50 mL), dried over $Na_2SO_4$, filtered, and concentrated in vacuum. The residue was purified by silica gel flash column chromatography (petroleum ether/ethyl acetate=20/1 to 0/1) to obtain compound 53-7. LCMS (ESI) m/z: 303.1 (M+1).

Step VII: Preparation of Compound 53-8

Compound 2-(iodomethyl)-4,4,5,5-tetramethyl-1,3,2-dioxaborolane (105.29 mg, 393.03 μmol, 1.1 eq) and compound 53-7 (108 mg, 357.30 μmol, 1 eq) were dissolved in acetonitrile (5 mL), potassium carbonate (74.07 mg, 535.94 μmol, 1.5 eq) was added to the mixture at 15° C., and the mixture was then stirred at 60° C. for 2 hours. 10 mL of water was added to the mixture, and the mixture was extracted with ethyl acetate (20 mL×3), washed with brine (30 mL×2), dried over anhydrous $Na_2SO_4$, filtered, and concentrated in vacuum to obtain compound 53-8. LCMS (ESI) m/z: 361.1 (M+1).

Step VIII: Preparation of Compound 53

Compound 53-8 (117 mg, 324.90 μmol, 1 eq) was dissolved in isopropanol (0.5 mL), sodium hydroxide (2 M, 324.90 μL, 2 eq) was added at 0° C., and the mixture was then stirred at 20° C. for 2 hours. The reaction liquid was filtered and purified by preparative HPLC (chromatographic column: Waters Xbridge 150-25 mm×5 μm; mobile phase: 10 mmol/L ammonium bicarbonate aqueous solution and acetonitrile, the proportion of acetonitrile in the mobile phase was from 1% to 6%, 4 min) to obtain compound 53. $^1H$ NMR (400 MHz, $D_2O$) δ=6.52 (d, J=8.8 Hz, 1H), 6.25 (d, J=8.8 Hz, 1H), 6.11-5.75 (m, 1H), 3.91 (t, J=6.1 Hz, 2H), 3.21 (s, 2H), 2.03-1.82 (m, 2H), 1.81-1.69 (m, 2H); LCMS (ESI) m/z: 285.1 (M−18+1).

Example 54

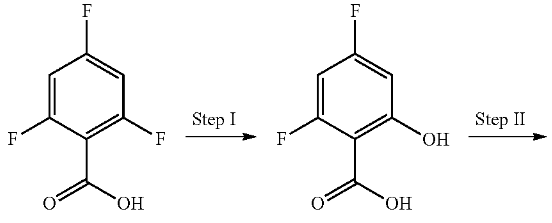

54-1

54-2

-continued

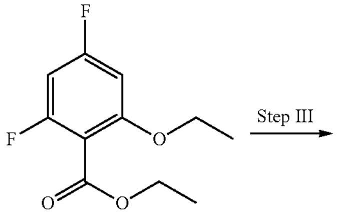

54-3

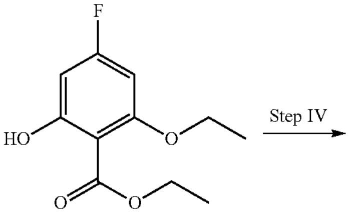

54-4

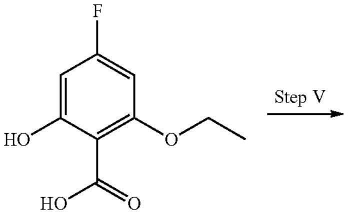

54-5

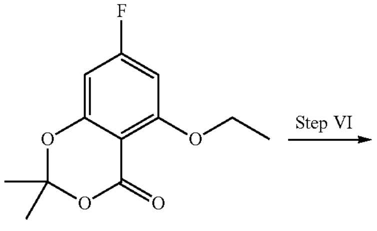

54-6

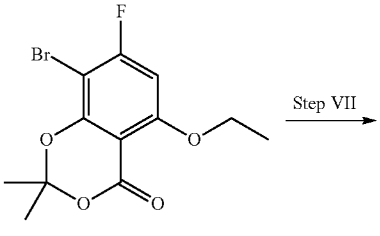

54-7

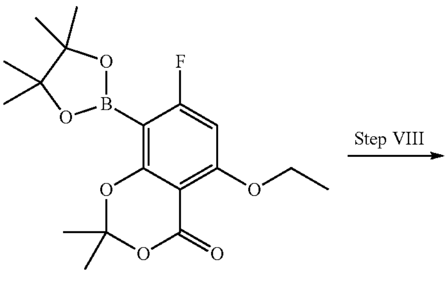

54-8

-continued

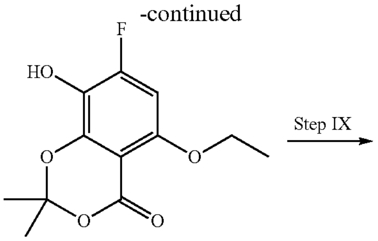

54-9

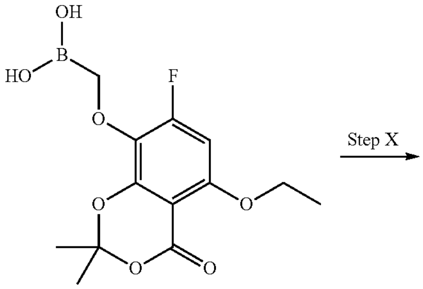

54-10

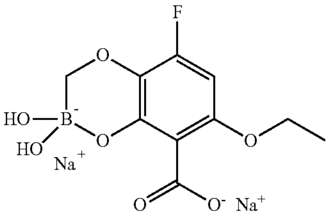

Compound 54

Step I: Preparation of Compound 54-2

Sodium hydroxide (25.44 g, 636.03 mmol, 4 eq) was added to a solution of compound 54-1 (28 g, 159.01 mmol, 1 eq) in N-methylpyrrolidone (280 mL). The mixture was stirred at 130° C. for 2 hours. Hydrochloric acid aqueous solution (350 mL, 2N) was added at 20° C. to quench the reaction mixture, which was then extracted with 500 mL of ethyl acetate. The organic layer was washed with 900 mL (300 mL×3) of brine, dried with anhydrous sodium sulfate, filtered, and concentrated under reduced pressure to obtain a residue. The residue was stirred with petroleum ether/methyl tert-butyl ether (5/1, 100 mL) and filtered to obtain a filter cake. The filtrate was concentrated and then purified by silica gel flash column chromatography (petroleum ether/ethyl acetate=10/1 to 0/1). The filter cake was combined with the product purified by column chromatography to obtain compound 54-2. $^1$H NMR (400 MHz, DMSO-$d_6$) δ=6.84-6.71 (m, 1H), 6.65 (br d, J=10.5 Hz, 1H).

Step II: Preparation of Compound 54-3

Compound 54-2 (7.5 g, 43.08 mmol, 1 eq), iodoethane (20.16 g, 129.23 mmol, 10.34 mL, 3 eq), and potassium carbonate (14.88 g, 107.70 mmol, 2.5 eq) were mixed in N,N-dimethylformamide (80 mL), the mixture was degassed, and after displacement with nitrogen 3 times, the mixture was then stirred at 80° C. for 12 hours in a nitrogen atmosphere. 50 mL of water was added to the reaction mixture, and the reaction mixture was then extracted with 50 mL of ethyl acetate. The organic layer was washed with aqueous saturated table salt (30 mL×3), dried over anhydrous sodium sulfate, filtered, and concentrated under reduced pressure to obtain compound 54-3. $^1$H NMR (400 MHz, $CDCl_3$) δ=6.46 (d, J=10.2 Hz, 2H), 4.47-4.36 (m, 2H), 4.07 (d, J=6.9 Hz, 2H), 1.41 (td, J=7.1, 18.6 Hz, 6H).

Step III: Preparation of Compound 54-4

At 0-5° C., sodium hydride (3.36 g, 84.10 mmol, 60% purity, 2.2 eq) was added in portions to a solution of compound 54-3 (8.8 g, 38.23 mmol, 1 eq) and 2-methylsulfonylethanol (5.22 g, 42.05 mmol, 1.1 eq) in N,N-dimethylformamide (90 mL). The mixture was stirred at 20° C. for 1 hour. The reaction mixture was quenched by adding a hydrochloric acid aqueous solution (200 mL, 0.5 N) and then extracted with 50 mL of ethyl acetate. The organic layer was washed with 50 mL of brine, dried over anhydrous sodium sulfate, filtered, and concentrated under reduced pressure, and the residue was purified by silica gel flash column chromatography (petroleum ether/ethyl acetate=100/1 to 50/1) to obtain 54-4. $^1$H NMR (400 MHz, $CDCl_3$) δ=12.01 (d, J=1.4 Hz, 1H), 6.30 (dd, J=2.4, 10.1 Hz, 1H), 6.13 (dd, J=2.4, 11.2 Hz, 1H), 4.40 (q, J=7.1 Hz, 2H), 4.04 (q, J=6.9 Hz, 2H), 1.52-1.36 (m, 6H). LCMS (ESI) m/z: 229.0 (M+1).

Step IV: Preparation of Compound 54-5

A solution of sodium hydroxide (4.42 g, 110.42 mmol, 4 eq) in water (20 mL) was added to a solution of compound 54-4 (6.3 g, 27.61 mmol, 1 eq) in ethanol (40 mL). The mixture was stirred at 80° C. for 12 hours. The reaction mixture was adjusted to pH<3 with a hydrochloric acid aqueous solution (200 mL, 1N) and then extracted with 100 mL of ethyl acetate. The organic layer was washed with 100 mL of brine, dried over anhydrous sodium sulfate, filtered, and concentrated under reduced pressure to obtain a residue. Compound 54-5 was obtained. LCMS (ESI) m/z: 201.1 (M+1); $^1$H NMR (400 MHz, $CDCl_3$) δ=12.53 (d, J=1.5 Hz, 1H), 6.44 (dd, J=2.4, 10.1 Hz, 1H), 6.24 (dd, J=2.3, 10.3 Hz, 1H), 4.32 (q, 1=7.1 Hz, 2H), 1.61 (t, J=7.0 Hz, 3H).

Step V: Preparation of Compound 54-6

At 0-5° C., acetone (23.70 g, 408.06 mmol, 30 mL, 16.02 eq) and trifluoroacetic anhydride (21.41 g, 101.92 mmol, 14.18 mL, 4 eq) were added to a solution of compound 54-5 (5.1 g, 25.48 mmol, 1 eq) in trifluoroacetic acid (30 mL). The mixture was stirred at 100° C. for 16 hours. The reaction mixture was concentrated under reduced pressure to remove the solvent. The residue was diluted with 100 mL of a sodium bicarbonate aqueous solution and extracted with 100 mL of ethyl acetate. The organic layer was washed with 30 mL of brine, dried over anhydrous sodium sulfate, filtered, and concentrated under reduced pressure to obtain a residue. The residue was purified by silica gel flash column chromatography (petroleum ether/ethyl acetate=20/1 to 10/1). The residue was stirred with petroleum ether (20 mL) and filtered, and the filter cake was dried to obtain compound 54-6. LCMS (ESI) m/z: 241.0 (M+1); $^1$H NMR (400 MHz, $CDCl_3$) δ=6.25 (dd, J=2.2, 11.3 Hz, 1H), 6.19 (dd, J=2.3, 9.1 Hz, 1H), 4.07 (q, J=7.0 Hz, 2H), 1.63 (s, 6H), 1.50-1.40 (m, 3H).

Step VI: Preparation of Compound 54-7

N-bromosuccinimide (2.78 g, 15.61 mmol, 1.5 eq.) and then acetic acid (2.50 g, 41.63 mmol, 2.38 mL, 4 eq) were added to a solution of compound 54-6 (2.5 g, 10.41 mmol, 1 eq) in tetrahydrofuran (25 mL), the mixture was stirred at 80° C. for 1 h, NBS (926.12 mg, 5.20 mmol, 0.5 eq) was then added, and the mixture was stirred at 80° C. for 1 hour. After another 2 hours, the reaction mixture was concentrated under reduced pressure to remove the solvent. The residue was diluted with 50 mL of a sodium bicarbonate aqueous solution and extracted with ethyl acetate (50 mL×2). The combined organic layers were washed with 20 mL of brine, dried over anhydrous sodium sulfate, filtered, and concentrated under reduced pressure to obtain a residue. The residue was purified by silica gel flash column chromatography (petroleum ether/ethyl acetate=20/1 to 10/1). Compound 54-7 was obtained. LCMS (ESI) m/z: 318.8/320.8 (M+1/M+3); $^1$H NMR (400 MHz, $CDCl_3$) δ=6.49 (d, J=10.9 Hz, 1H), 4.17 (q, J=7.0 Hz, 2H), 1.78 (s, 6H), 1.57-1.49 (m, 3H).

Step VII: Preparation of Compound 54-8

Compound 54-7 (1.8 g, 5.64 mmol, 1 eq), 4,4,5,5-tetramethyl-2-(4,4,5,5-tetramethyl-1,3,2-dioxaborolane-2-yl)-1,3,2-dioxaborolane (4.30 g, 16.92 mmol, 3 eq), potassium acetate (1.94 g, 19.74 mmol, 3.5 eq), and Pd(dppf)$Cl_2 \cdot CH_2Cl_2$ (460.62 mg, 564.05 μmol, 0.1 eq) were mixed in dioxane (20 mL), the mixture was degassed, and after displacement with nitrogen 3 times, the mixture was then stirred and reacted at 90° C. for 12 hours in a nitrogen atmosphere. The reaction mixture was quenched by adding 100 mL of water and extracted with 100 mL of ethyl acetate. The organic layer was washed with 50 mL of brine, dried over anhydrous sodium sulfate, filtered, and concentrated under reduced pressure to obtain a residue. The residue was purified by silica gel flash column chromatography (petroleum ether/ethyl acetate=10/1 to 6/1). Compound 54-8 was obtained. LCMS (ESI) m/z: 367.0 (M+1).

Step VIII: Preparation of Compound 54-9

Compound 54-8 (550 mg, 1.50 mmol, 1 eq) was dissolved in tetrahydrofuran (5 mL) and water (5 mL), and sodium perborate tetrahydrate (462.18 mg, 3.00 mmol, 577.73 μL, 2 eq) was added. The mixture was stirred at 20° C. for 1 hour. The reaction mixture was diluted with 10 mL of water, and the mixture was adjusted to pH<7 with a hydrochloric acid aqueous solution (0.5 N) and then extracted with 20 mL of ethyl acetate. The organic layer was washed with 10 mL of brine, dried over sodium sulfate, filtered, and concentrated under reduced pressure to obtain a residue. The residue was purified by silica gel flash column chromatography (petroleum ether/ethyl acetate=5/1 to 3/1). Compound 54-9 was obtained. LCMS (ESI) m/z: 257.1 (M+1).

Step IX: Preparation of Compound 54-10

Compound 54-9 (180 mg, 702.50 μmol, 1 eq), 2-(iodomethyl)-4,4,5,5-tetramethyl-1,3,2-dioxaborolane (263.48 mg, 983.50 μmol, 1.4 eq), and potassium carbonate (145.64 mg, 1.05 mmol, 1.5 eq) were mixed in acetonitrile (2 mL), the mixture was degassed, and after displacement with nitrogen 3 times, it was then stirred at 60° C. for 4 hours in a nitrogen atmosphere. The reaction mixture was adjusted to pH<3 with a hydrochloric acid aqueous solution (1 N) and then extracted with 10 mL of ethyl acetate, and the organic layer was washed with 10 mL of brine, dried over anhydrous sodium sulfate, filtered, and concentrated under reduced pressure to obtain compound 54-10. LCMS (ESI) m/z: 315.1 (M+1).

Step X: Preparation of Compound 54

Compound 54-10 (220 mg, 700.48 μmol, 1 eq) was dissolved in isopropanol (2 mL), and sodium hydroxide (2 M, 875.60 μL, 2.5 eq) was added. The mixture was stirred at 20° C. for 1 hour. The mixture was filtered to obtain a filtrate. The residue was purified by preparative HPLC (chromatographic column: Waters Xbridge 150×25 mm×5 μm; mobile phase: 10 mmol/L ammonium bicarbonate aqueous solution and acetonitrile; the proportion of acetonitrile in the mobile phase was from 1% to 6%, 4 min). Compound 54 was obtained. $^{1}H$ NMR (400 MHz, $D_2O$) δ=6.20 (d, J=12.8 Hz, 1H), 3.87 (q, J=7.0 Hz, 2H), 3.23 (s, 2H), 1.18 (t, J=7.0 Hz, 3H); LCMS (ESI) m/z: 257.0 (M+1).

Example 55

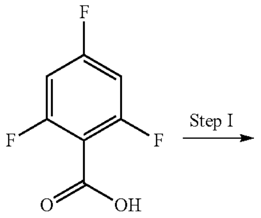

54-2

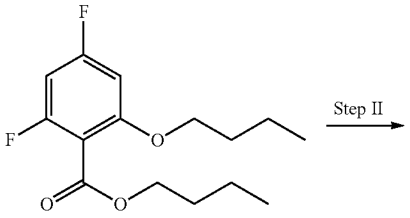

55-2

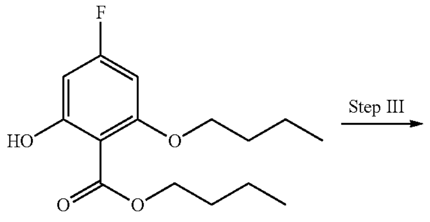

55-3

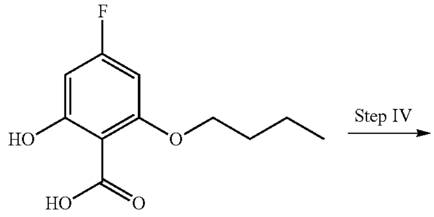

55-4

-continued

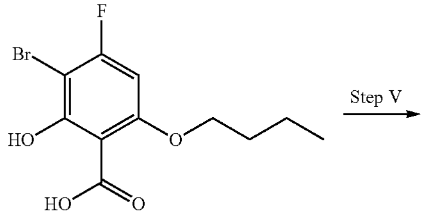

55-5

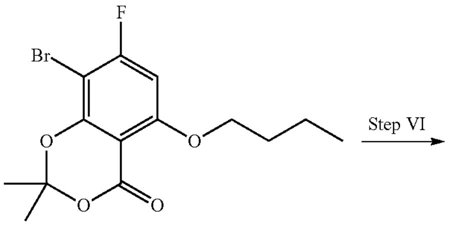

55-6

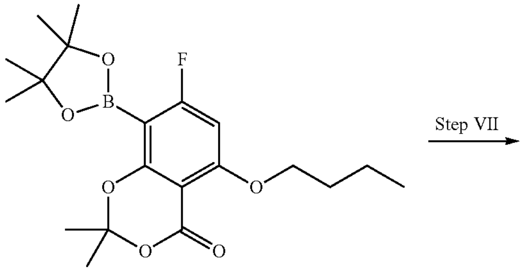

55-7

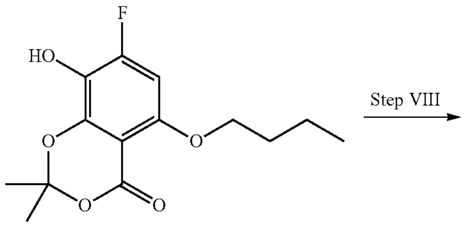

55-8

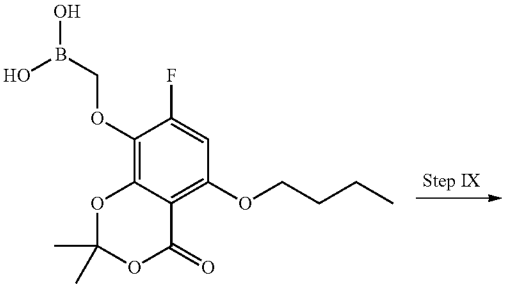

55-9

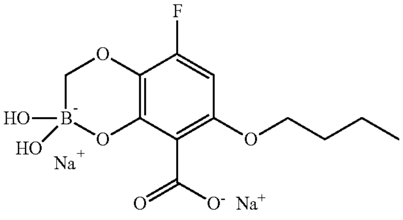

Compound 55

Step I: Preparation of Compound 55-2

Compound 54-2 (10 g, 57.44 mmol, 1 eq) was dissolved in a dimethylformamide solution (100 mL), potassium carbonate (19.85 g, 143.59 mmol, 2.5 eq) and 1-bromobutane (19.68 g, 143.59 mmol, 15.49 mL, 2.5 eq) were added at 25° C., and the mixture was then stirred at 80° C. for 16 hours. The residue was concentrated in vacuum, water (50 mL) was added, and the aqueous phase was extracted with ethyl acetate (100 mL 1). The combined organic phases were washed with brine (100 mL×1), dried with anhydrous $Na_2SO_4$, filtered, and concentrated in vacuum. The crude product was purified by silica gel chromatography (petroleum ether/ethyl acetate=100/1, 10/1). 55-2 was obtained. LCMS: 287.1 (M+1); $^1$H NMR (400 MHz, $CDCl_3$) δ=6.52-6.40 (m, 2H), 4.35 (t, J=6.6 Hz, 2H), 3.99 (t, J=6.4 Hz, 2H), 1.86-1.68 (m, 4H), 1.48 (quind, J=7.4, 14.9 Hz, 4H), 0.98 (t, J=7.4 Hz, 6H).

Step II: Preparation of Compound 55-3

Compound 55-2 (14 g, 48.90 mmol, 1 eq) and 2-methylsulfonylethanol (6.37 g, 51.34 mmol, 1.05 eq) were dissolved in a dimethylformamide solution (160 mL), and NaH (4.11 g, 102.68 mmol, 60% purity, 2.1 eq) was added in portions at 0-5° C. The mixture was stirred at 20° C. for 1 hour. The reaction mixture was quenched by adding an HCl aqueous solution (200 mL, 0.5 N) and then extracted with 300 mL of EA. The organic layer was washed with 300 mL of brine, dried over $Na_2SO_4$, filtered, and concentrated under reduced pressure, and the crude product was purified by silica gel chromatography (petroleum ether/ethyl acetate=300/1, 10/1). Compound 55-3 was obtained. LCMS: 285.4 (M+1); $^1$H NMR (400 MHz, $CDCl_3$) δ=12.01 (d, J=1.5 Hz, 1H), 6.20 (dd, J=2.4, 10.0 Hz, 1H), 6.05 (dd, J=2.4, 11.4 Hz, 1H), 4.26 (t, J=6.5 Hz, 2H), 3.87 (t, J=6.3 Hz, 2H), 1.81-1.59 (m, 4H), 1.54-1.32 (m, 4H), 0.91 (dt, J=3.7, 7.4 Hz, 6H).

Step III: Preparation of Compound 55-4

Compound 55-3 (430 mg, 1.51 mmol, 1 eq) was dissolved in an ethanol solution (5 mL), and NaOH (241.96 mg, 6.05 mmol, 4 eq) in $H_2O$ (1 mL) was added at 20° C. The mixture was stirred at 85° C. for 16 hours. The reaction mixture was adjusted to pH<3 with an HCl aqueous solution (10 mL, 1N) and then extracted with 10 mL of EA. The organic layer was washed with 10 mL of brine, dried over $Na_2SO_4$, filtered, and concentrated under reduced pressure to obtain a residue. 55-4 was obtained. LCMS (ESI) m/z: 229.1 (M+1).

Step IV: Preparation of Compound 55-5

Compound 55-5 (500 mg, 2.19 mmol, 1 eq) was dissolved in a dichloromethane solution (5 mL), a solution of liquid bromine (350.12 mg, 2.19 mmol, 112.94 μL, 1 eq) in dichloromethane (0.5 mL) was added at −30° C., and the mixture was then slowly heated to 20° C. and stirred for 1 hour. The crude product was poured into $Na_2SO_3$ (10 mL) and stirred for 10 minutes. The aqueous phase was extracted with dichloromethane (10 mL×2). The combined organic phases were washed with brine (20 mL×1), dried with anhydrous $Na_2SO_4$, filtered, and concentrated in vacuum to obtain 55-5. LCMS (ESI) m/z: 307.3 (M+1); $^1$H NMR (400 MHz, $CDCl_3$) δ=13.31 (d, J=1.6 Hz, 1H), 11.34 (s, 1H), 6.40 (d, J=10.0 Hz, 1H), 4.26 (t, J=6.5 Hz, 2H), 2.05-1.87 (m, 2H), 1.55 (s, =7.5 Hz, 2H), 1.05 (t, J=7.3 Hz, 3H).

Step V: Preparation of Compound 55-6

Compound 55-5 (4.9 g, 15.96 mmol, 1 eq) was dissolved in a trifluoroacetic acid solution (30 mL), acetone (23.70 g, 408.06 mmol, 30 mL, 25.58 eq) and trifluoroacetic anhydride (13.40 g, 63.82 mmol, 8.88 mL, 4 eq) were added, and the mixture was stirred at 0° C. and then at 100° C. for 16 hours. The solution was concentrated in vacuum, $H_2O$ (50 mL) was then added, and the mixture was extracted with ethyl acetate (50 mL×2). The combined organic phases were washed with $NaHCO_3$ (100 mL×1) and brine (100 mL×1), dried with anhydrous $Na_2SO_4$, filtered, and concentrated in vacuum. The residue was purified by silica gel column chromatography (petroleum ether/ethyl acetate=100/1, 50/1). Compound 55-6 was obtained. LCMS (ESI) m/z: 347 (M+1); $^1$H NMR (400 MHz, $CDCl_3$) δ=6.40 (d, J=10.9 Hz, 1H), 3.98 (t, J=6.5 Hz, 2H), 1.86-1.76 (m, 2H), 1.68 (s, 6H), 1.48 (qd, J=7.4, 15.0 Hz, 2H), 0.92 (t, J=7.4 Hz, 3H).

Step VI: Preparation of Compound 55-7

Compound 55-6 (2.5 g, 7.20 mmol, 1 eq), 4,4,5,5-tetramethyl-2-(4,4,5,5-tetramethyl-1,3,2-dioxaborolane-2-yl)-1,3,2-dioxaborolane (4.57 g, 18.00 mmol, 2.5 eq), potassium acetate (2.12 g, 21.60 mmol, 3 eq) and $Pd(dppf)Cl_2 \cdot CH_2Cl_2$ (588.06 mg, 720.10 μmol, 0.1 eq) were dissolved in a dioxane solution (25 mL), and the mixture was then stirred at 82° C. for 16 h. The reaction mixture was concentrated under reduced pressure to remove the solvent. $H_2O$ (30 mL) was added to the solution, and the aqueous phase was extracted with ethyl acetate (50 mL×2). The combined organic phases were washed with brine (100 mL), dried with anhydrous $Na_2SO_4$, filtered, and concentrated in vacuum. The residue was purified by silica gel chromatography (petroleum ether/ethyl acetate=10/1 to 0/1). Compound 55-7 was obtained. LCMS (ESI) m/z: 395.2 (M+1).

Step VII: Preparation of Compound 55-8

Compound 55-7 (3.7 g, 9.39 mmol, 1 eq) was dissolved in tetrahydrofuran (20 mL) and $H_2O$ (20 mL), and sodium perborate tetrahydrate (4.33 g, 28.16 mmol, 5.41 mL, 3 eq) was added at 25° C. and stirred for 2 hours. $H_2O$ (50 mL) was added to the solution, and the mixed solution was extracted with ethyl acetate (50 mL×2). The combined organic phases were washed with brine (100 mL×1), dried with anhydrous $Na_2SO_4$, filtered, and concentrated in vacuum. The crude product was purified by silica gel chromatography (petroleum ether/ethyl acetate=10/1 to 5/1). Compound 55-8 was obtained. LCMS (ESI) m/z: 285.3 (M+1); $^1$H NMR (400 MHz, $CDCl_3$) δ=6.42 (d, J=12.8 Hz, 1H), 4.01 (t, 0.1=6.6 Hz, 2H), 1.88 (br d, J=7.0 Hz, 2H), 1.77 (s, 6H), 1.60-1.52 (m, 2H), 1.00 (t, J=7.4 Hz, 3H).

Step VIII: Preparation of Compound 55-9

Compound 55-8 (300 mg, 1.06 mmol, 1 eq) was dissolved in an acetonitrile solution (5 mL), and 2-(iodomethyl)-4,4,5,5-tetramethyl-1,3,2-dioxaborolane (424.07 mg, 1.58 mmol, 1.5 eq) and $K_2CO_3$ (218.78 mg, 1.58 mmol, 1.5 eq) were added at 25° C. and then stirred at 60° C. for 2 hours. $H_2O$ (5 mL) was added to the solution, and the aqueous phase was extracted with ethyl acetate (10 mL×2). The combined organic phases were washed with brine (30 mL), dried with anhydrous $Na_2SO_4$, filtered, and concentrated in vacuum. Compound 55-9 was obtained. LCMS (ESI) m/z: 343.3 (M+1).

Step IX: Preparation of Compound 55

Compound 55-9 (200 mg, 479.36 μmol, 82% purity, 1 eq) was dissolved in an i-PrOH solution (2 mL), and NaOH (3 M, 319.57 μL, 2 eq) was added and then stirred at 25° C. for 2 hours. The mixture was filtered, and the filtrate was used for preparative HPLC. The filtrate was purified by preparative HPLC (chromatographic column: Waters Xbridge 150×25 mm×5 μm; mobile phase: 10 mmol/L ammonium bicarbonate aqueous solution and acetonitrile; the proportion of acetonitrile in the mobile phase was from 1% to 20%, 7 min). Compound 55 was obtained. LCMS (ESI) m/z: 285 (M+1), 267.1 (M−18+1); $^1H$ NMR (400 MHz, $D_2O$) δ=6.19 (br d, J=12.8 Hz, 1H), 3.81 (t, J=6.5 Hz, 2H), 3.32-3.18 (m, 2H), 1.59-1.50 (m, 2H), 1.34-1.25 (m, 2H), 0.79 (t, J=7.4 Hz, 3H).

Example 56

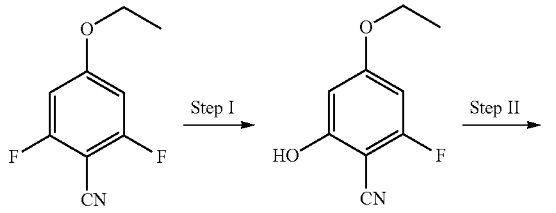

56-1 56-2

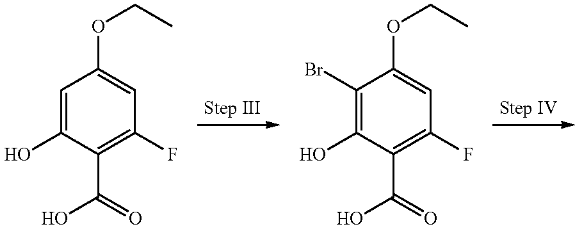

56-3 56-4

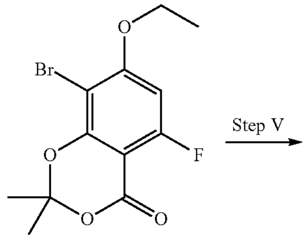

56-5

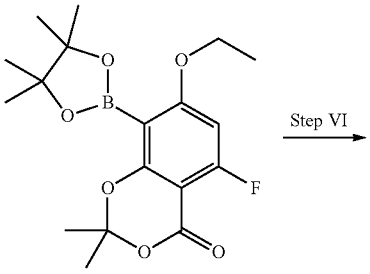

56-6

-continued

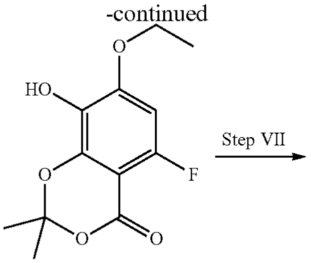

56-7

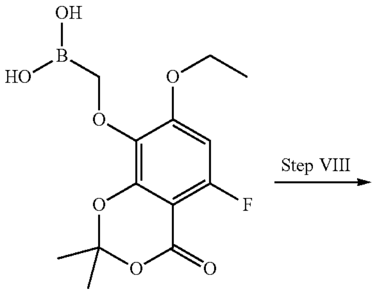

56-8

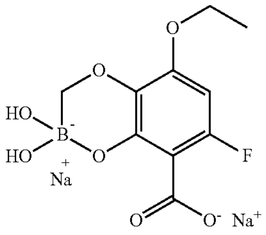

Compound 56

Step I: Preparation of Compound 56-2

Compound 56-1 (7.2 g, 39.31 mmol, 1 eq) and 2-methanesulfonylethanol (4.88 g, 39.31 mmol, 1 eq) were dissolved in DMF (72 mL), NaH (3.14 g, 78.62 mmol, 60% purity, 2 eq) was added in portions at 0° C., and the mixture was stirred at 20° C. for 0.5 hour. The reaction mixture was slowly poured into ice water (100 mL) and extracted with ethyl acetate (150 mL). The aqueous phase was adjusted to pH=2 with HCl and extracted with 300 mL of ethyl acetate 400 mL (400 mL×2). The combined organic phases were washed with brine (300 mL), dried with $Na_2SO_4$, filtered, and concentrated under reduced pressure to obtain compound 56-2.

Step I: Preparation of Compound 56-3

Compound 56-2 (6.2 g, 34.22 mmol, 1 eq) was dissolved in ethanol (20 mL), NaOH (8 M, 42.78 mL, eq) was added at room temperature, and the mixture was stirred at 120° C. for 48 hours. Concentration under reduced pressure was carried out to remove ethanol, the concentrate was then diluted with 100 mL of $H_2O$, adjusted to pH=3 with HCl, and then extracted with 150 mL of ethyl acetate (150 mL×1), the aqueous phase was adjusted to pH=2 with HCl, and after filtration, the filter cake was dried under reduced pressure to obtain a crude product, which was stirred with petroleum ether/ethyl acetate=10/1 (55 mL) at 20° C. for 30 minutes and filtered, and the filter cake was dried to obtain compound 56-3. LCMS (ESI) m/z: 201.1 (M+1).

Step III: Preparation of Compound 56-4

Compound 56-3 (3.12 g, 15.59 mmol, 1 eq) was dissolved in DCM (30 mL), and NBS (2.77 g, 15.59 mmol, 1 eq) was added at room temperature. The mixture was stirred at 0° C. for 2 hours, and the reaction mixture was concentrated under reduced pressure to remove the solvent. The residue was diluted with 60 mL of $H_2O$, extracted with EA (30 mL×2), washed with brine (30 mL×2), dried with $Na_2SO_4$, filtered, and concentrated under reduced pressure to obtain a crude product, which was purified by preparative HPLC (chromatographic column: Phenomenex Synergi Max-RP 250×50 mm×10 μm; mobile phase: water (0.1% TFA) and acetonitrile, the proportion of acetonitrile in the mobile phase was from 30% to 60%, 20 min) to obtain compound 56-4. $^1H$ NMR (400 MHz, DMSO-$d_6$) δ=6.73-6.64 (m, 1H), 4.24-4.13 (m, 2H), 1.41-1.31 (m, 3H).

Step IV: Preparation of Compound 56-5

Compound 56-4 (637 mg, 2.28 mmol, 1 eq) was dissolved in TFA (6 mL), acetone (1.33 g, 22.83 mmol, 1.68 mL, 10 eq) was added at 0° C., TFAA (1.44 g, 6.85 mmol, 952.51 μL, 3 eq) was added dropwise, and after displacement with nitrogen several times, the reaction product was stirred at 100° C. under $N_2$ for 12 hours. Concentration under reduced pressure was carried out to remove the solvent, and the concentrate was diluted with 20 mL of $H_2O$ and extracted with EA (30 mL×2). It was washed with 30 mL of brine (30 mL), dried over $Na_2SO_4$, filtered, and concentrated under reduced pressure to obtain a residue, which was purified by column chromatography ($SiO_2$, petroleum ether/ethyl acetate=10/1) to obtain compound 56-5. LCMS (ESI) m/z: 321.0 (M+3).

Step V: Preparation of Compound 56-6

Compound 56-5 (484 mg, 758.33 μmol, 50% purity, 1 eq) was dissolved in dioxane (10 mL), and pinacol boronate (577.70 mg, 2.27 mmol, 3 eq), potassium acetate (260.48 mg, 2.65 mmol, 3.5 eq) and Pd(dppf)$Cl_2$ (262.89 mg, 227.50 μmol, 0.3 eq) were then added under nitrogen flow. The mixture was stirred at 70° C. for 48 hours under nitrogen protection. The reaction mixture was filtered, then diluted with 30 mL of water, extracted with ethyl acetate (30 mL×2), washed with 30 mL of brine (30 mL×1), dried over $Na_2SO_4$, filtered, and concentrated under reduced pressure to obtain a residue. The residue was purified by column chromatography ($SiO_2$, petroleum ether/ethyl acetate=5/1 to 2/1) to obtain compound 56-6. LCMS (ESI) m/z: 367.2 (M+1).

Step VI: Preparation of Compound 56-7

Compound 56-6 (806 mg, 2.20 mmol, 1 eq) was dissolved in a mixed solution of THF (8 mL) and $H_2O$ (8 mL). Sodium perborate tetrahydrate (1.02 g, 6.60 mmol, 3 eq) was added at 20° C., and the mixture was stirred at 20° C. for 1 hour. The reaction liquid was diluted with 20 mL of water, then extracted with 80 mL of ethyl acetate (40 mL×2), washed with brine (40 mL), dried with anhydrous $Na_2SO_4$, filtered, and concentrated in vacuum. The residue was purified by column chromatography ($SiO_2$, petroleum ether/ethyl acetate=10/1 to 4/1) to obtain compound 56-7. LCMS (ESI) m/z: 257.2 (M+1).

Step VII: Preparation of Compound 56-8

Compound 56-7 (20 mg, 78.06 μmol, 1 eq) was dissolved in $CH_3CN$ (1 mL), and 2-iodomethyl pinacol boronate (25.09 mg, 93.67 μmol, 1.2 eq) and $K_2CO_3$ (12.95 mg, 93.67 μmol, 1.2 eq) were added in sequence at room temperature; and after the addition was complete, displacement with nitrogen was performed 3 times, and the mixture was then stirred at 60° C. for 6 hours under $N_2$. The reaction mixture was concentrated under reduced pressure to remove the solvent $CH_3CN$. The residue was diluted with 20 mL of $H_2O$, adjusted to pH=3 with 1M HCl, and extracted with 60 mL of ethyl acetate (30 mL×2). The combined organic layers were washed with 20 mL of brine (20 mL×1), dried over $Na_2SO_4$, filtered, and concentrated under reduced pressure to obtain compound 56-8 as a yellow oil. LCMS (ESI) m/z: 315.1 (M+1).

Step VIII: Preparation of Compound 56

Compound 56-8 (24 mg, 76.42 μmol, 1 eq) was dissolved in i-PrOH (1 mL), and NaOH (2 M, 76.42 μL, 2 eq) was added dropwise at room temperature. The mixture was stirred at 20° C. for 2 hours. The reaction mixture was diluted with 1 mL of $H_2O$ and purified by preparative HPLC (chromatographic column: Waters Xbridge 150×25 mm×5 μm; mobile phase: 10 mmol/L ammonium bicarbonate aqueous solution and acetonitrile; the proportion of acetonitrile in the mobile phase was from 0% to 10%, 10 min) to obtain compound 56. LCMS (ESI) m/z: 257.1 (M+1). $^1H$ NMR (400 MHz, $D_2O$) δ=6.33 (d, J=12.72 Hz, 1H), 4.03 (q, J=6.97 Hz, 2H), 3.27 (s, 2H), 1.31 (t, J=7.03 Hz, 3H).

Example 57

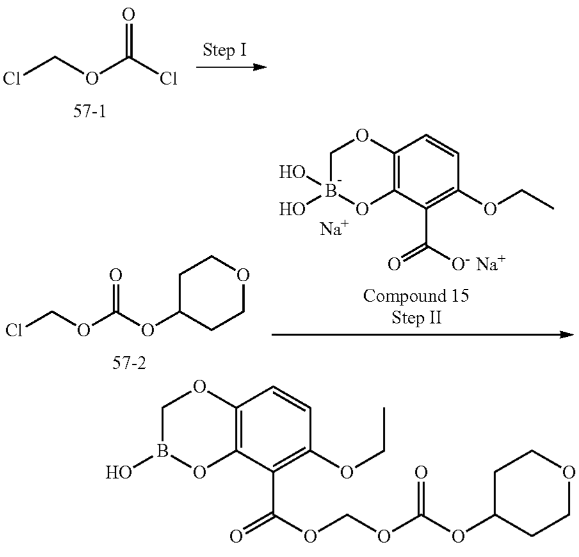

Step I: Preparation of Compound 57-2

Compound 57-1 (5.12 g, 39.71 mmol, 3.53 mL, 1 eq) was dissolved in DCM (100 mL), pyridine (3.20 g, 40.50 mmol, 3.27 mL, 1.02 eq) was added at room temperature, and 4-hydroxytetrahydropyran (5 g, 48.96 mmol, 4.90 mL, 1.23 eq) was added at 0° C. The mixture was stirred at 20° C. for 4 hours, quenched by adding 50 mL of $H_2O$ at 20° C., and extracted with 100 mL of DCM (50 mL×2), and the combined organic phases were washed with 200 mL (100 mL×2)

of brine, dried over $Na_2SO_4$, filtered, and concentrated under reduced pressure to obtain compound 57-2, $^1H$ NMR (400 MHz, $CDCl_3$) δ=5.73-5.63 (s, 2H), 4.90-4.77 (m, 1H), 3.93-3.81 (m, 2H), 3.53-3.40 (m, 2H), 2.01-1.91 (m, 2H), 1.77-1.63 (m, 2H).

Step II: Preparation of Compound 57

Compound 15 (126.04 mg, 420.17 μmol, 1 eq), compound 57-2 (163.54 mg, 840.33 μmol, 2 eq), 5 $K_2CO_3$ (116.14 mg, 840.33 μmol, 2 eq), and potassium iodide (139.50 mg, 840.33 μmol, 2 eq) were dissolved in DMF (2 mL), and after displacement with nitrogen 3 times, the mixture was stirred at 50° C. for 12 hours under $N_2$. The reaction mixture was 1 mL of $H_2O$ and 1 mL of acetonitrile and purified by preparative HPLC (chromatographic column: Waters Xbridge 150×25 mm×5 μm; mobile phase: 10 mmol/L ammonium bicarbonate aqueous solution and acetonitrile; the proportion of acetonitrile in the mobile phase was from 10% to 40%, 10 min) to obtain compound 57. LCMS (ESI) m/z: 792.1 (2M); $^1H$ NMR (400 MHz, $CD_3OD$) δ=6.69 (d, J=8.78 Hz, 1H), 6.29 (d, J=8.78 Hz, 1H), 5.92 (s, 2H), 3.99 (s, 1H), 3.99-3.93 (m, 1H), 3.93-3.88 (m, 2H), 3.57 (ddd, J=11.80, 8.78, 3.01 Hz, 2H), 3.44 (s, 2H), 2.07-1.95 (m, 2H), 1.72 (dtd, J=13.05, 8.75, 8.75, 3.95 Hz, 2H), 1.31 (t, J=6.96 Hz, 3H).

Example 58

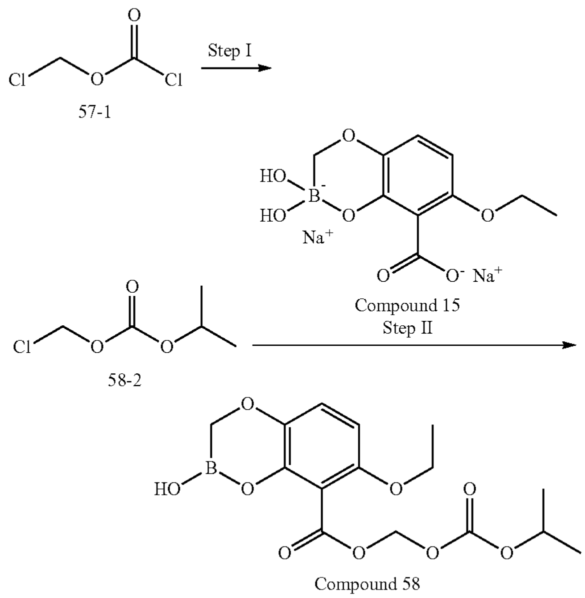

57-1
Compound 15
58-2
Compound 58

Step I: Preparation of Compound 58-2

Compound 57-1 (5 g, 38.78 mmol, 3.45 mL, 1 eq), and pyridine (3.13 g, 39.55 mmol, 3.19 mL, 1.02 eq) were dissolved in a dichloromethane solution, isopropanol (2.33 g, 38.78 mmol, 2.97 mL, 1 eq) was then added at 0° C., and the mixture was then slowly heated to 20° C. and stirred for 5 hours. Ice water (50 mL) was added to the solution and stirred for 10 minutes. The aqueous phase was extracted with DCM (50 mL×2). The combined organic phases were washed with brine (200 mL×1), dried with anhydrous $Na_2SO_4$, filtered, and concentrated in vacuum. Compound 58-2 was obtained. $^1H$ NMR (400 MHz, $CDCl_3$) δ=5.70-5.64 (m, 2H), 4.89 (s, J=6.3 Hz, 1H), 1.27 (d, J=6.3 Hz, 6H).

Step II: Preparation of Compound 58

Compound 15 (0.1 g, 333.36 μmol, 1 eq), potassium carbonate (138.22 mg, 1.00 mmol, 3 eq), and potassium iodide (166.01 mg, 1.00 mmol, 3 eq) were added to DMF (2 mL) and isopropyl chloromethyl carbonate (i.e., compound 58-2, 101.72 mg, 666.71 μmol, 2 eq) at 25° C. in a nitrogen atmosphere. The mixture was heated to 50° C. and maintained for 12 hours. $H_2O$ (2 mL) was added to the solution, the solution was filtered, and the filtrate was purified by preparative HPLC (column: Waters Xbridge 150×25 mm×5 μm; mobile phase: 10 mmol/L ammonium bicarbonate aqueous solution and acetonitrile; the proportion of acetonitrile in the mobile phase was from 14% to 44%, 10 min). Compound 58 was obtained. LCMS (ESI) m/z: 708 (2M); $^1H$ NMR (400 MHz, $CD_3OD$) δ=6.67 (d, J=8.7 Hz, 1H), 6.26 (d, J=9.0 Hz, 1H), 5.90 (s, 2H), 3.96 (q, J=7.0 Hz, 2H), 3.42 (s, 2H), 3.34 (br s, 1H), 1.32 (d, J=6.4 Hz, 9H).

Example 59

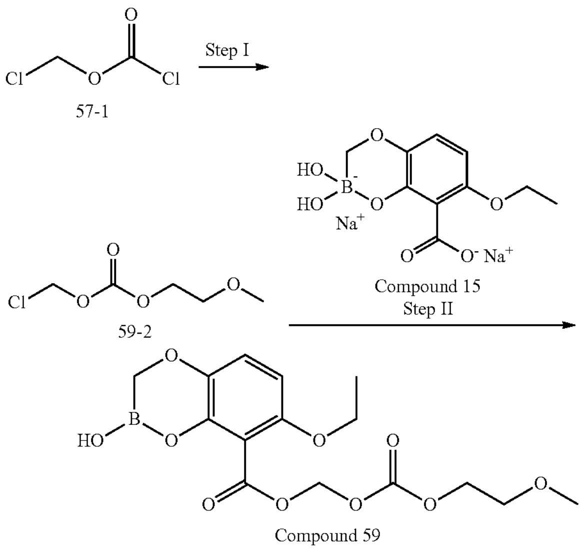

57-1
Compound 15
59-2
Compound 59

Step I: Preparation of Compound 59-2

At 0-5° C., pyridine (1.93 g, 24.43 mmol, 1.97 mL, 1.05 eq) and 2-methoxyethanol (1.86 g, 24.43 mmol, 1.05 eq) were added to a solution of 57-1 (3 g, 23.27 mmol, 2.07 mL, 1 eq) in dichloromethane (50 mL). The mixture was stirred at 20° C. for 12 hours. The reaction mixture was quenched by adding 50 mL of water, and the organic layer was then washed with 20 mL of a hydrochloric acid aqueous solution and water (20 mL×2), dried over anhydrous sodium sulfate, filtered, and concentrated under reduced pressure to obtain compound 59-2. $^1H$ NMR (400 MHz, $CDCl_3$) δ=5.76 (s, 2H), 4.39 (dd, J=3.8, 5.4 Hz, 2H), 3.66 (dd, J=3.9, 5.4 Hz, 2H), 3.42 (s, 3H).

Step II: Preparation of Compound 59

Compound 15 (100 mg, 333.36 μmol, 1 eq), compound 59-2 (112.39 mg, 666.72 μmol, 2 eq), potassium iodide (166.01 mg, 1.00 mmol, 3 eq), and potassium carbonate (92.15 mg, 666.72 μmol, 2 eq) were mixed in N,N-dimethylformamide (1 mL), the mixture was degassed, and after displacement with nitrogen 3 times, the mixture was then stirred at 50° C. for 12 h in a nitrogen atmosphere. The reaction mixture was quenched by adding 0.5 mL of water and then filtered to obtain a filtrate. The filtrate was purified by preparative HPLC (column: Waters Xbridge 150×25 mm/5 μm; mobile phase: water with 10 mmol/L ammonium bicarbonate and acetonitrile; the proportion of acetonitrile in the mobile phase was from 5% to 35%, 8 min). Compound 59 was obtained. LCMS (ESI) m/z: 739.9 (2M); $^1$H NMR (400 MHz, $CD_3OD$) δ=6.65 (d, J=8.7 Hz, 1H), 6.22 (d, J=8.8 Hz, 1H), 5.92 (s, 2H), 4.36-4.30 (m, 2H), 3.95 (q, J=6.9 Hz, 2H), 3.68-3.60 (m, 2H), 3.38 (s, 5H), 1.30 (t, J=7.0 Hz, 3H).

Example 60

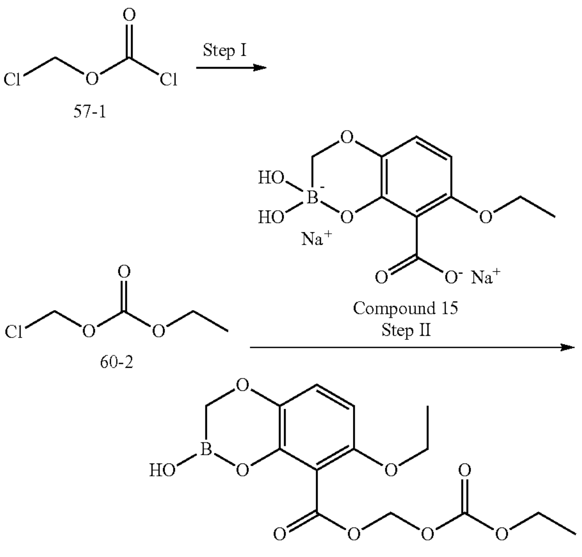

57-1

Compound 15

60-2

Compound 60

Step I: Synthesis of Compound 60-2

At 0-5° C., 57-1 (3 g, 23.27 mmol, 2.07 mL, 1 eq) was dissolved in dichloromethane (100 mL), and pyridine (1.88 g, 23.73 mmol, 1.92 mL, 1.02 eq) and ethanol (1.07 g, 23.27 mmol, 1 eq) were added. The mixture was stirred at 25° C. for another 8 hours. The reaction mixture was diluted with 20 mL of water and extracted with 60 mL (30 mL×2) of dichloromethane. The combined organic layers were washed with 30 mL of brine (30 mL×1), dried over sodium sulfate, filtered, and concentrated under reduced pressure to obtain compound 60-2. $^1$H NMR (400 MHz, $CDCl_3$) δ=5.78-5.66 (m, 2H), 4.29 (q, 1=7.2 Hz, 2H), 1.41-1.30 (m, 3H).

Step II: Synthesis of Compound 60

Compound 15 (100 mg, 333.36 μmol, 1 eq), potassium carbonate (138.22 mg, 1.00 mmol, 3 eq), and potassium iodide (166.01 mg, 1.00 mmol, 3 eq) were mixed in N,N-dimethylformamide (2 mL), the mixture was purged with nitrogen 3 times, and compound 60-2 (184.74 mg, 1.33 mmol, 4 eq) was then added at 25° C. in a nitrogen atmosphere. The mixture was then stirred at 50° C. for 16 hours. 10 mL of water was added to the mixture. The crude product was purified by preparative HPLC (chromatographic column: Waters Xbridge 150×25 mm×5 μm; mobile phase: water with 10 mmol/L ammonium bicarbonate and acetonitrile; the proportion of acetonitrile in the mobile phase was from 11% to 41%, 10 min). Compound 60 was obtained. LCMS (ESI) m/z: 680.1 (2M). $^1$H NMR (400 MHz, $CD_3OD$ δ=6.70 (d, J=8.9 Hz, 1H), 6.30 (d, J=8.9 Hz, 1H), 5.92 (s, 2H), 4.24 (q, J=7.2 Hz, 2H), 4.04-3.90 (m, 2H), 3.44 (s, 2H), 1.31 (dt, J=4.6, 7.0 Hz, 6H).

Biological Activity Test

Experimental Example 1: Detection of Compounds Restoring Antibacterial Effect of Antibiotics (MIC Shift)

The test compound was tested for minimum inhibitory concentration against three strains of *Klebsiella pneumoniae* ATCC BAA-1705 (KPC-2), ATCC BAA-2470 (NDM-1), and ARLG-1196 (CTM-1 group, SHV, NDM, TEM), and one strain of *Escherichia coli* ARLG-2829 (NDM-5, OXA-1). According to the requirements of the Institute of Clinical And Laboratory Standard (CLSI), the minimum inhibitory concentration (MIC) of each drug combination was determined by liquid microdilution method under the premise of fixing the concentration of meropenem at 4 μg/mL.

Preparation of compound mother plate: On the day of the experiment, the compound to be tested (the final concentration was 0.3125 to 20 μg/mL) and meropenem (the final concentration ranged from 1 to 64 μg/mL) were dissolved in a corresponding solvent (sterile $ddH_2O$ or DMSO) to form 100× mother liquors with the highest test concentration, and the compound to be tested and meropenem were then subjected to 2-fold series gradient dilution in a V-bottom 96-well plate to obtain 100× working solutions with the final concentration.

Preparation of inoculation solution: Fresh bacterial clones were picked from an overnight Mueller Hinton II Agar medium (MHA, Cat. No. 211438, BD BBLTM) plate, suspended in sterilized physiological saline, and adjusted to a concentration of $1\times10^8$ CFU/mL, and the suspension was further diluted to $5\text{-}10^5$ CFU/mL with Cation-Adjusted Mueller Hinton II Broth (MHB, Catalog #212332, BD BBLTM).

Detection of minimum inhibitory concentration (MIC): 1 μL of the compound to be tested and the meropenem working solution were transferred to the corresponding wells to be tested in a round-bottomed 96-well plate (Catalog #3788, Corning), and 98 μL of the inoculation solution was added to the round-bottomed 96-well plate containing drugs, which was an MIC test plate; and after the plate was inverted and cultured at 37° C. for 20-24 h, the MIC value was read, and the minimum inhibitory concentration for inhibiting bacterial growth was defined as MIC. The results were shown in Table 1.

The experimental results showed that the series of compounds of the present invention could restore the inhibitory activity of meropenem on the tested strains, and compared with meropenem alone, the combination with each compound at a certain concentration could restore the minimum inhibitory concentration (MIC) of meropenem to below the drug resistance breakpoint (MIC=4 μg/mL), with obvious MIC transition, indicating that the synthesized series of compounds had good inhibitory effects on β-lactamase (KPC-2, SHV, CTM-1 and isoforms thereof, NDM, TEM, OXA-1, etc.) expressed by the tested strains.

TABLE 1

Data of the detection (MIC shift) of the antibacterial effect of the compound of the present invention to restore the bacteriostatic effects of antibiotics

| Compound | Strain Drug resistance gene | MIC (μg/mL) *K. pneumoniae* ATCC BAA-1705 KPC-2 | *K. pneumoniae* ATCC BAA-2470 NDM-1 | *K. pneumoniae* ARLG-1196 CTM-1 and isoforms thereof, SHV, NDM, TEM | *E. coli* ARLG-2829 (Urine clinical isolate) NDM-5, OXA-1 |
|---|---|---|---|---|---|
| Meropenem | | 32 | 64 | 64 | >64 |
| 1 + meropenem (4 μg/mL) | | 0.0625 | >20 | >20 | >20 |
| 2 + meropenem (4 μg/mL) | | 20 | >20 | >20 | >20 |
| 3 + meropenem (4 μg/mL) | | ≤0.3125 | 5 | 2.5 | 5 |
| 4 + meropenem (4 μg/mL) | | ≤0.03 | 2.5 | 2.5 | 10 |
| 5 + meropenem (4 μg/mL) | | ≤0.3125 | 20 | 10 | >20 |
| 6 + meropenem (4 μg/mL) | | ≤0.03 | 10 | 10 | 20 |
| 7 + meropenem (4 μg/mL) | | ≤0.03 | 20 | 20 | >20 |
| 8 + meropenem (4 μg/mL) | | ≤0.3125 | 20 | 10 | 20 |
| 9 + meropenem (4 μg/mL) | | ≤0.3125 | >20 | >20 | >20 |
| 10 + meropenem (4 μg/mL) | | ≤0.03 | 5 | 2.5 | 10 |
| 11 + meropenem (4 μg/mL) | | ≤0.03 | 2.5 | 2.5 | 10 |
| 12 + meropenem (4 μg/mL) | | 0.06 | 5 | 2.5 | 10 |
| 14 + meropenem (4 μg/mL) | | ≤0.3125 | 5 | 2.5 | 10 |
| 15 + meropenem (4 μg/mL) | | ≤0.3125 | 0.625 | 0.625 | 1.25 |
| 16 + meropenem (4 μg/mL) | | 0.625 | 5 | 5 | 10 |
| 17 + meropenem (4 μg/mL) | | ≤0.3125 | 10 | 10 | 20 |
| 18 + meropenem (4 μg/mL) | | ≤0.3125 | 2.5 | 1.25 | 5 |
| 19 + meropenem (4 μg/mL) | | 0.625 | 1.25 | 1.25 | 5 |
| 20 + meropenem (4 μg/mL) | | 1.25 | 2.5 | 2.5 | 2.5 |
| 21 + meropenem (4 μg/mL) | | 1.25 | 5 | 1.25 | 2.5 |
| 22 + meropenem (4 μg/mL) | | ≤0.3125 | >20 | 20 | >20 |
| 23 + meropenem (4 μg/mL) | | 0.625 | 1.25 | 1.25 | 5 |
| 24 + meropenem (4 μg/mL) | | 0.625 | 2.5 | 2.5 | 5 |
| 25 + meropenem (4 μg/mL) | | ≤0.3125 | 1.25 | 0.625 | 2.5 |
| 26 + meropenem (4 μg/mL) | | 0.625 | 0.625 | 0.625 | 2.5 |
| 27 + meropenem (4 μg/mL) | | 0.625 | 1.25 | 0.625 | 1.25 |
| 28 + meropenem (4 μg/mL) | | 1.25 | 5 | 10 | 10 |
| 29 + meropenem (4 μg/mL) | | 0.625 | 2.5 | 1.25 | 5 |
| 30 + meropenem (4 μg/mL) | | ≤0.3125 | 10 | 2.5 | 2.5 |
| 31 + meropenem (4 μg/mL) | | <0.3125 | 5 | 1.25 | 2.5 |

Experimental Example 2: Detection of Compounds Restoring Antibacterial Effect of Antibiotics (MIC Shift)

The test compound was tested for minimum inhibitory concentration against 5 strains of *Klebsiella pneumoniae* ATCC BAA-1705 (KPC-2), ATCC BAA-2470 (NDM-1), ARLG-1196 (CTM-1 group, SHA NDM, TEM), NCTC 13440 (VIM-1), and NCTC 13439 (VIM), and one strain of *Escherichia coli* ARLG-2829 (NDM-5, OXA-1). According to the requirements of the Institute of Clinical And Laboratory Standard (CLSI), the minimum inhibitory concentration (MIC) of each drug combination was determined by liquid microdilution method under the premise of fixing the concentration of the compound to be tested at 8 μg/mL. The test method was the same as above, and the concentration of meropenem ranged from 0.125 to 8 μg/mL. The results were shown in Table 2.

The experimental results showed that the series of compounds of the present invention could restore the inhibitory activity of meropenem on the tested strains, and compared with meropenem alone, the combination with 8 μg/mL of each compound could significantly reduce the minimum inhibitory concentration (MIC) of meropenem, with obvious MIC transition, indicating that the synthesized series of compounds had good inhibitory effects on β-lactamase (KPC-2, SHV, CTM-1 isoforms thereof, NDM, NDM-12 NDM-5, TEM VIM, VIM-1, OXA-1, etc.) expressed by the tested strains.

TABLE 2

Data of the detection (MIC shift) of the antibacterial effect of the compound of the present invention to restore the bacteriostatic effects of antibiotics

| | | MIC (μg/mL) | | | | | |
|---|---|---|---|---|---|---|---|
| | | *K. pneumoniae* | | | | | *E. coli* |
| | Strain | ATCC BAA-1705 | ATCC BAA-2470 | ARLG-1196 | NCTC 13440 | NCTC 13439 | ARLG-2829 (Urine clinical isolate) |
| Compound | Drug resistance gene | KPC-2 | NDM-1 | CTM-1 and isoforms thereof, SHV, NDM, TEM | VIM-1 | VIM | NDM-5, OXA-1 |
| Meropenem | | 32 | 128 | 64 | 16 | 4 | 128 |
| 13 (8 μg/mL) + meropenem | | ≤0.125 | 0.25 | 0.5 | 8 | 2 | 0.25 |
| 15 (8 μg/mL) + meropenem | | ≤0.125 | ≤0.125 | ≤0.125 | 1 | 0.5 | 0.5 |
| 32 (8 μg/mL) + meropenem | | ≤0.125 | 0.25 | ≤0.125 | 2 | 0.5 | 0.5 |
| 33 (8 μg/mL) + meropenem | | ≤0.125 | 0.5 | 0.25 | 1 | 0.5 | 0.25 |
| 34 (8 μg/mL) + meropenem | | ≤0.125 | 0.5 | ≤0.125 | 4 | 0.5 | 0.5 |
| 35 (8 μg/mL) + meropenem | | 4 | >8 | 8 | 8 | 4 | >8 |
| 36 (8 μg/mL) + meropenem | | ≤0.125 | ≤0.125 | ≤0.125 | 1 | 0.5 | ≤0.125 |
| 37 (8 μg/mL) + meropenem | | ≤0.125 | 0.5 | ≤0.125 | 2 | 0.5 | 1 |
| 40 (8 μg/mL) + meropenem | | ≤0.125 | 1 | 0.25 | 0.5 | 0.25 | 2 |
| 41 (8 μg/mL) + meropenem | | ≤0.125 | 0.25 | ≤0.125 | 0.5 | 0.5 | 0.25 |
| 43 (8 μg/mL) + meropenem | | ≤0.125 | 0.5 | 0.25 | 2 | 0.5 | 1 |
| 44 (8 μg/mL) + meropenem | | ≤0.125 | 1 | 0.5 | 2 | 0.5 | 2 |
| 45 (8 μg/mL) + meropenem | | 0.5 | 8 | 0.5 | 8 | 2 | 2 |
| 46 (8 μg/mL) + meropenem | | 4 | >8 | >8 | 4 | 2 | 8 |
| 47 (8 μg/mL) + meropenem | | ≤0.125 | ≤0.125 | 1 | 4 | 4 | ≤0.125 |
| 48 (8 μg/mL) + meropenem | | 8 | >8 | >8 | >8 | 8 | >8 |
| 49 (8 μg/mL) + meropenem | | 4 | >8 | 2 | 4 | 2 | 4 |
| 52 (8 μg/mL) + meropenem | | ≤0.125 | 0.25 | 0.5 | 8 | 2 | 2 |
| 53 (8 μg/mL) + meropenem | | ≤0.125 | 1 | 0.5 | 8 | 2 | 2 |
| $4 (8 μg/mL) + meropenem | | ≤0.125 | ≤0.125 | ≤0.125 | 4 | 0.5 | ≤0.125 |
| 55 (8 μg/mL) + meropenem | | ≤0.125 | 0.5 | ≤0.125 | 4 | 1 | 0.25 |

Experimental Example 3: Experiment of the Pharmacokinetics of the Compound in Rats The pharmacokinetic characteristics of the compound in rodents after intravenous injection and oral administration were tested by standard protocol. Specifically, the fasting SD male rats in the experiment were given the candidate compounds by intravenous injection and oral administration. Both oral preparation and intravenous preparation were prepared into 10 mg/mL or 30 mg/mL clear solutions with physiological saline and were administered by intravenous bolus or gavage for 5 minutes. Plasma samples were collected and analyzed by LC-MS/MS method, and pharmacokinetic parameters were calculated. The pharmacokinetic parameters of compound 15 were shown in Table 3.

The experimental results showed that the series of compounds of the present invention had good exposure when administered whether orally or intravenously, no obvious toxic and side effects at intravenous bolus of 300 mg/kg, good safety, and excellent pharmacokinetic properties.

TABLE 3

Pharmacokinetic data of the compounds of the present invention in rats

| Pharmacokinetic parameters in rats | | Example 15 |
|---|---|---|
| Intravenous bolus (100 mpk) | $C_0$ (μg/mL) | 579.7 |
| | Cl(mL/min/kg) | 3.02 |
| | $Vd_{ss}$ (L/kg) | 0.583 |
| | $T_{1/2}$ (h) | 3.9 |
| | $AUC_{0\text{-}last}$ (h*μg/mL) | 549.3 |
| Intravenous bolus (300 mpk) | $C_0$ (μg/mL) | 1385.1 |
| | Cl(mL/min/kg) | 4.29 |
| | $Vd_{ss}$ (L/kg) | 0.96 |
| | $T_{1/2}$ (h) | 4.56 |
| | $AUC_{0\text{-}last}$ (h*μg/mL) | 1155.2 |
| Oral (100 mpk) | $C_{max}$ (μg/mL) | 35.2 |
| | $T_{max}$ (h) | 2.0 |
| | $T_{1/2}$ (h) | 4.99 |
| | $AUC_{0\text{-}last}$ (h*μg/mL) | 278.3 |
| | Bioavailability (%)[#] | 52.2 |

[#]Note:
The calculation formula was bioavailability = $AUC_{0\text{-}inf}$ (100 mpk PO administration)/$AUC_{0\text{-}inf}$ (100 mpk IV administration)

Experimental Example 4: Pharmacodynamic Experiment of the Compound in Thigh Muscle and Lung 1) Thigh Muscle Model 36 CD-1 female mice were divided into 12 cages with 3 rats in each cage. The day of infection was denoted as day 0.

Immunosuppressant cyclophosphamide at 150 mg/kg was injected intraperitoneally on day −4 and immunosuppressant cyclophosphamide at 100 mg/kg was injected intraperitoneally on day −1 to induce immunodeficient mice.

On day −1, the strain *Klebsiella pneumoniae* ATCC BAA-1705 was resuscitated on an MHA plate. Resuscitated colonies were picked and dissolved in sterile physiological saline to prepare a bacterial solution with a concentration of 5.6E+07 CFU/mL for thigh muscle infection in mice. The initial time of infection was denoted as 0 h, and 100 μL of the bacterial solution was injected into each mouse at the thigh muscle at 0 h, that is, the inoculation amount was 5.6E+06 CFU/mouse. 2 h after infection, dosing was performed according to the experimental scheme. The specific experimental scheme was as follows (see Table 4):

(1) 2 h after infection: for the 1st cage of mice, at the endpoint, thigh muscle tissue was taken and placed in 10 mL of sterile physiological saline, the tissue was homogenized by a homogenizer, and the homogenate was diluted in a gradient and spotted in a plate, with two replicates for each mouse.

(2) 2 h after infection: the 2nd to 12th cages were respectively treated at 10 mL/kg by volume according to the body weight of the mice, the 2nd cage of mice were given a vehicle by intravenous injection every 2 h, and the endpoint was 12 h; the 3rd cage of mice were given 100 mg/kg of meropenem by intravenous injection every 2 h, and the endpoint was 12 h; the 4th cage of mice were given 100 mg/kg of meropenem and 20 mg/kg of QPX7728 by intravenous injection every 2 h, and the endpoint was 12 h; the 5th cage of mice were given 100 mg/kg of meropenem and 100 mg/kg of compound 15 by intravenous injection every 2 h, and the endpoint was 12 h; the 6th cage of mice were given 100 mg/kg of meropenem and 20 mg/kg of compound 15 by intravenous injection every 2 h, and the endpoint was 12 h; the 7th cage of mice were given 100 mg/kg of meropenem and 4 mg/kg of compound 15 by intravenous injection every 2 h, and the endpoint was 12 h; the 8th cage of mice were given 100 mg/kg of cefepime by intravenous injection every 2 h, and the endpoint was 12 h; the 9th cage of mice were given 100 mg/kg of cefepime and 20 mg/kg of QPX7728 by intravenous injection every 2 h, and the endpoint was 12 h; the 10th cage of mice were given 100 mg/kg of cefepime and 100 mg/kg of compound 15 by intravenous injection every 2 h, and the endpoint was 12 h; the 11th cage of mice were given 100 mg/kg of cefepime and 20 mg/kg of compound 15 by intravenous injection every 2 h, and the endpoint was 12 h; and the 12th cage of mice were given 100 mg/kg of cefepime and 4 mg/kg of compound 15 by intravenous injection every 2 h, and the endpoint was 12 h. At the endpoint of 12 h, thigh muscle tissue was taken and placed in 10 mL of sterile physiological saline, the tissue was homogenized by a homogenizer, and the homogenate was diluted in a gradient and spotted in a plate, with two replicates for each mouse. The bacterial load in the thigh muscle tissue of the mice was counted, and the experiment was summarized as follows (see Table 5):

TABLE 4

Experimental scheme for thigh muscle model

| Experimental groupe | Number of animals | Compound | Inoculation dose | Mode of administration | Experiment endpoint |
|---|---|---|---|---|---|
| 1 | 3 | 2 h control group | *Klebsiella* | — | 2 h |
| 2 | 3 | 12 h infection group | *pneumoniae* ATCC-BAA | 3% DMSO + 1% Tween 80 brine i.v. | 12 h |

TABLE 4-continued

| Experimental scheme for thigh muscle model | | | | | |
|---|---|---|---|---|---|
| Experimental groupe | Number of animals | Compound | Inoculation dose | Mode of administration | Experiment endpoint |
| 3 | 3 | Meropenem | 1705 5.60E+06 | 100 mpk, q2 h, 2, 4, 6, 8, 10 h, i.v. | 12 h |
| 4 | 3 | Meropenem + QPX7728 | CFU/mouse | 100 mpk + 20 mpk, q2 h, 2, 4, 6, 8, 10 h, i.v. | 12 h |
| 5 | 3 | Meropenem + compound 15 | | 100 mpk + 100 mpk, q2 h, 2, 4, 6, 8, 10 h, i.v. | 12 h |
| 6 | 3 | Meropenem + compound 15 | | 100 mpk + 20 mpk, q2 h, 2, 4, 6, 8, 10 h, i.v. | 12 h |
| 7 | 3 | Meropenem + compound 15 | | 100 mpk + 4 mpk, q2 h, 2, 4, 6, 8, 10 h, i.v. | 12 h |
| 8 | 3 | Cefepime | | 100 mpk, q2 h, 2, 4, 6, 8, 10 h, i.v. | 12 h |
| 9 | 3 | Cefepime + QPX7728 | | 100 mpk + 20 mpk, q2 h, 2, 4, 6, 8, 10 h, i.v. | 12 h |
| 10 | 3 | Cefepime + compound 15 | | 100 mpk + 100 mpk, q2 h, 2, 4, 6, 8, 10 h, i.v. | 12 h |
| 11 | 3 | Cefepime + compound 15 | | 100 mpk + 20 mpk, q2 h, 2, 4, 6, 8, 10 h, i.v. | 12 h |
| 12 | 3 | Cefepime + compound 15 | | 100 mpk + 4 mpk, q2 h, 2, 4, 6, 8, 10 h, i.v. | 12 h |

TABLE 5

| Experimental results of bacterial load in thigh muscle tissue of mice | |
|---|---|
| Group | Average CFU in mice |
| 2 h control group | 3.87E+07 CFU/mouse |
| 12 h infection group | 8.80E+08 CFU/mouse |
| Meropenem (100 mg/kg) | 4.83E+08 CFU/mouse |
| Meropenem (100 mg/kg) + QPX7728 (20 mg/kg) | 1.02E+07 CFU/mouse |
| Meropenem (100 mg/kg) + compound 15 (100 mg/kg) | 2.02E+06 CFU/mouse |
| Meropenem (100 mg/kg) + compound 15 (20 mg/kg) | 4.08E+06 CFU/mouse |
| Meropenem (100 mg/kg) + compound 15 (4 mg/kg) | 1.65E+07 CFU/mouse |
| Cefepime (100 mg/kg) | 4.25E+07 CFU/mouse |
| Cefepime (100 mg/kg) + QPX7728 (20 mg/kg) | 1.50E+07 CFU/mouse |
| Cefepime (100 mg/kg) + compound 15 (100 mg/kg) | 1.24E+06 CFU/mouse |
| Cefepime (100 mg/kg) + compound 15 (20 mg/kg) | 2.06E+06 CFU/mouse |
| Cefepime (100 mg/kg) + compound 15 (4 mg/kg) | 5.68E+06 CFU/mouse |

2) Lung Infection Model

36 CD-1 female mice were divided into 12 cages with 3 rats in each cage. The day of infection was denoted as day 0.

Immunosuppressant cyclophosphamide at 150 mg/kg was injected intraperitoneally on day −4 and immunosuppressant cyclophosphamide at 100 mg/kg was injected intraperitoneally on day −1 to induce immunodeficient mice.

On day −1, the strain *Klebsiella pneumoniae* ATCC BAA-1705 was resuscitated on an MHA plate. Resuscitated colonies were picked and dissolved in sterile physiological saline to prepare a bacterial solution with a concentration of 2.75E+08 CFU/mL for lung infection by nasal drip. The initial time of infection was denoted as 0 h, and 50 μL of the bacterial solution was injected into each mouse by nasal drip at 0 h, that is, the inoculation amount was 1.38E+07 CFU/mouse. 2 h after infection, dosing was performed according to the experimental scheme. The specific experimental scheme was as follows (see Table 6):

(1) 2 h after infection: for the 1st cage of mice, at the endpoint, lung tissue was taken and placed in 10 mL of sterile physiological saline, the tissue was homogenized by a homogenizer, and the homogenate was diluted in a gradient and spotted in a plate, with two replicates for each mouse.

(2) 2 h after infection: the 2nd to 12th cages were respectively treated at 10 mL/kg by volume according to the body weight of the mice, the 2nd cage of mice were given a vehicle by intravenous injection every 2 h, and the endpoint was 12 h; the 3rd cage of mice were given 100 mg/kg of meropenem by intravenous injection every 2 h, and the endpoint was 12 h; the 4th cage of mice were given 100 mg/kg of meropenem and 20 mg/kg of QPX7728 by intravenous injection every 2 h, and the endpoint was 12 h; the 5th cage of mice were given 100 mg/kg of meropenem and 100 mg/kg of compound 15 by intravenous injection every 2 h, and the endpoint was 12 h; the 6th cage of mice were given 100 mg/kg of meropenem and 20 mg/kg of compound 15 by intravenous injection every 2 h, and the endpoint was 12 h; the 7th cage of mice were given 100 mg/kg of meropenem and 4 mg/kg of compound 15 by intravenous injection every 2 h, and the endpoint was 12 h; the 8th cage of mice were given 100 mg/kg of cefepime by intravenous injection every 2 h, and the endpoint was 12 h; the 9th cage of mice were given 100 mg/kg of cefepime and 20 mg/kg of QPX7728 by intravenous injection every 2 h, and the endpoint was 12 h; the 10th cage of mice were given 100 mg/kg of cefepime and 100 mg/kg of compound 15 by intravenous injection every 2 h, and the endpoint was 12 h: the 11th cage of mice were given 100 mg/kg of cefepime and 20 mg/kg of compound 15 by intravenous injection every 2 h, and the endpoint was 12 h; and the 12th cage of mice were given 100 mg/kg of cefepime and 4 mg/kg of compound 15 by intravenous injection every 2 h, and the endpoint was 12 h. At the endpoint, lung tissue was taken and placed in 10 mL of sterile physiological saline, the tissue was homogenized by a homogenizer, and the homogenate was diluted in a gradient and spotted in a plate, with two replicates for each mouse.

The bacterial load in the lung tissue of the mice was counted, and the experiment was summarized as follows (see Table 7):

TABLE 6

Experimental scheme for lung infection model

| Experimental groupe | Number of animals | Compound | Inoculation dose | Mode of administration | Experiment endpoint |
|---|---|---|---|---|---|
| 1 | 3 | 2 h control group | *Klebsiella* | — | 2 h |
| 2 | 3 | 12 h infection group | *pneumoniae* ATCC-BAA 1705 | 3% DMSO + 1% Tween 80 brine i.v. | 12 h |
| 3 | 3 | Meropenem | 1.38E+07 CFU/mouse | 100 mpk, q2 h, 2, 4, 6, 8, 10 h, i.v. | 12 h |
| 4 | 3 | Meropenem + QPX7728 | | 100 mpk + 20 mpk, q2 h, 2, 4, 6, 8, 10 h, i.v. | 12 h |
| 5 | 3 | Meropenem + compound 15 | | 100 mpk + 100 mpk, q2 h, 2, 4, 6, 8, 10 h, i.v. | 12 h |
| 6 | 3 | Meropenem + compound 15 | | 100 mpk + 20 mpk, q2 h, 2, 4, 6, 8, 10 h, i.v. | 12 h |
| 7 | 3 | Meropenem + compound 15 | | 100 mpk + 4 mpk, q2 h, 2, 4, 6, 8, 10 h, i.v. | 12 h |
| 8 | 3 | Cefepime | | 100 mpk, q2 h, 2, 4, 6, 8, 10 h, i.v. | 12 h |
| 9 | 3 | Cefepime + QPX7728 | | 100 mpk + 20 mpk, q2 h, 2, 4, 6, 8, 10 h, i.v. | 12 h |
| 10 | 3 | Cefepime + compound 15 | | 100 mpk + 100 mpk, q2 h, 2, 4, 6, 8, 10 h, i.v. | 12 h |
| 11 | 3 | Cefepime + compound 15 | | 100 mpk + 20 mpk, q2 h, 2, 4, 6, 8, 10 h, i.v. | 12 h |
| 12 | 3 | Cefepime + compound 15 | | 100 mpk + 4 mpk, q2 h, 2, 4, 6, 8, 10 h, i.v. | 12 h |

TABLE 7

Experimental results of bacterial load in the tissue of the lung infection model of mice

| Group | Average CFU in mice |
|---|---|
| 2 h control group | 1.53E+07 CFU/mouse |
| 12 h infection group | 4.70E+08 CFU/mouse |
| Meropenem (100 mg/kg) | 2.73E+08 CFU/mouse |
| Meropenem (100 mg/kg) + QPX7728 (20 mg/kg) | 8.42E+06 CFU/mouse |
| Meropenem (100 mg/kg) + compound 15 (100 mg/kg) | 7.67E+05 CFU/mouse |
| Meropenem (100 mg/kg) + compound 15 (20 mg/kg) | 6.04E+06 CFU/mouse |
| Meropenem (100 mg/kg) + compound 15 (4 mg/kg) | 6.83E+07 CFU/mouse |
| Cefepime (100 mg/kg) | 1.90E+08 CFU/mouse |
| Cefepime (100 mg/kg) + QPX7728 (20 mg/kg) | 2.68E+06 CFU/mouse |
| Cefepime (100 mg/kg) + compound 15 (100 mg/kg) | 1.84E+05 CFU/mouse |
| Cefepime (100 mg/kg) + compound 15 (20 mg/kg) | 3.73E+05 CFU/mouse |
| Cefepime (100 mg/kg) + compound 15 (4 mg/kg) | 2.38E+06 CFU/mouse |

Conclusion: The mouse thigh muscle infection model and the mouse lung infection model showed that the compound of the present invention combined with meropenem or cefepime had significant in vivo infection inhibition effects.

The invention claimed is:

1. A compound represented by Formula (II) or (II') or a pharmaceutically acceptable salt thereof, (II)

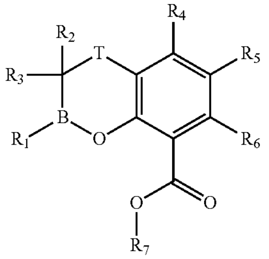

or (II')

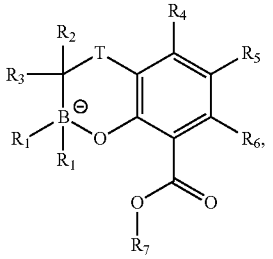

wherein B is boron;

T is —O—, —S—, or —Se—;

each $R_1$ is independently —OH or $C_{1-3}$ alkoxy;

$R_2$ and $R_3$ are each independently H or $C_{1-3}$ alkyl, wherein the $C_{1-3}$ alkyl is optionally substituted with 1, 2, or 3 substituents independently selected from F, Cl, Br, I, —OH, and —$OCH_3$;

$R_4$ is H, F, Cl, Br, I, $C_{1-3}$ alkyl, or $C_{1-3}$ alkoxy, wherein the $C_{1-3}$ alkyl and $C_{1-3}$ alkoxy are each independently and optionally substituted with 1, 2, or 3 substituents independently selected from F, Cl, Br, I, –OH, and —$OCH_3$;

$R_5$ is H, F, Cl, Br, I, or $C_{1-3}$ alkoxy;

$R_6$ is H, F, Cl, Br, I, —$OR_a$, or $C_{1-3}$ alkyl, wherein the $C_{1-3}$ alkyl is optionally substituted with 1, 2, or 3 substituents independently selected from F, Cl, Br, I, —OH, and —$OCH_3$;

or $R_5$ and $R_6$ together with the carbon atom to which they are attached form a 5-6-membered oxygen-containing non-aromatic heterocyclic ring, wherein the 5-6-membered oxygen-containing non-aromatic heterocyclic ring is optionally substituted with 1, 2, or 3 substituents independently selected from F, Cl, Br, I, –OH, and —$OCH_3$;

$R_7$ is H, $C_{1-3}$ alkyl, —$C(R_b)_2OC(=O)R_c$, or —$C(R_b)_2OC(=O)OR_c$, wherein the $C_{1-3}$ alkyl is optionally substituted with 1, 2, or 3 substituents independently selected from F, Cl, Br, I, —OH, and —$OCH_3$;

$R_a$ is H, $C_{1-6}$ alkyl,

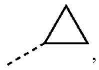 , 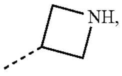 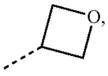 or 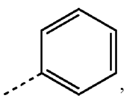 , wherein the $C_{1-6}$ alkyl,

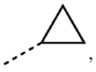 , 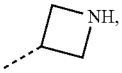 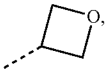 and 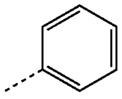

are each independently and optionally substituted with 1, 2, or 3 $R_{a1}$;

each $R_b$ is independently H or $C_{1-3}$ alkyl;

$R_c$ is H, $C_{1-3}$ alkyl,

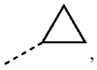 , or 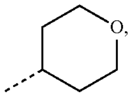

wherein the $C_{1-3}$ alkyl,

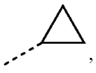 , and 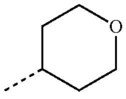

are each independently and optionally substituted with 1, 2, or 3 $R_{c1}$;

each $R_{a1}$ is independently F, Cl, Br, I, $C_{1-3}$ alkyl, $C_{1-3}$ alkoxy,

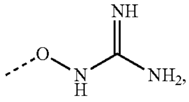 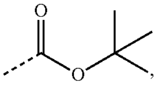 , 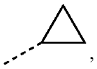 ,

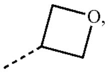 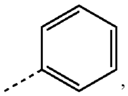 , or 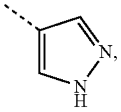

wherein the $C_{1-3}$ alkyl, $C_{1-3}$ alkoxy,

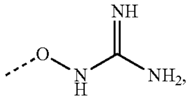 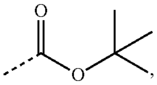 , 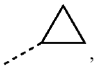 ,

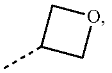 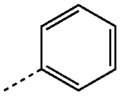 , and 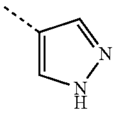

are each independently and optionally substituted with 1, 2, or 3 R;

each $R_{c1}$ is independently F, Cl, Br, I, —OH, $C_{1-3}$ alkyl, or $C_{1-3}$ alkoxy; and each R is independently F, Cl, Br, I, —OH, or $C_{1-3}$ alkyl, wherein the $C_{1-3}$ alkyl is optionally substituted with 1, 2, or 3 substituents independently selected from F, Cl, Br, I, and

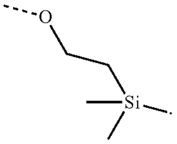

2. The compound or the pharmaceutically acceptable salt thereof according to claim 1, wherein the compound has a structure represented by Formula (II-1), (II'-1), (II-2), or (II'-2):

(II-1)

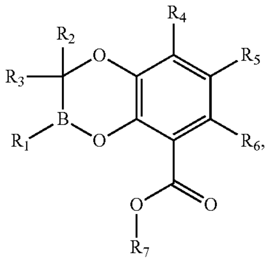

-continued (II'-1)

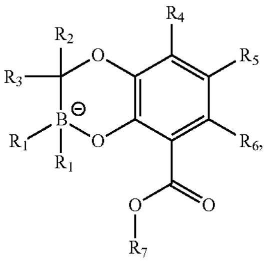

(II-2)

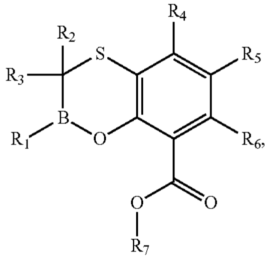 or (II'-2)

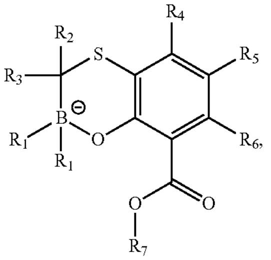

wherein $R_1$, $R_2$, $R_3$, $R_4$, $R_5$, $R_6$, and $R_7$ are as defined in claim 1.

3. The compound or the pharmaceutically acceptable salt thereof according to claim 1, wherein each $R_1$ is independently —OH or —$OCH_3$; and/or each $R_2$ and $R_3$ are each independently H or —$CH_3$; and/or $R_4$ is H, F, Cl, —$CH_3$, or —$OCH_2CH_3$; and/or $R_5$ is H, F, Cl, or —$OCH_3$; and/or each R is independently F, Cl, Br, I, —$CH_3$, or

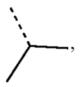, wherein the —$CH_3$ or

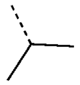

is each independently and optionally substituted with 1, 2, or 3 substituents independently selected from F, Cl, Br, I, and

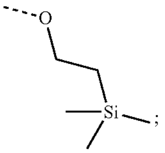;

and/or each $R_{a1}$ is independently F, Cl, Br, I, —$OCH_3$,

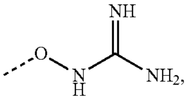, 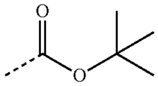, 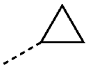, 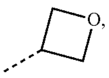, 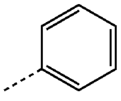, or 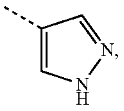

wherein the —$OCH_3$,

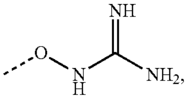, 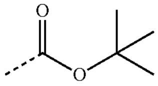, 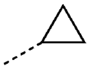, 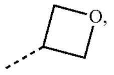, 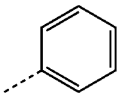, and 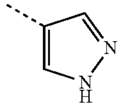

are each independently and optionally substituted with 1, 2, or 3 R; and/or $R_a$ is H, —$CH_3$, —$CH_2CH_3$,

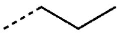, 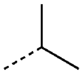, 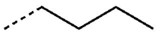, 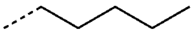, 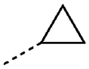, 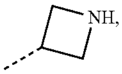, 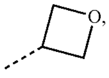 or 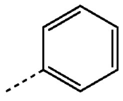, wherein the —$CH_3$, —$CH_2CH_3$,

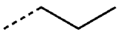, 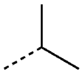, 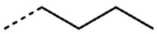, 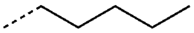, 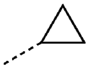, 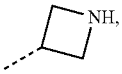, 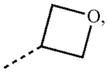 and 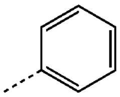

are each independently and optionally substituted with 1, 2, or 3 $R_{a1}$; and/or $R_6$ is H, F, Cl, Br, I, —$OR_a$, or —$CH_3$, wherein the —$CH_3$ is optionally substituted with 1, 2, or 3 substituents independently selected from F, Cl, Br, I, —OH, and —$OCH_3$; and/or each $R_b$ is independently H; and/or each $R_{c1}$ is independently —$OCH_3$; and/or $R_c$ is H, —$CH_3$, —$CH_2CH_3$,

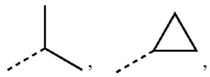

or

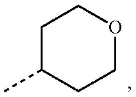

wherein the —$CH_3$, —$CH_2CH_3$,

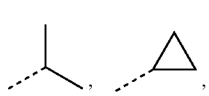

and

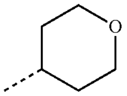

are each independently and optionally substituted with 1, 2, or 3 $R_{c1}$; and/or $R_7$ is H

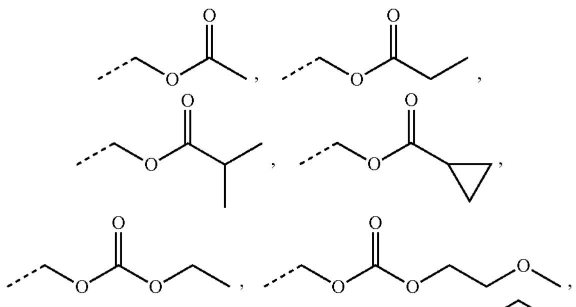

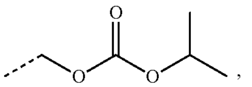

or

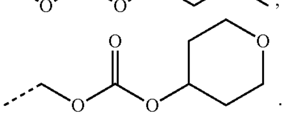

4. The compound or the pharmaceutically acceptable salt thereof according to claim 1, wherein each R is independently F, Cl, Br, I, —$CH_3$,

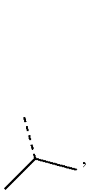

or

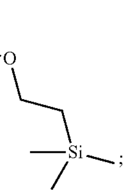

and/or each $R_{a1}$ is independently F, Cl, Br, I, —$OCH_3$,

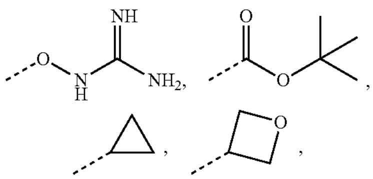

-continued

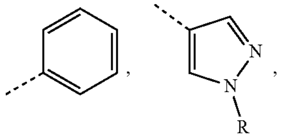

or

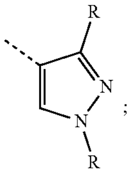

and/or $R_a$ is H, —$CH_3$,

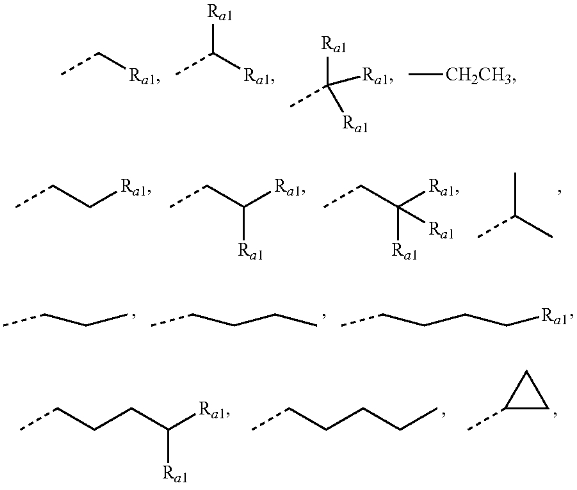

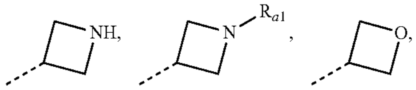

or

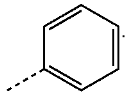

5. The compound or the pharmaceutically acceptable salt thereof according to claim 1, wherein each $R_{a1}$ is independently F, Cl, Br, I, —$OCH_3$,

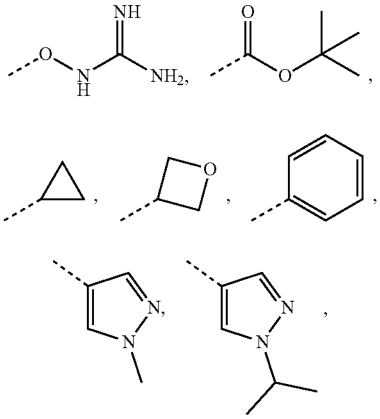

-continued
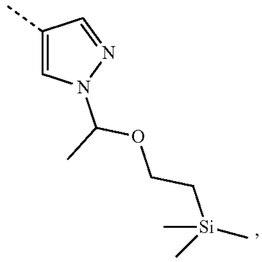
, or
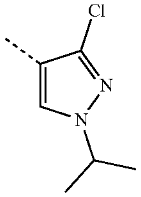
;
and/or
$R_a$ is H, $—CH_3$,
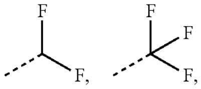
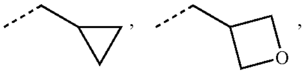
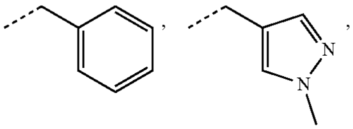
,
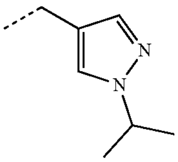
,
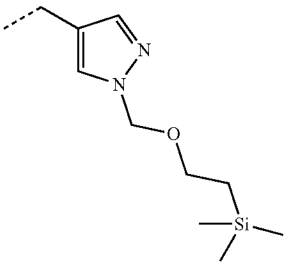
,
$—CH_2CH_3$,
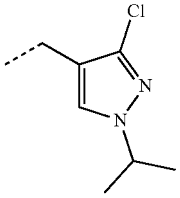
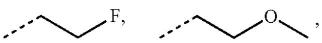
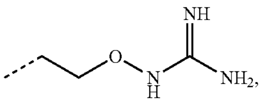
,
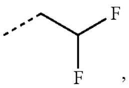
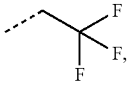
,
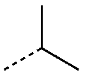
,
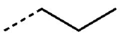
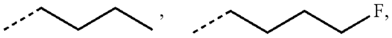
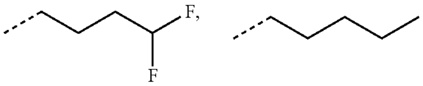
,
-continued
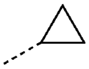
,
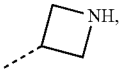
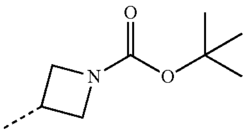
,
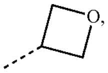
or
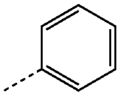
; and/or
$R_6$ is H, F, Cl, Br, I, —OH, $—OCH_3$, $—OCH_2CH_3$, $—CH_3$, $—CH_2OH$, $—CH_2OCH_3$,
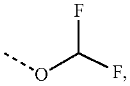
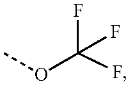
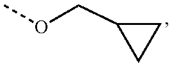
,
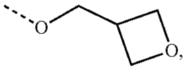
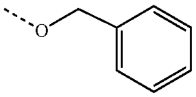
,
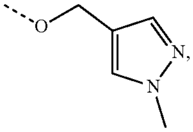
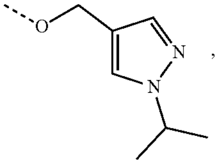
,
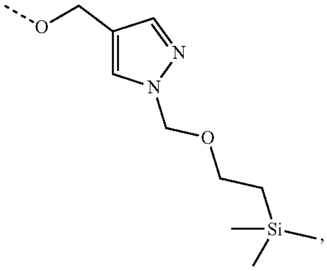
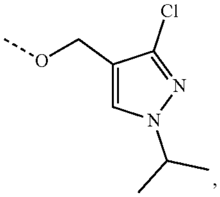
,
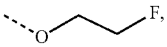
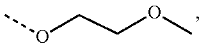
,
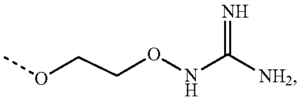
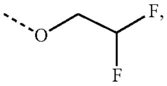
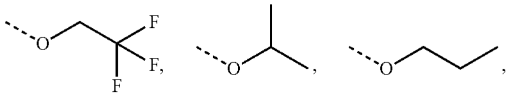
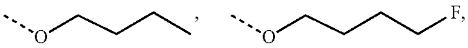
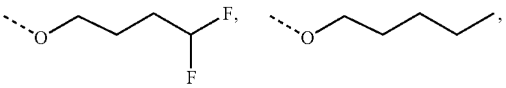
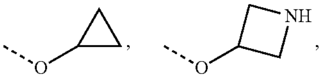
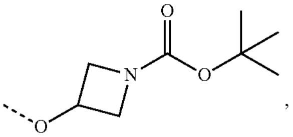
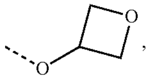
or -continued

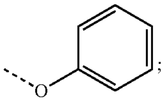

and/or $R_c$ is H, $-CH_3$, $-CH_2CH_3$,

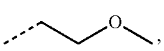, 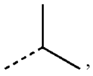, 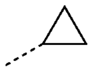, or 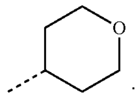.

6. The compound or the pharmaceutically acceptable salt thereof according to claim 1, wherein the structural unit

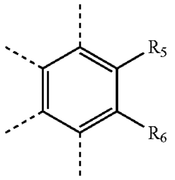 is 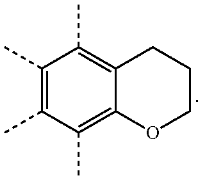.

7. The compound or the pharmaceutically acceptable salt thereof according to claim 1, wherein the compound has a structure represented by Formula (I) or (I'):

(I)

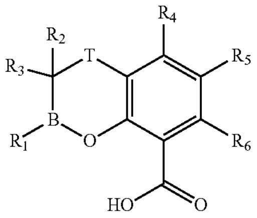

or (I')

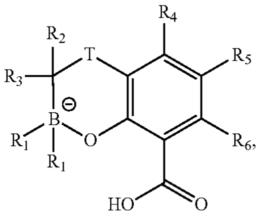

wherein T, $R_1$, $R_2$, $R_3$, $R_4$, $R_5$, and $R_6$ are as defined in claim 1.

8. The compound or the pharmaceutically acceptable salt thereof according to claim 7, wherein the compound has a structure represented by Formula (I-1), (I'-1), (I-2), or (I'-2):

(I-1)

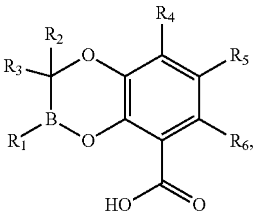

(I'-1)

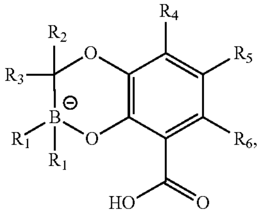

(I-2)

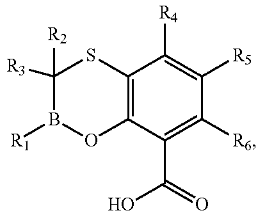

or (I'-2)

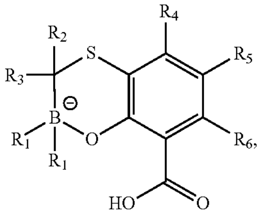

wherein $R_1$, $R_2$, $R_3$, $R_4$, $R_5$, and $R_6$ are as defined in claim 7.

9. The compound or the pharmaceutically acceptable salt thereof according to claim 8, wherein the pharmaceutically acceptable salt thereof has a structure represented by Formula (I-3), (I-4), (I-5), or (I-6):

(I-3)

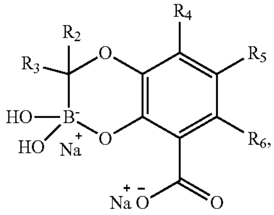

(I-4)

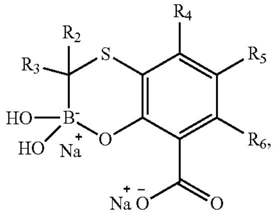

-continued
(I-5)
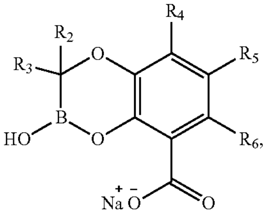
or
(I-6)
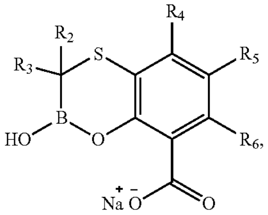
wherein $R_2$, $R_3$, $R_4$, $R_5$, and $R_6$ are as defined in claim 8.
10. A compound of the following formula or a pharmaceutically acceptable salt thereof:
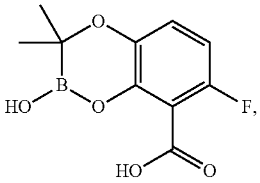
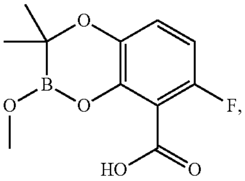
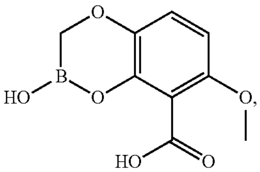
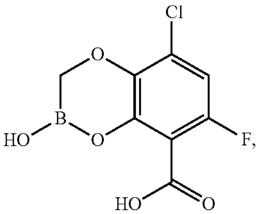
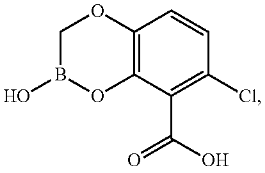
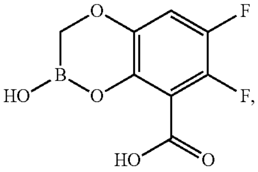
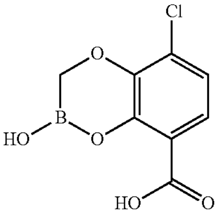
,
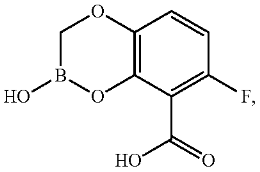
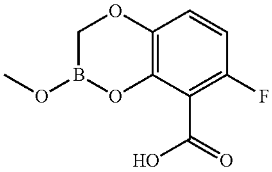
,
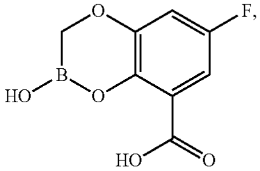
-continued
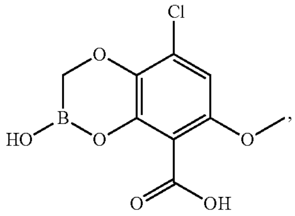
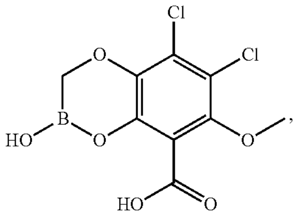
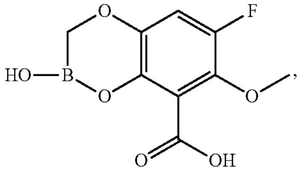
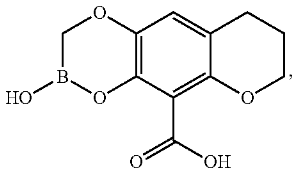
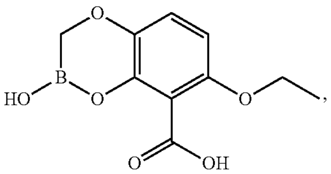
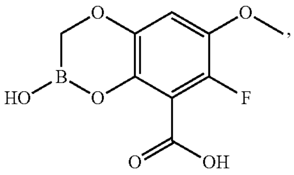
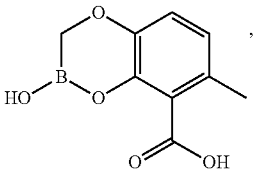
,
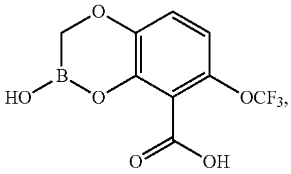
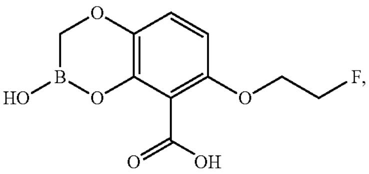
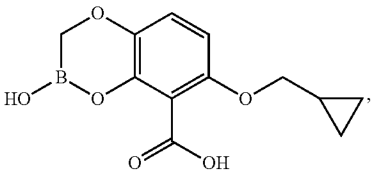

-continued
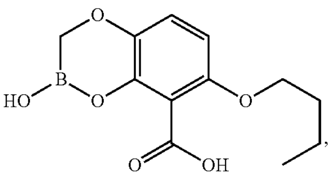
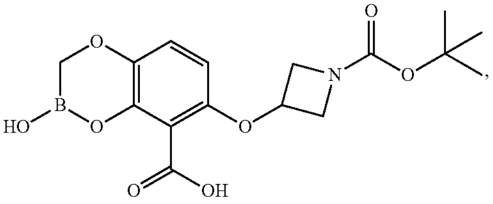
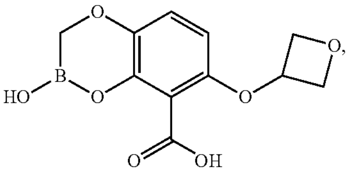
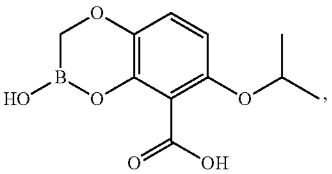
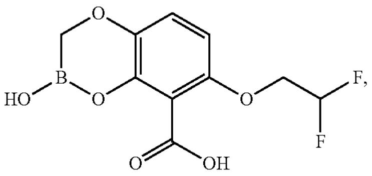
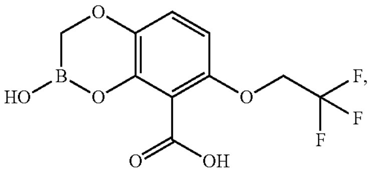
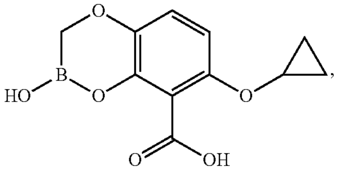
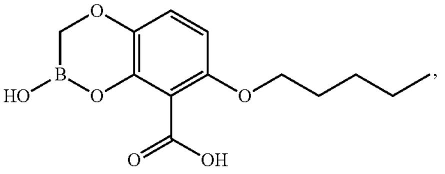
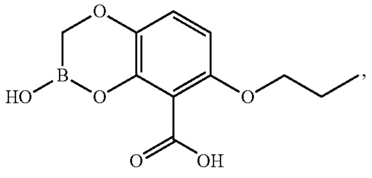
-continued
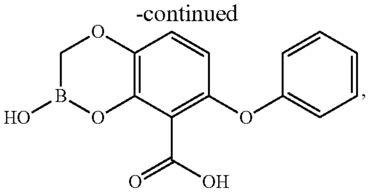
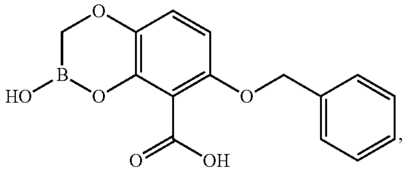
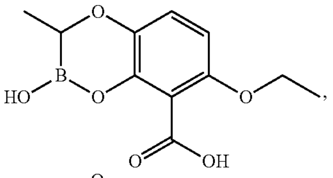
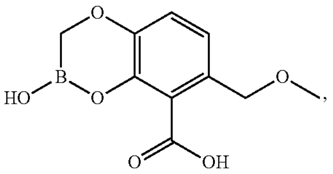
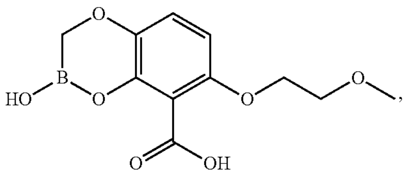
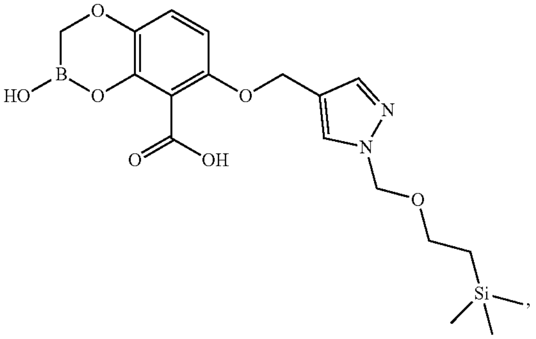
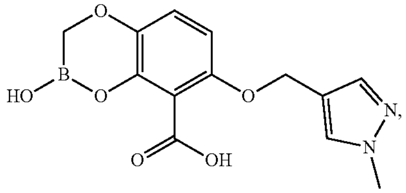
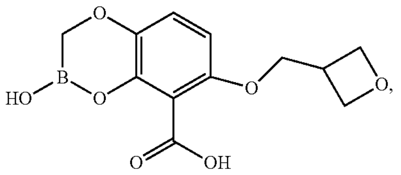
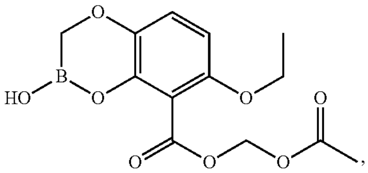

-continued
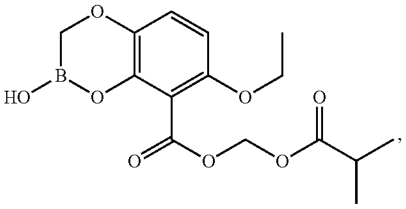
,
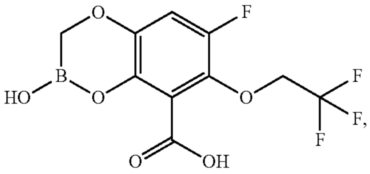
,
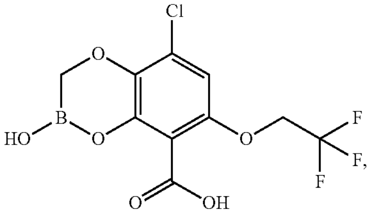
,
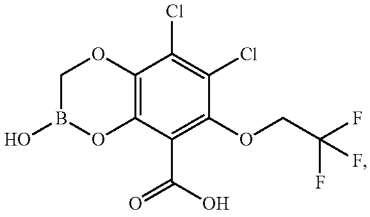
,
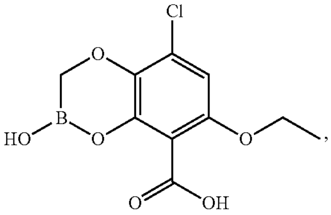
,
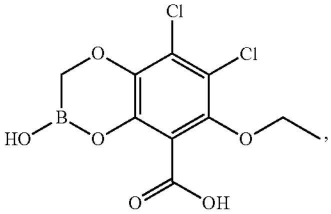
,
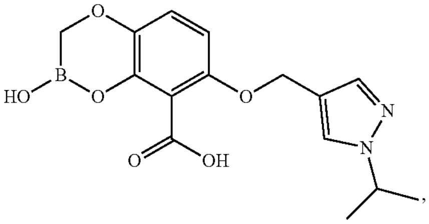
,
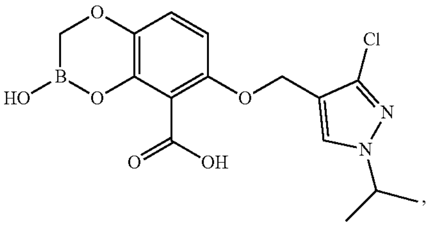
,
-continued
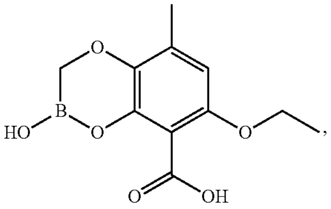
,
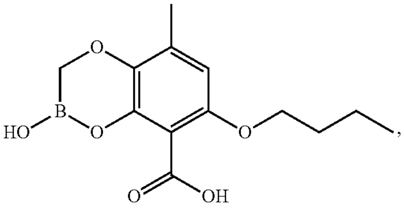
,
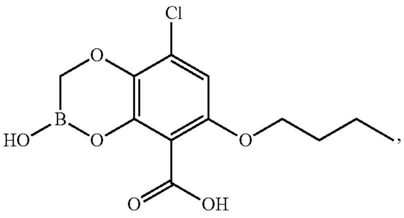
,
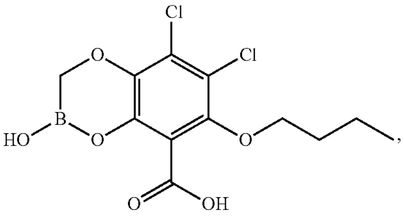
,
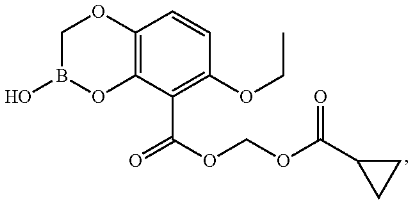
,
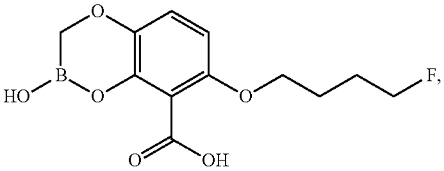
,
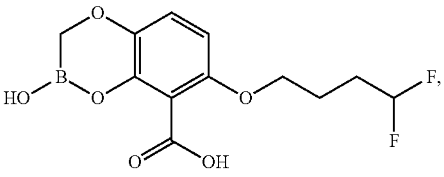
,
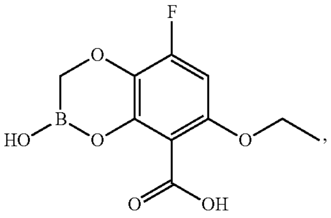
, -continued
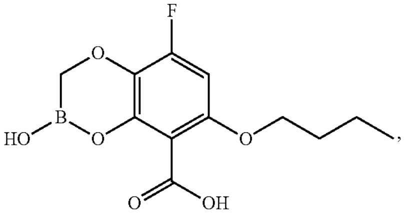
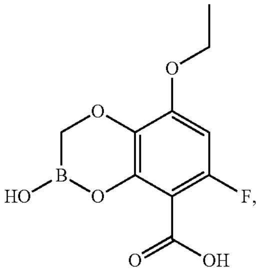
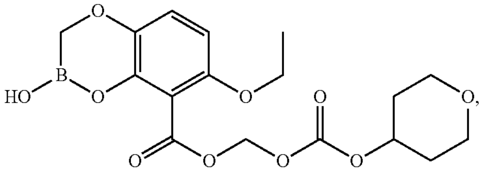
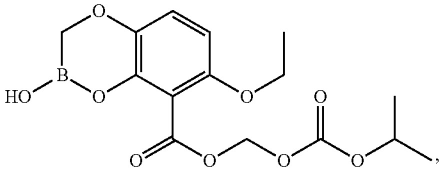
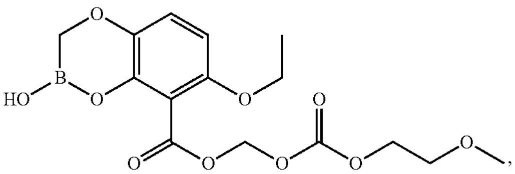
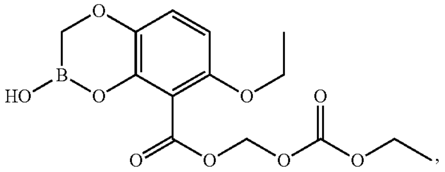
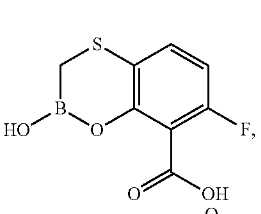
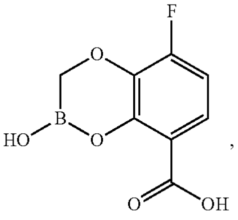
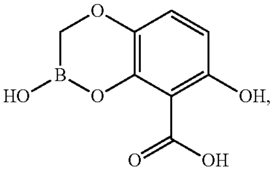
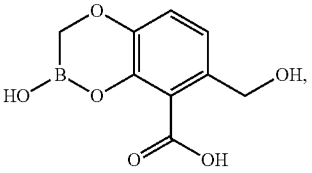
-continued
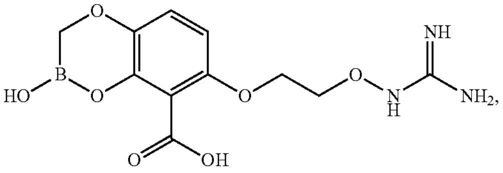
or
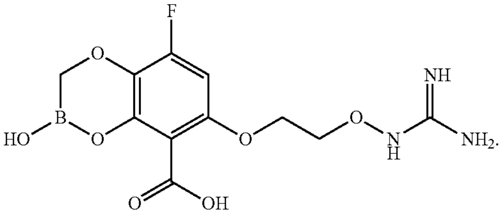
11. A compound of the following formula:
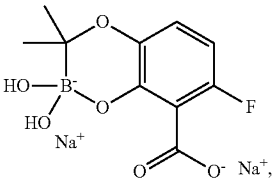
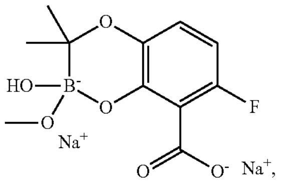
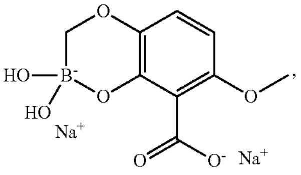
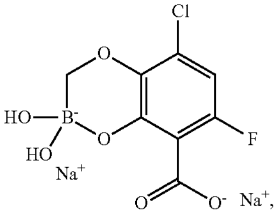
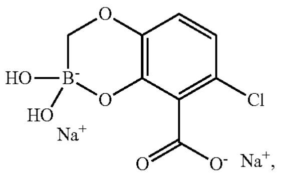
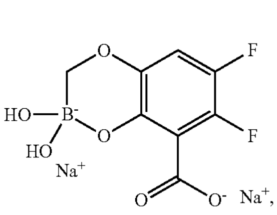
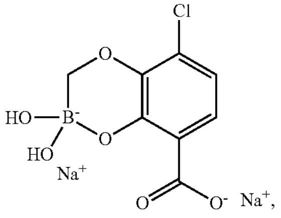
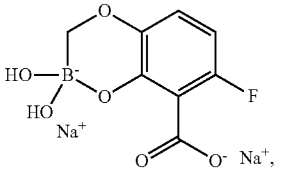
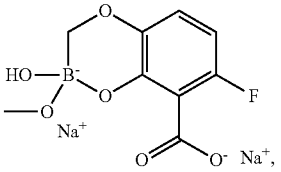

-continued
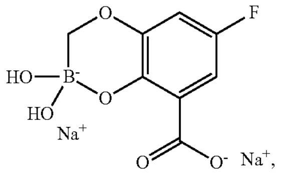
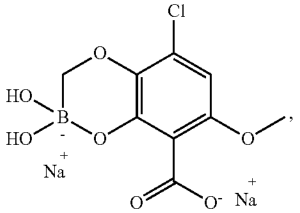
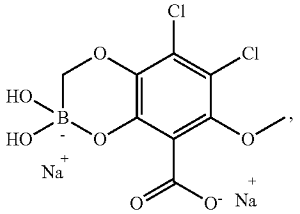
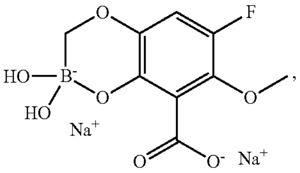
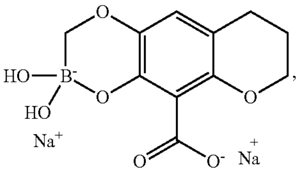
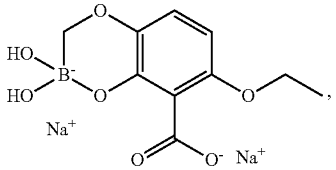
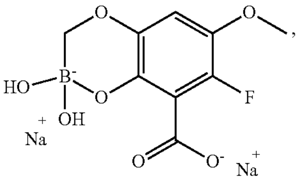
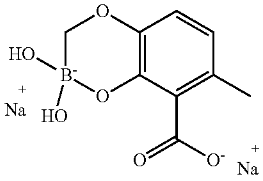
,
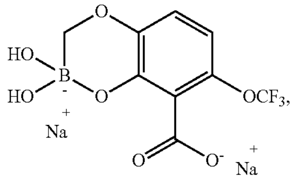
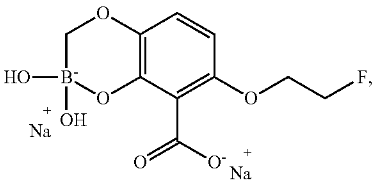
-continued
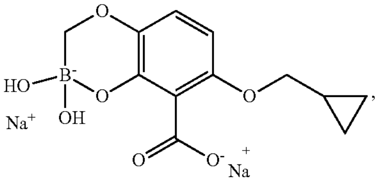
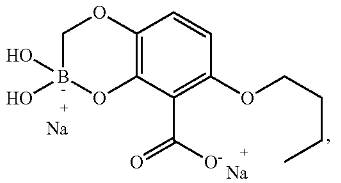
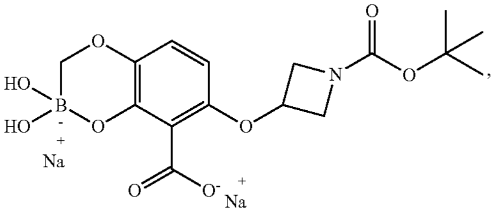
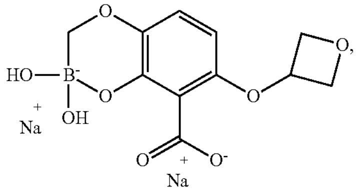
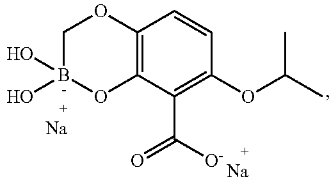
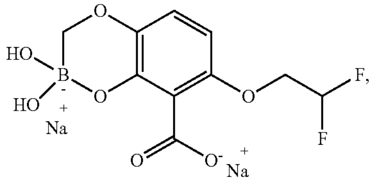
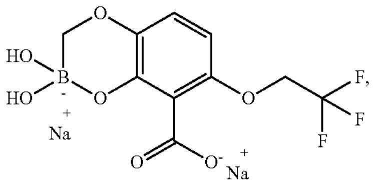
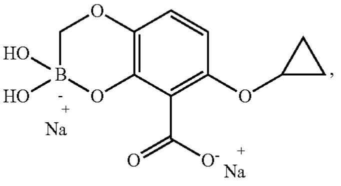
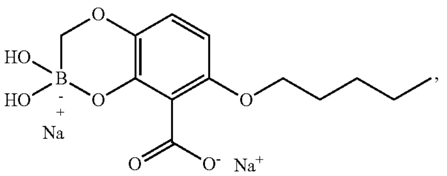

-continued
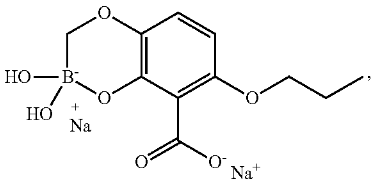
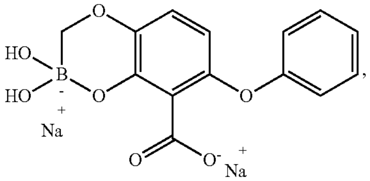
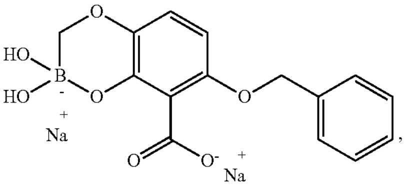
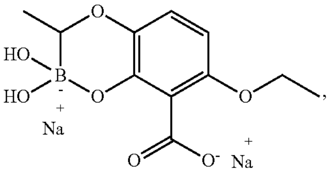
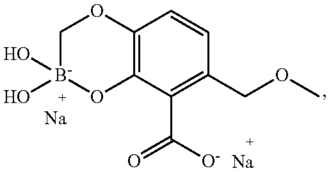
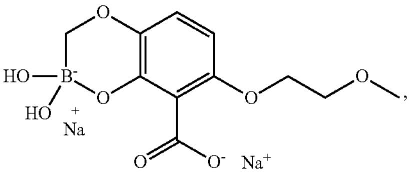
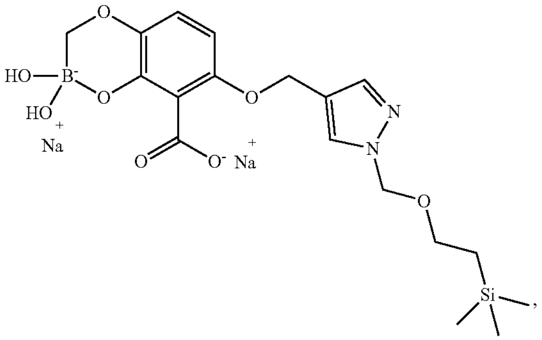
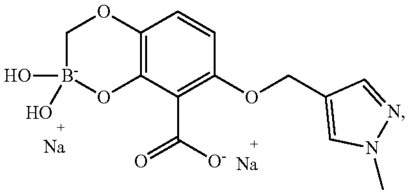
-continued
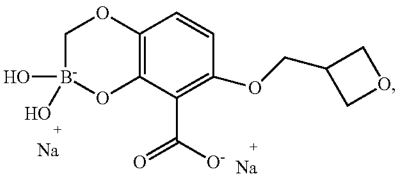
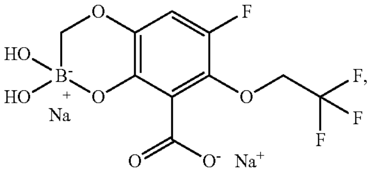
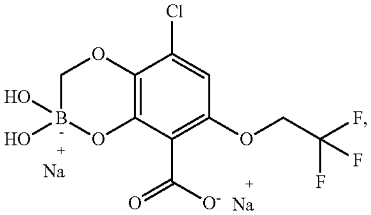
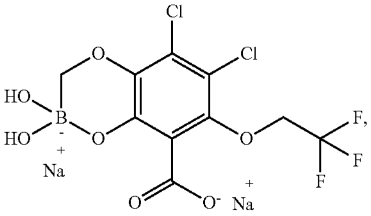
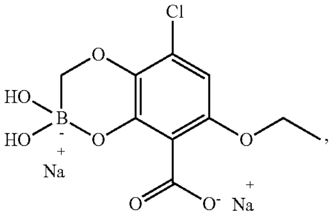
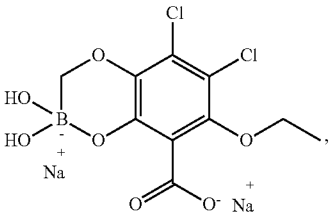
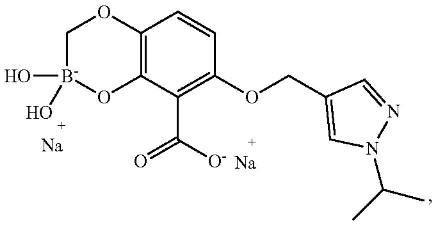
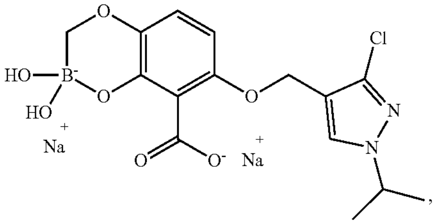

-continued
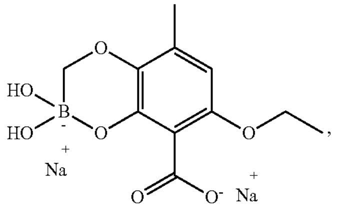
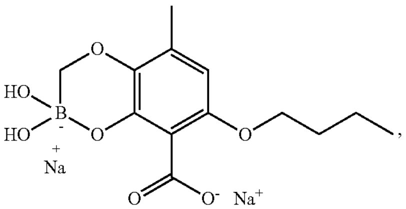
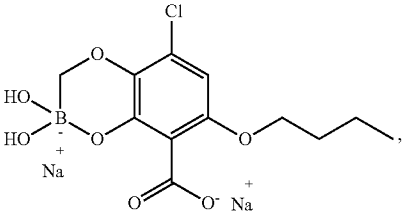
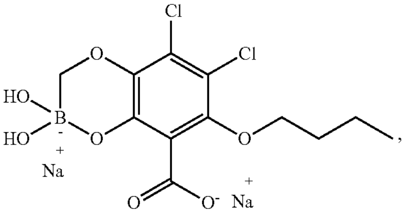
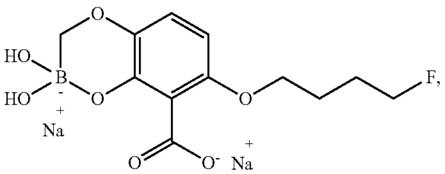
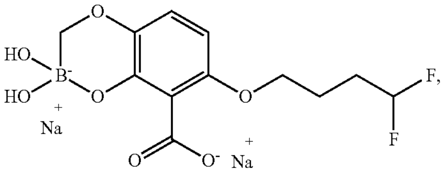
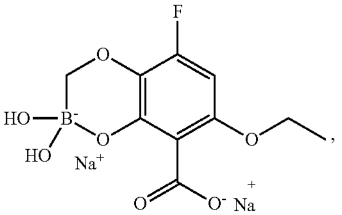
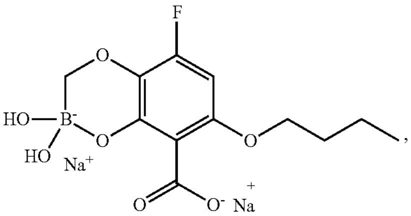
-continued
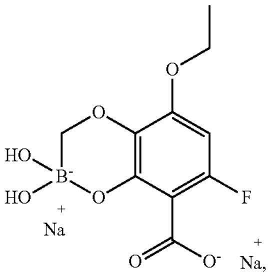
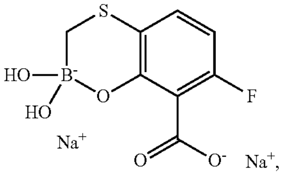
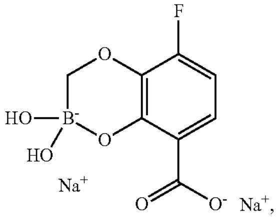
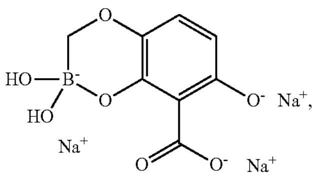
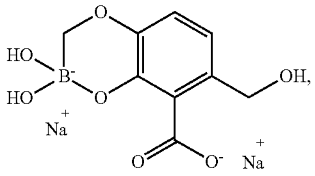
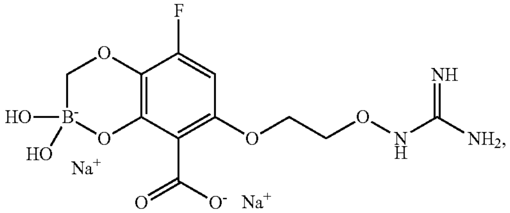
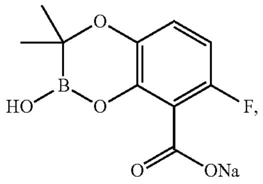
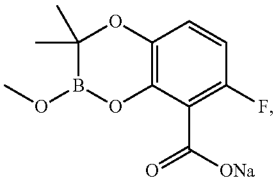
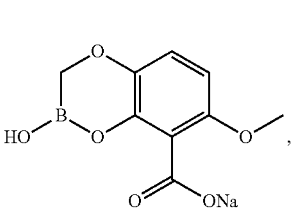
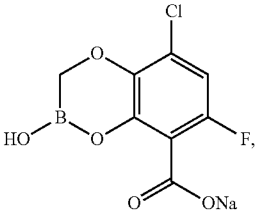
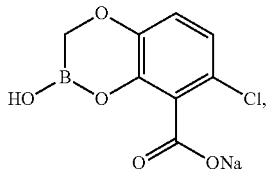
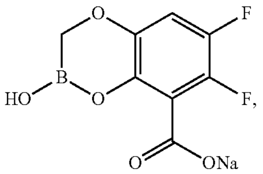

-continued
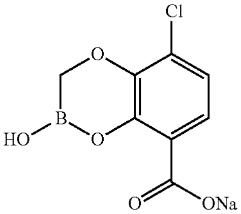
,
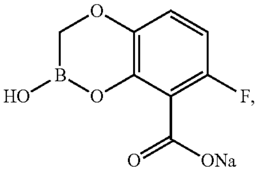
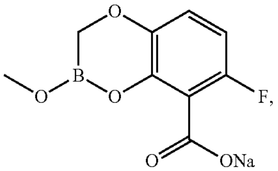
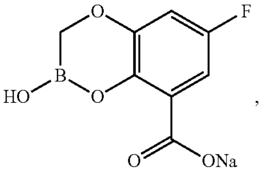
,
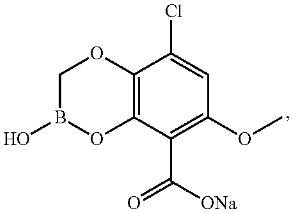
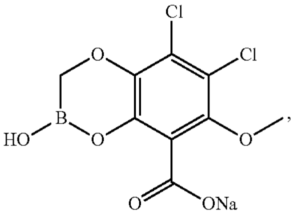
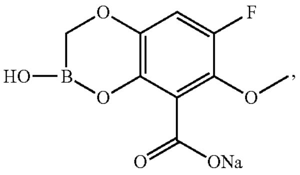
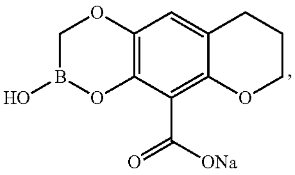
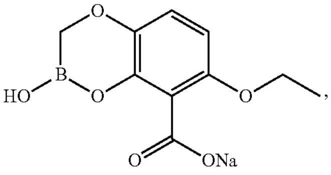
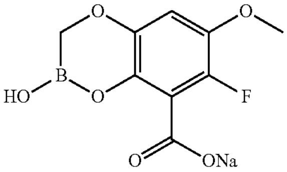
,
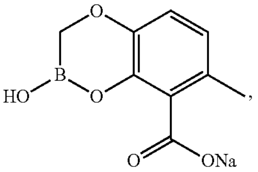
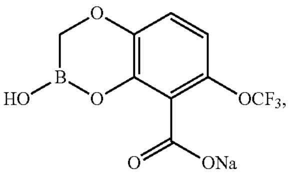
-continued
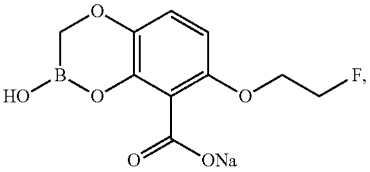
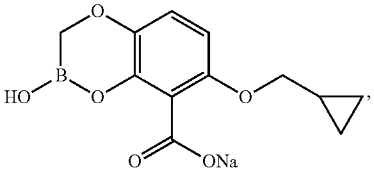
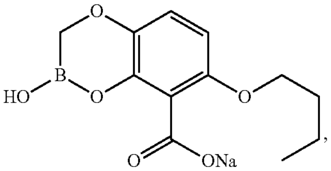
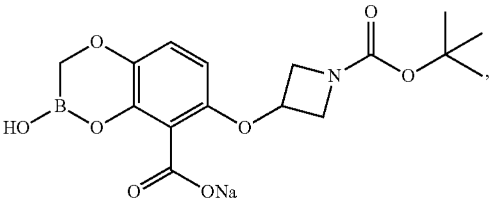
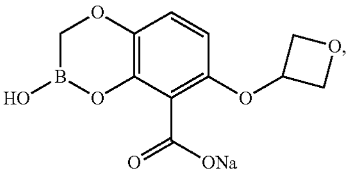
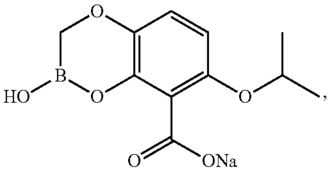
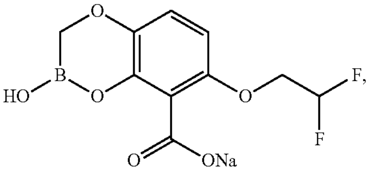
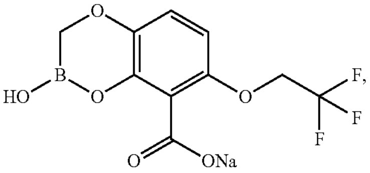
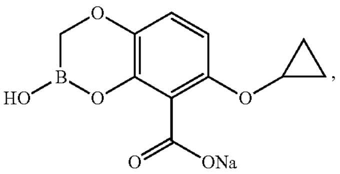

-continued
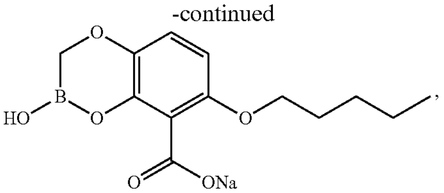
,
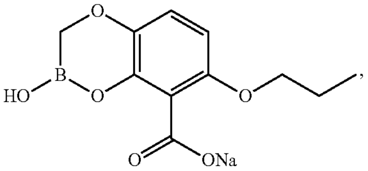
,
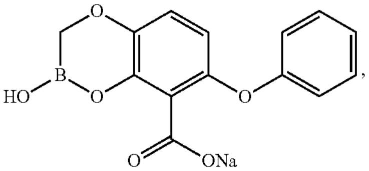
,
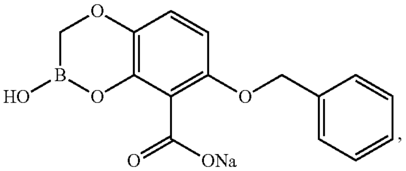
,
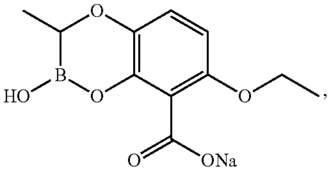
,
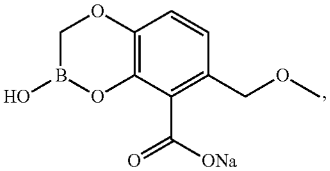
,
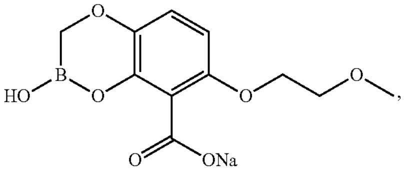
,
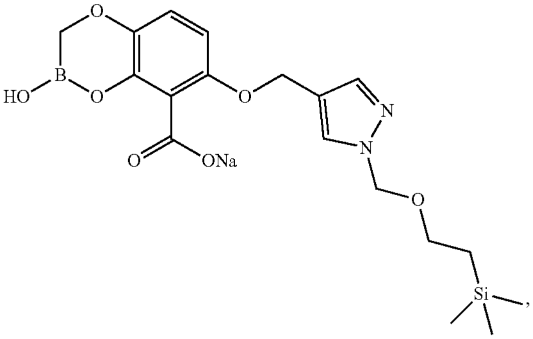
,
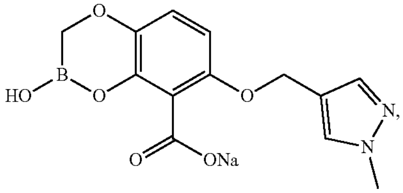
-continued
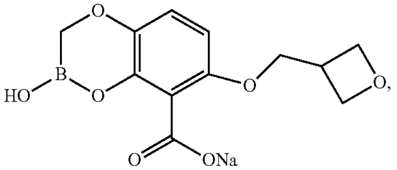
,
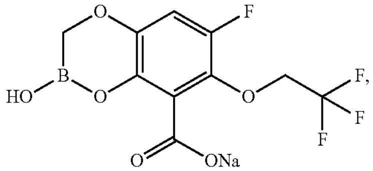
,
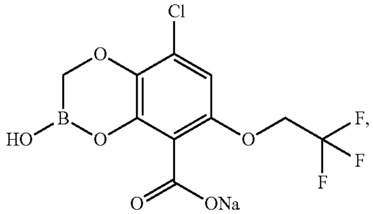
,
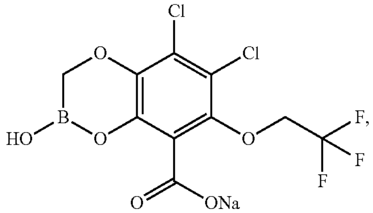
,
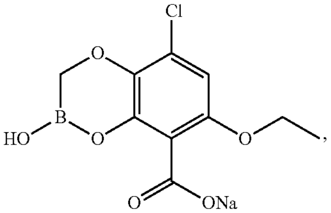
,
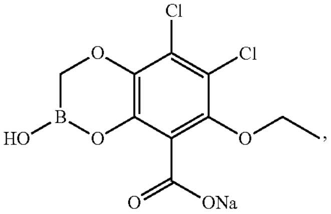
,
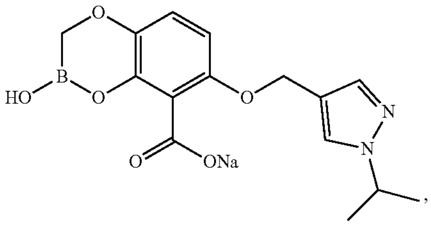
,
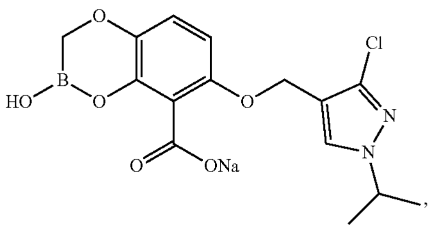
, -continued

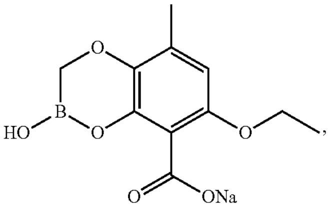,

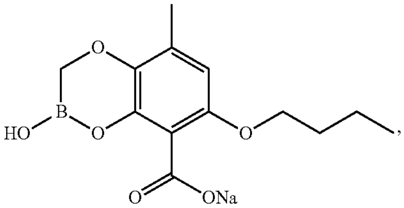,

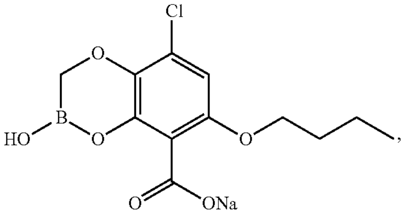,

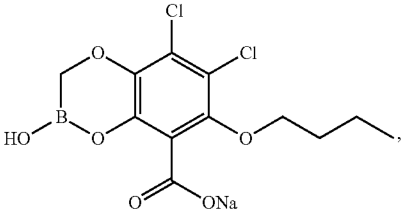,

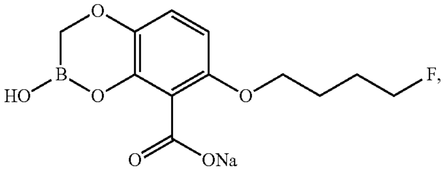,

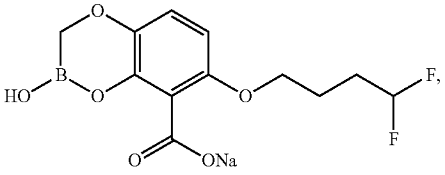,

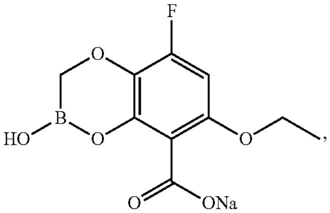,

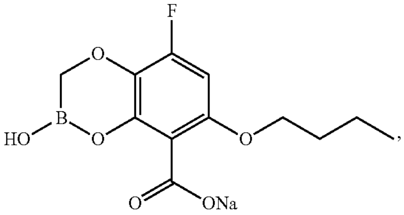,

-continued

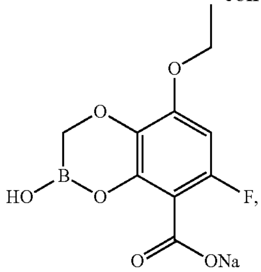,

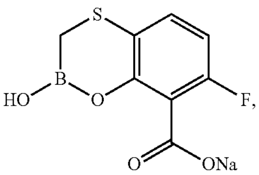,

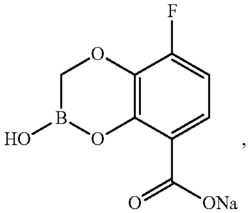,

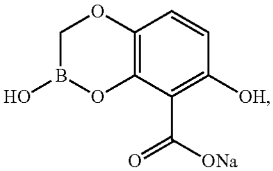,

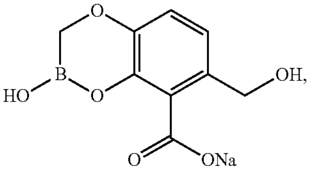,

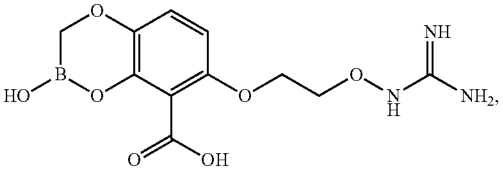, or

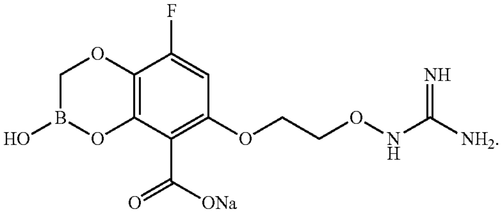.

12. The compound or the pharmaceutically acceptable salt thereof according to claim 1, wherein the pharmaceutically acceptable salt is a sodium salt.

13. A pharmaceutical composition comprising a therapeutically effective amount of the compound or the pharmaceutically acceptable salt thereof according to claim 1, a β-lactam antibacterial agent, and a pharmaceutically acceptable carrier.

14. The pharmaceutical composition according to claim 13, wherein the β-lactam antibacterial agent is based on penicillin, cephalosporin, cephamycin, oxacephem, carbapenem, or monocyclic lactam.

15. The pharmaceutical composition according to claim 14, wherein the β-lactam antibacterial agent is amoxicillin, piperacillin, ticarcillin, azlocillin, mezlocillin, cefazolin, cefradine, cefotaxime, cefuroxime, cefaclor, cefotiam, cefprozil, cefotaxime, ceftriaxone, ceftazidime, cefoperazone, ceftizoxime, cefmenoxime, cefodizime, cefpodoxime, cefixime, ceftibuten, cefpirome, cefepime, cefoxitin, cefmetazole, panipenem, aztreonam, carumonam, cefoxitin, cefmetazole, latamoxef, flomoxef, imipenem, meropenem, ceftolozane, or cefiderocol.

16. A method of preparing a β-lactamase inhibitor medicament, comprising combining a compound or a pharmaceutically acceptable salt thereof according to claim 1, a β-lactam antibacterial agent, and a pharmaceutically acceptable carrier.

17. A method for treating a disease associated with bacterial infection, the method comprising administering a therapeutically effective amount of a compound or pharmaceutically acceptable salt thereof according to claim 1.

* * * * *